US008916550B2

(12) United States Patent
Chong et al.

(10) Patent No.: US 8,916,550 B2
(45) Date of Patent: *Dec. 23, 2014

(54) COMPOUNDS FOR MODULATING TRPV3 FUNCTION

(75) Inventors: Jayhong A. Chong, Brookline, MA (US); Christopher Fanger, Bolton, MA (US); Glenn R. Larsen, Sudbury, MA (US); William C. Lumma, Jr., Helena, MT (US); Magdalene M. Moran, Brookline, MA (US); Amy Ripka, Wintrop, MA (US); Dennis John Underwood, Jamaica Plain, MA (US); Manfred Weigele, Cambridge, MA (US); Xiaoguang Zhen, Newton, MA (US); Anu Mahadevan, Westford, MA (US); Peter Meltzer, Lexington, MA (US)

(73) Assignee: Hydra Biosciences, Inc., Cambridge, MA (US)

( * ) Notice: Subject to any disclaimer, the term of this patent is extended or adjusted under 35 U.S.C. 154(b) by 77 days.

This patent is subject to a terminal disclaimer.

(21) Appl. No.: 11/600,514

(22) Filed: Nov. 15, 2006

(65) Prior Publication Data
US 2007/0213321 A1 Sep. 13, 2007

Related U.S. Application Data

(63) Continuation-in-part of application No. 11/431,942, filed on May 9, 2006, now Pat. No. 7,803,790.

(60) Provisional application No. 60/679,438, filed on May 9, 2005, provisional application No. 60/679,436, filed on May 9, 2005, provisional application No. 60/702,584, filed on Jul. 25, 2005.

(51) Int. Cl.
| *A61K 31/55* | (2006.01) |
| *A61K 31/47* | (2006.01) |
| *A61K 31/40* | (2006.01) |
| *A61K 31/165* | (2006.01) |
| *A61K 31/428* | (2006.01) |
| *C07D 417/12* | (2006.01) |
| *C07D 513/04* | (2006.01) |
| *C07D 401/12* | (2006.01) |
| *A61K 31/4709* | (2006.01) |

(52) U.S. Cl.
CPC ............ *C07D 417/12* (2013.01); *A61K 31/428* (2013.01); *C07D 513/04* (2013.01); *C07D 401/12* (2013.01); *A61K 31/4709* (2013.01); *A61K 31/55* (2013.01)
USPC ....... 514/217.07; 514/314; 514/423; 514/617

(58) Field of Classification Search
None
See application file for complete search history.

(56) References Cited

U.S. PATENT DOCUMENTS

| 4,273,927 A | 6/1981 | White, Jr. et al. |
| 4,461,896 A | 7/1984 | Portluck |
| 4,509,971 A | 4/1985 | Forster et al. |
| 4,784,682 A | 11/1988 | Forster et al. |
| 4,833,243 A | 5/1989 | Forster et al. |
| 5,101,034 A | 3/1992 | Schmidt et al. |
| 5,356,864 A | 10/1994 | Forster et al. |
| 5,442,074 A | 8/1995 | Forster et al. |
| 5,990,126 A | 11/1999 | Park et al. |
| 6,121,284 A | 9/2000 | Urbahns et al. |
| 6,245,817 B1 | 6/2001 | Connell et al. |
| 6,403,607 B1 | 6/2002 | Hidaka et al. |
| 2002/0156253 A1 | 10/2002 | Curtis et al. |
| 2003/0027164 A1 | 2/2003 | Gaughan et al. |
| 2003/0027232 A1 | 2/2003 | Davis et al. |
| 2003/0157633 A1 | 8/2003 | Bevan et al. |
| 2003/0219806 A1 | 11/2003 | Glucksmann et al. |
| 2004/0009537 A1 | 1/2004 | Roos et al. |
| 2004/0044031 A1 | 3/2004 | Yamada et al. |
| 2005/0059823 A1 | 3/2005 | McNaughton-Smith et al. |
| 2005/0070570 A1 | 3/2005 | Garcia et al. |
| 2005/0203159 A1 | 9/2005 | Zelle et al. |
| 2006/0270688 A1 | 11/2006 | Chong et al. |
| 2007/0179164 A1 | 8/2007 | Chong et al. |
| 2008/0146611 A1 | 6/2008 | Moran et al. |
| 2011/0144135 A1 | 6/2011 | Chong et al. |
| 2011/0151559 A1 | 6/2011 | Chong et al. |
| 2012/0015979 A1 | 1/2012 | Moran et al. |

FOREIGN PATENT DOCUMENTS

| DE | 3018075 A1 | 11/1981 |
| DE | 3038599 A1 | 5/1982 |
| DE | 3038652 A1 | 5/1982 |
| EP | 0318859 A2 | 6/1989 |
| EP | 0572893 A1 | 5/1993 |
| EP | 0573882 A1 | 6/1993 |
| EP | 0979823 A1 | 2/2000 |
| EP | 0665834 B1 | 5/2001 |
| JP | 56158702 | 7/1981 |
| WO | WO-95/01334 | 1/1995 |
| WO | WO-99/52875 A1 | 10/1999 |

(Continued)

OTHER PUBLICATIONS

Vippagunta SR, Brittain HG, Grant DJ. Crystalline solids. Adv Drug Deliv Rev. May 16, 2001;48(1):3-26. Review.*
Wolff, Manfred E ((Burger's Medicinal Chemistry 5ed, Part I) John Wiley & Sons, 1995, pp. 975-977).*
Banker ((Modern Pharmaceutics) Banker, G.S. et al, "Modern Pharmaceutics, 3ed.", Marcel Dekker, New York, 1996, pp. 451 and 596.*
STN Summary Accession No. 1980:146745 (containing summary of Foerster et al (DE 2822155 )).*
Anderson (Chem and Biol 10:787-797, 2003).*
Thiel (Nature Biotechnol 2:513-519, 2004).*
STN Registry File Records III.
Database Chemcats [Online], Chemical Abstracts Service, Columbus, Ohio, US; Aurora Screening Library, Order Nos. kuk-232311, ken-123216, ken-116846, Sep. 6, 2007.

(Continued)

*Primary Examiner* — Craig Ricci
(74) *Attorney, Agent, or Firm* — Lando & Anatasi LLP

(57) ABSTRACT

The present application relates to compounds and methods for treating pain and other conditions related to TRPV3.

26 Claims, 33 Drawing Sheets

(56) References Cited

FOREIGN PATENT DOCUMENTS

| WO | WO-02/04448 A2 | 1/2002 |
|---|---|---|
| WO | WO-02/101045 | 12/2002 |
| WO | WO-2004/069792 A2 | 8/2004 |
| WO | WO-2004/100865 A2 | 11/2004 |
| WO | WO-2005/023242 A1 | 3/2005 |
| WO | WO-2005/044221 A2 | 5/2005 |
| WO | WO-2005/049613 A1 | 6/2005 |
| WO | WO-2005/097112 A2 | 10/2005 |

OTHER PUBLICATIONS

Database Chemcats [Online], Chemical Abstracts Service, Columbus, Ohio, US; AKos Screening Library, Order Nos. AKL-P-1811372, AKL-P-0790097, Feb. 7, 2006.
International Search Report from PCT/US2007/020195, mailed Jan. 28, 2008.
Chung et al., "Biphasic Currents Evoked by Chemical or Thermal Activation of the Heat-gated Ion Channel, TRPV3," J. of Biological Chemistry 280: 15928-15941(2005).
Clapham et al., "The TRP Ion Channel Family," Nature Reviews, 2: 387-396(2001).
Clapham, David E., "Hot and Cold TRP Ion Channels," Science, 295: 2228-2229(2002).
Clapham, David E., "TRP channels as cellular sensors," Nature, 426: 517-524(2003).
Moqrich et al, "Impaired Thermosensation in Mice Lacking TRPV3, a Heat and Camphor Sensor in the Skin," Science 307(5714): 1468-1472(2005).
Moran et al., "TRP Ion Channels in the Nervous System," Current Opinion in Neurobiology, 14: 362-369(2004).
Peier et al., "A Heat-Sensitive TRP Channel Expressed in Keratinocytes," Science, 296: 2046-2049(2002).
Ramsey et al., "An Introduction to TRP Channels," Annual Rev. Physiology, 68: 619-647(2006).
Smith et al., "TRPV3 is a temperature-sensitive vallinoid receptor-like protein," Nature, 418: 186-190 (2002).
STN Registry File Records.
Xu et al., "Oregano, thyme and clove-derived flavors and skin sensitizers activate TRP channels," Nature Neuroscience Advance Online Publication, doi: 10.1038/nn1692, pp. 1-8(2006).
Xu et al., "TRPV3 is a calcium-permeable temperature-sensitive cation channel," Nature, 418: 181-186(2002).
RD 201017 (Research Disclosure), "Herbicidal Agents," 201:9-17(1981).
Burnstock, G. and Williams, M., "P2 Purinergic Receptors: Modulation of Cell Function and Therapeutic Potential," The Journal of Pharmacology and Experimental Therapeutics, 295(3):862-869(2000).
Burnstock, Geoffrey, "Pathophysiology and Therapeutic Potential of Purinergic Signaling," Pharmacological Reviews, 58(1):58-86(2006).
Foresta et al., "Extracellular ATP Is a Trigger for the Acrosome Reaction in Human Spermatozoa," J. Biol. Chem., 267(27)19443-19447(1992).
Gopinath et al., "Increased capsaicin receptor TRPV1 in skin nerve fibres and related vallinoid receptors TRPV3 and TRPV4 in keratinocytes in human breast pain," BMC Women's Health, 5:2(2005). (Also available at http://www.biomedcentral.com/1472-6874/5/2).
STN Registry File Records II.
Wang et al, "Extracellular ATP shows synergistic enhancement of DNA synthesis when combined with agents that are active in wound healing or as neurotransmitters," Biochemical and Biophysical Research Communications, 166(1):251-258(1990).
International Search Report from PCT/US2006/017995, mailed Nov. 22, 2006.
Written Opinion of the International Searching Authority for PCT/US2006/017995.
Written Opinion of the International Searching Authority for PCT/US2007/020195.
Levine, J.D., et al., "TRP channels: Targets for the relief of pain," Biochimica et Biophysica Acta, 1772:989-1003 (2007).
U.S. Appl. No. 11/431,942, filed May 9, 2006, Chong et al.
U.S. Appl. No. 11/592,783, filed Nov. 3, 2006, Chong et al.
U.S. Appl. No. 11/901,253, filed Sep. 14, 2007, Moran et al.
International Search Report and Written Opinion of the International Searching Authority for PCT/US2007/024100 issued Mar. 26, 2009.
European Search Report from EP 11006999 dated Oct. 26, 2011.
CAplus Accession No. 1986:14516.
CAplus Accession No. 1970: 443484.
Database Chemcats (online), Chemical Library, "Quinoline, 1-[[5-chloro-2-benzothiazolyl)thio]acetyl]-1,2,3,4-tetrahydro", CAS Registry No. 399010-02-7, Interchim Intermediates, Order No. BAS 06988536, Montlucon, France, Jan. 18, 2005.
Database Chemcats (online), Chemical Library, "Quinoline, 1-[(2-benzothiazolylthio)acetyl]- 1,2,3,4-tetrahydro", CAS Registry No. 296790-83-5, ChemDiv, Inc. Product Library, San Diego, CA, Apr. 25, 2003.
Gavva, N. R. et al., "AMG 9810 [(E)-3-(4-t-Butylphenyl)-N-(2,3-dihydrobenzo[b][1,4]dioxin-6-yl)acrylamide], a Novel Vanilloid Receptor 1 (TRPV1) Antagonist with Antihyperalgesic Properties", Journal of Pharmacology and Experimental Therapeutics, 313(1):474-484 (American Society for Pharmacology and Experimental Therapeutics, Dec. 22, 2004).
Ma, H.T. et al., Requirement of the inositol trisphosphate receptor for activation of store-operated Ca2+ channels, Science, 287:1647-1651 (2000).
Examination Report from related Australian application No. 2006244074 dated Feb. 23, 2011.
Examination Report from related Australian patent application No. 2006244074 dated May 3, 2012.
Office Action from related Canadian application No. 2,608,194 dated Oct. 9, 2012.
Examination Report from related European regional application No. EP 06759445.7 dated Mar. 16, 2010.
Examination Report from related European regional application No. EP 06759445.7 dated Sep. 13, 2011.
Extended European Search Report from related European regional application No. EP 11006999.4 dated Nov. 8, 2011.
Examination Report from related European regional application No. EP 11006999.4 dated Mar. 15, 2013.
Office Action from related Japanese patent application No. 2008-511295 dated Feb. 14, 2012.
Examination Report from related Taiwan patent application No. 095116362 dated Oct. 5, 2012.
Ma et al., "Requirement of the Inositol Trisphosphate Receptor for Activation of Store-Operated $Ca^{2=}$ Channels," Science, 287:1647-1651 (2000).
U.S. Appl. No. 11/920,184, filed Nov. 9, 2007, Chong et al.
U.S. Appl. No. 12/084,610, filed May 5, 2008, Chong et al.
U.S. Appl. No. 12/152,131, filed May 12, 2008, Chong et al.

* cited by examiner

| Compound | Structure | Mol. Weight |
|---|---|---|
| Compounds IC50 (patch, inward) < 0.2 uM ||| 
| 23 | 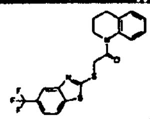 | 408.47 |
| 15 | 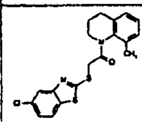 | 388.94 |
| 32 | 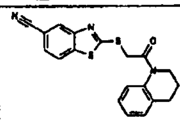 | 365.48 |
| 46 | 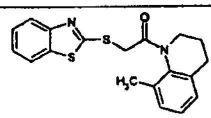 | 354.50 |
| 31 | 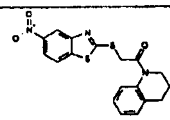 | 385.47 |
| 101 | 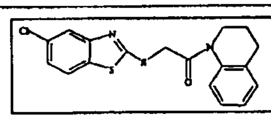 | 374.91 |
| 102 | 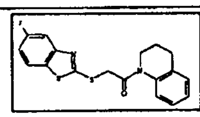 | 358.45 |
|  |  | 370.49 |
| Compounds IC50 (patch, inward) 0.21 - 1.0 uM |||
| 29 | 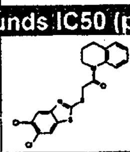 | 409.36 |
| 64 | 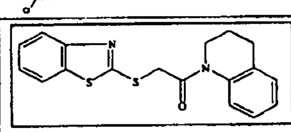 | 340.47 |
|  |  | 356.46 |

Figure 14B

| | | |
|---|---|---|
| Compounds IC50 (patch, inward) 0.21 - 1.0 uM | | |
| | | 406.28 |
| 25 | | 374.91 |
| 22 | | 374.91 |
| 18 | | 370.50 |
| 30 | | 354.50 |
| | | 388.49 |
| | | 389.48 |
| | | 349.82 |
| Compounds IC50 (patch, inward) 1.1 - 5.0 uM | | |
| 38 | | 354.50 |
| 44 | | 342.44 |
| | | 384.52 |
| 47 | | 354.50 |

| Compounds | IC50 (patch, inward) 1.1 -5.0 uM | |
|---|---|---|
| 39 |  | 370.50 |
| 62 |  | 324.40 |
| 70 |  | 341.46 |
|  |  | 390.48 |
|  |  | 314.43 |
|  |  | 324.40 |
|  |  | 306.45 |
|  |  | 475.66 |
| 21 |  | 385.47 |
| 40 |  | 354.50 |
| 45 |  | 354.50 |
| 17 |  | 337.45 |

| | Compounds IC50 (patch, inward) 1.1 -5.0 uM | |
|---|---|---|
| 37 |  | 368.48 |
| 26 |  | 374.91 |
| 82 |  | 323.42 |
| 56 |  | 329.83 |
| |  | 351.79 |
| |  | 313.38 |
| |  | 378.22 |
| | Compounds IC50 (patch, inward) 5.1-10 uM | |
| 33 |  | 318.46 |
| |  | 315.35 |
| |  | 348.43 |
| 27 |  | 349.46 |
| 34 |  | 346.52 |

| | Compounds IC50 (patch, inward) 5.1-10 uM | |
|---|---|---|
| 73 |  | 339.48 |
| 41 |  | 341.46 |
| 42 |  | 344.43 |
| |  | 335.79 |
| 20 |  | 426.54 |
| 77 |  | 353.51 |
| |  | 341.46 |
| 50 |  | 355.48 |
| 52 |  | 397.52 |
| |  | 329.38 |
| |  | 340.47 |
| |  | 455.60 |
| |  | 341.46 |

| | Compounds IC50 (patch, inward) 5.1-10 uM | |
|---|---|---|
| |  | 341.46 |
| |  | 341.46 |
| |  | 372.45 |
| |  | 321.76 |
| |  | 362.82 |
| |  | 417.57 |
| 59 |  | 433.57 |
| 30 |  | 363.49 |
| |  | 356.21 |
| |  | 339.75 |
| 26 |  | 431.57 |

Figure 14G

| | Compounds IC50 (patch, inward) 5.1-10 uM | |
|---|---|---|
| 60 | (structure) | 459.59 |
| | (structure) | 322.42 |
| | (structure) | 336.45 |
| | (structure) | 370.51 |
| | (structure) | 518.72 |
| | (structure) | 453.65 |
| | (structure) | 384.52 |

Figure 15

| Compound ID | MW | Structure | IC$_{50}$ patch P1 (nM) inward | IC$_{50}$ patch P1 (nM) outward | IC$_{50}$ patch P2 (nM) inward | IC$_{50}$ patch P2 (nM) outward | FDSS IC50 |
|---|---|---|---|---|---|---|---|
| B1 | 216.24 | pyridine-O-CH2CH2-O-pyridine | 501-5000 | | | | 501-5000 |
| B2 | 308.76 | 2,6-dimethoxyphenyl-O-CH2CH2-O-(3-chlorophenyl) | 501-5000 | >5000 | 501-5000 | >5000 | >5000 |
| B3 | 387.66 | 2,6-dimethoxyphenyl-O-CH2CH2CH2-O-(2-chloro-4-bromophenyl) | | | | | >5000 |

Figure 16A

| Compound ID | MW | Structure | IC$_{50}$ patch P1 (nM) inward / outward | IC$_{50}$ patch P2 (nM) inward / outward | FDSS IC50 |
|---|---|---|---|---|---|
| C1 | 467.95 | 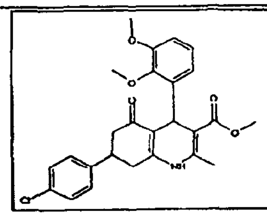 | / | 501-5000 / | >5000 |
| C2 | 425.89 | 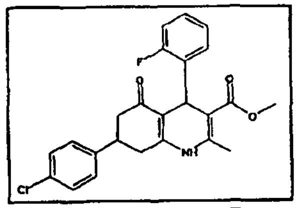 | 501-5000 / | >5000 / | >5000 |
| C3 | 409.51 | 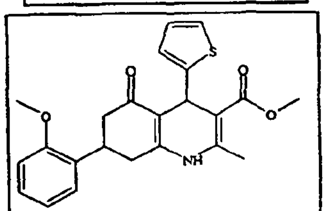 | 501-5000 / | >5000 / | >5000 |
| C4 | 403.48 | 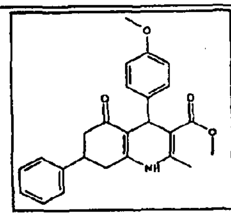 | 501-5000 / | >5000 / | >5000 |

| Compound ID | MW | Structure | IC$_{50}$ patch P1 (nM) inward / outward | IC$_{50}$ patch P2 (nM) inward / outward | FDSS IC50 |
|---|---|---|---|---|---|
| C5 | 419.48 | 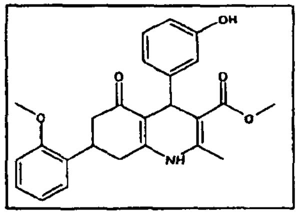 | 501-5000 | >5000 | >5000 |
| C6 | 393.51 | 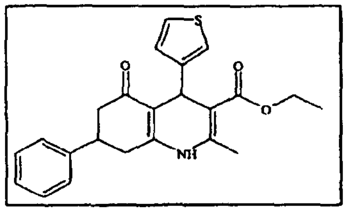 | >5000 | >5000 | >5000 |
| C7 | 463.53 | 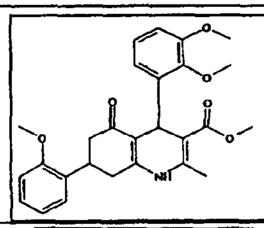 | >5000 | >5000 | >5000 |
| C8 | 461.52 | 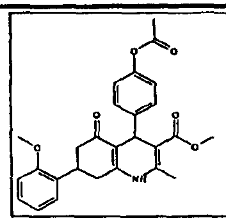 | >5000 | >5000 | >5000 |

| Compound ID | MW | Structure | IC$_{50}$ patch P1 (nM) | | IC$_{50}$ patch P2 (nM) | | FDSS IC50 |
|---|---|---|---|---|---|---|---|
| | | | inward | outward | inward | outward | |
| C9 | 458.37 | 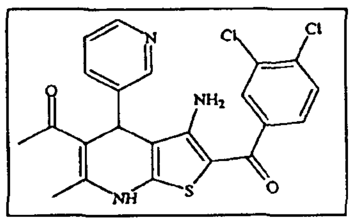 | | | | | 501-5000 |

Figure 17

| Compound ID | MW | Structure | IC50 patch P1 (nM) inward | IC50 patch P1 (nM) outward | IC50 patch P2 (nM) inward | IC50 patch P2 (nM) outward | FDSS IC50 |
|---|---|---|---|---|---|---|---|
| D1 | 368.46 | 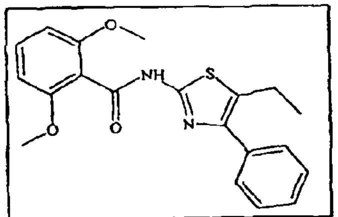 | 501-5000 | | 501-5000 | 501-5000 | 501-5000 |
| D2 | 336.14 | 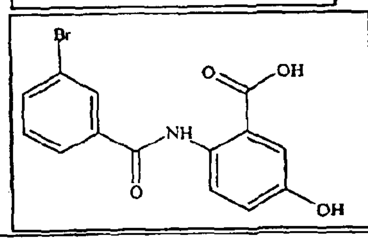 | >5000 | >5000 | >5000 | >5000 | 501-5000 |
| D3 | 364.38 | 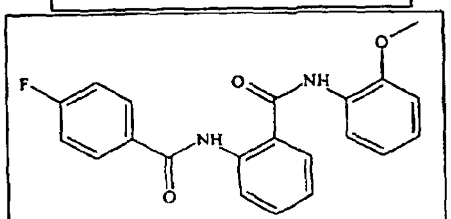 | | >5000 | >5000 | >5000 | >5000 |
| D4 | 349.46 | 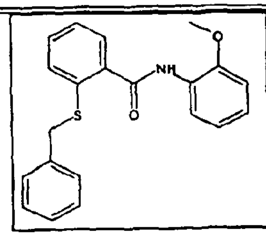 | 501-5000 | | 501-5000 | >5000 | >5000 |

| MW | Structure | IC$_{50}$ patch P1 (nM) | | IC$_{50}$ patch P2 (nM) | |
|---|---|---|---|---|---|
| | | inward | outward | inward | outward |
| 449.47 | 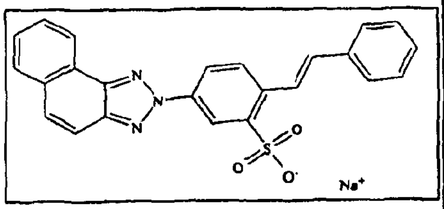 | 0-500 | 0-500 | | |
| 302.33 | 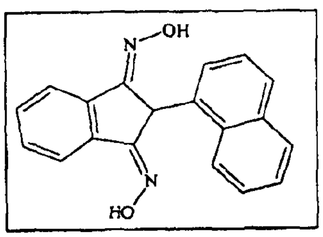 | 0-500 | 501-5000 | | |
| 421.55 | 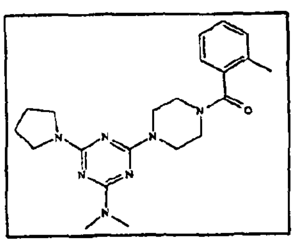 | 0-500 | 501-5000 | 501-5000 | |
| 299.4 | 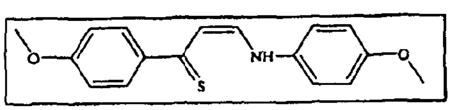 | 501-5000 | 501-5000 | | |

| MW | Structure | IC$_{50}$ patch P1 (nM) | | IC$_{50}$ patch P2 (nM) | |
|---|---|---|---|---|---|
| | | inward | outward | inward | outward |
| 352.34 | 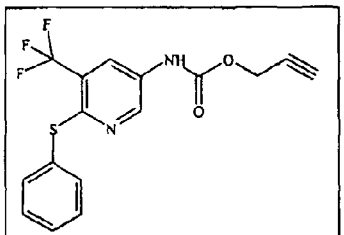 | 501-5000 | 501-5000 | | |
| 273.31 | 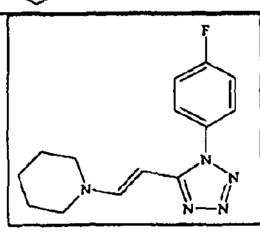 | 501-5000 | >5000 | 501-5000 | >5000 |
| |  | 501-5000 | 501-5000 | | |
| |  | 501-5000 | 501-5000 | 501-5000 | 501-5000 |

| MW | Structure | IC$_{50}$ patch P1 (nM) | | IC$_{50}$ patch P2 (nM) | |
|---|---|---|---|---|---|
| | | inward | outward | inward | outward |
| |  | 501-5000 | 501-5000 | | |
| |  | 501-5000 | >5000 | | |

Figure 19A

| Structure | M. Wt. | hTRPV3 Phase 1 Inwd (IC50, micro molar) | hTRPV3 Phase 2 Inwd (IC50, micro molar) | NaV1.2 (IC50, micro molar) | hTRPV1 Inwd (IC50, micro molar) | hERG (IC50, micro molar) |
|---|---|---|---|---|---|---|
| 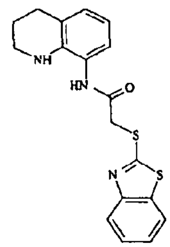 | 355.48 | ≤10.0 | ≤10.0 | | | |
| 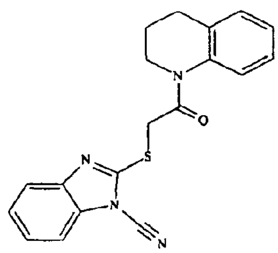 | 348.42 | ≤1.0 | ≤0.2 | ≥30 | ≥20 | ≥15 |
| 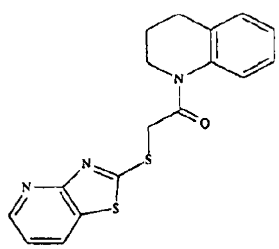 | 341.45 | ≤10.0 | ≤10.0 | | | |
| 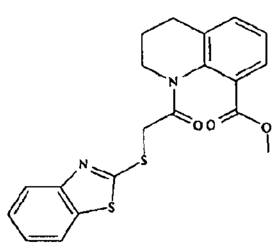 | 398.5 | ≤0.2 | ≤0.2 | ≥30 | ≥20 | |
| 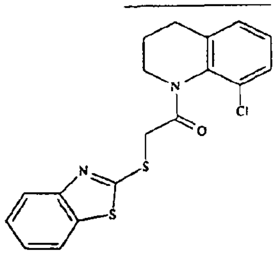 | 374.91 | ≤0.2 | | | | |

Figure 19B

| Structure | M. Wt. | hTRPV3 Phase 1 Inwd (IC50, micro molar) | hTRPV3 Phase 2 Inwd (IC50, micro molar) | NaV1.2 (IC50, micro molar) | hTRPV1 Inwd (IC50, micro molar) | hERG (IC50, micro molar) |
|---|---|---|---|---|---|---|
| | 383.53 | ≤5.0 | ≤1.0 | | | |
| 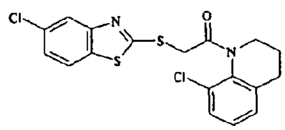 | 409.35 | ≤0.2 | ≤0.2 | | | |
| 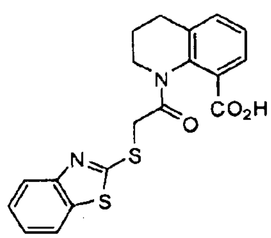 | 384.47 | ≤10.0 | ≤10.0 | | | |
| 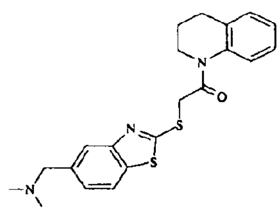 | 397.56 | ≤10.0 | ≤10.0 | | | |
| | 383.53 | ≤5.0 | ≤5.0 | | | |

Figure 19C

| Structure | M. Wt. | hTRPV3 Phase 1 Inwd (IC50, micro molar) | hTRPV3 Phase 2 Inwd (IC50, micro molar) | NaV1.2 (IC50, micro molar) | hTRPV1 Inwd (IC50, micro molar) | hERG (IC50, micro molar) |
|---|---|---|---|---|---|---|
| 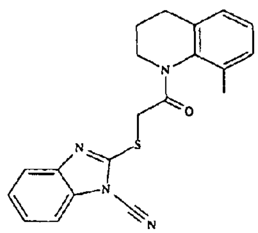 | 362.45 | ≤1.0 | ≤0.2 | | | |
| 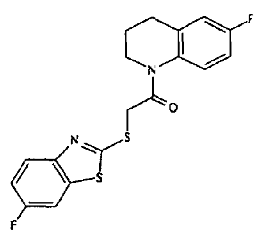 | 376.44 | ≤1.0 | ≤1.0 | | | |
| 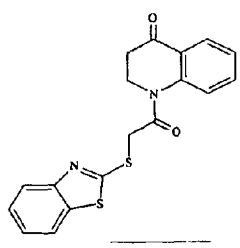 | 354.45 | ≤10.0 | ≤5.0 | | | |
| 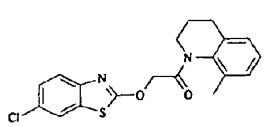 | 372.87 | ≤1.0 | ≤0.2 | | | |

US 8,916,550 B2

COMPOUNDS FOR MODULATING TRPV3 FUNCTION

RELATED APPLICATIONS

This application is a continuation-in-part of and claims priority to U.S. application Ser. No. 11/431,942, filed May 9, 2006, which claims priority to U.S. provisional application Ser. No. 60/679,438, filed May 9, 2005, 60/679,436, filed May 9, 2005, and 60/702,584, filed Jul. 25, 2005. The disclosures of each of the foregoing applications are hereby incorporated by reference in their entirety.

BACKGROUND

A variety of ion channel proteins exist to mediate ion flux across cellular membranes. The proper expression and function of ion channel proteins is essential for the maintenance of cell function, intracellular communication, and the like. Numerous diseases are the result of misregulation of membrane potential or aberrant calcium handling. Given the central importance of ion channels in modulating membrane potential and ion flux in cells, identification of agents that can promote or inhibit particular ion channels are of great interest as research tools and as possible therapeutic agents.

One such channel is the Transient Receptor Potential V3 (TRPV3) channel. TRPV3 is a calcium permeable channel, specifically a calcium permeable non-selective cation channel. In addition to calcium ions, TRPV3 channels are permeable to other cations, for example sodium. Thus, TRPV3 channels modulate membrane potential by modulating the flux of cations such as calcium and sodium ions. Although non-selective cation channels such as TRPV3 modulate, among other things, calcium ion flux, they are mechanistically distinct from voltage-gated calcium channels. Generally, voltage-gated calcium channels respond to membrane depolarization and open to permit an influx of calcium from the extracellular medium that results in an increase in intracellular calcium levels or concentrations. In contrast, TRP channels which are non-selective cation channels are generally signal transduction gated, long lasting, and produce more prolonged changes in ion concentration. These mechanistic differences are accompanied by structural differences among voltage-gated and TRP channels. Thus, although many diverse channels act to regulate ion flux and membrane potential in various cell types and in response to numerous stimuli, it is important to recognize the significant structural, functional, and mechanistic differences among different classes of ion channels.

TRPV3 function has been implicated in, among other things, the reception and transduction of pain. Accordingly, it would be desirable to identify and make compounds that can modulate one or more functions of TRPV3. Such compounds have a variety of in vitro and in vivo uses.

SUMMARY

An important aspect of achieving cellular homeostasis is the maintenance of appropriate ion concentrations in various cell types during the development of and in response to numerous stimuli. Large numbers of diverse types of ion channels act to maintain cellular homeostasis by moving ions into and out of cells across the plasma membrane, and within cells by moving ions across membranes of intracellular organelles including, for example, the endoplasmic reticulum, sarcoplasmic reticulum, mitochondria and endocytic organelles including endosomes and lysosomes. One such ion channel is the non-selective cation channel TRPV3. TRPV3 is cation permeable and belongs to the larger family of TRP ion channels.

TRP channels have been classified into at least six groups: TRPC (short), TRPV (vanilloid), TRPM (long, melastatin), TRPP (polycystins), TRPML (mucolipins), and TRPA (ANKTM1). The TRPC group can be divided into 4 subfamilies (TRPC1, TRPC4,5, TRPC3,6,7 and TRPC2) based on sequence homology and functional similarities. Currently the TRPV family has 6 members. TRPV5 and TRPV6 are more closely related to each other than to TRPV1, TRPV2, TRPV3, or TRPV4. TRPV3 is most closely related to TRPV4, and is more closely related to TRPV1 and TRPV2 than to TRPV5 and TRPV6. The TRPM family has 8 members. Constituents include the following: the founding member TRPM1 (Melastatin or LTRPC1), TRPM3 (KIAA1616 or LTRPC3), TRPM7 (TRP-PLIK, ChaK(1), LTRPC7), TRPM6 (ChaK2), TRPM2 (TRPC7 or LTRPC2), TRPM8 (Trp-p8 or CMR1), TRPM5 (Mtr1 or LTRPC5), and TRPM4 (FLJ20041 or LTRPC4). The sole mammalian member of the TRPA family is ANKTM1. The TRPML family consists of the mucolipins, which include TRPML1 (mucolipins 1), TRPML2 (mucolipins 2), and TRPML3 (mucolipin3). The TRPP family consists of two groups of channels: those predicted to have six transmembrane domains and those that have 11. TRPP2 (PKD2), TRPP3 (PKD2L1), TRPP5 (PKD2L2) are all predicted to have six transmembrane domains. TRPP1 (PKD1, PC1), PKD-REJ and PKD-1L1 are all thought to have 11 transmembrane domains.

The TRP channels constitute a large and important class of channels involved in modulating cellular homeostasis. The present invention provides methods and compositions that modulate at least one TRP family member. Specifically, the present invention provides methods and compositions for antagonizing a function of TRPV3. Modulating a function of TRPV3 provides a means for modulating calcium homeostasis, sodium homeostasis, intracellular calcium levels, membrane polarization (resting membrane potential), and/or cation levels in a cell. Compounds that can modulate one or more TRPV3 functions are useful in many aspects including, but not limited to, maintaining calcium homeostasis; maintaining sodium homeostasis; modulating intracellular calcium levels; modulating membrane polarization (membrane potential); modulating cation levels; and/or treating or preventing diseases, disorders, or conditions associated with calcium homeostasis, sodium homeostasis, calcium or sodium dyshomeostasis, or membrane polarization/hyperpolarization (including hypo and hyperexcitability), and/or treating or preventing diseases, disorders, or conditions associated with regulation or misregulation of TRPV3 expression or function. Additionally, the present invention provides, in certain embodiments, methods and compositions that antagonize both a function of TRPV3 and a function of one or more additional TRP channels.

The present application provides compounds that can modulate TRPV3 function. Methods employing these compounds are also provided. Certain embodiments provide a method of modulating a TRPV3 function in a cell comprising administering to the cell an effective amount of a compound that inhibits a TRPV3 mediated current. Certain embodiments provide a method of modulating a TRPV3 function in a cell comprising administering to the cell an effective amount of a compound that inhibits TRPV3 function, wherein the compound inhibits the Phase II outward current mediated by TRPV3. Certain embodiments provide a method of preventing or treating a disease or condition related to TRPV3 function in a subject comprising administering to the subject a therapeutically effective amount of a compound that inhibits TRPV3 function, wherein the compound inhibits the Phase II outward current mediated by TRPV3. Certain embodiments provide a method of modulating a TRPV3 function in a cell comprising administering to the cell an effective amount of a compound that inhibits TRPV3 function, wherein the compound inhibits the Phase II inward current mediated by TRPV3. Certain embodiments also provide a method of preventing or treating a disease or condition related to TRPV3 function in a subject comprising administering to the subject a therapeutically effective amount of a compound that inhibits TRPV3 function, wherein the compound inhibits the Phase II inward current mediated by TRPV3. Certain embodiments provide a method of modulating TRPV3 function in a cell comprising administering to the cell an effective amount of a compound that inhibits TRPV3 function, wherein the compound inhibits the Phase I inward current mediated by TRPV3. Certain embodiments also provide a method of preventing or treating a disease or condition related to TRPV3 function in a subject comprising administering to the subject a therapeutically effective amount of a compound that inhibits TRPV3 function, wherein the compound inhibits the Phase I inward current mediated by TRPV3. Certain embodiments also provide a method of preventing or treating a disease or condition related to TRPV3 function in a subject comprising administering to the subject a therapeutically effective amount of a compound that inhibits TRPV3 function, wherein the compound inhibits the Phase I outward current mediated by TRPV3. Certain embodiments provide a method of modulating TRPV3 function in a cell comprising administering to the cell an effective amount of a compound that inhibits TRPV3 function, wherein the compound inhibits the Phase I outward current mediated by TRPV3. Certain embodiments also provide a method of preventing or treating a disease or condition involving activation of TRPV3 or for which reduced TRPV3 activity can reduce the severity in a subject comprising administering to the subject a therapeutically effective amount of a compound that inhibits TRPV3 function, wherein the compound inhibits one or more of a Phase I inward current mediated by TRPV3, a Phase II inward current mediated by TRPV3, a Phase I outward current mediated by TRPV3, or a Phase II outward current mediated by TRPV3. In any of the foregoing, the invention additionally provides compounds and methods that inhibit both the Phase I outward current and the Phase II outward current. Furthermore, in any of the foregoing, the invention provides compounds and methods that inhibit both the Phase I inward current and the Phase II inward current, as well as compounds that inhibit any combination of Phase I and Phase II currents. Note that inhibition of a particular current refers to the ability of a compound to inhibit that current (e.g., Phase I inward, Phase I outward, Phase II inward, and/or Phase II outward) in either an in vitro or in vivo assay. Inhibition of a particular current in either an in vivo or an in vitro assay serves as a proxy for the particular functional activity of the particular compound.

The biphasic currents mediated by TRPV3 are discussed in, for example, Chung et al. (Chung et al., 2005, Journal of Biological Chemistry 280: 15928-15941). Briefly, a unique property of TRPV3 is that there is a phase change in the current. The current-voltage relationship changes upon repeated stimulation, so that the amount of inward current increases dramatically. For ease, two phases of TRPV3 current have been described: Phase I and Phase II. Throughout, we have defined phase I as currents that show a 10:1 ratio or greater of outward current amplitude (at +100 mV) to inward current amplitude (at −120 mV). In other words, the current shows strong outward rectification and minimal inward current. Phase II is defined as a ration of 2:1 or less of outward current amplitude (at +100 mV) to inward current amplitude (at −120 mV). The current-voltage relationship is fairly linear in this case.

The following articles are exemplary of the state of the art regarding the structure and function of TRPV (Ramsey et al. (2006) Annual Rev Physiology 68: 619-647; Clapham. (2003) Nature 426: 517-524; Xu et al. (2002) Nature 418: 181-186; Clapham et al. (2001) Nature Reviews of Neuroscience 2: 387-396). The foregoing articles are incorporated by reference in their entirety.

One aspect of the present invention relates to a method for treating or preventing a condition involving activation of TRPV3 or for which reduced TRPV3 activity can reduce the severity by administering a TRPV3 antagonist that inhibits TRPV3-mediated current. Described in greater detail below are TRPV3 antagonists that have measured $IC_{50}$'s for inhibition of TRPV3 of 10 micromolar or less, 1 micromolar or less, 500 nanomolar or less, 200 nanomolar or less, 100 nanomolar or less, and even 10 nanomolar or less. In certain embodiments, the TRPV3 antagonist inhibit one or both of inward and outward TRPV3-mediated current with an $IC_{50}$ of 1 micromolar or less, and more with an $IC_{50}$ of 500 nanomolar or less, 200 nanomolar or less, 100 nanomolar or less, 25 nanomolar or less and even 10 nanomolar or less. In certain embodiments, the TRPV3 antagonist inhibits at least 95% of TRPV3-mediated current at 5 micromolar or less, and even more preferably at 1 micromolar or less.

In certain embodiments, the subject TRPV3 antagonists inhibit TRPV3 with an $IC_{50}$ at least one order of magnitude lower than its $IC_{50}$ for inhibition of one or more of TRPV5, TRPV6, NaV 1.2, TRPV1, mitochondrial uniporter and hERG channel activities, and even more preferably two or even three orders of magnitude lower.

In certain embodiments, the TRPV3 antagonists inhibit TRPV3 with an $IC_{50}$ at least one order of magnitude lower than its $IC_{50}$ for inhibition of TRPV1, and even more preferably two or even three orders of magnitude lower. In certain embodiments, the subject TRPV3 antagonists can be selected for selectivity for TRPV3 versus TRPV1 on the basis of having $IC_{50}$ for TRPV1 inhibition greater than 10 micromolar.

In certain embodiments, the subject TRPV3 antagonists inhibit TRPV3 with an $IC_{50}$ at least one order of magnitude more potent than its Ki for the AMPA receptor. In certain other embodiments, the subject TRPV3 antagonists inhibit TRPV3 with an $IC_{50}$ at least two orders of magnitude, or even three orders of magnitude, or four orders of magnitude more potent than its Ki for the AMPA receptor. In certain embodiments, the subject TRPV3 antagonists do not appreciably bind the AMPA receptor. In other words, the subject antagonists inhibit TRPV3 with a particular $IC_{50}$ and, when administered at that concentration, the antagonist does not appreciably bind AMPA receptor (e.g., does specifically and appreciably bind the AMPA receptor). In certain embodiments, compounds of the invention inhibit a TRPV3-mediated current with an $IC_{50}$ that is more potent than its Ki for the AMPA receptor. In such embodiments, the ability of the subject TRPV3 inhibitors to decrease pain would thus be independent of binding to and modulation of the alpha-amino-3-hydroxy-5-methyl-4-isoxazolepropionic acid (AMPA) receptor which has been implicated in neuropathic pain reception.

In certain embodiments, the TRPV3 antagonists inhibit one or more of TRPV2, TRPV4, ANKTM1 and/or TRPM8 with an $IC_{50}$ of 10 micromolar or less.

In certain embodiments, the TRPV3 antagonist has a therapeutic index (T.I.) for treating the condition with the compound of 10 or greater, and even more preferably has a T.I. of at least 25, 50 or even 100.

In preferred embodiments, the TRPV3 inhibitor has an $IC_{50}$ for TRPV3 inhibition that, at that concentration, does not cause QT interval elongation in the patient and/or does not alter temperature regulation in the patient.

In certain embodiments, the TRPV3 inhibitor is used to treat or ameliorate pain. Exemplary classes of pain that can treated using a TRPV3 inhibitor include, but are not limited to nociceptive pain, inflammatory pain, and neuropathic pain. Pain that can be treated with a TRPV3 inhibitor can be chronic or acute.

In certain embodiments, the TRPV3 inhibitor is non-narcotic and has little or no narcotic side-effects. In certain other embodiments, the TRPV3 inhibitor can be used to treat or ameliorate pain with fewer side-effects than narcotic pain relievers. Exemplary side-effects that may be substantially absent at effective dosages of TRPV3 inhibitors include one or more of exopthalmos, catalepsy, disruption of gut motility, and inhibition of sensation in non-injured areas of the body.

In certain embodiments, the TRPV3 antagonist is "small molecule", e.g., an organic molecule having a molecular weight of 2000 amu or less. Exemplary TRPV3 antagonists include a compound of Formula I or a salt thereof, or a solvate, hydrate, oxidative metabolite or prodrug of the compound or its salt:

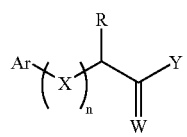

I wherein: Ar represents an aryl or heteroaryl group; Y represents Ph, OArl, SArl, or N(U)(Arl); R represents H or a lower alkyl; X represents $CH_2$, O, S, $NR_{10}$, $CF_2$, or $C(CN)_2$; W represents O, S, or NR'; n is 1, or when X is $CH_2$, n is 1 or 2; Arl represents an aralkyl, heteroaralkyl, aryl, or heteroaryl group, which may be monocyclic or bicyclic; Ph represents a substituted or unsubstituted phenyl ring, optionally fused to a substituted or unsubstituted 5- to 7-membered cycloalkyl, heterocyclyl, aryl, or heteroaryl ring; R', independently for each occurrence, represents H or a lower alkyl; U represents hydrogen or lower alkyl, alkenyl, alkynyl, cycloalkyl, heterocyclyl, aryl, heteroaryl, cycloalkylalkyl, heterocyclylalkyl, aralkyl, or heteroaralkyl, or, U, N and R' taken together form a 5- to 7-membered heterocyclic ring, or, U, Arl and N taken together form a ring fused to the aryl or heteroaryl ring of Arl, thereby forming a bicyclic structure; $R_{10}$ represents H, lower alkyl, or cyano; and wherein said compound inhibits TRPV3 with an with an $IC_{50}$ of 10 micromolar or less.

In certain embodiments, R is H, W is O or S, and X is O or S.

In certain embodiments, X is $CH_2$.

In certain preferred embodiments, the TRPV3 antagonist is represented in Formula Ia, or a salt thereof, or a solvate, hydrate, oxidative metabolite or prodrug of the compound or its salt:

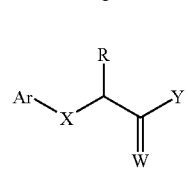

Ia wherein: Ar represents an aryl or heteroaryl group; Y represents Ph, OArl, SArl, or N(U)(Arl); R represents H or a lower alkyl; X represents O, S, $NR_{10}$, $CF_2$, or $C(CN)_2$; W represents O, S, or NR'; Arl represents an aralkyl, heteroaralkyl, aryl, or heteroaryl group, which may be monocyclic or bicyclic; Ph represents a substituted or unsubstituted phenyl ring, optionally fused to a substituted or unsubstituted 5- to 7-membered cycloalkyl, heterocyclyl, aryl, or heteroaryl ring; R', independently for each occurrence, represents H or a lower alkyl; U represents hydrogen or lower alkyl, alkenyl, alkynyl, cycloalkyl, heterocyclyl, aryl, heteroaryl, cycloalkylalkyl, heterocyclylalkyl, aralkyl, or heteroaralkyl, or, U, N and R' taken together form a 5- to 7-membered heterocyclic ring, or, U, Arl and N taken together form a ring fused to the aryl or heteroaryl ring of Arl, thereby forming a bicyclic structure; and $R_{10}$ represents H, lower alkyl, or cyano.

In certain embodiments of Formulas I and Ia, Y is N(U)(Arl), and in such embodiments, Y can represent, for example,

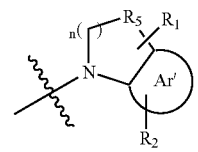

wherein: $R_1$ and $R_2$, each independently, is absent or represents one or more substituents on the ring to which it is attached; Ar' represents an aryl or heteroaryl group; $R_5$ represents $CH_2$, O, $NR_6$; $R_6$ represents H or lower alkyl; and n represents 1, 2, or 3. In certain embodiments of the above-referenced compounds, one or more of the following conditions may be true:

Ar' represents phenyl, thiophene, imidazole, thiazole, furan, oxazole, tetrazole, thiadiazole, pyridine, pyrimadine, or triazole;

each $R_1$ is independently selected from H, lower alkyl, alkoxy, carboxyl, ester, amido, sulfonamido, heterocyclyl, cycloalkyl, hydroxyl, amino, acylamino, thioether, sulfonylamino, or $R_1$ taken together with the carbon to which it is attached forms a carbonyl or thiocarbonyl;

each R2 is independently selected from H, lower alkyl, alkoxy, carboxyl, ester amido, sulfonamido, heterocyclyl, cycloalkyl, hydroxyl, amino, acylamino, thioether, sulfonylamino, halogen, $CF_3$, or cyano;

In certain preferred embodiments of Formulas I and Ia, Y represents

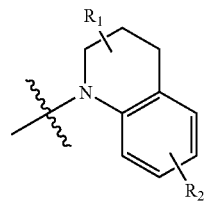

wherein $R_1$ and $R_2$ each, independently, are absent or represent one or more substituents on the ring to which they are attached. Even more preferably, independently for each occurrence, $R_1$ is selected from H, lower alkyl, alkoxy, carboxyl, ester, amido, sulfonamido, heterocyclyl, cycloalkyl, hydroxyl, amino, acylamino, thioether, sulfonylamino, or R1 taken together with the carbon to which it is attached forms a carbonyl or thiocarbonyl; and independently for each occurrence, $R_2$ is selected from H, lower alkyl, alkoxy, carboxyl, ester, amido, sulfonamido, heterocyclyl, cycloalkyl, hydroxyl, amino, acylamino, thioether, sulfonylamino, halogen, $CF_3$, or cyano.

For further illustration, Y can represent

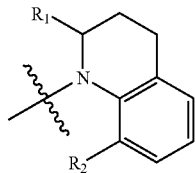

wherein $R_1$ represents H, lower alkyl, alkoxy, carboxyl, ester, amido, sulfonamido, heterocyclyl, cycloalkyl, hydroxyl, amino, acylamino, thioether, sulfonylamino, or $R_1$ taken together with the carbon to which it is attached forms a carbonyl or thiocarbonyl; and $R_2$ represents H, lower alkyl, alkoxy, carboxyl, ester, amido, sulfonamido, heterocyclyl, cycloalkyl, hydroxyl, amino, acylamino, thioether, sulfonylamino, halogen, $CF_3$, or cyano. In certain preferred embodiments, $R_1$ represents H, lower alkyl, alkoxy, or $R_1$ taken together with the carbon to which it is attached forms a carbonyl, and $R_2$ represents H, lower alkyl, alkoxy or halogen.

In certain preferred embodiments of Formulas I and Ia, Ar represents

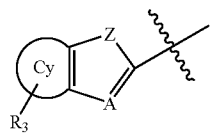

wherein: Cy represents an aryl or heteroaryl ring; Z represents O, S, $NR_{11}$, $CF_2$, or $C(CN)_2$; $R_3$ is absent or represents one or more substituents on the ring to which it is attached; $R_{11}$ represents H, lower alkyl, or cyano; A represents N or $C(R_{2a})$; and $R_{2a}$ represents H, lower alkyl, alkoxy, or halogen.

For example, Cy can represent a phenyl, thiophene, imidazole, thiazole, furan, oxazole, tetrazole, thiadiazole, pyridine, pyrimadine, or triazole, and $R_3$ can be absent, or independently for each occurrence, selected from lower alkyl, alkoxy, carboxyl, ester, amido, sulfonamido, heterocyclyl, cycloalkyl, hydroxyl, amino, acylamino, thioether, sulfonylamino, nitro, halogen, $CF_3$, or cyano. In certain preferred embodiments, A represents N, and Z represents O or S.

To further illustrate, Ar can represent

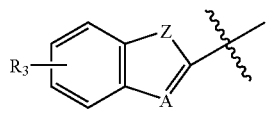

wherein: Z represents O, S, $NR_{11}$, $CF_2$, NR, or $C(CN)_2$; A represents N or $C(R_{2a})$; $R_3$ is absent or represents one or more substituents on the ring to which it is attached; $R_{11}$ represents H, lower alkyl, or cyano; and $R_{2a}$ represents H, lower alkyl, alkoxy, or halogen. In certain preferred embodiments: Z represents O or S; and $R_3$ is absent or each $R_3$ is independently selected from lower alkyl, alkoxy, carboxyl, ester, amido, sulfonamido, heterocyclyl, cycloalkyl, hydroxyl, amino, acylamino, thioether, sulfonylamino, nitro, halogen, $CF_3$, or cyano;

In certain preferred embodiments, Ar can represent

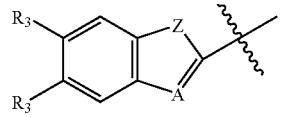

wherein: Z represents O, S, $NR_{11}$, $CF_2$, or $C(CN)_2$; A represents N or $C(R_{2a})$; $R_3$ independently for each occurrence represents H, lower alkyl, alkoxy, carboxyl, ester, amido, sulfonamido, heterocyclyl, cycloalkyl, hydroxyl, amino, acylamino, thioether, sulfonylamino, halogen, $CF_3$, or cyano; $R_{11}$ represents H, lower alkyl, or cyano; and $R_{2a}$ represents H, lower alkyl, alkoxy, or halogen. Preferably Z represents O or S, and $R_3$ independently for each occurrence represents H, lower alkyl, alkoxy, $CF_3$, nitro, or halogen.

In certain other preferred embodiments of Formulas I and La, Ar represents

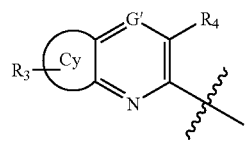

wherein: G' represents N or $C(R_5)$; $R_3$ is absent or represents one or more substituents on Cy; $R_5$ represents H or a substituent; $R_4$ represents H or a substituent; and Cy represents an aryl or heteroaryl ring. In certain preferred embodiments, Cy can be a phenyl, thiophene, imidazole, thiazole, furan, oxazole, tetrazole, thiadiazole, pyridine, pyrimadine, or triazole. In certain embodiments, $R_3$ is absent, or independently for each occurrence, is selected from lower alkyl, alkoxy, carboxyl, ester, amido, sulfonamido, heterocyclyl, cycloalkyl, hydroxyl, amino, acylamino, thioether, sulfonylamino, nitro, halogen, $CF_3$, or cyano; and $R_4$ and $R_5$, independently for each occurrence, are selected from H, lower alkyl, alkoxy, carboxyl, ester, amido, sulfonamido, heterocyclyl, cycloalkyl, hydroxyl, amino, acylamino, thioether, sulfonylamino, halogen, $CF_3$, or cyano.

In still other embodiments, the TRPV3 antagonist is a compound of Formula V or a salt thereof, or a solvate, hydrate, oxidative metabolite or prodrug of the compound or its salt:

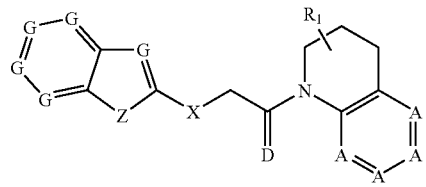

V wherein: X represents O, S, $NR_{10}$, $CF_2$, or $C(CN)_2$; Z represents O, S, $NR_{11}$, $CF_2$, or $C(CN)_2$; $R_{10}$ represents H, lower alkyl, or cyano; $R_{11}$ represents H, lower alkyl, or cyano; A represents N or $C(R_2)$; G represents N or $C(R_3)$; $R_1$ is absent or represents one or more substituents on the ring to which it is attached; $R_2$ represents, independently for each occurrence, H or a substituent; $R_3$ represents, independently for each occurrence, H or a substituent; and D represents O or N.

In certain preferred embodiments of formula V: X represents S and D represents O; $R_1$ is absent, or independently for each occurrence, is selected from lower alkyl, alkoxy, carboxyl, ester, amido, sulfonamido, heterocyclyl, cycloalkyl, hydroxyl, amino, acylamino, thioether, sulfonylamino, or $R_1$ taken together with the carbon to which it is attached forms a carbonyl or thiocarbonyl; and $R_2$ and $R_3$, independently for each occurrence, are selected from H, lower alkyl, alkoxy, carboxyl, ester, amido, sulfonamido, heterocyclyl, cycloalkyl, hydroxyl, amino, acylamino, thioether, sulfonylamino, nitro, halogen, $CF_3$, or cyano.

To further illustrate, the TRPV3 antagonist can be represented by Formula Va or a salt thereof, or a solvate, hydrate, oxidative metabolite or prodrug of the compound or its salt:

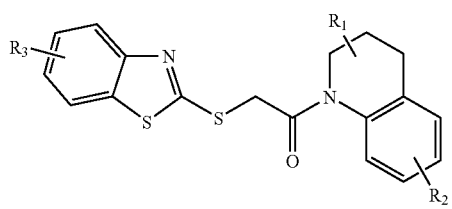

Va wherein: $R_1$, $R_2$ and $R_3$ are absent or represent one or more substituents on the ring to which they are attached. For instance, $R_1$ is absent, or independently for each occurrence, is selected from lower alkyl, alkoxy, carboxyl, ester, amido, sulfonamido, heterocyclyl, cycloalkyl, hydroxyl, amino, acylamino, thioether, sulfonylamino, or $R_1$ taken together with the carbon to which it is attached forms a carbonyl or thiocarbonyl; and $R_2$ and $R_3$ are absent, or independently for each occurrence, are selected from lower alkyl, alkoxy, carboxyl, ester, amido, sulfonamido, heterocyclyl, cycloalkyl, hydroxyl, amino, acylamino, thioether, sulfonylamino, nitro, halogen, $CF_3$, or cyano. In certain preferred embodiments, $R_1$ is absent, or independently for each occurrence, is selected from lower alkyl, or alkoxy, or $R_1$ taken together with the carbon to which it is attached forms a carbonyl; $R_2$ is absent, or independently for each occurrence, is selected from lower alkyl, alkoxy, or halogen; and $R_3$ is absent, or independently for each occurrence, is selected from lower alkyl, alkoxy, $CF_3$, nitro, or halogen. In even more preferred embodiments, $R_1$ represents H; $R_2$ represents H or $CH_3$ and is positioned ortho to the N of the ring system; and $R_3$ represents one or more substituents positioned meta or para to the nitrogen of the ring system.

In still another illustration, the TRPV3 antagonist can be represented by Formula Vb or a salt thereof, or a solvate, hydrate, oxidative metabolite or prodrug of the compound or its salt:

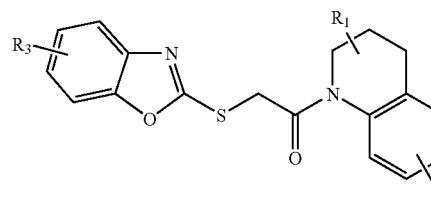

Vb wherein $R_1$, $R_2$ and $R_3$ are absent or represent one or more substituents on the ring to which they are attached. For instance, $R_1$ is absent, or independently for each occurrence, is selected from lower alkyl, alkoxy, carboxyl, ester, amido, sulfonamido, heterocyclyl, cycloalkyl, hydroxyl, amino, acylamino, thioether, sulfonylamino, or $R_1$ taken together with the carbon to which it is attached forms a carbonyl or thiocarbonyl; and $R_2$ and $R_3$ are absent, or independently for each occurrence, are selected from lower alkyl, alkoxy, carboxyl, ester, amido, sulfonamido, heterocyclyl, cycloalkyl, hydroxyl, amino, acylamino, thioether, sulfonylamino, nitro, halogen, $CF_3$, or cyano. In certain preferred embodiments, $R_1$ is absent, or independently for each occurrence, is selected from lower alkyl, or alkoxy, or $R_1$ taken together with the carbon to which it is attached forms a carbonyl; $R_2$ is absent, or independently for each occurrence, is selected from lower alkyl, alkoxy, or halogen; and $R_3$ is absent, or independently for each occurrence, is selected from lower alkyl, alkoxy, $CF_3$, nitro, or halogen. In certain embodiments, $R_1$, $R_2$, and $R_3$ are absent.

In still other embodiments, the TRPV3 antagonist is a compound of Formula VI or a salt thereof, or a solvate, hydrate, oxidative metabolite or prodrug of the compound or its salt:

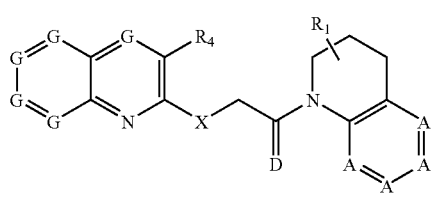

VI wherein: X represents O, S, $NR_{10}$, $CF_2$, or $C(CN)_2$; $R_{10}$ represents H, lower alkyl, or cyano; A represents N or $C(R_2)$; G represents N or $C(R_3)$; $R_1$ is absent or represents one or more substituents on the ring to which it is attached; $R_2$ represents, independently for each occurrence, H or a substituent; $R_3$ represents, independently for each occurrence, H or a substituent; $R_4$ represents H or a substituent; D represents O or N; and wherein said compound inhibits TRPV3 with an with an $IC_{50}$ of 10 micromolar or less.

In certain preferred embodiments, X represents S and D represents O.

In certain embodiments, the compound can be represented by Formula VIa or a salt thereof, or a solvate, hydrate, oxidative metabolite or prodrug of the compound or its salt:

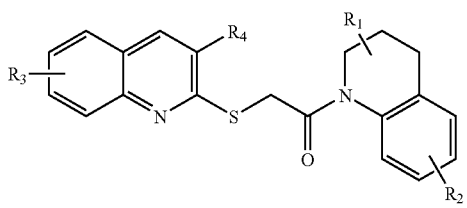

VIa wherein: $R_1$, $R_2$ and $R_3$ are absent or represent one or more substituents on the ring to which they are attached; and $R_4$ represents H or a substituent. In certain preferred embodiments, $R_1$ is absent, or independently for each occurrence, is selected from lower alkyl, alkoxy, carboxyl, ester, amido, sulfonamido, heterocyclyl, cycloalkyl, hydroxyl, amino, acylamino, thioether, sulfonylamino, or $R_1$ taken together with the carbon to which it is attached forms a carbonyl or thiocarbonyl; and $R_2$, $R_3$ and $R_4$ are absent, or independently for each occurrence, is selected from H, lower alkyl, alkoxy, carboxyl, ester, amido, sulfonamido, heterocyclyl, cycloalkyl, hydroxyl, amino, acylamino, thioether, sulfonylamino, nitro, halogen, $CF_3$, or cyano. In preferred embodiments, the $R_1$ is absent, or independently for each occurrence, is selected from lower alkyl, or alkoxy, or $R_1$ taken together with the carbon to which it is attached forms a carbonyl; $R_2$ is absent, or independently for each occurrence, is selected from lower alkyl, alkoxy, or halogen; $R_3$ absent, or independently for each occurrence, is selected from H, lower alkyl, alkoxy, $CF_3$, nitro, or halogen; and $R_4$ is selected from H, lower alkyl, or cyano. In other preferred embodiments, $R_1$ and $R_2$ are absent; $R_3$ represents methoxy positioned para to the N of the ring system; and $R_4$ represents cyano.

In certain embodiments, the compound can be represented by Formula VIb or a salt thereof, or a solvate, hydrate, oxidative metabolite or prodrug of the compound or its salt:

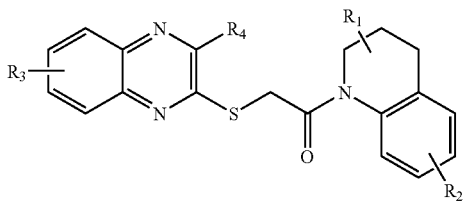

VIb wherein: $R_1$, $R_2$ and $R_3$ are absent or represent one or more substituents on the ring to which they are attached; and $R_4$ represents H or a substituent. For instance, $R_1$ is absent, or independently for each occurrence, is selected from lower alkyl, alkoxy, carboxyl, ester, amido, sulfonamido, heterocyclyl, cycloalkyl, hydroxyl, amino, acylamino, thioether, sulfonylamino, or $R_1$ taken together with the carbon to which it is attached forms a carbonyl or thiocarbonyl; and $R_2$, $R_3$ and $R_4$ are absent, or independently for each occurrence, is selected from lower alkyl, alkoxy, carboxyl, ester, amido, sulfonamido, heterocyclyl, cycloalkyl, hydroxyl, amino, acylamino, thioether, sulfonylamino, nitro, halogen, $CF_3$, or cyano. In certain preferred embodiments, $R_1$ is absent, or independently for each occurrence, is selected from lower alkyl, alkoxy, or halogen or $R_1$ taken together with the carbon to which it is attached forms a carbonyl; $R_2$ is absent, or independently for each occurrence, is selected from lower alkyl, alkoxy, or halogen; $R_3$ is absent, or independently for each occurrence, is selected from lower alkyl, alkoxy, $CF_3$, nitro, or halogen; and $R_4$ is selected from H, lower alkyl, or cyano.

In still other illustrative embodiments, the compound can be represented by Formula II or a salt thereof, or a solvate, hydrate, oxidative metabolite or prodrug of the compound or its salt:

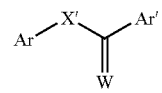

II wherein: W represents O or S; X' represents $NR_{12}$; $R_{12}$ represents H or lower alkyl; Ar and Ar' independently represent substituted or unsubstituted aryl or heteroaryl rings; and wherein said compound inhibits TRPV3 with an with an $IC_{50}$ of 10 micromolar or less. For instance, Ar can represents phenyl, as can Ar'.

In yet another illustrative embodiments, the compound can be represented by Formula III or a salt thereof, or a solvate, hydrate, oxidative metabolite or prodrug of the compound or its salt:

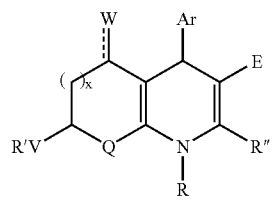

III wherein: Ar represents a substituted or unsubstituted aryl or heteroaryl ring; Q represents O, S, NR, or $CH_2$; R, independently for each occurrence, represents H or lower alkyl; R' represents H or a substituted or unsubstituted lower alkyl, alkenyl, alkynyl, cycloalkyl, heterocyclyl, aryl, heteroaryl, cycloalkylalkyl, heterocyclylalkyl, aralkyl, or heteroaralkyl; R", independently for each occurrence, represents H or lower alkyl; V is absent or represents C=O, C=S, or $SO_2$; W represents a hydrogen-bond acceptor, such as =O, =S, amino, hydroxyl, or ether; E represents H, a substituted or unsubstituted lower alkyl, alkenyl, alkynyl, cycloalkyl, heterocyclyl, aryl, heteroaryl, cycloalkylalkyl, heterocyclylalkyl, aralkyl, or heteroaralkyl, or halogen, carbonyl (e.g., ester, carboxyl, or formyl), thiocarbonyl (e.g., thioester, thiocarboxylate, or thioformate), ketone, aldehyde, amino, acylamino, amido, amidino, cyano, nitro, azido, sulfonyl, sulfoxido, sulfate, sulfonate, sulfamoyl, sulfonamido, or phosphoryl; x represents 0 or 1 wherein when x is 0, the carbons bearing W and V are directly linked by a single or double bond; and wherein said compound inhibits TRPV3 with an with an $IC_{50}$ of 10 micromolar or less.

In certain embodiments, the compounds of Formula III are characterized by one or more of the following: Q represents S or $CH_2$; R represents H; R' represents a substituted or unsubstituted aryl or heteroaryl ring; R" represents lower alkyl; and/or E represents $CO_2Me$ or $CO_2Et$.

Additional illustrative embodiments of TRPV3 antagonists include compounds can be represented by Formula IV or a salt thereof, or a solvate, hydrate, oxidative metabolite or prodrug of the compound or its salt:

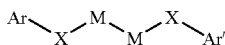

IV wherein: Ar and Ar' independently represent substituted or unsubstituted aryl or heteroaryl rings; R, independently for each occurrence, represents H or lower alkyl; X, independently for each occurrence, represents O, S, NR, $CF_2$, or $CR_2$; M, independently for each occurrence, represents a substituted or unsubstituted methylene group; and wherein said compound inhibits TRPV3 with an with an $IC_{50}$ of 10 micromolar or less. For instance In certain embodiments, the compounds of Formula IV are characterized by one or more of the following: Ar and Ar' represent phenyl or pyridyl rings; R represents H; X represents O or S; M represents $CH_2$.

In certain embodiments the TRPV3 inhibitor for use in methods or pharmaceutical preparations of the present invention is selected from a compound depicted in any of FIGS. 14A-19C. In certain embodiments, the present invention contemplates the use of any compound as depicted in FIGS. 14A-19C in any of the methods or pharmaceutical preparations of the present invention.

The TRPV3 antagonists of the subject invention can be used as part of a prophylaxis or treatment for a variety of disorders and conditions, including, but not limited to, acute and/or chronic pain, touch sensitivity, burns, inflammation, diabetic neuropathy, psoriasis, eczema, dermatitis, post-herpetic neuralgia (shingles), migraine, incontinence, fever, hot flashes, osteoarthritis, oral mucositis, cancer pain, bladder cystitis, pain associated with Crohn's disease and Irritable Bowel Syndrome (IBS), rheumatoid arthritis, Grierson-Gopalan syndrome (better known as burning feet syndrome), burning mouth syndrome (BMS) and cough, or is used as a depilatory to promote loss of or inhibit the growth of hair on a patient. Other exemplary diseases or conditions that can be treated using a TRPV3 antagonist of the present invention are detailed throughout the specification. The invention contemplates the use of compounds having any of the structures provided in the specification in the treatment of or to reduce the symptoms of any of the diseases or conditions disclosed in the application. The invention further contemplates the use of compounds having any of the structures provided in the specification in the manufacture of a medicament or pharmaceutical preparation to treat or reduce the symptoms of any of the diseases or conditions provided in the specification. Compounds for use in treating a particular disease or condition can be formulated for administration via a route appropriate for the particular disease or condition.

The TRPV3 antagonists can be administered alone or in combination with other therapeutic agents. For instance, the TRPV3 antagonists is administered conjointly with one more of an anti-inflammatory agent, anti-acne agent, anti-wrinkle agent, anti-scarring agent, anti-psoriatic agent, anti-proliferative agent, anti-fungal agent, anti-viral agent, anti-septic agent, anti-migraine agent, keratolytic agent, or a hair growth inhibitor.

The TRPV3 antagonists can be administered topically, orally, transdermally, rectally, vaginally, parenterally, intranasally, intraocularly, intravenously, intramuscularly, intraarterially, intrathecally, intracapsularly, intraorbitally, intracardiacly, intradermally, intraperitoneally, transtracheally, subcutaneously, subcuticularly, intraarticularly, subcapsularly, subarachnoidly, intraspinally, intrasternally or by inhalation.

In certain preferred embodiments, the TRPV3 antagonists is administered topically.

In certain preferred embodiments, the TRPV3 antagonists is administered orally.

In certain preferred embodiments, the TRPV3 antagonists is administered parenterally.

In certain preferred embodiments, the TRPV3 antagonists is administered to prevent, treat or alleviate signs and symptoms of acute pain, chronic pain, touch sensitivity, itching sensitivity, or as part of treating a burn, such as, for example, post-surgical pain, cancer pain, or neuropathic pain.

In certain preferred embodiments, the TRPV3 antagonists is administered to prevent, treat or alleviate signs and symptoms of migraine.

In certain preferred embodiments, the TRPV3 antagonists is administered to prevent, treat or alleviate signs and symptoms of a disorder or condition selected from the group consisting of diabetic neuropathy, inflammation, psoriasis, eczema, dermatitis, post-herpetic neuralgia (shingles), incontinence, bladder incontinence, fever, hot flashes, and cough.

In certain preferred embodiments, the TRPV3 antagonists is administered to prevent, treat or alleviate signs and symptoms of osteoarthritis.

In certain preferred embodiments, the TRPV3 antagonists is administered to prevent, treat or alleviate signs and symptoms of rheumatoid arthritis.

In certain preferred embodiments, the TRPV3 antagonists is administered to prevent, treat or alleviate signs and symptoms of oral mucositis.

In certain preferred embodiments, the TRPV3 antagonists is administered to promote loss of or inhibit the growth of hair on a patient.

In certain embodiments, the TPRV 3 antagonist is administered to prevent, treat or alleviate signs and symptoms of oral pain.

In certain embodiments, the TRPV3 antagonist is administered to prevent, treat or alleviate signs and symptoms of pancreatitis, for example pain associated with pancreatitis.

In certain embodiments, the TRPV3 antagonist is administered to prevent, treat or alleviate signs and symptoms of chronic regional pain syndrome.

Still another aspect of the present invention relates to the use of a TRPV3 antagonist, e.g., a small molecule agent that inhibits inward TRPV3-mediated current with an $IC_{50}$ of 1 micromolar or less, in the manufacture of a medicament to prevent, treat or alleviate symptoms of a disease, disorder or condition involving activation of TRPV3, or for which reduced TRPV3 activity can reduce the severity, in a patient.

Yet another aspect of the present invention relates to a pharmaceutical preparation comprising an agent that inhibits inward TRPV3-mediated current with an $IC_{50}$ of 1 micromolar or less; and a pharmaceutically acceptable excipient or solvent wherein the agent is provided in a dosage form providing an amount effective to prevent, treat or alleviate symptoms of a disease, disorder or condition involving activation of TRPV3, or for which reduced TRPV3 activity can reduce the severity, in a patient. In certain preferred embodiments, the pharmaceutical preparation does not cause QT interval elongation in the patient. In certain embodiments, the pharmaceutical preparation does not alter normal temperature regulator or sensation in said patient.

In certain illustrative embodiments, the pharmaceutical preparation comprises an agent that inhibits TRPV3-mediated current with an $IC_{50}$ of at least one order of magnitude lower than its $IC_{50}$ for inhibition of NaV 1.2 function, TRPV1 function, TRPV5 function, TRPV6 function, mitochondrial uniporter function and HERG function; and a pharmaceutically acceptable excipient or solvent, wherein the agent is provided in a dosage form providing an amount effective to prevent, treat or alleviate symptoms of a disease, disorder or condition involving activation of TRPV3, or for which reduced TRPV3 activity can reduce the severity, in a patient, but which does not cause QT interval elongation.

In another illustrative embodiment, the pharmaceutical preparation comprises an agent that inhibits heat-induced TRPV3-mediated current with an $IC_{50}$ of 1 micromolar or less; and a pharmaceutically acceptable excipient or solvent, wherein the agent is provided in a dosage form providing an amount effective to prevent, treat or alleviate symptoms of a disease, disorder or condition involving activation of TRPV3, or for which reduced TRPV3 activity can reduce the severity, in a patient, but which does not cause QT interval elongation.

One preferred preparation is a topical formulation for reducing TRPV3 activity in skin or mucosa, comprising an agent that inhibits both 2-APB (2-aminoethyl diphenylborinate) and heat induced TRPV3-mediated current with an $IC_{50}$ of 1 micromolar or less.

Another preferred preparation is a removable patch or bandage, comprising: (i) a polymeric base; and (ii) an agent that inhibits both 2-APB and heat induced TRPV3-mediated current with an $IC_{50}$ of 1 micromolar or less.

Still another illustrative formulation is a skin exfoliant composition for topical application to an animal subject comprising a topical vehicle; one or more skin exfoliant ingredients selected from the group consisting of carboxylic acids, keto acids, α-hydroxy acids, β-hydroxy acids, retinoids, peroxides, and organic alcohols, said one or more skin exfoliant ingredients contained in a total amount of at least about 12% by weight and capable of inducing skin irritation and effecting exfoliation of the skin of said subject; and an agent that inhibits both 2-APB and heat induced TRPV3-mediated current with an $IC_{50}$ of 1 micromolar or less, which agent is provided in an amount effective for analgesic, anti-irritant and/or anti-inflammatory effects when applied to skin.

Yet another embodiment is an antitussive composition for peroral administration comprising an agent that inhibits both 2-APB and heat induced TRPV3-mediated current with an $IC_{50}$ of 1 micromolar or less, and an orally-acceptable pharmaceutical carrier in the form of an aqueous-based liquid, or solid dissolvable in the mouth, selected from the group consisting of syrup, elixer, suspension, spray, lozenge, chewable lozenge, powder, and chewable tablet. Such antitussive compositions can include one or more additional agents for treating cough, allergy or asthma symptom selected from the group consisting of: antihistamines, 5-lipoxygenase inhibitors, leukotriene inhibitors, H3 inhibitors, β-adrenergic receptor agonists, xanthine derivatives, α-adrenergic receptor agonists, mast cell stabilizers, expectorants, NK1, NK2 and NK3 tachykinin receptor antagonists, and $GABA_B$ agonists.

Still another embodiment is a metered dose aerosol dispenser containing an aerosol pharmaceutical composition for pulmonary or nasal delivery comprising an agent that inhibits both 2-APB and heat induced TRPV3-mediated current with an $IC_{50}$ of 1 micromolar or less. For instance, it can be a metered dose inhaler, a dry powder inhaler or an air-jet nebulizer.

Still another embodiment is an eye ointment or eyedrops for ocular administration. Such ocular compositions may be useful for the treatment or alleviation of ocular pain including pain resulting from eye abrasion or post-surgical pain.

In certain embodiments, the TRPV3 inhibitor for use in methods or pharmaceutical preparations of the present invention is selected from a compound depicted in FIGS. 14A-19C. In certain embodiments, the present invention contemplates the use of any compound as depicted in FIGS. 14A-19C in any of the methods or pharmaceutical preparations of the present invention.

The present invention also relates to certain novel compounds, including purified preparations of those compounds. For instance, the invention provides compounds of Formula VII or a salt thereof, or a solvate, hydrate, oxidative metabolite or prodrug of the compound or its salt:

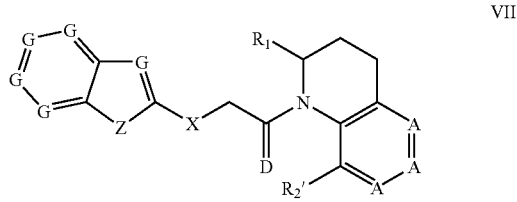

VII wherein: X represents O, S, N(CN), $CF_2$, or $C(CN)_2$; Z represents O, S, N(CN), $CF_2$, or $C(CN)_2$; A represents N or $C(R_2)$; G represents N or $C(R_3)$; $R_1$ represents H or a substituent; $R_2'$ represents a substituent; $R_2$ represents, independently for each occurrence, H or a substituent; $R_3$ represents, independently for each occurrence, H or a substituent; and D represents O or N. In certain preferred embodiments: X represents S and D represents O; and/or $R_1$ is selected from H, lower alkyl, alkoxy, carboxyl, ester, amido, sulfonamido, heterocyclyl, cycloalkyl, hydroxyl, amino, acylamino, thioether, sulfonylamino, or $R_1$ taken together with the carbon to which it is attached forms a carbonyl or thiocarbonyl; and $R_2'$, $R_2$ and $R_3$, independently for each occurrence, are selected from H, lower alkyl, alkoxy, carboxyl, ester, amido, sulfonamido, heterocyclyl, cycloalkyl, hydroxyl, amino, acylamino, thioether, sulfonylamino, nitro, halogen, $CF_3$, or cyano.

In certain embodiments, the compound can be represented by Formula VIIa or a salt thereof, or a solvate, hydrate, oxidative metabolite or prodrug of the compound or its salt:

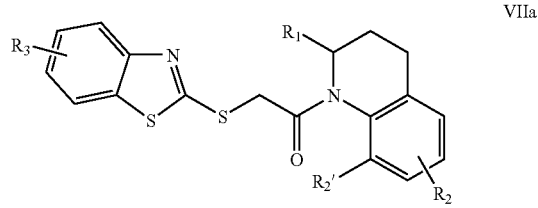

VIIa wherein: $R_1$ represents H or a substituent; $R_2$ and $R_3$ are absent or represent one or more substituents on the ring to which they are attached; and $R_2'$ represents a substituent. In certain preferred embodiments, $R_1$ is selected from H, lower alkyl, alkoxy, carboxyl, ester, amido, sulfonamido, heterocyclyl, cycloalkyl, hydroxyl, amino, acylamino, thioether, sulfonylamino, or $R_1$ taken together with the carbon to which it is attached forms a carbonyl or thiocarbonyl; $R_2$ and $R_3$ are absent or, independently for each occurrence, are selected from lower alkyl, alkoxy, carboxyl, ester, amido, sulfonamido, heterocyclyl, cycloalkyl, hydroxyl, amino, acylamino, thioether, sulfonylamino, nitro, halogen, $CF_3$, or cyano; and $R_2'$ is selected from lower alkyl, alkoxy, carboxyl, ester, amido, sulfonamido, heterocyclyl, cycloalkyl, hydroxyl, amino, acylamino, thioether, sulfonylamino, halogen, $CF_3$, or cyano. In more preferred embodiments, each $R_1$ is independently selected from H, lower alkyl, or alkoxy, or $R_1$ taken together with the carbon to which it is attached forms a carbonyl. In certain embodiments, each $R_2$ is absent or is independently selected from lower alkyl, alkoxy, or halogen;

$R_2'$ is selected from lower alkyl, alkoxy, or halogen; and each $R_3$ is absent or is independently selected from lower alkyl, alkoxy, $CF_3$, nitro, or halogen.

In certain preferred embodiments, $R_1$ and $R_2$ are absent; $R_2'$ represents $CH_3$; and $R_3$ represents one or more substituents positioned meta or para to the nitrogen of the ring system.

In certain embodiments, the compound can be represented by Formula VIIb or a salt thereof, or a solvate, hydrate, oxidative metabolite or prodrug of the compound or its salt:

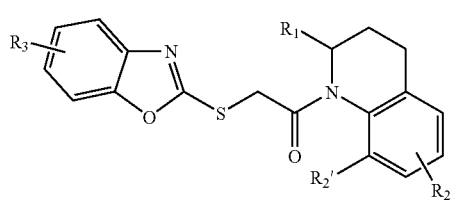

VIIb wherein: $R_1$ represents H or a substituent; $R_2$ and $R_3$ are absent or represent one or more substituents on the ring to which they are attached; and $R_2'$ represents a substituent.

For instance, $R_1$ can be selected from H, lower alkyl, alkoxy, carboxyl, ester, amido, sulfonamido, heterocyclyl, cycloalkyl, hydroxyl, amino, acylamino, thioether, sulfonylamino, or $R_1$ taken together with the carbon to which it is attached forms a carbonyl or thiocarbonyl; $R_2$ and $R_3$ are absent or, independently for each occurrence, are selected from lower alkyl, alkoxy, carboxyl, ester, amido, sulfonamido, heterocyclyl, cycloalkyl, hydroxyl, amino, acylamino, thioether, sulfonylamino, nitro, halogen, $CF_3$, or cyano; and $R_2'$ is selected from lower alkyl, alkoxy, carboxyl, ester, amido, sulfonamido, heterocyclyl, cycloalkyl, hydroxyl, amino, acylamino, thioether, sulfonylamino, halogen, $CF_3$, or cyano.

In certain preferred embodiments, $R_1$ is independently selected from H, lower alkyl, or alkoxy, or $R_1$ taken together with the carbon to which it is attached forms a carbonyl.

In certain preferred embodiments, $R_2$ is absent or each $R_2$ is independently selected from lower alkyl, alkoxy, or halogen.

In certain preferred embodiments, $R_2'$ is selected from lower alkyl, alkoxy, or halogen.

In certain preferred embodiments, $R_3$ is absent or each $R_3$ is independently selected from lower alkyl, alkoxy, $CF_3$, nitro, or halogen.

In certain preferred embodiments, $R_1$, $R_2$, and $R_3$ are absent.

In certain embodiments, the TRPV3 antagonist can be represented by Formula VIII or a salt thereof, or a solvate, hydrate, oxidative metabolite or prodrug of the compound or its salt:

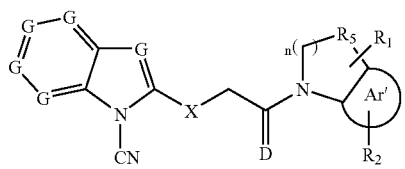

VIII wherein: X represents O, S, N(CN), $CF_2$, or $C(CN)_2$; G represents N or $C(R_3)$; $R_1$ and $R_2$, each independently, is absent or represents one or more substituents on the ring to which it is attached; Ar' represents an aryl or heteroaryl group; n represents 1, 2, or 3; $R_3$ represents, independently for each occurrence, H or a substituent; $R_5$ represents $CH_2$, O, $NR_6$; $R_6$ represents H or lower alkyl; and D represents O or N.

In certain embodiments, Ar' represents phenyl, thiophene, imidazole, thiazole, furan, oxazole, tetrazole, thiadiazole, pyridine, pyrimadine, or triazole.

In certain embodiments, X represents S and D represents O.

In certain embodiments, $R_1$ is absent or, independently for each occurrence, is selected from lower alkyl, alkoxy, carboxyl, ester, amido, sulfonamido, heterocyclyl, cycloalkyl, hydroxyl, amino, acylamino, thioether, sulfonylamino, or $R_1$ taken together with the carbon to which it is attached forms a carbonyl or thiocarbonyl; and $R_2$ and $R_3$, independently for each occurrence, are selected from H, lower alkyl, alkoxy, carboxyl, ester, amido, sulfonamido, heterocyclyl, cycloalkyl, hydroxyl, amino, acylamino, thioether, sulfonylamino, nitro, halogen, $CF_3$, or cyano.

In certain embodiments, the TRPV3 antagonist can be represented by Formula VIIIa or a salt thereof, or a solvate, hydrate, oxidative metabolite or prodrug of the compound or its salt:

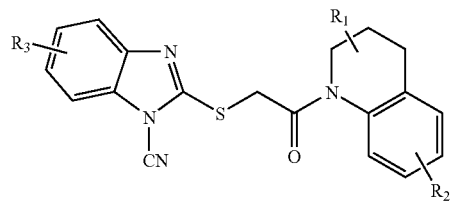

VIIIa wherein: $R_1$, $R_2$ and $R_3$ are absent or represent one or more substituents on the ring to which they are attached.

In certain embodiments, $R_1$ is absent or, independently for each occurrence, is selected from lower alkyl, alkoxy, carboxyl, ester, amido, sulfonamido, heterocyclyl, cycloalkyl, hydroxyl, amino, acylamino, thioether, sulfonylamino, or $R_1$ taken together with the carbon to which it is attached forms a carbonyl or thiocarbonyl; and $R_2$ and $R_3$ are absent or, independently for each occurrence, are selected from lower alkyl, alkoxy, carboxyl, ester, amido, sulfonamido, heterocyclyl, cycloalkyl, hydroxyl, amino, acylamino, thioether, sulfonylamino, nitro, halogen, $CF_3$, or cyano.

In certain embodiments, the TRPV3 antagonist is a compound of Formula IX or a salt thereof, or a solvate, hydrate, oxidative metabolite or prodrug of the compound or its salt:

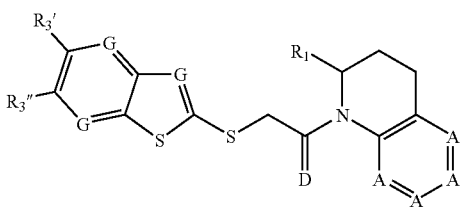

IX wherein: A represents N or $C(R_2)$; G represents N or $C(R_3)$; $R_1$ represents H or a substituent; $R_2$ represents, independently for each occurrence, H or a substituent; $R_3$ represents, independently for each occurrence, H or a substituent; $R_3'$ represents H, halogen, alkoxy, lower alkyl, perfluoroalkyl, aryl, heteroaryl, or CH₂R₃ₐ; R₃" represents H, halogen, lower alkyl, aryl, heteroaryl, or CH₂R₃ₐ; R₃ₐ represents amino, heterocyclyl, carboxyl, ester, aryl, or heteroaryl; and D represents O or N, provided that when R₃' is H, R₃" is not H or lower alkyl, and when R₃' is halogen, R₃" is not H.

In certain embodiments, R₁ is selected from H, lower alkyl, alkoxy, carboxyl, ester, amido, sulfonamido, heterocyclyl, cycloalkyl, hydroxyl, amino, acylamino, thioether, sulfonylamino, or R₁ taken together with the carbon to which it is attached forms a carbonyl or thiocarbonyl; and R₂ and R₃, independently for each occurrence, are selected from H, lower alkyl, alkoxy, carboxyl, ester, amido, sulfonamido, heterocyclyl, cycloalkyl, hydroxyl, amino, acylamino, thioether, sulfonylamino, halogen, CF₃, or cyano.

In certain embodiments, the TRPV3 antagonist is a compound represented by formula Ixa or a salt thereof, or a solvate, hydrate, oxidative metabolite or prodrug of the compound or its salt:

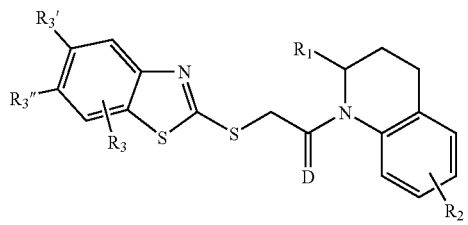

IXa wherein R₁ represents H or a substituent; R₂ is absent or represents a substituent; R₃ is absent or represents a substituent; R₃' represents H, halogen, alkoxy, lower alkyl, perfluoroalkyl, aryl, heteroaryl, or CH₂R₃ₐ; R₃" represents H, halogen, lower alkyl, aryl, heteroaryl, or CH₂R₃ₐ; R₃ₐ represents amino, heterocyclyl, carboxyl, ester, aryl, or heteroaryl; and D represents O or N, provided that when R₃' is H, R₃" is not H or lower alkyl, and when R₃' is halogen, R₃" is not H.

In certain embodiments, R₁ is selected from H, lower alkyl, alkoxy, carboxyl, ester, amido, sulfonamido, heterocyclyl, cycloalkyl, hydroxyl, amino, acylamino, thioether, sulfonylamino, or R₁ taken together with the carbon to which it is attached forms a carbonyl or thiocarbonyl; and R₂ and R₃ are absent or, independently for each occurrence, are selected from lower alkyl, alkoxy, carboxyl, ester, amido, sulfonamido, heterocyclyl, cycloalkyl, hydroxyl, amino, acylamino, thioether, sulfonylamino, halogen, CF₃, or cyano.

In certain embodiments, the TRPV3 antagonist is a compound of Formula X or a salt thereof, or a solvate, hydrate, oxidative metabolite or prodrug of the compound or its salt:

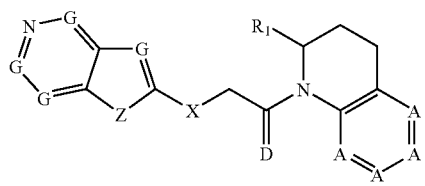

X wherein: X represents O, S, N(CN), CF₂, or C(CN)₂; Z represents O, S, N(CN), CF₂, or C(CN)₂; A represents N or C(R₂); G represents N or C(R₃); R₁ represents H or a substituent; R₂ represents, independently for each occurrence, H or a substituent; R₃ represents, independently for each occurrence, H or a substituent; and D represents O or N.

In certain embodiments, X represents S and D represents O.

In certain embodiments, R₁ is selected from H, lower alkyl, alkoxy, carboxyl, ester, amido, sulfonamido, heterocyclyl, cycloalkyl, hydroxyl, amino, acylamino, thioether, sulfonylamino, or R₁ taken together with the carbon to which it is attached forms a carbonyl or thiocarbonyl; and R₂ and R₃, independently for each occurrence, are selected from H, lower alkyl, alkoxy, carboxyl, ester, amido, sulfonamido, heterocyclyl, cycloalkyl, hydroxyl, amino, acylamino, thioether, sulfonylamino, nitro, halogen, CF₃, or cyano.

In certain embodiments, the TRPV3 antagonist is a compound can be represented by Formula Xa or a salt thereof, or a solvate, hydrate, oxidative metabolite or prodrug of the compound or its salt:

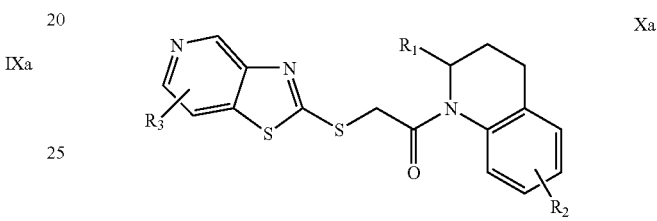

Xa wherein: R₁ represents H or a substituent; and R₂ and R₃ are absent or represent one or more substituents on the ring to which they are attached.

In certain embodiments, R₁ is selected from H, lower alkyl, alkoxy, carboxyl, ester, amido, sulfonamido, heterocyclyl, cycloalkyl, hydroxyl, amino, acylamino, thioether, sulfonylamino, or R₁ taken together with the carbon to which it is attached forms a carbonyl or thiocarbonyl; and R₂ and R₃ are absent or, independently for each occurrence, are selected from lower alkyl, alkoxy, carboxyl, ester, amido, sulfonamido, heterocyclyl, cycloalkyl, hydroxyl, amino, acylamino, thioether, sulfonylamino, nitro, halogen, CF₃, or cyano.

In certain embodiments, R₁ is H; and R₂ and R₃ are absent.

In certain embodiments, the TRPV3 antagonist is a compound represented by Formula Xb or a salt thereof, or a solvate, hydrate, oxidative metabolite or prodrug of the compound or its salt:

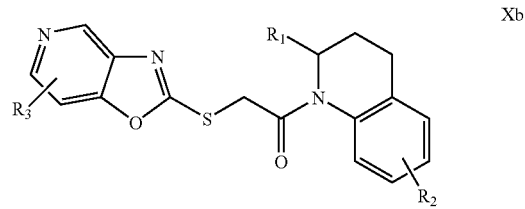

Xb wherein: R₁ represents H or a substituent; and R₂ and R₃ are absent or represent one or more substituents on the ring to which they are attached.

In certain embodiments, wherein R₁ is selected from H, lower alkyl, alkoxy, carboxyl, ester, amido, sulfonamido, heterocyclyl, cycloalkyl, hydroxyl, amino, acylamino, thioether, sulfonylamino, or R₁ taken together with the carbon to which it is attached forms a carbonyl or thiocarbonyl; and R₂ and R₃ are absent or, independently for each occurrence, are selected from lower alkyl, alkoxy, carboxyl, ester, amido, sulfonamido, heterocyclyl, cycloalkyl, hydroxyl, amino, acylamino, thioether, sulfonylamino, nitro, halogen, $CF_3$, or cyano.

In certain embodiments, the TRPV3 antagonist is a compound of Formula XI or a salt thereof, or a solvate, hydrate, oxidative metabolite or prodrug of the compound or its salt:

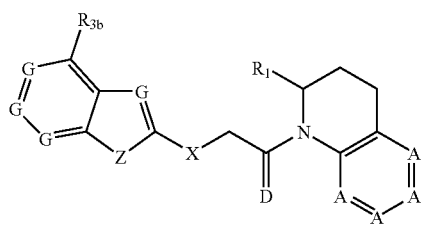

XI wherein: X represents O, S, N(CN), $CF_2$, or $C(CN)_2$; Z represents O, S, N(CN), $CF_2$, or $C(CN)_2$; A represents N or $C(R_2)$; G represents N or $C(R_3)$; $R_1$ represents H or a substituent; $R_2$ represents, independently for each occurrence, H or a substituent; $R_3$ represents, independently for each occurrence, H or a substituent; $R_{3b}$ represents a substituent; and D represents O or N.

In certain embodiments, X represents S and D represents O.

In certain embodiments, $R_1$ is selected from H, lower alkyl, alkoxy, carboxyl, ester, amido, sulfonamido, heterocyclyl, cycloalkyl, hydroxyl, amino, acylamino, thioether, sulfonylamino, or $R_1$ taken together with the carbon to which it is attached forms a carbonyl or thiocarbonyl; and $R_2$ and $R_3$ are absent or, independently for each occurrence, are selected from lower alkyl, alkoxy, carboxyl, ester, amido, sulfonamido, heterocyclyl, cycloalkyl, hydroxyl, amino, acylamino, thioether, sulfonylamino, nitro, halogen, $CF_3$, or cyano; and $R_{3b}$ is selected from lower alkyl, alkoxy, carboxyl, ester, amido, sulfonamido, heterocyclyl, cycloalkyl, hydroxyl, amino, acylamino, thioether, sulfonylamino, halogen, $CF_3$, or cyano.

In certain embodiments, the TRPV3 antagonist is a compound represented by Formula XIa or a salt thereof, or a solvate, hydrate, oxidative metabolite or prodrug of the compound or its salt:

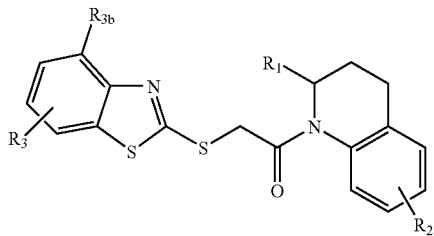

XIa wherein: $R_1$ represents H or a substituent; $R_2$ and $R_3$ are absent or represent one or more substituents on the ring to which they are attached; and $R_{3b}$ represents a substituent.

In certain embodiments, $R_1$ is selected from H, lower alkyl, alkoxy, carboxyl, ester, amido, sulfonamido, heterocyclyl, cycloalkyl, hydroxyl, amino, acylamino, thioether, sulfonylamino, or $R_1$ taken together with the carbon to which it is attached forms a carbonyl or thiocarbonyl; $R_2$ and $R_3$ are absent or, independently for each occurrence, are selected from lower alkyl, alkoxy, carboxyl, ester, amido, sulfonamido, heterocyclyl, cycloalkyl, hydroxyl, amino, acylamino, thioether, sulfonylamino, nitro, halogen, $CF_3$, or cyano; and $R_{3b}$ is selected from lower alkyl, alkoxy, carboxyl, ester, amido, sulfonamido, heterocyclyl, cycloalkyl, hydroxyl, amino, acylamino, thioether, sulfonylamino, halogen, $CF_3$, or cyano.

In certain embodiments, $R_1$ is H; $R_2$ and $R_3$ are absent; and $R_{3b}$ is a halogen.

In certain embodiments, the TRPV3 antagonist is a compound can be represented by Formula XIb or a salt thereof, or a solvate, hydrate, oxidative metabolite or prodrug of the compound or its salt:

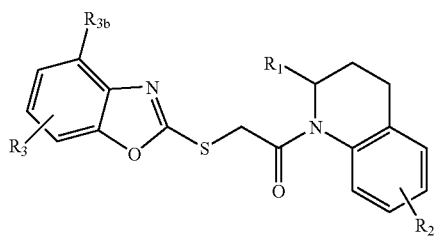

XIb wherein: $R_1$ represents H or a substituent; $R_2$ and $R_3$ are absent or represent one or more substituents on the ring to which they are attached; and $R_{3b}$ represents a substituent.

In certain embodiments, $R_1$ is selected from H, lower alkyl, alkoxy, carboxyl, ester, amido, sulfonamido, heterocyclyl, cycloalkyl, hydroxyl, amino, acylamino, thioether, sulfonylamino, or $R_1$ taken together with the carbon to which it is attached forms a carbonyl or thiocarbonyl; $R_2$ and $R_3$ are absent or, independently for each occurrence, are selected from lower alkyl, alkoxy, carboxyl, ester, amido, sulfonamido, heterocyclyl, cycloalkyl, hydroxyl, amino, acylamino, thioether, sulfonylamino, nitro, halogen, $CF_3$, or cyano; and $R_{3b}$ is selected from lower alkyl, alkoxy, carboxyl, ester, amido, sulfonamido, heterocyclyl, cycloalkyl, hydroxyl, amino, acylamino, thioether, sulfonylamino, halogen, $CF_3$, or cyano.

One aspect of the present invention provides a pharmaceutical preparation suitable for use in a human patient, or for veterinary use, comprising an effective amount of any of the compounds shown above (e.g., a compound of Formula I, Formula Ia, Formula II, Formula III, Formula IV, Formula V, Formula Va, Formula Vb, Formula VI, Formula VIa, Formula VIb, Formula VII, Formula VIIa, Formula VIIb, Formula VIII, Formula VIIIa, Formula IX, Formula IXa, Formula X, Formula Xa, Formula Xb, Formula XI, Formula XIa, or Formula XIb, or a salt thereof, or a solvate, hydrate, oxidative metabolite or prodrug of the compound or its salt), and one or more pharmaceutically acceptable excipients. In certain embodiments, the pharmaceutical preparations may be for use in treating or preventing a condition involving activation of TRPV3 or for which reduced TRPV3 activity can reduce the severity. In certain embodiments, the pharmaceutical preparations have a low enough pyrogen activity to be suitable for use in a human patient, or for veterinary use. In certain embodiments, the pharmaceutical preparation comprises an effective amount of any of the compounds shown above, wherein the compound inhibits TRPV3 with an $IC_{50}$ of 10 micromolar or less. In certain embodiments, the pharmaceutical preparation comprises an effective amount of any of the compounds shown above, wherein the compound inhibits one or more members of the vanilloid receptor family with an $IC_{50}$ of 10 micromolar or less. In certain embodiments, the pharmaceutical preparation comprises a compound which inhibits TRPV3 with an $IC_{50}$ of 1 micromolar or less, or even with an $IC_{50}$ of 500 nM or less, 250 nM or less, 200 nM or less, or even 100 nM or less.

In certain embodiments, the present invention provides a pharmaceutical preparation, having a low enough pyrogen activity to be suitable for use in a human patient, or for veterinary use, comprising a compound of Formula XII or a salt thereof, or a solvate, hydrate, oxidative metabolite or prodrug of the compound or its salt, and one or more pharmaceutically acceptable excipients:

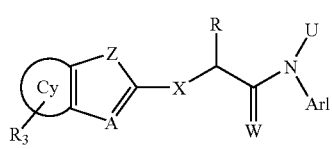

XII wherein: R represents H or a lower alkyl; X represents O, S, $NR_{10}$, $CF_2$, or $C(CN)_2$; W represents O, S, or NR'; Cy represents an aryl or heteroaryl ring; Z represents O, S, $NR_{11}$, $CF_2$, or $C(CN)_2$; A represents N or $C(R_{2a})$; $R_3$ is absent or represents one or more substituents on the ring to which it is attached; Arl represents an aralkyl, heteroaralkyl, aryl, or heteroaryl group, which may be monocyclic or bicyclic; U represents hydrogen or lower alkyl, alkenyl, alkynyl, cycloalkyl, heterocyclyl, aryl, heteroaryl, cycloalkylalkyl, heterocyclylalkyl, aralkyl, or heteroaralkyl, or, U, N and R' taken together form a 5- to 7-membered heterocyclic ring, or, U, Arl and N taken together form a ring fused to the aryl or heteroaryl ring of Arl, thereby forming a bicyclic structure; R', independently for each occurrence, represents H or a lower alkyl; $R_{2a}$ represents H, lower alkyl, alkoxy, or halogen; $R_{10}$ represents H, lower alkyl, or cyano; and $R_{11}$ represents H, lower alkyl, or cyano; wherein said compound inhibits one or more members of the vanilloid receptor family with an $IC_{50}$ of 10 micromolar or less.

In another aspect of any of the foregoing, the invention contemplates that any of the TRPV3 inhibitors of the present invention, including inhibitors having one or more of the characteristics disclosed herein, can be used to inhibit a function of TRPV3, for example a TRPV3-mediated current. In some embodiments, the compounds can be used to inhibit a TRPV3 mediated current in vitro, for example in cells in culture. In some embodiments, the compounds can be used to inhibit a TRPV3 mediated current in vivo. In certain embodiments, the compounds inhibit both an inward and an outward TRPV3-mediated current.

The invention contemplates pharmaceutical preparations and uses of TRPV3 antagonists having any combination of the foregoing or following characteristics, as well as any combination of the structural or functional characteristics of the TRPV3 antagonists described herein. Any such antagonists or preparations can be used in the treatment of any of the diseases or conditions described herein.

DETAILED DESCRIPTION OF THE DRAWINGS

FIG. 1 provides a schematic representation of experiments performed using a thermal injury model.

FIG. 2 summarizes experiments showing the effectiveness of a TRPV3 inhibitor in diminishing pain in the thermal injury model. The reduction in pain is dose dependent.

Figure 5:
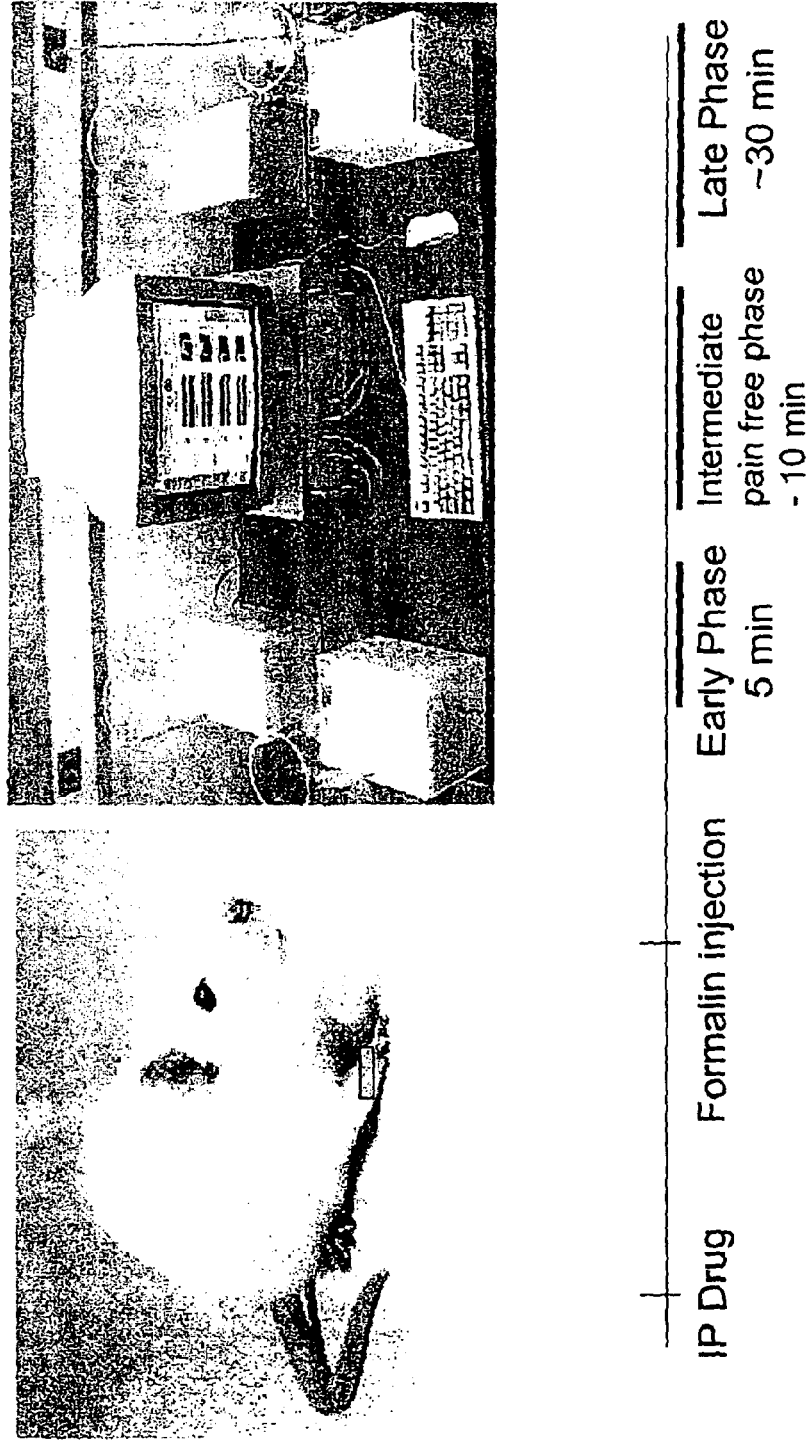

FIG. 5 provides a schematic representation of experiments performed using an automated formalin model.

Figure 6:
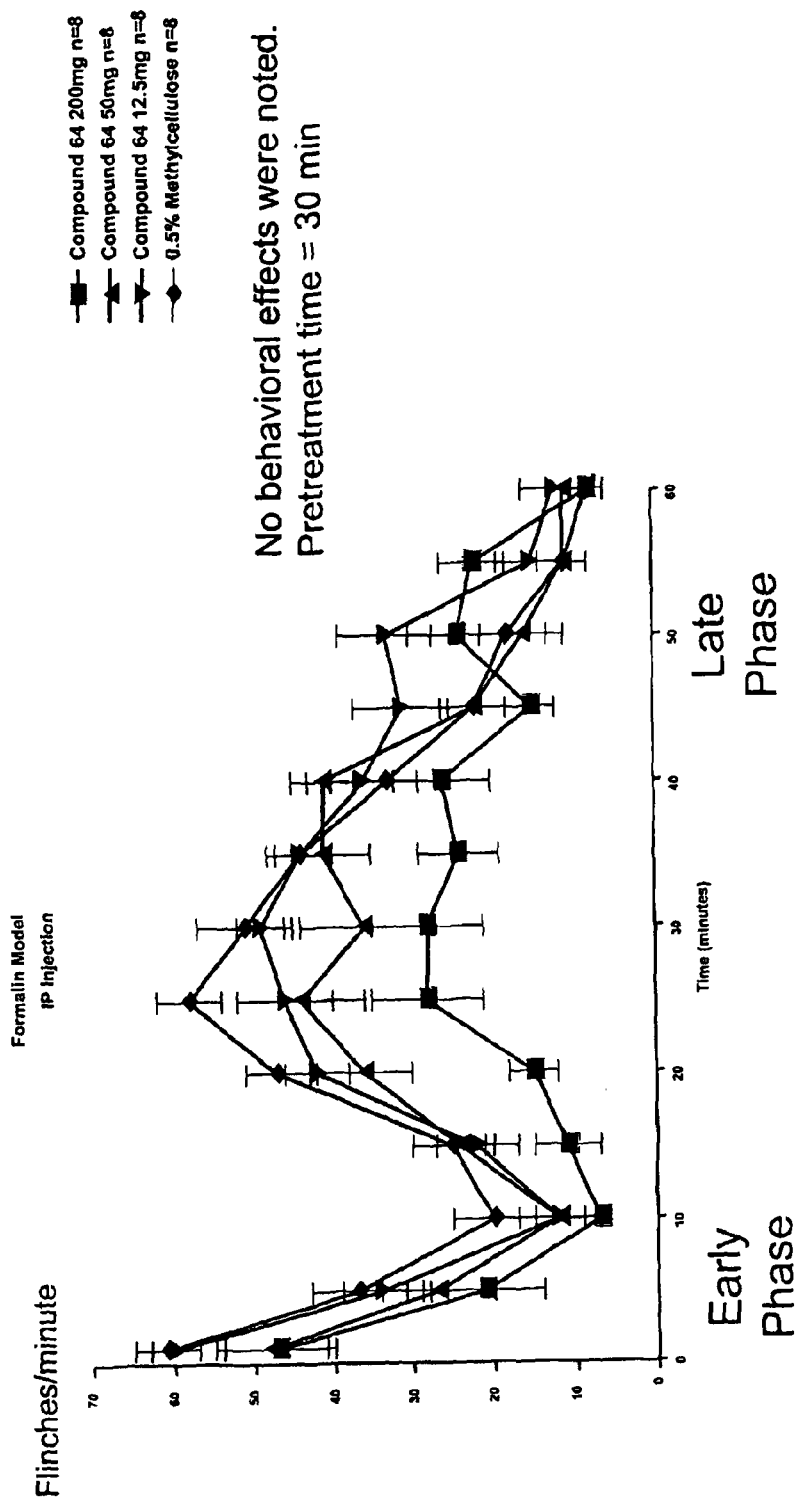

FIG. 6 summarizes experiments showing the effectiveness of a TRPV3 inhibitor in diminishing pain in the formalin model. The TRPV3 inhibitor reduces pain during the second phase (also known as the Late Phase or the facilitated phase) following formalin injection. There is also a trend towards a reduction in the first phase (also known as the Early Phase).

Figure 7:
Figure 7:
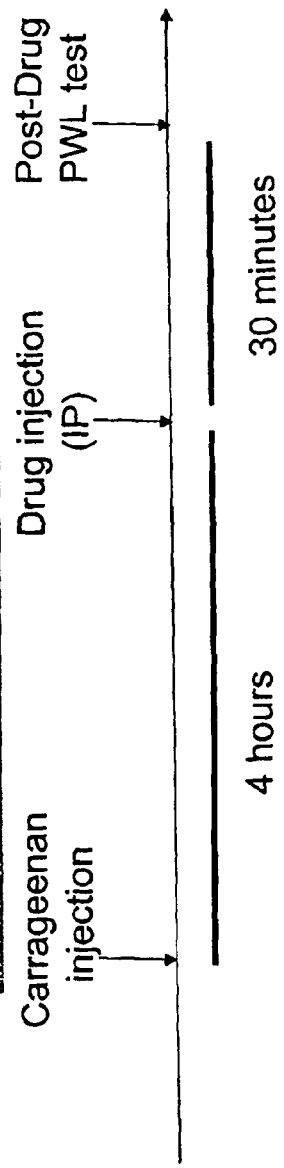

FIG. 7 provides a schematic representation of experiments performed using the carrageenan model of acute inflammatory pain.

Figure 8:
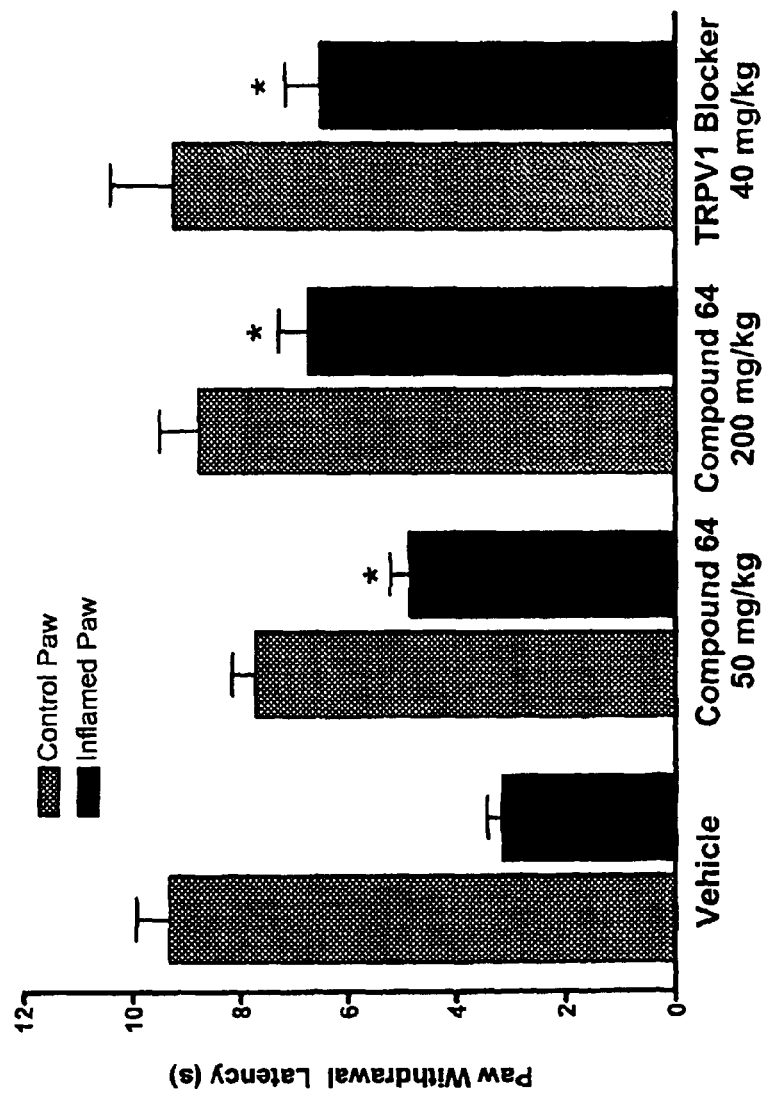

FIG. 8 summarizes experiments showing that a TRPV3 inhibitor reduces thermal hyperalgesia in the carrageenan model of acute inflammatory pain. The effectiveness of the TRPV3 inhibitor is similar to that of a TRPV1 inhibitor.

Figure 9:
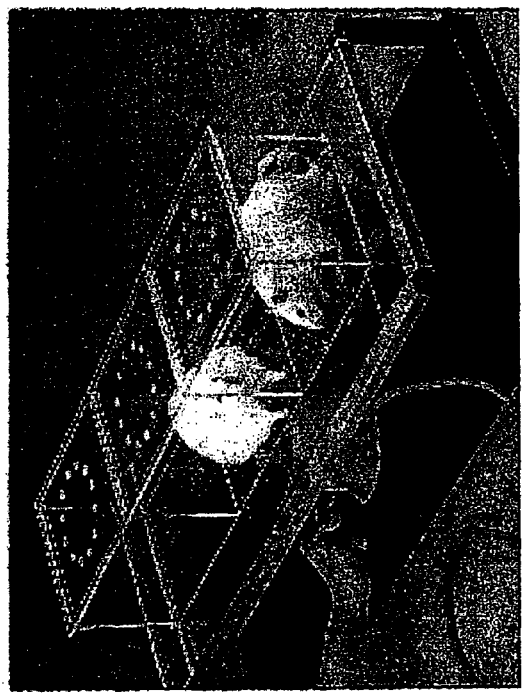
Figure 9:
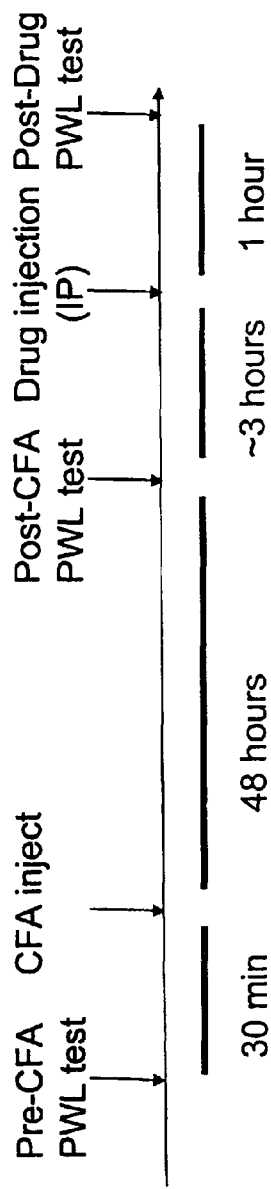

FIG. 9 provides a schematic representation of experiments performed using the Complete Freund's Adjuvant (CFA) model of inflammatory pain.

Figure 10:
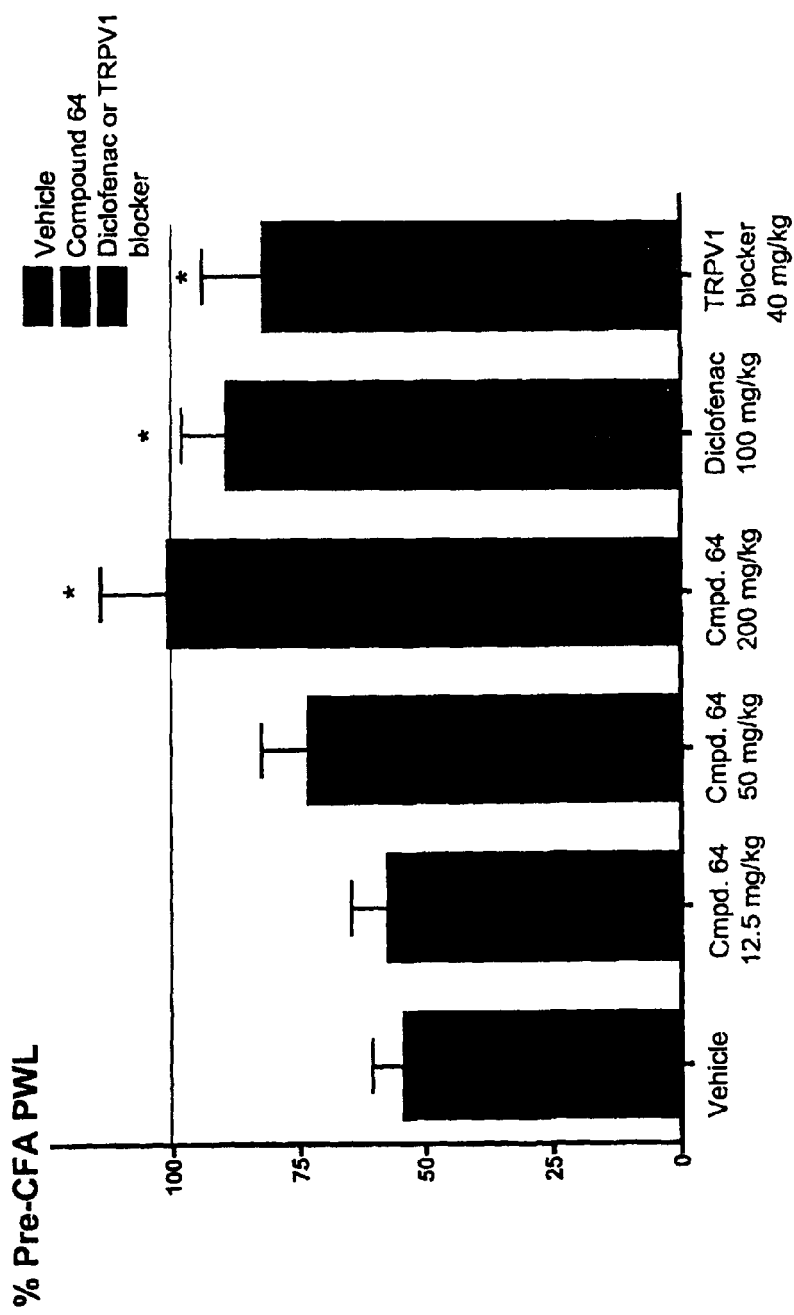

FIG. 10 summarizes experiments showing that a TRPV3 inhibitor reduces inflammatory pain in the CFA model. The effectiveness of the TRPV3 inhibitor is comparable or superior to that of diclofenac (a non-steroidal anti-inflammatory), as well as a TRPV1 inhibitor.

Figure 11:
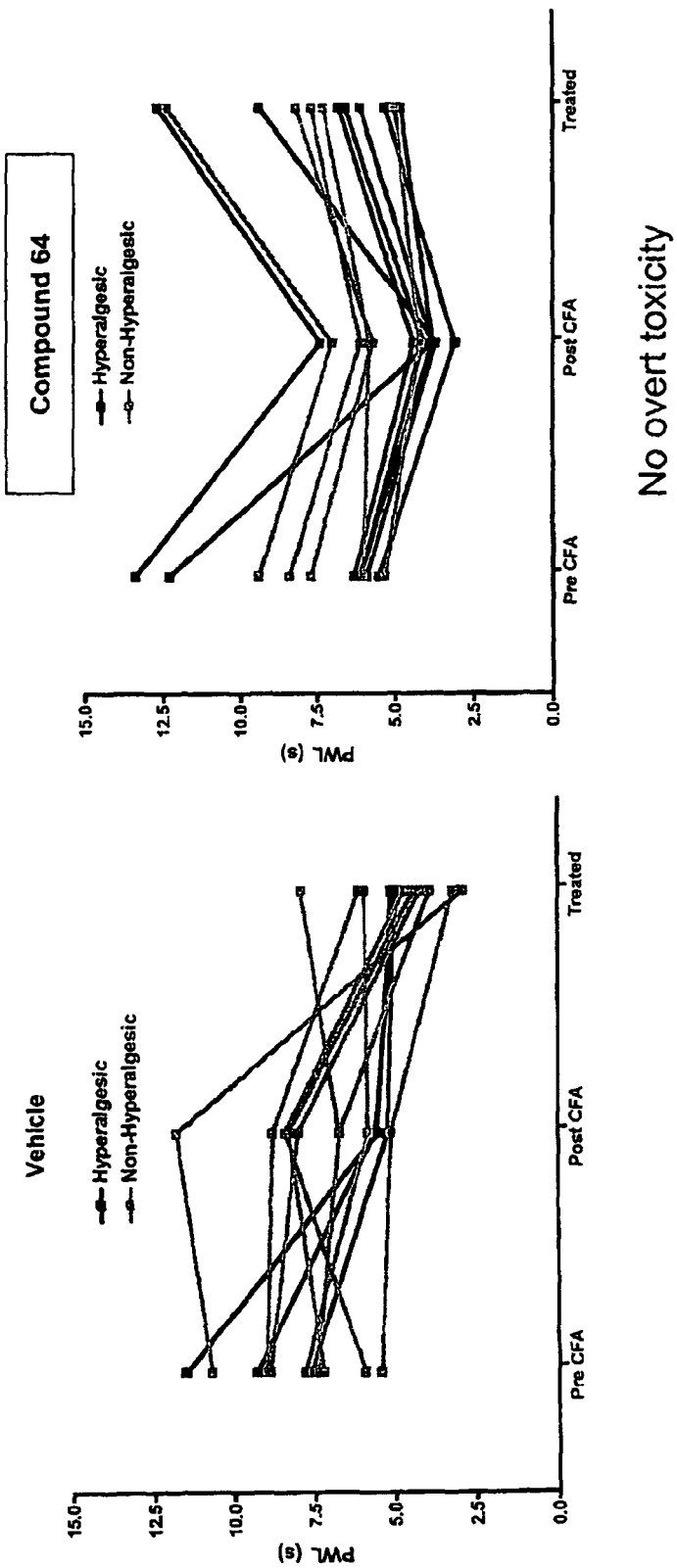

FIG. 11 summarizes experiments showing the responses for individual rats. TRPV3 inhibitor restores pain sensitivity to baseline after injection of CFA.

Figure 12:
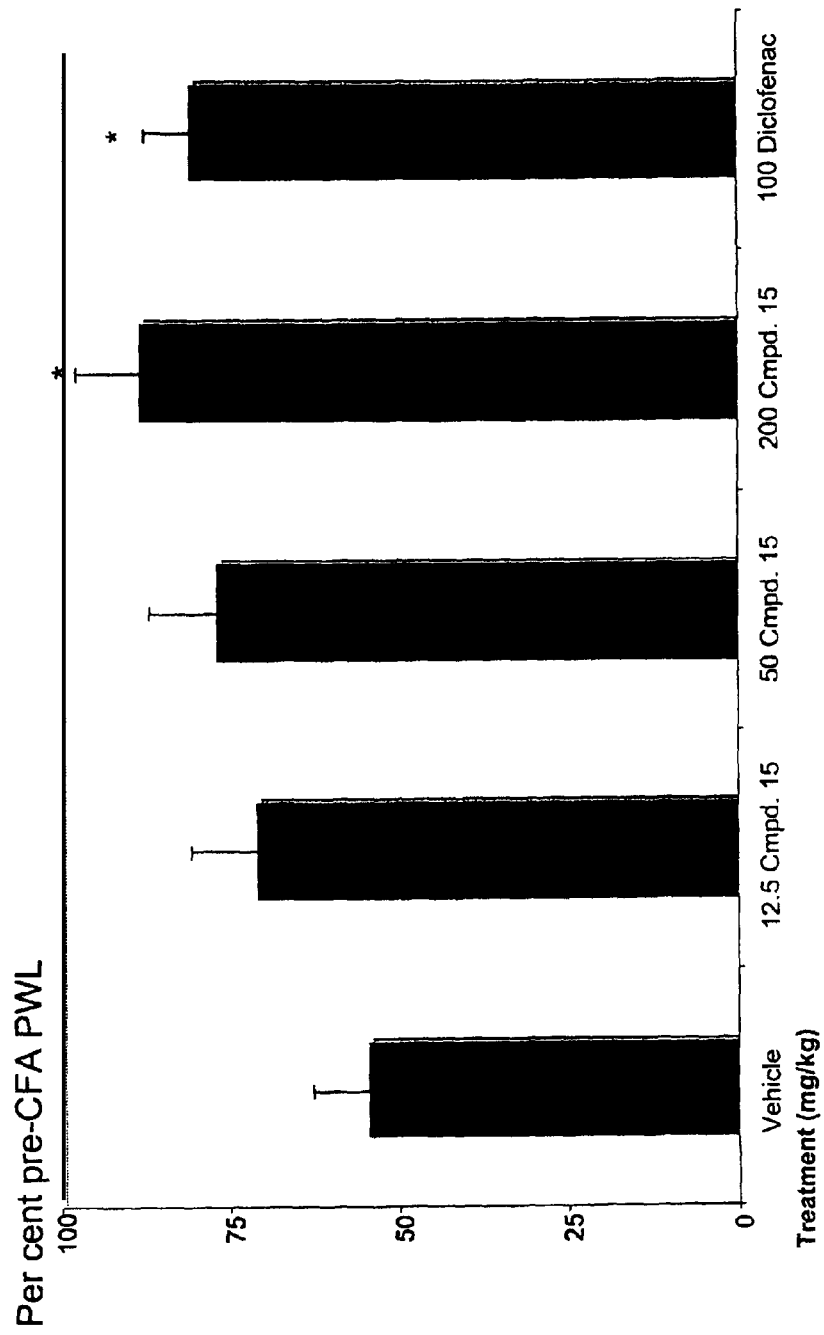

FIG. 12 summarizes experiments performed using a second TRPV3 inhibitor. This second TRPV3 inhibitor also reduces pain in the CFA model. Furthermore, the effectiveness of the TRPV3 inhibitor in reducing pain in the CFA model is similar to that of the non-steroidal anti-inflammatory, diclofenac.

Figures 13A, 13B:
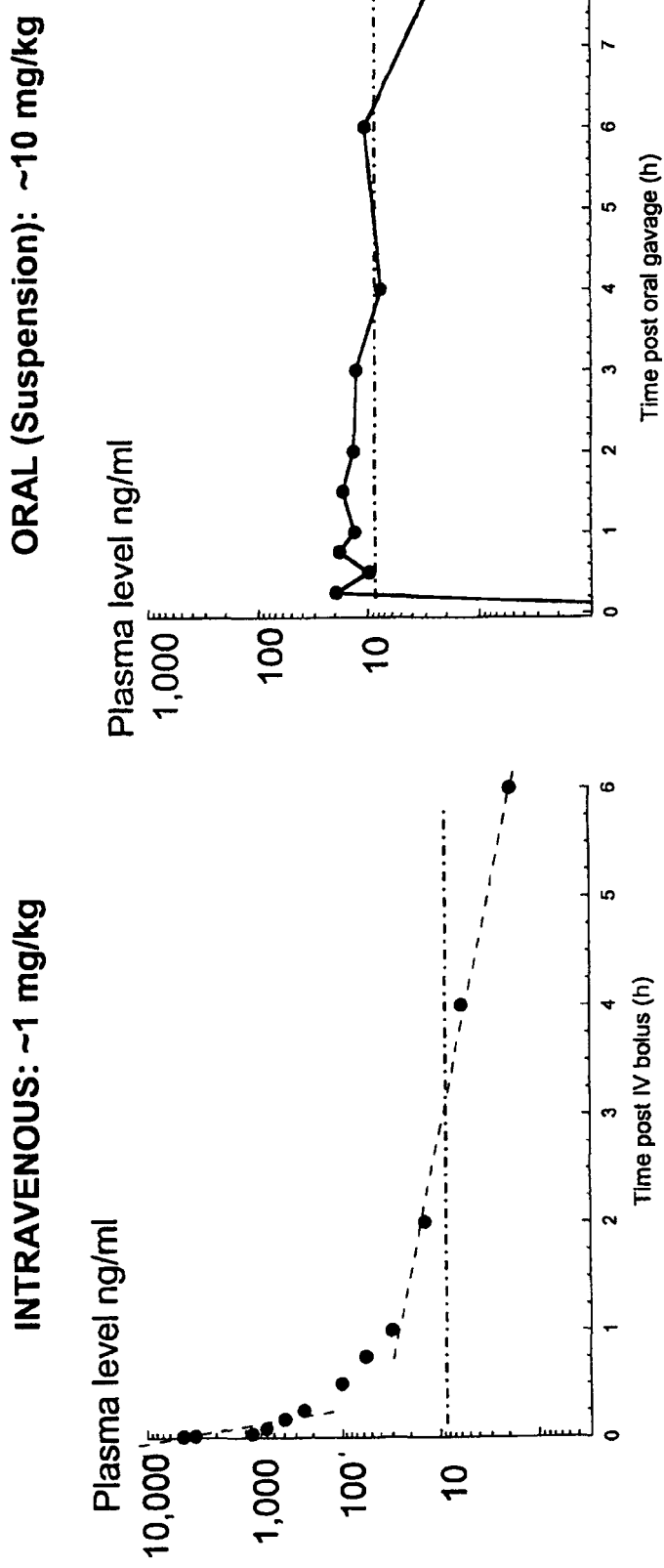
Figure 14A:
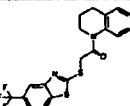
Figure 14A:
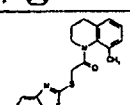
Figure 14A:
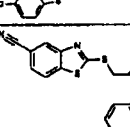
Figure 14A:
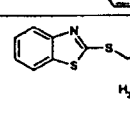
Figure 14A:
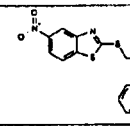
Figure 14A:
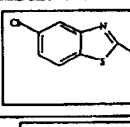
Figure 14A:
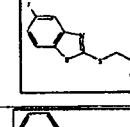
Figure 14A:
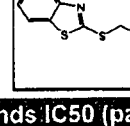
Figure 14A:
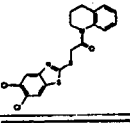
Figure 14A:
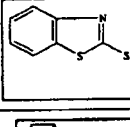
Figure 14A:
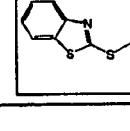
Figure 14C:
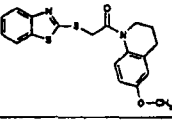
Figure 14C:
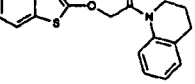
Figure 14C:
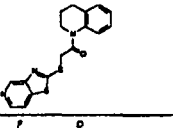
Figure 14C:
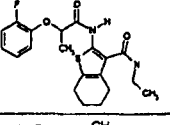
Figure 14C:
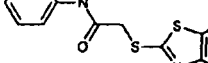
Figure 14C:
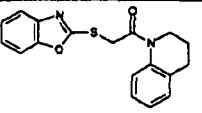
Figure 14C:
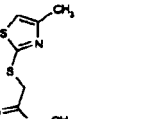
Figure 14C:
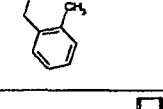
Figure 14C:
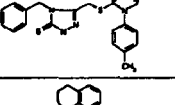
Figure 14C:
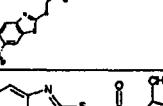
Figure 14C:
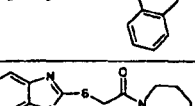
Figure 14C:
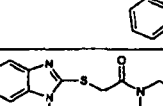
Figure 14D:
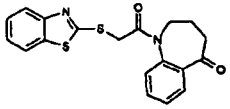
Figure 14D:
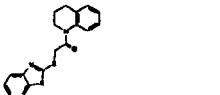
Figure 14D:
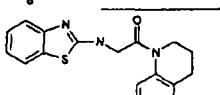
Figure 14D:
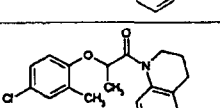
Figure 14D:
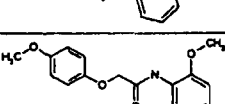
Figure 14D:
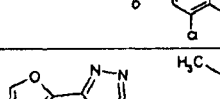
Figure 14D:
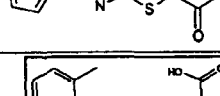
Figure 14D:
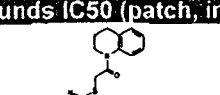
Figure 14D:
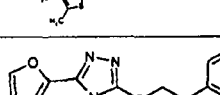
Figure 14D:
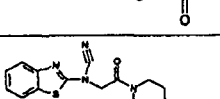
Figure 14D:
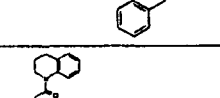
Figure 14D:
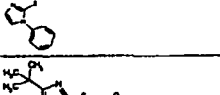
Figure 14E:
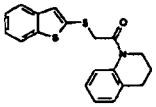
Figure 14E:
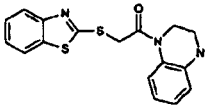
Figure 14E:
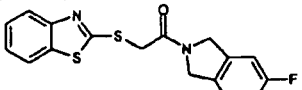
Figure 14E:
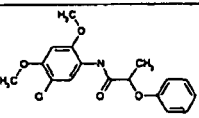
Figure 14E:
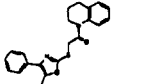
Figure 14E:
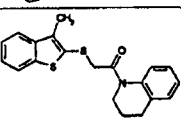
Figure 14E:
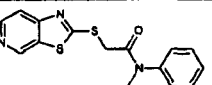
Figure 14E:
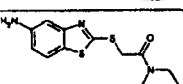
Figure 14E:
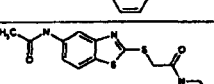
Figure 14E:
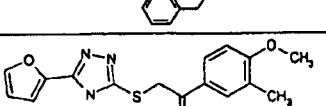
Figure 14E:
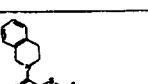
Figure 14E:
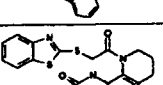
Figure 14E:
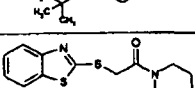
Figure 14F:
Figure 14F:
Figure 14F:
Figure 14F:
Figure 14F:
Figure 14F:
Figure 14F:
Figure 14F:
Figure 14F:
Figure 14F:
Figure 14F:

FIGS. 13A and 13B summarize experiments measuring plasma levels of a potent TRPV3 inhibitor described in the example below. The TRPV3 inhibitor was administered intravenously (a) or orally in a suspension (b).

FIGS. 14A-14G show the SAR for various compounds of Formula I versus TRPV3.

FIG. 15 shows the SAR for various compounds of Formula IV versus TRPV3 and in some instances versus other channels.

Figure 16B:
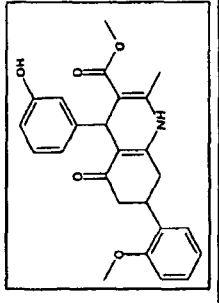
Figure 16B:
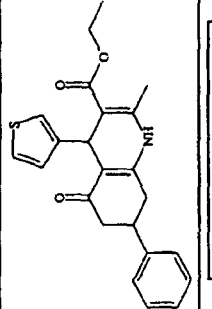
Figure 16B:
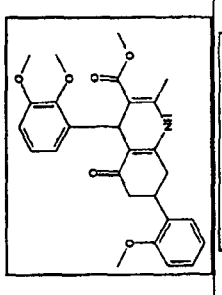
Figure 16B:
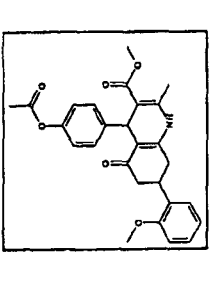
Figure 16C:
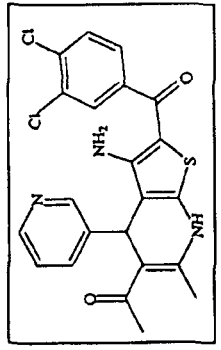

FIGS. 16A-16C show the SAR for various compounds of Formula III versus TRPV3 and in some instances versus other channels.

FIG. 17 shows the SAR for various compounds of Formula II versus TRPV3 and in some instances versus other channels.

FIG. 18 shows the SAR for various compounds versus TRPV3.

Figure 18A:
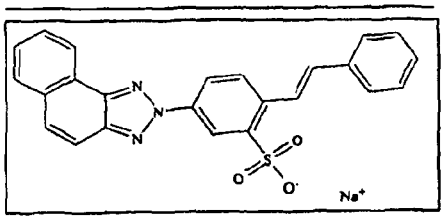
Figure 18A:
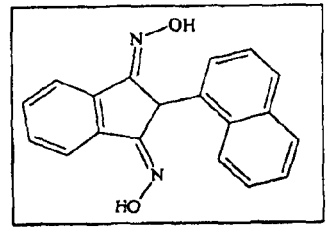
Figure 18A:
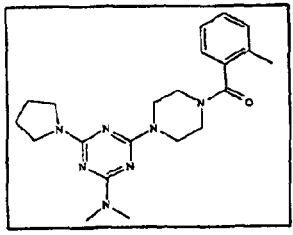
Figure 18A:
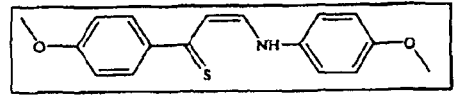
Figure 18B:
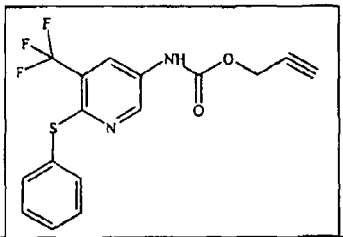
Figure 18B:
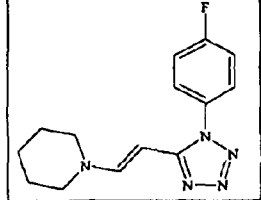
Figure 18B:
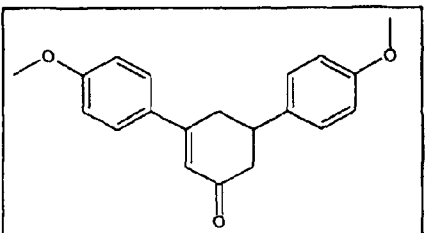
Figure 18B:
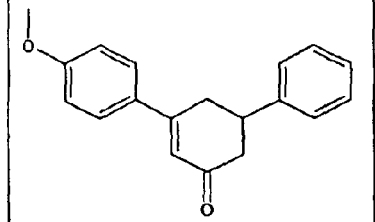
Figure 18C:
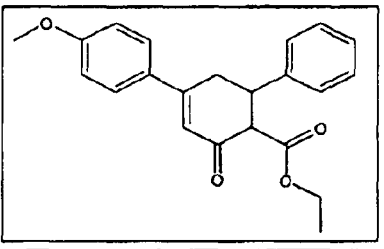
Figure 18C:
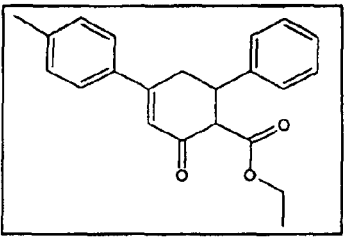

FIGS. 18A-18C show the SAR for various compounds versus TRPV3.

FIGS. 19A-19C show the SAR for various compounds versus TRPV3.

Figure 20:
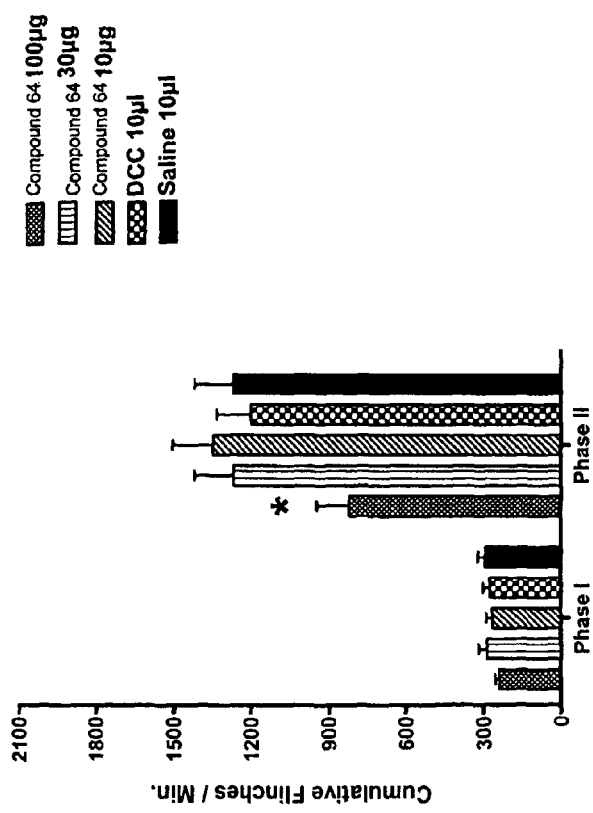

FIG. 20 summarizes experiments showing the effectiveness of a TRPV3 inhibitor in diminishing pain in the formalin model following intrathecal delivery.

Figure 21:
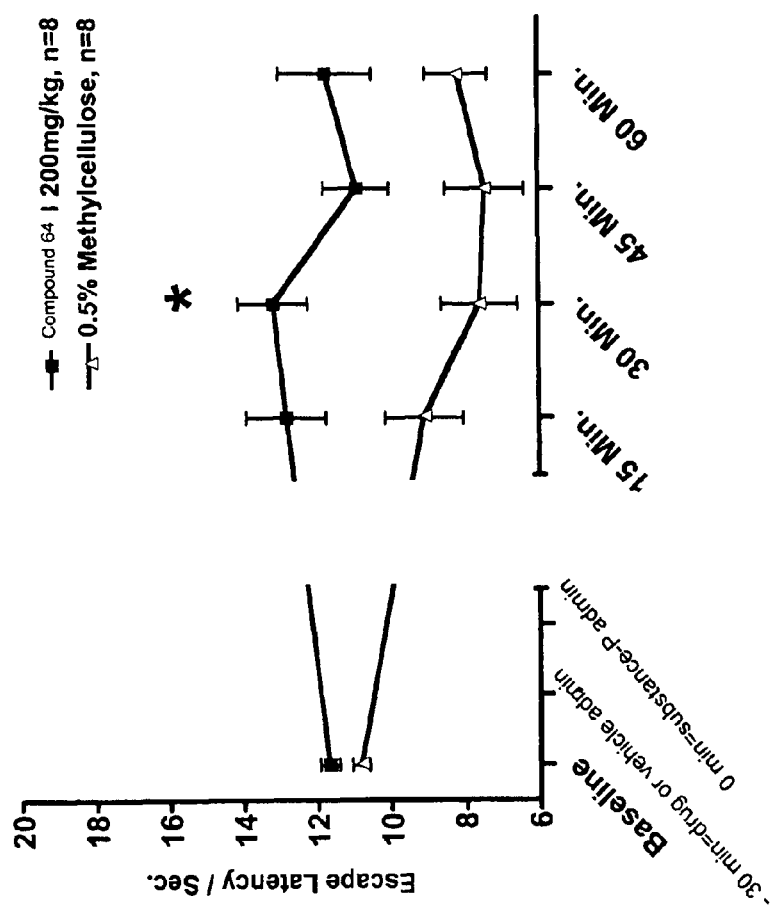

FIG. 21 summarizes experiments showing the efficacy of a systemically delivered TRPV3 inhibitor in reducing hyperalgesia induced by intrathecal administration of substance-P.

DETAILED DESCRIPTION OF THE INVENTION

Cellular homeostasis is a result of the summation of regulatory systems involved in, amongst other things, the regulation of ion flux and membrane potential. Cellular homeostasis is achieved, at least in part, by movement of ions into and out of cells across the plasma membrane and within cells by movement of ions across membranes of intracellular organelles including, for example, the endoplasmic reticulum, sarcoplasmic reticulum, mitochondria and endocytic organelles including endosomes and lysosomes.

Movement of ions across cellular membranes is carried out by specialized proteins. TRP channels are one large family of non-selective cation channels that function to help regulate ion flux and membrane potential. TRP channels are subdivided into 6 sub-families including the TRPV (vanilloid receptor) family. TRPV3 is a member of the TRPV class of TRP channels.

Non-selective cation channels such as TRPV3 modulate the flux of calcium and sodium ions across cellular membranes. Sodium and calcium influx leads to a depolarization of the cell. This increases the probability that voltage-gated ion channels will reach the threshold required for activation. As a result, activation of non-selective cation channels can increase electrical excitability and increase the frequency of voltage-dependent events. Voltage dependent events include, but are not limited to, neuronal action potentials, cardiac action potentials, smooth muscle contraction, cardiac muscle contraction, and skeletal muscle contraction.

TRPV3 is also highly expressed in skin. In a keratinocyte cell line, stimulation of TRPV3 leads to release of inflammatory mediators including interleukin-1. Thus TRPV3 may also play an important role in regulating inflammation and pain that results from the release of inflammatory stimuli (Xu et al., 2006)

TRPV3 proteins are thermosensitive channels expressed in skin cells (see, e.g., Peier et al. (2002) Science 296:2046-2049) and dorsal root ganglion, trigeminal ganglion, spinal cord and brain (see, e.g., Xu et al. (2002) Nature 418:181-185; Smith et al. (2002) Nature 418:186-188). Particular TRPV3 proteins that may be used in screening assays, as described herein, to identify compounds that modulate a function of TRPV3 include, but are not limited to human TRPV3, mouse TRPV3, and *Drosophila* TRPV3. U.S. Patent Application Publication 2004/0009537 (the "'537 publication") disclosed sequences corresponding to human, mouse, and *Drosophila* TRPV3. For example, SEQ ID NOs 106 and 107 of the '537 publication correspond to the human nucleic acid and amino acid sequences, respectively. SEQ ID Nos 108 and 109 of the '537 publication correspond to the mouse nucleic acid and amino acid sequences, respectively. The *Drosophila* protein is approximately 25% identical and 41% homologous to the human protein over approximately 49% of the length of the protein, and approximately 26% identical and 42% homologous to the mouse protein over approximately 49% of the length of the protein.

Other exemplary human TRPV3 nucleic acid and amino acid sequences are disclosed in GenBank at the following accession numbers: gi:21912412 (accession no. AJ487035); gi:21435923 (accession no. AF514998); gi:22651775 (accession no. AY118268); gi:85397600 (accession no. BC104868); and gi:22651773 (accession no. AY118267). The TRPV3 sequences and disclosures provided at these accession numbers are hereby incorporated by reference in their entirety. Compounds that inhibit one or more functions or activities of TRPV3, according to the present invention, inhibit one or more functions of any of the TRPV3 proteins provided herein. Furthermore, compounds that inhibit one or more functions or activities of TRPV3, according to the present invention, inhibit one or more functions of a TRPV3 protein encoded by a nucleic acid sequence that hybridizes under stringent conditions, including a wash step of 0.2×SSC at 65° C., to a TRPV3 nucleic acid sequence provided herein.

TRPV3 is expressed in a pattern consistent with a role in, among other things, pain. TRPV3 is expressed in tissues containing pain-sensing neurons (nociceptors). Nociceptors mediate responsiveness to force, heat, cold, chemicals, and inflammation. In addition, skin which expresses high levels of TRPV3 plays a significant role in pain. Further evidence indicates that TRPV3 expression increases in the skin cells of breast cancer patients who report significant pain (Gopinath et al., 2005).

Accordingly, modulating the function of TRPV3 proteins provides a means of modulating calcium homeostasis, sodium homeostasis, membrane polarization, and/or intracellular calcium levels, and compounds that can modulate TRPV3 function are useful in many aspects, including, but not limited to, maintaining calcium homeostasis, modulating intracellular calcium levels, modulating membrane polarization, and treating or preventing diseases, disorders, or conditions associated with calcium and/or sodium homeostasis or dyshomeostasis. In one embodiment, compounds that modulate TRPV3 function can be used in the treatment of diseases, injuries, disorders, or conditions caused or exacerbated, in whole or in part, by regulation or misregulation of TRPV3 activity. In one embodiment, compounds that inhibit a TRPV3 function can be used in the treatment of diseases, injuries, disorders, or conditions caused or exacerbated, in whole or in part, by regulation or misregulation of TRPV3 activity. In still another embodiment, compounds that inhibit a TRPV3 function can be used in the treatment of pain.

In certain embodiments, the TRPV3 antagonist is "small molecule", e.g., an organic molecule having a molecular weight of 2000 amu or less. Exemplary TRPV3 antagonists include a compound of Formula I or a salt thereof, or a solvate, hydrate, oxidative metabolite or prodrug of the compound or its salt:

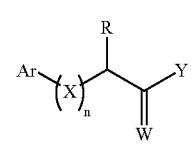

I wherein: Ar represents an aryl or heteroaryl group; Y represents Ph, OArl, SArl, or N(U)(Arl); R represents H or a lower alkyl; X represents $CH_2$, O, S, $NR_{10}$, $CF_2$, or $C(CN)_2$; W represents O, S, or NR'; n is 1, or when X is $CH_2$, n is 1 or 2; Arl represents an aralkyl, heteroaralkyl, aryl, or heteroaryl group, which may be monocyclic or bicyclic; Ph represents a substituted or unsubstituted phenyl ring, optionally fused to a substituted or unsubstituted 5- to 7-membered cycloalkyl, heterocyclyl, aryl, or heteroaryl ring; R', independently for each occurrence, represents H or a lower alkyl; U represents hydrogen or lower alkyl, alkenyl, alkynyl, cycloalkyl, heterocyclyl, aryl, heteroaryl, cycloalkylalkyl, heterocyclylalkyl, aralkyl, or heteroaralkyl, or, U, N and R' taken together form a 5- to 7-membered heterocyclic ring, or, U, Arl and N taken together form a ring fused to the aryl or heteroaryl ring of Arl, thereby forming a bicyclic structure; $R_{10}$ represents H, lower alkyl, or cyano; and wherein said compound inhibits TRPV3 with an with an $IC_{50}$ of 10 micromolar or less.

In certain embodiments, R is H, W is O or S, and X is O or S.

In certain embodiments, X is CH₂.

In certain preferred embodiments, the TRPV3 antagonist is represented in Formula Ia, or a salt thereof, or a solvate, hydrate, oxidative metabolite or prodrug of the compound or its salt:

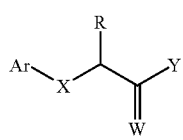

Ia wherein: Ar represents an aryl or heteroaryl group; Y represents Ph, OArl, SArl, or N(U)(Arl); R represents H or a lower alkyl; X represents O, S, NR$_{10}$, CF$_2$, or C(CN)$_2$; W represents O, S, or NR'; Arl represents an aralkyl, heteroaralkyl, aryl, or heteroaryl group, which may be monocyclic or bicyclic; Ph represents a substituted or unsubstituted phenyl ring, optionally fused to a substituted or unsubstituted 5- to 7-membered cycloalkyl, heterocyclyl, aryl, or heteroaryl ring; R', independently for each occurrence, represents H or a lower alkyl; U represents hydrogen or lower alkyl, alkenyl, alkynyl, cycloalkyl, heterocyclyl, aryl, heteroaryl, cycloalkylalkyl, heterocyclylalkyl, aralkyl, or heteroaralkyl, or, U, N and R' taken together form a 5- to 7-membered heterocyclic ring, or, U, Arl and N taken together form a ring fused to the aryl or heteroaryl ring of Arl, thereby forming a bicyclic structure; and R$_{10}$ represents H, lower alkyl, or cyano.

Exemplary compounds of Formula I and Ia include:

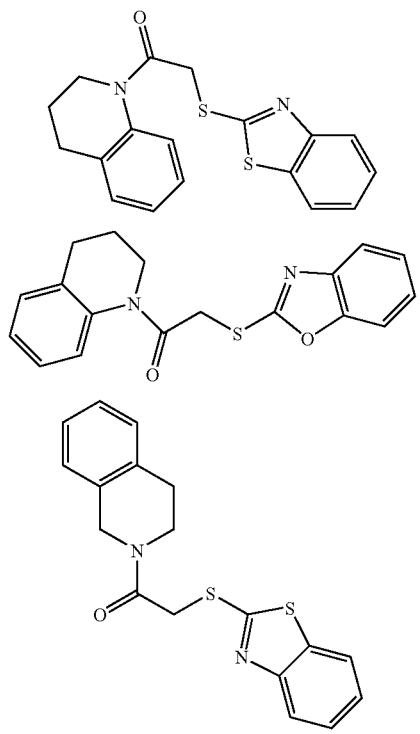

-continued

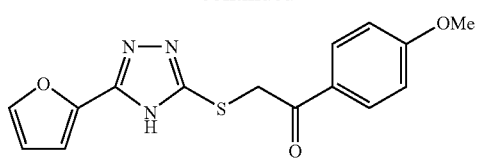

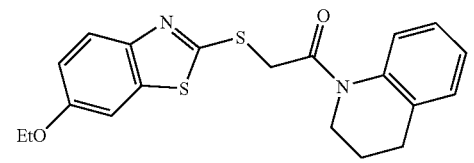

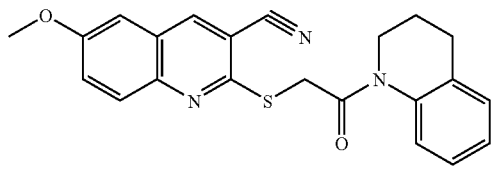

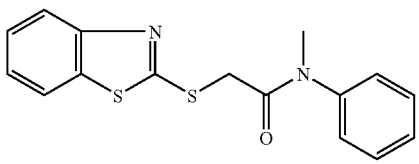

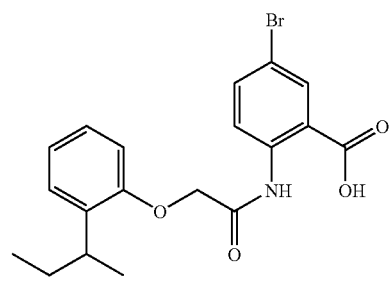

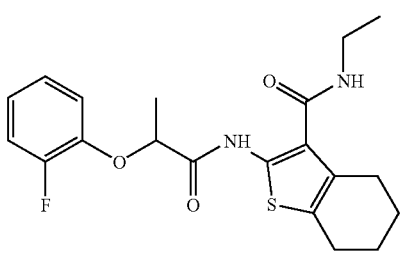

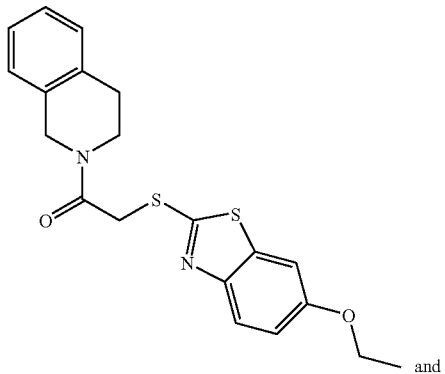

and

-continued

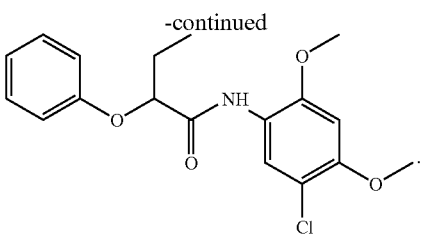

Other exemplary compounds of Formula I are shown in FIG. 14A-14G. FIGS. 14A-14G show the SAR for various compounds of Formula I versus TRPV3.

In certain embodiments of Formulas I and Ia, Y is N(U)(ArI), and in such embodiments, Y can represent, for example,

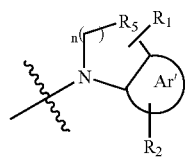

wherein: $R_1$ and $R_2$, each independently, is absent or represents one or more substituents on the ring to which it is attached; Ar' represents an aryl or heteroaryl group; $R_5$ represents $CH_2$, O, $NR_6$; $R_6$ represents H or lower alkyl; and n represents 1, 2, or 3. In certain embodiments of the above-referenced compounds, one or more of the following conditions may be true:

- Ar' represents phenyl, thiophene, imidazole, thiazole, furan, oxazole, tetrazole, thiadiazole, pyridine, pyrimadine, or triazole;
- each $R_1$ is independently selected from H, lower alkyl, alkoxy, carboxyl, ester, amido, sulfonamido, heterocyclyl, cycloalkyl, hydroxyl, amino, acylamino, thioether, sulfonylamino, or $R_1$ taken together with the carbon to which it is attached forms a carbonyl or thiocarbonyl;
- each $R_2$ is independently selected from H, lower alkyl, alkoxy, carboxyl, ester amido, sulfonamido, heterocyclyl, cycloalkyl, hydroxyl, amino, acylamino, thioether, sulfonylamino, halogen, $CF_3$, or cyano;

In certain preferred embodiments of Formulas I and Ia, Y represents

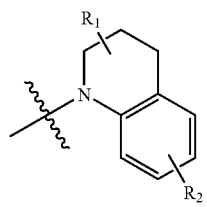

wherein $R_1$ and $R_2$ each, independently, are absent or represent one or more substituents on the ring to which they are attached. Even more preferably, independently for each occurrence, $R_1$ is selected from H, lower alkyl, alkoxy, carboxyl, ester, amido, sulfonamido, heterocyclyl, cycloalkyl, hydroxyl, amino, acylamino, thioether, or R1 taken together with the carbon to which it is attached forms a carbonyl or thiocarbonyl; and independently for each occurrence, $R_2$ is selected from H, lower alkyl, alkoxy, carboxyl, ester, amido, sulfonamido, heterocyclyl, cycloalkyl, hydroxyl, amino, acylamino, thioether, sulfonylamino, halogen, $CF_3$, or cyano.

For further illustration, Y can represent

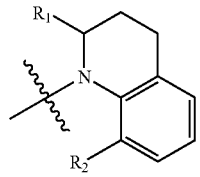

wherein $R_1$ represents H, lower alkyl, alkoxy, carboxyl, ester, amido, sulfonamido, heterocyclyl, cycloalkyl, hydroxyl, amino, acylamino, thioether, sulfonylamino, or $R_1$ taken together with the carbon to which it is attached forms a carbonyl or thiocarbonyl; and $R_2$ represents H, lower alkyl, alkoxy, carboxyl, ester, amido, sulfonamido, heterocyclyl, cycloalkyl, hydroxyl, amino, acylamino, thioether, sulfonylamino, halogen, $CF_3$, or cyano. In certain preferred embodiments, $R_1$ represents H, lower alkyl, alkoxy, or $R_1$ taken together with the carbon to which it is attached forms a carbonyl, and $R_2$ represents H, lower alkyl, alkoxy or halogen.

In certain preferred embodiments of Formulas I and Ia, Ar represents

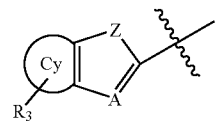

wherein: Cy represents an aryl or heteroaryl ring; Z represents O, S, $NR_{11}$, $CF_2$, or $C(CN)_2$; $R_3$ is absent or represents one or more substituents on the ring to which it is attached; $R_{11}$ represents H, lower alkyl, or cyano; A represents N or $C(R_{2a})$; and $R_{2a}$ represents H, lower alkyl, alkoxy, or halogen.

For example, Cy can represent a phenyl, thiophene, imidazole, thiazole, furan, oxazole, tetrazole, thiadiazole, pyridine, pyrimadine, or triazole, and $R_3$ can be absent, or independently for each occurrence, selected from lower alkyl, alkoxy, carboxyl, ester, amido, sulfonamido, heterocyclyl, cycloalkyl, hydroxyl, amino, acylamino, thioether, sulfonylamino, nitro, halogen, $CF_3$, or cyano. In certain preferred embodiments, A represents N, and Z represents O or S.

To further illustrate, Ar can represent

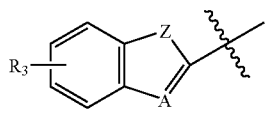

wherein: Z represents O, S, $NR_{11}$, $CF_2$, NR, or $C(CN)_2$; A represents N or $C(R_{2a})$; $R_3$ is absent or represents one or more substituents on the ring to which it is attached; $R_{11}$ represents H, lower alkyl, or cyano; and $R_{2a}$ represents H, lower alkyl, alkoxy, or halogen. In certain preferred embodiments: Z represents O or S; and $R_3$ is absent or each $R_3$ is independently selected from lower alkyl, alkoxy, carboxyl, ester, amido, sulfonamido, heterocyclyl, cycloalkyl, hydroxyl, amino, acylamino, thioether, sulfonylamino, nitro, halogen, $CF_3$, or cyano;

In certain preferred embodiments, Ar can represent

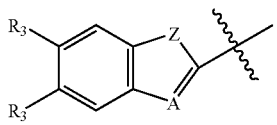

wherein: Z represents O, S, $NR_{11}$, $CF_2$, or $C(CN)_2$; A represents N or $C(R_{2a})$; $R_3$ independently for each occurrence represents H, lower alkyl, alkoxy, carboxyl, ester, amido, sulfonamido, heterocyclyl, cycloalkyl, hydroxyl, amino, acylamino, thioether, sulfonylamino, halogen, $CF_3$, or cyano; $R_{11}$ represents H, lower alkyl, or cyano; and $R_{2a}$ represents H, lower alkyl, alkoxy, or halogen. Preferably Z represents O or S, and $R_3$ independently for each occurrence represents H, lower alkyl, alkoxy, $CF_3$, nitro, or halogen.

In certain other preferred embodiments of Formulas I and Ia, Ar represents

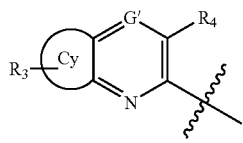

wherein: G' represents N or $C(R_5)$; $R_3$ is absent or represents one or more substituents on Cy; $R_5$ represents H or a substituent; $R_4$ represents H or a substituent; and Cy represents an aryl or heteroaryl ring. In certain preferred embodiments, Cy can be a phenyl, thiophene, imidazole, thiazole, furan, oxazole, tetrazole, thiadiazole, pyridine, pyrimidine, or triazole. In certain embodiments, $R_3$ is absent, or independently for each occurrence, is selected from lower alkyl, alkoxy, carboxyl, ester, amido, sulfonamido, heterocyclyl, cycloalkyl, hydroxyl, amino, acylamino, thioether, sulfonylamino, nitro, halogen, $CF_3$, or cyano; and $R_4$ and $R_5$, independently for each occurrence, are selected from H, lower alkyl, alkoxy, carboxyl, ester, amido, sulfonamido, heterocyclyl, cycloalkyl, hydroxyl, amino, acylamino, thioether, sulfonylamino, halogen, $CF_3$, or cyano.

In still other embodiments, the TRPV3 antagonist is a compound of Formula V or a salt thereof, or a solvate, hydrate, oxidative metabolite or prodrug of the compound or its salt:

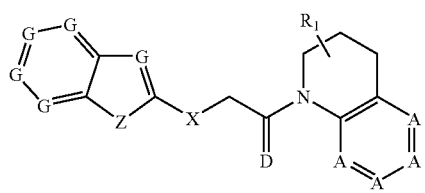

wherein: X represents O, S, $NR_{10}$, $CF_2$, or $C(CN)_2$; Z represents O, S, $NR_{11}$, $CF_2$, or $C(CN)_2$; $R_{10}$ represents H, lower alkyl, or cyano; $R_{11}$ represents H, lower alkyl, or cyano; A represents N or $C(R_2)$; G represents N or $C(R_3)$; $R_1$ is absent or represents one or more substituents on the ring to which it is attached; $R_2$ represents, independently for each occurrence, H or a substituent; $R_3$ represents, independently for each occurrence, H or a substituent; and D represents O or N.

In certain preferred embodiments of formula V: X represents S and D represents O; $R_1$ is absent, or independently for each occurrence, is selected from lower alkyl, alkoxy, carboxyl, ester, amido, sulfonamido, heterocyclyl, cycloalkyl, hydroxyl, amino, acylamino, thioether, sulfonylamino, or $R_1$ taken together with the carbon to which it is attached forms a carbonyl or thiocarbonyl; and $R_2$ and $R_3$, independently for each occurrence, are selected from H, lower alkyl, alkoxy, carboxyl, ester, amido, sulfonamido, heterocyclyl, cycloalkyl, hydroxyl, amino, acylamino, thioether, sulfonylamino, nitro, halogen, $CF_3$, or cyano.

To further illustrate, the TRPV3 antagonist can be represented by Formula Va or a salt thereof, or a solvate, hydrate, oxidative metabolite or prodrug of the compound or its salt:

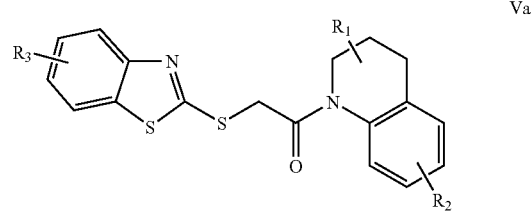

wherein: $R_1$, $R_2$ and $R_3$ are absent or represent one or more substituents on the ring to which they are attached. For instance, $R_1$ is absent, or independently for each occurrence, is selected from lower alkyl, alkoxy, carboxyl, ester, amido, sulfonamido, heterocyclyl, cycloalkyl, hydroxyl, amino, acylamino, thioether, sulfonylamino, or $R_1$ taken together with the carbon to which it is attached forms a carbonyl or thiocarbonyl; and $R_2$ and $R_3$ are absent, or independently for each occurrence, are selected from lower alkyl, alkoxy, carboxyl, ester, amido, sulfonamido, heterocyclyl, cycloalkyl, hydroxyl, amino, acylamino, thioether, sulfonylamino, nitro, halogen, $CF_3$, or cyano. In certain preferred embodiments, $R_1$ is absent, or independently for each occurrence, is selected from lower alkyl, or alkoxy or $R_1$ taken together with the carbon to which it is attached forms a carbonyl; $R_2$ is absent, or independently for each occurrence, is selected from lower alkyl, alkoxy, or halogen; and $R_3$ is absent, or independently for each occurrence, is selected from lower alkyl, alkoxy, $CF_3$, nitro, or halogen. In even more preferred embodiments, $R_1$ represents H; $R_2$ represents H or $CH_3$ and is positioned ortho to the N of the ring system; and $R_3$ represents one or more substituents positioned meta or para to the nitrogen of the ring system.

In still another illustration, the TRPV3 antagonist can be represented by Formula Vb or a salt thereof, or a solvate, hydrate, oxidative metabolite or prodrug of the compound or its salt:

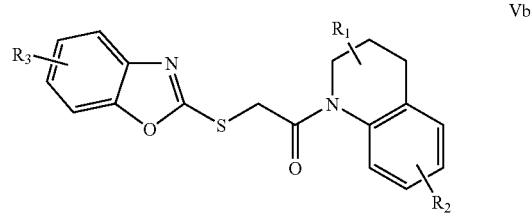

wherein $R_1$, $R_2$ and $R_3$ are absent or represent one or more substituents on the ring to which they are attached. For instance, $R_1$ is absent, or independently for each occurrence, is selected from lower alkyl, alkoxy, carboxyl, ester, amido, sulfonamido, heterocyclyl, cycloalkyl, hydroxyl, amino, acylamino, thioether, sulfonylamino, or $R_1$ taken together with the carbon to which it is attached forms a carbonyl or thiocarbonyl; and $R_2$ and $R_3$ are absent, or independently for each occurrence, are selected from lower alkyl, alkoxy, carboxyl, ester, amido, sulfonamido, heterocyclyl, cycloalkyl, hydroxyl, amino, acylamino, thioether, sulfonylamino, nitro, halogen, $CF_3$, or cyano. In certain preferred embodiments, $R_1$ is absent, or independently for each occurrence, is selected from lower alkyl, or alkoxy, or $R_1$ taken together with the carbon to which it is attached forms a carbonyl; $R_2$ is absent, or independently for each occurrence, is selected from lower alkyl, alkoxy, or halogen; and $R_3$ is absent, or independently for each occurrence, is selected from lower alkyl, alkoxy, $CF_3$, nitro, or halogen. In certain embodiments, $R_1$, $R_2$, and $R_3$ are absent.

In still other embodiments, the TRPV3 antagonist is a compound of Formula VI or a salt thereof, or a solvate, hydrate, oxidative metabolite or prodrug of the compound or its salt:

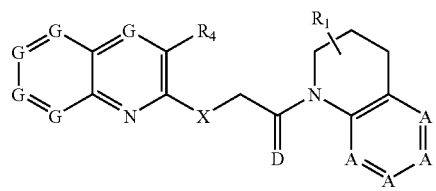

VI wherein: X represents O, S, $NR_{10}$, $CF_2$, or $C(CN)_2$; $R_{10}$ represents H, lower alkyl, or cyano; A represents N or $C(R_2)$; G represents N or $C(R_3)$; $R_1$ is absent or represents one or more substituents on the ring to which it is attached; $R_2$ represents, independently for each occurrence, H or a substituent; $R_3$ represents, independently for each occurrence, H or a substituent; $R_4$ represents H or a substituent; D represents O or N; and wherein said compound inhibits TRPV3 with an with an $IC_{50}$ of 10 micromolar or less.

In certain preferred embodiments, X represents S and D represents O.

In certain embodiments, the compound can be represented by Formula VIa or a salt thereof, or a solvate, hydrate, oxidative metabolite or prodrug of the compound or its salt:

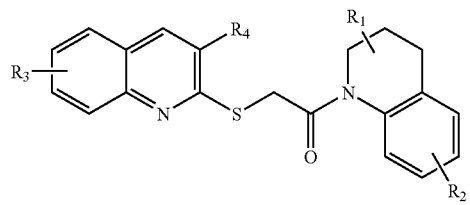

VIa wherein: $R_1$, $R_2$ and $R_3$ are absent or represent one or more substituents on the ring to which they are attached; and $R_4$ represents H or a substituent. In certain preferred embodiments, $R_1$ is absent, or independently for each occurrence, is selected from lower alkyl, alkoxy, carboxyl, ester, amido, sulfonamido, heterocyclyl, cycloalkyl, hydroxyl, amino, acylamino, thioether, sulfonylamino, or $R_1$ taken together with the carbon to which it is attached forms a carbonyl or thiocarbonyl; and $R_2$, $R_3$ and $R_4$ are absent, or independently for each occurrence, is selected from H, lower alkyl, alkoxy, carboxyl, ester, amido, sulfonamido, heterocyclyl, cycloalkyl, hydroxyl, amino, acylamino, thioether, sulfonylamino, nitro, halogen, $CF_3$, or cyano. In preferred embodiments, the $R_1$ is absent, or independently for each occurrence, is selected from lower alkyl, or alkoxy, or $R_1$ taken together with the carbon to which it is attached forms a carbonyl; $R_2$ is absent, or independently for each occurrence, is selected from lower alkyl, alkoxy, or halogen; $R_3$ absent, or independently for each occurrence, is selected from H, lower alkyl, alkoxy, $CF_3$, nitro, or halogen; and $R_4$ is selected from H, lower alkyl, or cyano. In other preferred embodiments, $R_1$ and $R_2$ are absent; $R_3$ represents methoxy positioned para to the N of the ring system; and $R_4$ represents cyano.

In certain embodiments, the compound can be represented by Formula VIb or a salt thereof, or a solvate, hydrate, oxidative metabolite or prodrug of the compound or its salt:

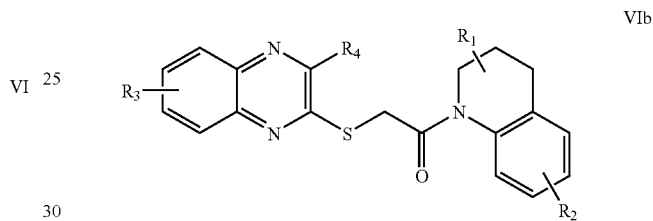

VIb wherein: $R_1$, $R_2$ and $R_3$ are absent or represent one or more substituents on the ring to which they are attached; and $R_4$ represents H or a substituent. For instance, $R_1$ is absent, or independently for each occurrence, is selected from lower alkyl, alkoxy, carboxyl, ester, amido, sulfonamido, heterocyclyl, cycloalkyl, hydroxyl, amino, acylamino, thioether, sulfonylamino, or $R_1$ taken together with the carbon to which it is attached forms a carbonyl or thiocarbonyl; and $R_2$, $R_3$ and $R_4$ are absent, or independently for each occurrence, is selected from lower alkyl, alkoxy, carboxyl, ester, amido, sulfonamido, heterocyclyl, cycloalkyl, hydroxyl, amino, acylamino, thioether, sulfonylamino, nitro, halogen, $CF_3$, or cyano. In certain preferred embodiments, $R_1$ is absent, or independently for each occurrence, is selected from lower alkyl, alkoxy, or halogen or $R_1$ taken together with the carbon to which it is attached forms a carbonyl; $R_2$ is absent, or independently for each occurrence, is selected from lower alkyl, alkoxy, or halogen; $R_3$ is absent, or independently for each occurrence, is selected from lower alkyl, alkoxy, $CF_3$, nitro, or halogen; and $R_4$ is selected from H, lower alkyl, or cyano.

In still other illustrative embodiments, the compound can be represented by Formula II or a salt thereof, or a solvate, hydrate, oxidative metabolite or prodrug of the compound or its salt:

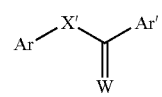

II wherein: W represents O or S; X' represents $NR_{12}$; $R_{12}$ represents H or lower alkyl; Ar and Ar' independently represent substituted or unsubstituted aryl or heteroaryl rings; and wherein said compound inhibits TRPV3 with an with an IC$_{50}$ of 10 micromolar or less. For instance, Ar can represents phenyl, as can Ar'.

Examples of compounds within the above formula include:

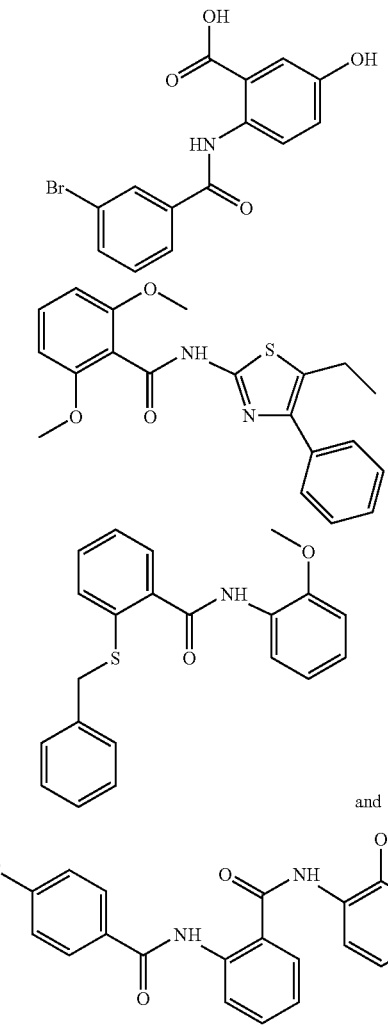

FIG. 17 shows the SAR for various compounds of Formula II versus TRPV3 and in some instances versus other channels.

In yet another illustrative embodiments, the compound can be represented by Formula III or a salt thereof, or a solvate, hydrate, oxidative metabolite or prodrug of the compound or its salt:

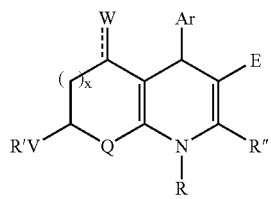

III wherein: Ar represents a substituted or unsubstituted aryl or heteroaryl ring; Q represents O, S, NR, or CH$_2$; R, independently for each occurrence, represents H or lower alkyl; R' represents H or a substituted or unsubstituted lower alkyl, alkenyl, alkynyl, cycloalkyl, heterocyclyl, aryl, heteroaryl, cycloalkylalkyl, heterocyclylalkyl, aralkyl, or heteroaralkyl; R", independently for each occurrence, represents H or lower alkyl; V is absent or represents C=O, C=S, or SO$_2$; W represents a hydrogen-bond acceptor, such as =O, =S, amino, hydroxyl, or ether; E represents H, a substituted or unsubstituted lower alkyl, alkenyl, alkynyl, cycloalkyl, heterocyclyl, aryl, heteroaryl, cycloalkylalkyl, heterocyclylalkyl, aralkyl, or heteroaralkyl, or halogen, carbonyl (e.g., ester, carboxyl, or formyl), thiocarbonyl (e.g., thioester, thiocarboxylate, or thioformate), ketone, aldehyde, amino, acylamino, amido, amidino, cyano, nitro, azido, sulfonyl, sulfoxido, sulfate, sulfonate, sulfamoyl, sulfonamido, or phosphoryl; x represents 0 or 1 wherein when x is 0, the carbons bearing W and V are directly linked by a single or double bond; and wherein said compound inhibits TRPV3 with an with an IC$_{50}$ of 10 micromolar or less.

In certain embodiments, the compounds of Formula III are characterized by one or more of the following: Q represents S or CH$_2$; R represents H; R' represents a substituted or unsubstituted aryl or heteroaryl ring; R" represents lower alkyl; and/or E represents CO$_2$Me or CO$_2$Et.

Exemplary compounds of Formula III include:

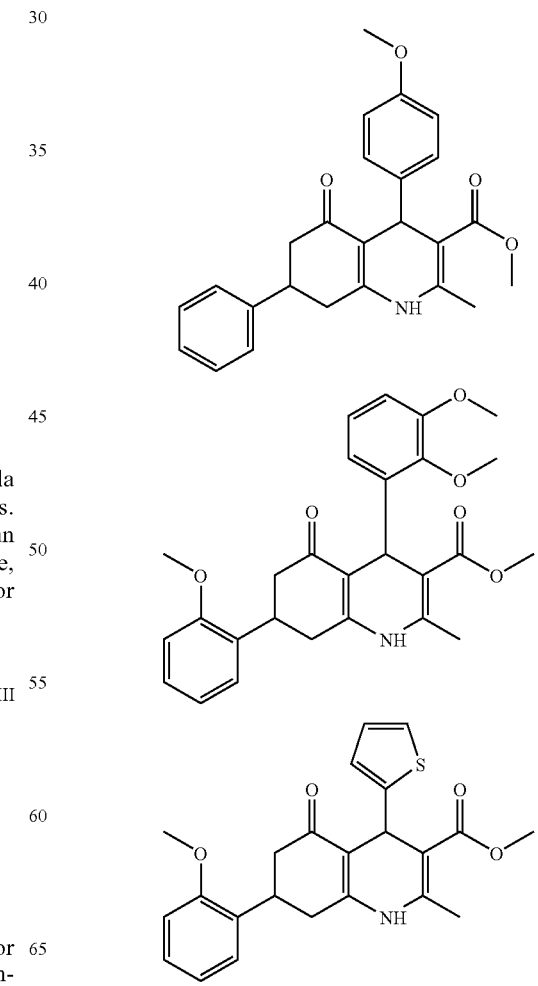

-continued

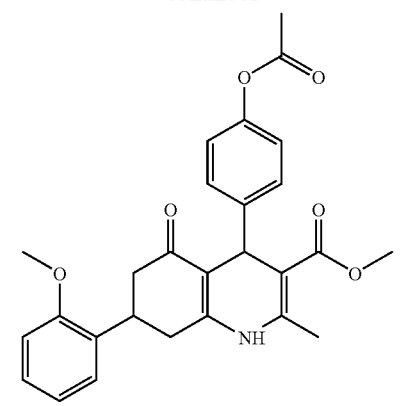

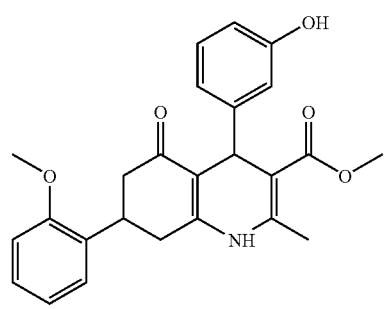

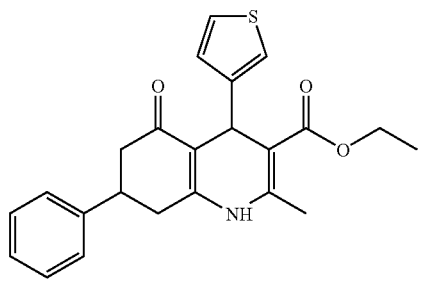

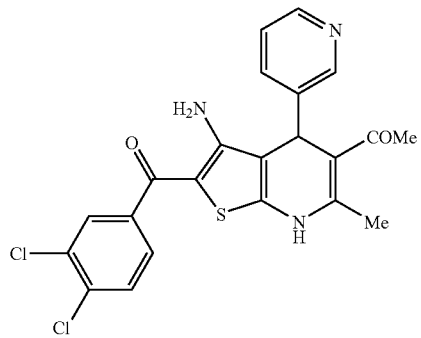

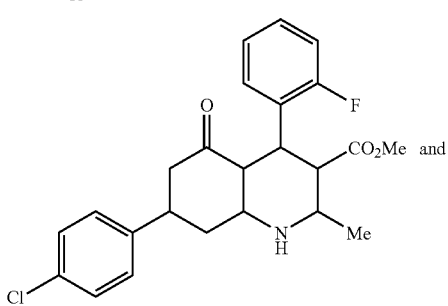

-continued

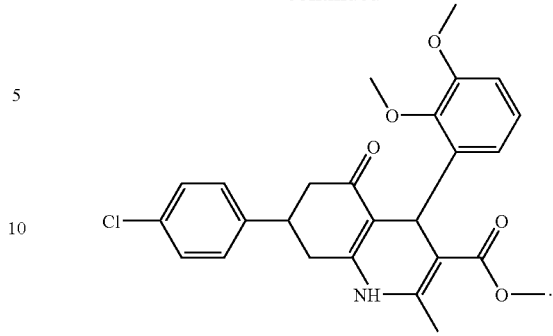

FIGS. 16A-16C show the SAR for various compounds of Formula III versus TRPV3 and in some instances versus other channels.

In yet another illustrative embodiments, the compound can be represented by Formula IIIA or a salt thereof, or a solvate, hydrate, oxidative metabolite or prodrug of the compound or its salt:

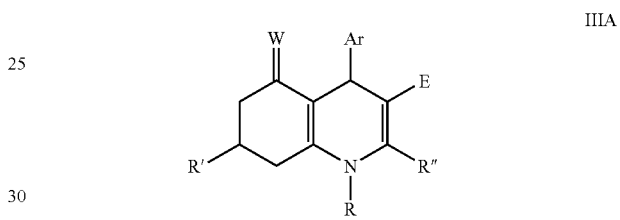

IIIA wherein: R, independently for each occurrence, represents H or lower alkyl, preferably H; R' represents substituted or unsubstituted alkyl, alkenyl, alkynyl, cycloalkyl, heterocyclyl, aryl, heteroaryl, cycloalkylalkyl, heterocyclylalkyl, aralkyl, or heteroaralkyl, preferably substituted or unsubstituted aryl or heteroaryl; R", independently for each occurrence, represents H or lower alkyl, preferably lower alkyl, such as methyl; W represents O or S; E represents H, a substituted or unsubstituted alkyl, alkenyl, alkynyl, cycloalkyl, heterocyclyl, aryl, heteroaryl, cycloalkylalkyl, heterocyclylalkyl, aralkyl, or heteroaralkyl, or halogen, carbonyl (e.g., ester, carboxyl, or formyl), thiocarbonyl (e.g., thioester, thiocarboxylate, or thioformate), ketone, aldehyde, amino, acylamino, amido, amidino, cyano, nitro, azido, sulfonyl, sulfoxido, sulfate, sulfonate, sulfamoyl, sulfonamido, or phosphoryl, preferably acyl, a cyano or nitro substituent, or a carboxylic acid or ester or amide derivative thereof, even more preferably a carboxylic acid or ester or amide derivative thereof, such as $CO_2Me$ or $CO_2Et$; and Ar represents a substituted or unsubstituted aryl or heteroaryl ring.

Additional illustrative embodiments of TRPV3 antagonists include compounds can be represented by Formula IV or a salt thereof, or a solvate, hydrate, oxidative metabolite or prodrug of the compound or its salt:

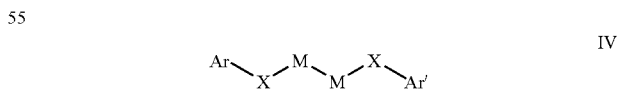

IV wherein: Ar and Ar' independently represent substituted or unsubstituted aryl or heteroaryl rings; R, independently for each occurrence, represents H or lower alkyl; X, independently for each occurrence, represents O, S, NR, $CF_2$, or $CR_2$; M, independently for each occurrence, represents a substituted or unsubstituted methylene group; and wherein said compound inhibits TRPV3 with an with an $IC_{50}$ of 10 micromolar or less.

In certain embodiments, the compounds of Formula IV are characterized by one or more of the following: Ar and Ar' represent phenyl or pyridyl rings; R represents H; X represents O or S; M represents CH$_2$.

Examples of compounds within the above formula include:

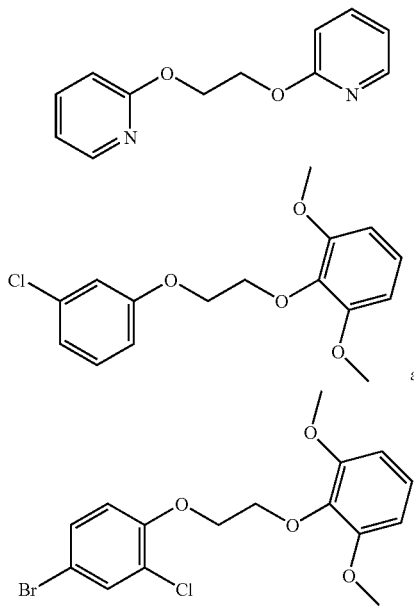

and

FIG. 15 shows the SAR for various compounds of Formula IV versus TRPV3 and in some instances versus other channels.

Additional illustrative embodiments of TRPV3 antagonists which applicants also observed to be TRPV3 inhibitors, include compounds which can be represented by the following structures or a salt thereof, or a solvate, hydrate, oxidative metabolite or prodrug of the compound or its salt:

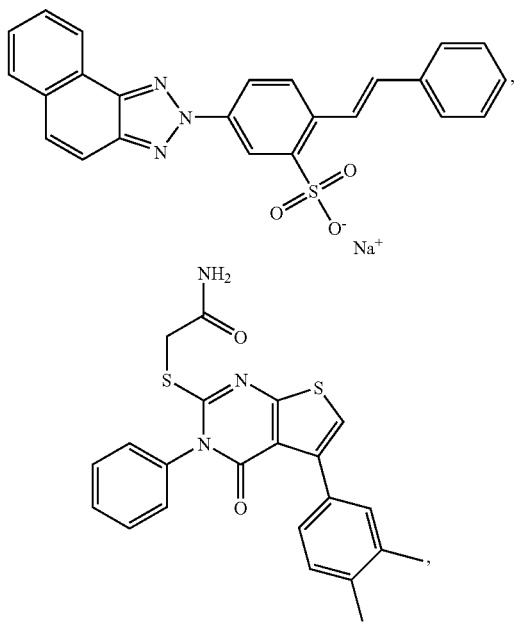

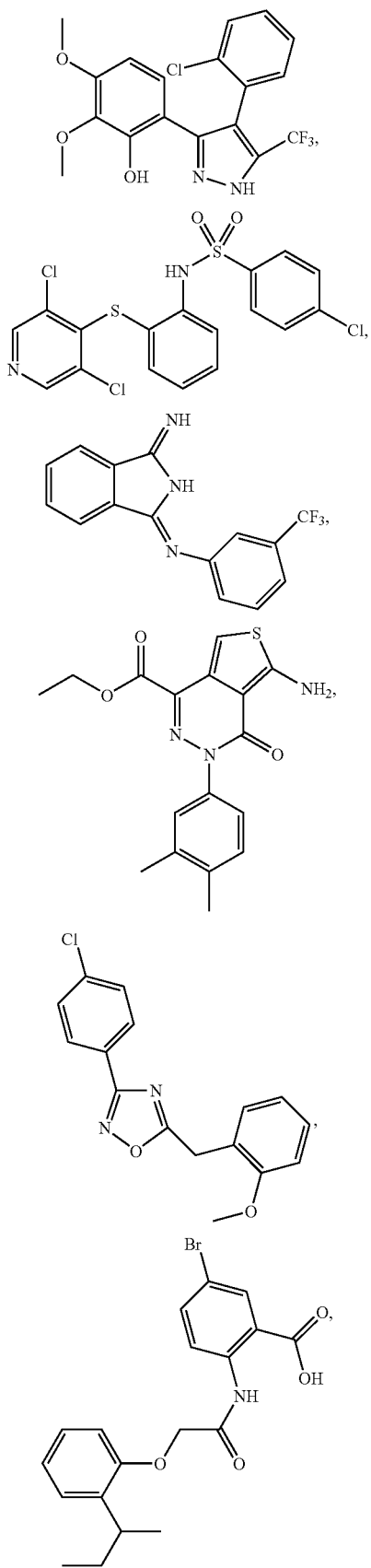

-continued

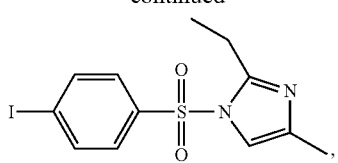

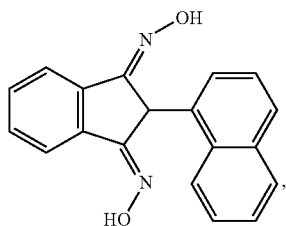

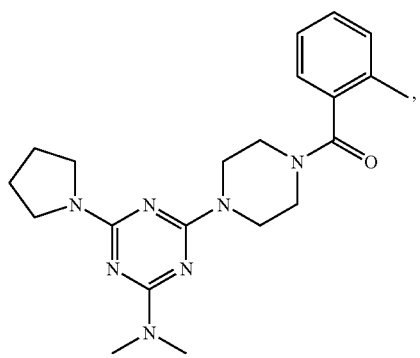

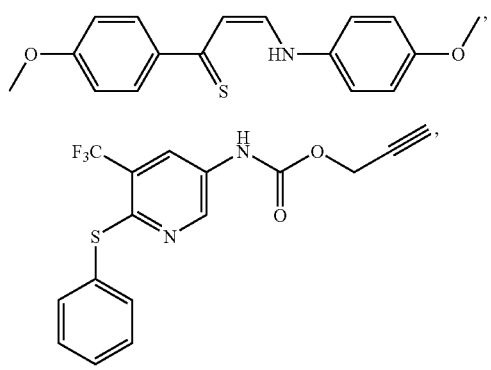

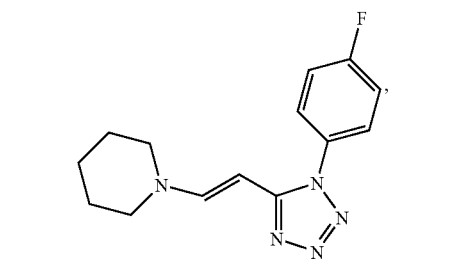

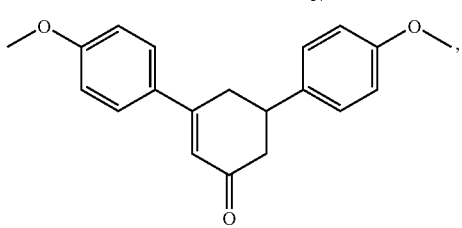

-continued

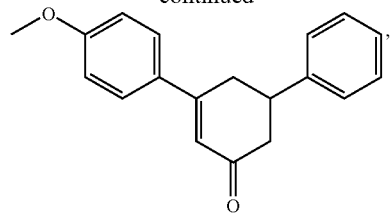

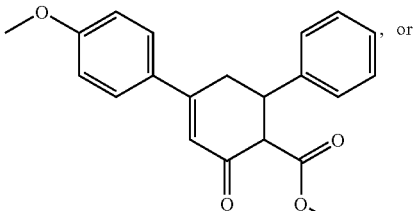

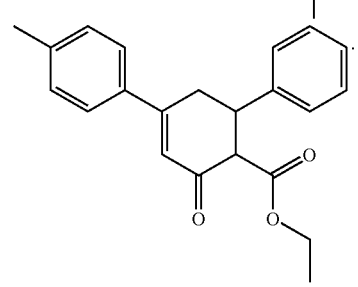

FIGS. 18A-18C show the SAR for various compounds versus TRPV3.

In certain embodiments, the TRPV3 inhibitor for use in methods or pharmaceutical preparations of the present invention is selected from a compound depicted in any of FIGS. 14A-19C. In certain embodiments, the present invention contemplates the use of any compound as depicted in FIGS. 14A-19C in any of the methods or pharmaceutical preparations of the present invention.

The present invention also relates to certain novel compounds, including purified preparations of those compounds. For instance, the invention provides compounds of Formula VII or a salt thereof, or a solvate, hydrate, oxidative metabolite or prodrug of the compound or its salt:

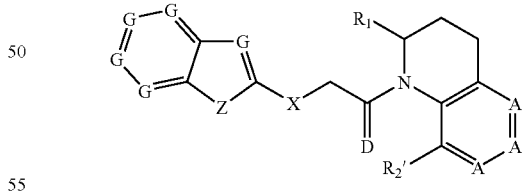

VII wherein: X represents O, S, N(CN), CF$_2$, or C(CN)$_2$; Z represents O, S, N(CN), CF$_2$, or C(CN)$_2$; A represents N or C(R$_2$); G represents N or C(R$_3$); R$_1$ represents H or a substituent; R$_2$' represents a substituent; R$_2$ represents, independently for each occurrence, H or a substituent; R$_3$ represents, independently for each occurrence, H or a substituent; and D represents O or N. In certain preferred embodiments: X represents S and D represents O; and/or R$_1$ is selected from H, lower alkyl, alkoxy, carboxyl, ester, amido, sulfonamido, heterocyclyl, cycloalkyl, hydroxyl, amino, acylamino, thioether, sulfonylamino, or R$_1$ taken together with the carbon to which it is attached forms a carbonyl or thiocarbonyl; and $R_2'$, $R_2$ and $R_3$, independently for each occurrence, are selected from H, lower alkyl, alkoxy, carboxyl, ester, amido, sulfonamido, heterocyclyl, cycloalkyl, hydroxyl, amino, acylamino, thioether, sulfonylamino, nitro, halogen, $CF_3$, or cyano.

In certain embodiments, the compound can be represented by Formula VIIa or a salt thereof, or a solvate, hydrate, oxidative metabolite or prodrug of the compound or its salt:

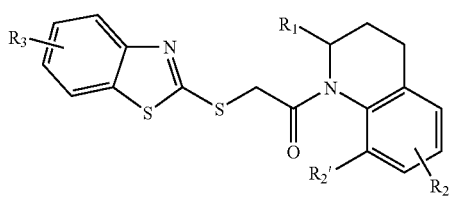

VIIa wherein: $R_1$ represents H or a substituent; $R_2$ and $R_3$ are absent or represent one or more substituents on the ring to which they are attached; and $R_2'$ represents a substituent. In certain preferred embodiments, $R_1$ is selected from H, lower alkyl, alkoxy, carboxyl, ester, amido, sulfonamido, heterocyclyl, cycloalkyl, hydroxyl, amino, acylamino, thioether, sulfonylamino, or $R_1$ taken together with the carbon to which it is attached forms a carbonyl or thiocarbonyl; $R_2$ and $R_3$ are absent or, independently for each occurrence, are selected from lower alkyl, alkoxy, carboxyl, ester, amido, sulfonamido, heterocyclyl, cycloalkyl, hydroxyl, amino, acylamino, thioether, sulfonylamino, nitro, halogen, $CF_3$, or cyano; and $R_2'$ is selected from lower alkyl, alkoxy, carboxyl, ester, amido, sulfonamido, heterocyclyl, cycloalkyl, hydroxyl, amino, acylamino, thioether, sulfonylamino, halogen, $CF_3$, or cyano. In more preferred embodiments, each $R_1$ is independently selected from H, lower alkyl, or alkoxy, or $R_1$ taken together with the carbon to which it is attached forms a carbonyl. In certain embodiments, each $R_2$ is absent or is independently selected from lower alkyl, alkoxy, or halogen; $R_2'$ is selected from lower alkyl, alkoxy, or halogen; and each $R_3$ is absent or is independently selected from lower alkyl, alkoxy, $CF_3$, nitro, or halogen.

In certain preferred embodiments, $R_1$ and $R_2$ are absent; $R_2'$ represents $CH_3$; and $R_3$ represents one or more substituents positioned meta or para to the nitrogen of the ring system.

In certain embodiments, the compound can be represented by Formula VIIb or a salt thereof, or a solvate, hydrate, oxidative metabolite or prodrug of the compound or its salt:

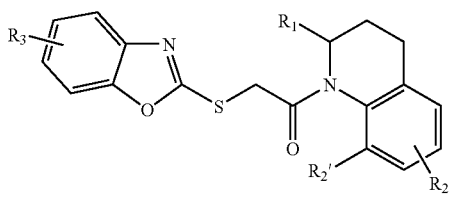

VIIb wherein: $R_1$ represents H or a substituent; $R_2$ and $R_3$ are absent or represent one or more substituents on the ring to which they are attached; and $R_2'$ represents a substituent.

For instance, $R_1$ can be selected from H, lower alkyl, alkoxy, carboxyl, ester, amido, sulfonamido, heterocyclyl, cycloalkyl, hydroxyl, amino, acylamino, thioether, sulfonylamino, or $R_1$ taken together with the carbon to which it is attached forms a carbonyl or thiocarbonyl; $R_2$ and $R_3$ are absent or, independently for each occurrence, are selected from lower alkyl, alkoxy, carboxyl, ester, amido, sulfonamido, heterocyclyl, cycloalkyl, hydroxyl, amino, acylamino, thioether, sulfonylamino, nitro, halogen, $CF_3$, or cyano; and $R_2'$ is selected from lower alkyl, alkoxy, carboxyl, ester, amido, sulfonamido, heterocyclyl, cycloalkyl, hydroxyl, amino, acylamino, thioether, sulfonylamino, halogen, $CF_3$, or cyano.

In certain preferred embodiments, $R_1$ is independently selected from H, lower alkyl, or alkoxy, or $R_1$ taken together with the carbon to which it is attached forms a carbonyl.

In certain preferred embodiments, $R_2$ is absent or each $R_2$ is independently selected from lower alkyl, alkoxy, or halogen.

In certain preferred embodiments, $R_2'$ is selected from lower alkyl, alkoxy, or halogen.

In certain preferred embodiments, $R_3$ is absent or each $R_3$ is independently selected from lower alkyl, alkoxy, $CF_3$, nitro, or halogen.

In certain preferred embodiments, $R_1$, $R_2$, and $R_3$ are absent.

In certain embodiments, the TRPV3 antagonist can be represented by Formula VIII or a salt thereof, or a solvate, hydrate, oxidative metabolite or prodrug of the compound or its salt:

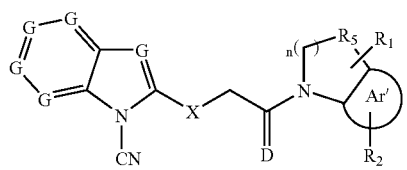

VIII wherein: X represents O, S, N(CN), $CF_2$, or $C(CN)_2$; G represents N or $C(R_3)$; $R_1$ and $R_2$, each independently, is absent or represents one or more substituents on the ring to which it is attached; Ar' represents an aryl or heteroaryl group; n represents 1, 2, or 3; $R_3$ represents, independently for each occurrence, H or a substituent; $R_5$ represents $CH_2$, O, $NR_6$; $R_6$ represents H or lower alkyl; and D represents O or N.

In certain embodiments, Ar' represents phenyl, thiophene, imidazole, thiazole, furan, oxazole, tetrazole, thiadiazole, pyridine, pyrimadine, or triazole.

In certain embodiments, X represents S and D represents O.

In certain embodiments, $R_1$ is absent or, independently for each occurrence, is selected from lower alkyl, alkoxy, carboxyl, ester, amido, sulfonamido, heterocyclyl, cycloalkyl, hydroxyl, amino, acylamino, thioether, sulfonylamino, or $R_1$ taken together with the carbon to which it is attached forms a carbonyl or thiocarbonyl; and $R_2$ and $R_3$, independently for each occurrence, are selected from H, lower alkyl, alkoxy, carboxyl, ester, amido, sulfonamido, heterocyclyl, cycloalkyl, hydroxyl, amino, acylamino, thioether, sulfonylamino, nitro, halogen, $CF_3$, or cyano.

In certain embodiments, the TRPV3 antagonist can be represented by Formula VIIIa or a salt thereof, or a solvate, hydrate, oxidative metabolite or prodrug of the compound or its salt:

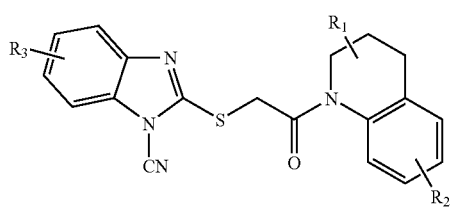

VIIIa

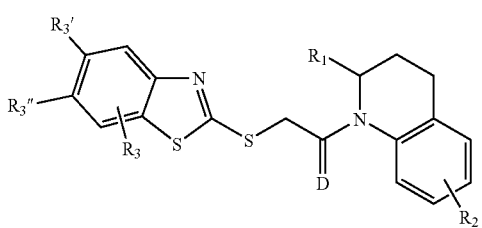

IXa wherein: $R_1$, $R_2$ and $R_3$ are absent or represent one or more substituents on the ring to which they are attached.

In certain embodiments, $R_1$ is absent or, independently for each occurrence, is selected from lower alkyl, alkoxy, carboxyl, ester, amido, sulfonamido, heterocyclyl, cycloalkyl, hydroxyl, amino, acylamino, thioether, sulfonylamino, or $R_1$ taken together with the carbon to which it is attached forms a carbonyl or thiocarbonyl; and $R_2$ and $R_3$ are absent or, independently for each occurrence, are selected from lower alkyl, alkoxy, carboxyl, ester, amido, sulfonamido, heterocyclyl, cycloalkyl, hydroxyl, amino, acylamino, thioether, sulfonylamino, nitro, halogen, $CF_3$, or cyano.

In certain embodiments, the TRPV3 antagonist is a compound of Formula IX or a salt thereof, or a solvate, hydrate, oxidative metabolite or prodrug of the compound or its salt:

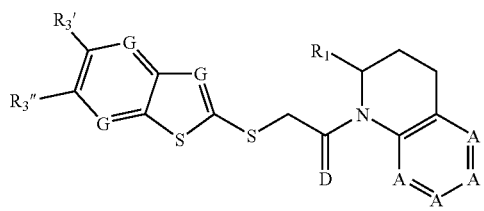

IX wherein: A represents N or $C(R_2)$; G represents N or $C(R_3)$; $R_1$ represents H or a substituent; $R_2$ represents, independently for each occurrence, H or a substituent; $R_3$ represents, independently for each occurrence, H or a substituent; $R_3'$ represents H, halogen, alkoxy, lower alkyl, perfluoroalkyl, aryl, heteroaryl, or $CH_2R_{3a}$; $R_3''$ represents H, halogen, lower alkyl, aryl, heteroaryl, or $CH_2R_{3a}$; $R_{3a}$ represents amino, heterocyclyl, carboxyl, ester, aryl, or heteroaryl; and D represents O or N, provided that when $R_3'$ is H, $R_3''$ is not H or lower alkyl, and when $R_3'$ is halogen, $R_3''$ is not H.

In certain embodiments, $R_1$ is selected from H, lower alkyl, alkoxy, carboxyl, ester, amido, sulfonamido, heterocyclyl, cycloalkyl, hydroxyl, amino, acylamino, thioether, sulfonylamino, or $R_1$ taken together with the carbon to which it is attached forms a carbonyl or thiocarbonyl; and $R_2$ and $R_3$, independently for each occurrence, are selected from H, lower alkyl, alkoxy, carboxyl, ester, amido, sulfonamido, heterocyclyl, cycloalkyl, hydroxyl, amino, acylamino, thioether, sulfonylamino, halogen, $CF_3$, or cyano.

In certain embodiments, the TRPV3 antagonist is a compound represented by formula Ixa or a salt thereof, or a solvate, hydrate, oxidative metabolite or prodrug of the compound or its salt:

wherein $R_1$ represents H or a substituent; $R_2$ is absent or represents a substituent; $R_3$ is absent or represents a substituent; $R_3'$ represents H, halogen, alkoxy, lower alkyl, perfluoroalkyl, aryl, heteroaryl, or $CH_2R_{3a}$; $R_3''$ represents H, halogen, lower alkyl, aryl, heteroaryl, or $CH_2R_{3a}$; $R_{3a}$ represents amino, heterocyclyl, carboxyl, ester, aryl, or heteroaryl; and D represents O or N, provided that when $R_3'$ is H, $R_3''$ is not H or lower alkyl, and when $R_3'$ is halogen, $R_3''$ is not H.

In certain embodiments, $R_1$ is selected from H, lower alkyl, alkoxy, carboxyl, ester, amido, sulfonamido, heterocyclyl, cycloalkyl, hydroxyl, amino, acylamino, thioether, sulfonylamino, or $R_1$ taken together with the carbon to which it is attached forms a carbonyl or thiocarbonyl; and $R_2$ and $R_3$ are absent or, independently for each occurrence, are selected from lower alkyl, alkoxy, carboxyl, ester, amido, sulfonamido, heterocyclyl, cycloalkyl, hydroxyl, amino, acylamino, thioether, sulfonylamino, halogen, $CF_3$, or cyano.

In certain embodiments, the TRPV3 antagonist is a compound of Formula X or a salt thereof, or a solvate, hydrate, oxidative metabolite or prodrug of the compound or its salt:

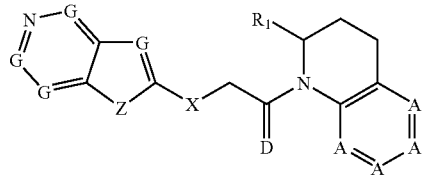

X wherein: X represents O, S, N(CN), $CF_2$, or $C(CN)_2$; Z represents O, S, N(CN), $CF_2$, or $C(CN)_2$; A represents N or $C(R_2)$; G represents N or $C(R_3)$; $R_1$ represents H or a substituent; $R_2$ represents, independently for each occurrence, H or a substituent; $R_3$ represents, independently for each occurrence, H or a substituent; and D represents O or N.

In certain embodiments, X represents S and D represents O.

In certain embodiments, $R_1$ is selected from H, lower alkyl, alkoxy, carboxyl, ester, amido, sulfonamido, heterocyclyl, cycloalkyl, hydroxyl, amino, acylamino, thioether, sulfonylamino, or $R_1$ taken together with the carbon to which it is attached forms a carbonyl or thiocarbonyl; and $R_2$ and $R_3$, independently for each occurrence, are selected from H, lower alkyl, alkoxy, carboxyl, ester, amido, sulfonamido, heterocyclyl, cycloalkyl, hydroxyl, amino, acylamino, thioether, sulfonylamino, nitro, halogen, $CF_3$, or cyano.

In certain embodiments, the TRPV3 antagonist is a compound can be represented by Formula Xa or a salt thereof, or a solvate, hydrate, oxidative metabolite or prodrug of the compound or its salt:

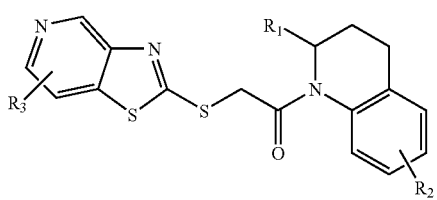

wherein: $R_1$ represents H or a substituent; and $R_2$ and $R_3$ are absent or represent one or more substituents on the ring to which they are attached.

In certain embodiments, $R_1$ is selected from H, lower alkyl, alkoxy, carboxyl, ester, amido, sulfonamido, heterocyclyl, cycloalkyl, hydroxyl, amino, acylamino, thioether, sulfonylamino, or $R_1$ taken together with the carbon to which it is attached forms a carbonyl or thiocarbonyl; and $R_2$ and $R_3$ are absent or, independently for each occurrence, are selected from lower alkyl, alkoxy, carboxyl, ester, amido, sulfonamido, heterocyclyl, cycloalkyl, hydroxyl, amino, acylamino, thioether, sulfonylamino, nitro, halogen, $CF_3$, or cyano.

In certain embodiments, $R_1$ is H; and $R_2$ and $R_3$ are absent.

In certain embodiments, the TRPV3 antagonist is a compound represented by Formula Xb or a salt thereof, or a solvate, hydrate, oxidative metabolite or prodrug of the compound or its salt:

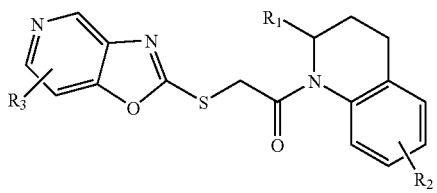

wherein: $R_1$ represents H or a substituent; and $R_2$ and $R_3$ are absent or represent one or more substituents on the ring to which they are attached.

In certain embodiments, wherein $R_1$ is selected from H, lower alkyl, alkoxy, carboxyl, ester, amido, sulfonamido, heterocyclyl, cycloalkyl, hydroxyl, amino, acylamino, thioether, sulfonylamino, or $R_1$ taken together with the carbon to which it is attached forms a carbonyl or thiocarbonyl; and $R_2$ and $R_3$ are absent or, independently for each occurrence, are selected from lower alkyl, alkoxy, carboxyl, ester, amido, sulfonamido, heterocyclyl, cycloalkyl, hydroxyl, amino, acylamino, thioether, sulfonylamino, nitro, halogen, $CF_3$, or cyano.

In certain embodiments, the TRPV3 antagonist is a compound of Formula XI or a salt thereof, or a solvate, hydrate, oxidative metabolite or prodrug of the compound or its salt:

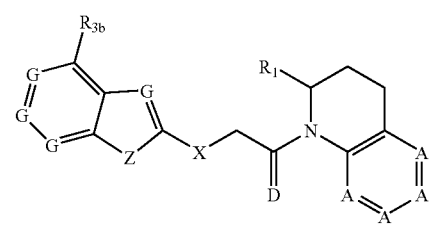

wherein: X represents O, S, N(CN), $CF_2$, or $C(CN)_2$; Z represents O, S, N(CN), $CF_2$, or $C(CN)_2$; A represents N or $C(R_2)$; G represents N or $C(R_3)$; $R_1$ represents H or a substituent; $R_2$ represents, independently for each occurrence, H or a substituent; $R_3$ represents, independently for each occurrence, H or a substituent; $R_{3b}$ represents a substituent; and D represents O or N.

In certain embodiments, X represents S and D represents O.

In certain embodiments, $R_1$ is selected from H, lower alkyl, alkoxy, carboxyl, ester, amido, sulfonamido, heterocyclyl, cycloalkyl, hydroxyl, amino, acylamino, thioether, sulfonylamino, or $R_1$ taken together with the carbon to which it is attached forms a carbonyl or thiocarbonyl; and $R_2$ and $R_3$ are absent or, independently for each occurrence, are selected from lower alkyl, alkoxy, carboxyl, ester, amido, sulfonamido, heterocyclyl, cycloalkyl, hydroxyl, amino, acylamino, thioether, sulfonylamino, nitro, halogen, $CF_3$, or cyano; and $R_{3b}$ is selected from lower alkyl, alkoxy, carboxyl, ester, amido, sulfonamido, heterocyclyl, cycloalkyl, hydroxyl, amino, acylamino, thioether, sulfonylamino, halogen, $CF_3$, or cyano.

In certain embodiments, the TRPV3 antagonist is a compound represented by Formula XIa or a salt thereof, or a solvate, hydrate, oxidative metabolite or prodrug of the compound or its salt:

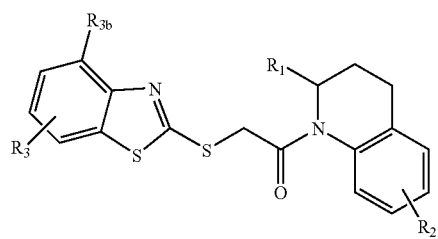

wherein: $R_1$ represents H or a substituent; $R_2$ and $R_3$ are absent or represent one or more substituents on the ring to which they are attached; and $R_{3b}$ represents a substituent.

In certain embodiments, $R_1$ is selected from H, lower alkyl, alkoxy, carboxyl, ester, amido, sulfonamido, heterocyclyl, cycloalkyl, hydroxyl, amino, acylamino, thioether, sulfonylamino, or $R_1$ taken together with the carbon to which it is attached forms a carbonyl or thiocarbonyl; $R_2$ and $R_3$ are absent or, independently for each occurrence, are selected from lower alkyl, alkoxy, carboxyl, ester, amido, sulfonamido, heterocyclyl, cycloalkyl, hydroxyl, amino, acylamino, thioether, sulfonylamino, nitro, halogen, $CF_3$, or cyano; and $R_{3b}$ is selected from lower alkyl, alkoxy, carboxyl, ester, amido, sulfonamido, heterocyclyl, cycloalkyl, hydroxyl, amino, acylamino, thioether, sulfonylamino, halogen, $CF_3$, or cyano.

In certain embodiments, $R_1$ is H; $R_2$ and $R_3$ are absent; and $R_{3b}$ is a halogen.

In certain embodiments, the TRPV3 antagonist is a compound can be represented by Formula XIb or a salt thereof, or a solvate, hydrate, oxidative metabolite or prodrug of the compound or its salt:

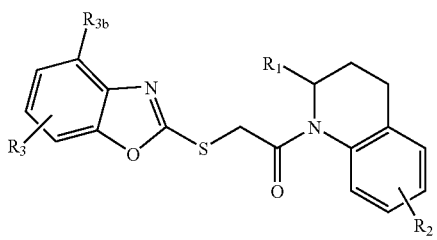

wherein: $R_1$ represents H or a substituent; $R_2$ and $R_3$ are absent or represent one or more substituents on the ring to which they are attached; and $R_{3b}$ represents a substituent.

In certain embodiments, $R_1$ is selected from H, lower alkyl, alkoxy, carboxyl, ester, amido, sulfonamido, heterocyclyl, cycloalkyl, hydroxyl, amino, acylamino, thioether, sulfonylamino, or $R_1$ taken together with the carbon to which it is attached forms a carbonyl or thiocarbonyl; $R_2$ and $R_3$ are absent or, independently for each occurrence, are selected from lower alkyl, alkoxy, carboxyl, ester, amido, sulfonamido, heterocyclyl, cycloalkyl, hydroxyl, amino, acylamino, thioether, sulfonylamino, nitro, halogen, $CF_3$, or cyano; and $R_{3b}$ is selected from lower alkyl, alkoxy, carboxyl, ester, amido, sulfonamido, heterocyclyl, cycloalkyl, hydroxyl, amino, acylamino, thioether, sulfonylamino, halogen, $CF_3$, or cyano.

One aspect of the present invention provides a pharmaceutical preparation suitable for use in a human patient, or for veterinary use, comprising an effective amount of any of the compounds shown above (e.g., a compound of Formula I, Formula Ia, Formula II, Formula III, Formula IV, Formula V, Formula Va, Formula Vb, Formula VI, Formula VIa, Formula VIb, Formula VII, Formula VIIa, Formula VIIb, Formula VIII, Formula VIIIa, Formula IX, Formula IXa, Formula X, Formula Xa, Formula Xb, Formula XI, Formula XIa, or Formula XIb, or a salt thereof, or a solvate, hydrate, oxidative metabolite or prodrug of the compound or its salt), and one or more pharmaceutically acceptable excipients. In certain embodiments, the pharmaceutical preparations may be for use in treating or preventing a condition involving activation of TRPV3 or for which reduced TRPV3 activity can reduce the severity. In certain embodiments, the pharmaceutical preparations have a low enough pyrogen activity to be suitable for use in a human patient, or for veterinary use. In certain embodiments, the pharmaceutical preparation comprises an effective amount of any of the compounds shown above, wherein the compound inhibits TRPV3 with an $IC_{50}$ of 10 micromolar or less. In certain embodiments, the pharmaceutical preparation comprises an effective amount of any of the compounds shown above, wherein the compound inhibits one or more members of the vanilloid receptor family with an $IC_{50}$ of 10 micromolar or less.

In certain embodiments, the present invention provides a pharmaceutical preparation, having a low enough pyrogen activity to be suitable for use in a human patient, or for veterinary use, comprising a compound of Formula XII or a salt thereof, or a solvate, hydrate, oxidative metabolite or prodrug of the compound or its salt, and one or more pharmaceutically acceptable excipients:

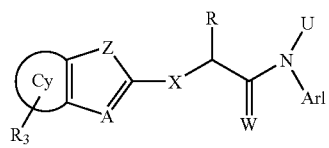

wherein: R represents H or a lower alkyl; X represents O, S, $NR_{10}$, $CF_2$, or $C(CN)_2$; W represents O, S, or NR'; Cy represents an aryl or heteroaryl ring; Z represents O, S, $NR_{11}$, $CF_2$, or $C(CN)_2$; A represents N or $C(R_{2a})$; $R_3$ is absent or represents one or more substituents on the ring to which it is attached; Arl represents an aralkyl, heteroaralkyl, aryl, or heteroaryl group, which may be monocyclic or bicyclic; U represents hydrogen or lower alkyl, alkenyl, alkynyl, cycloalkyl, heterocyclyl, aryl, heteroaryl, cycloalkylalkyl, heterocyclylalkyl, aralkyl, or heteroaralkyl, or, U, N and R' taken together form a 5- to 7-membered heterocyclic ring, or, U, Arl and N taken together form a ring fused to the aryl or heteroaryl ring of Arl, thereby forming a bicyclic structure; R', independently for each occurrence, represents H or a lower alkyl; $R_{2a}$ represents H, lower alkyl, alkoxy, or halogen; $R_{10}$ represents H, lower alkyl, or cyano; and $R_{11}$ represents H, lower alkyl, or cyano; wherein said compound inhibits one or more members of the vanilloid receptor family with an $IC_{50}$ of 10 micromolar or less.

In certain embodiments, the invention contemplates that any of the particular compounds depicted in FIGS. 14A-19C can be administered to treat any of the diseases or conditions disclosed herein. In some embodiments, the compound is formulated as a pharmaceutical preparation prior to administration. In certain embodiments, the TRPV3 inhibitor for use in methods or pharmaceutical preparations of the present invention is selected from a compound depicted in FIGS. 14A-19C. In certain embodiments, the present invention contemplates the use of any compound as depicted in FIGS. 14A-19C in any of the methods or pharmaceutical preparations of the present invention.

In certain embodiments of the above formulae, substituents may include one or more of: alkyl, alkenyl, alkynyl, cycloalkyl, heterocyclyl, aryl, heteroaryl, cycloalkylalkyl, heterocyclylalkyl, aralkyl, or heteroaralkyl, any of which may itself be further substituted, or halogen, carbonyl (e.g., ester, carboxyl, or formyl), thiocarbonyl (e.g., thioester, thiocarboxylate, or thioformate), ketone, aldehyde, a hydroxyl, an alkoxyl, a sulfhydryl, an alkylthio, amino, acylamino, amido, amidino, cyano, nitro, azido, sulfonyl, sulfoxido, sulfate, sulfonate, sulfamoyl, sulfonamido, a phosphate, and a phosphoryl.

Compounds of any of the above structures may be used in the manufacture of medicaments for the treatment of any diseases disclosed herein. Furthermore, TRPV3 inhibitors, according to the present invention, can be used in the manufacture of medicaments for the treatment of any diseases disclosed herein. In certain embodiments, compounds (e.g., inhibitors) of the invention can be used in the treatment of pain.

Compounds of any of the above structures may be used to inhibit an activity of TRPV3 in vitro or in vivo, and/or can be used in the manufacture of medicaments to inhibit an activity of TRPV3 in vitro or in vivo. TRPV3 inhibitors, according to the present invention, can be used to inhibit an activity of TRPV3, and/or can be used in the manufacture of medicaments to inhibit an activity of TRPV3 in vitro or in vivo.

For any of the aspects or embodiments of the invention, an exemplary function of TRPV3 that may be inhibited or modulated by a compound of the invention is a TRPV3-mediated current (e.g., an inward or outward Phase I and/or Phase II current).

In particular embodiments, the small molecule is chosen for use because it is more selective for one TRP isoform than others, e.g., 10-fold, and more preferably at least 100- or even 1000-fold more selective for TRPV3 over one or more of TRPC6, TRPV5, TRPV6, TRPM8, TRPV1, and/or TRPV4. In other embodiments, the differential is smaller, e.g., it more strongly inhibits TRPV3 than TRPM8, TRPV1 and/or TRPV4, preferably at least twice, three times, five times, or even ten times more strongly. Such comparisons may be made, for example, by comparing $IC_{50}$ values.

In certain embodiments, a compound which is an antagonist of TRPV3 is chosen to selectively antagonize TRPV3 over other ion channels, e.g., the compound modulates the activity of TRPV3 at least an order of magnitude more strongly than it modulates the activity of NaV1.2, Cav1.2, Cav3.1, HERG, and/or mitochondrial uniporter, preferably at least 1.5 orders of magnitude, two orders of magnitude more strongly, even more preferably at least three orders of magnitude more strongly. Such comparisons may be made, for example, by comparing $IC_{50}$ values.

Similarly, in particular embodiments, the small molecule is chosen for use because it lacks significant activity against one or more targets other than TRPV3. For example, the compound may have an $IC_{50}$ above 500 nM, above 1 μM, or even above 10 μM for inhibiting one or more of TRPC6, TRPV5, TRPV6, TRPV1, NaV1.2, Cav1.2, Cav3.1, HERG, and the mitochondrial uniporter.

In certain embodiment, the small molecule is chosen because it antagonizes the function of both TRPV3 and TRPM8, TRPV1 and/or TRPV4. Although such compounds selectively antagonize the function of both ion channels, the $IC_{50}$ values need not be identical.

In certain embodiments of any of the foregoing, the small molecule may be chosen because it is capable of inhibiting heat-induced activation of TRPV3. In certain embodiments, the TRPV3 antagonist inhibits heat-induced activation of TRPV3 and 2-APB induced activation of TRPV3. In certain other embodiments, the TRPV3 antagonist inhibits heat-induced activation of TRPV3 but does not inhibit 2-APB induced activation of TRPV3.

In certain embodiments, a compound which is an antagonist of TRPV3 is chosen to selectively antagonize TRPV3 over AMPA, e.g., the compound modulates the activity of TRPV3 at least an order of magnitude more strongly than it modulates the activity of AMPA. Such comparisons may be made, for example, by comparing $IC_{50}$ values. In certain embodiments, the subject TRPV3 antagonists do not appreciably bind the AMPA receptor. In other words, the subject antagonists inhibit TRPV3 with a particular $IC_{50}$ and, when administered at that concentration, the antagonist does not substantially bind the AMPA receptor. In such embodiments, the ability of the subject TRPV3 inhibitors to decrease pain would thus be independent of binding to and modulating the alpha-amino-3-hydroxy-5-methyl-4-isoxazolepropionic acid (AMPA) receptor which has been implicated in neuropathic pain reception. In certain embodiments, the subject TRPV3 antagonists inhibit TRPV3 with an $IC_{50}$ at least one order of magnitude more potent than its Ki for the AMPA receptor. In certain embodiments, the subject TRPV3 antagonists inhibit TRPV3 with an $IC_{50}$ at least two orders of magnitude more potent than its Ki for the AMPA receptor, or even three or four orders of magnitude more potent than its Ki for the AMPA receptor.

In certain embodiments of any of the foregoing, the small molecule may be chosen because it inhibits a TRPV3 function with an $IC_{50}$ less than 1 uM, or even less than 700, 600, 500, 400, 300, 200, or 100 nM. In other embodiments, the small molecule is chosen because it inhibits a TRPV3 function with an $IC_{50}$ less than 50 nM, or even less than 25, 20, 10, or 1 nM.

In certain embodiments of any of the foregoing, the compound may be chosen based on the rate of inhibition of a TRPV3 function. In one embodiment, the compound inhibits a TRPV3 function in less than 5 minutes, preferably less than 4, 3, or 2 minutes. In another embodiment, the compound inhibits a TRPV3 function in less than 1 minute.

In any of the foregoing embodiments, the small molecule antagonist of TRPV3 function may inhibit the Phase I outward current, the Phase I inward current, the Phase II outward current, the Phase II inward current, or any combination of one or more of these currents. Compounds that inhibit more than one of the foregoing currents may do so with the same or with differing $IC_{50}$ values. In any of the foregoing, the ability of a compound to inhibit a particular Phase I and/or Phase II current can be assessed either in vitro or in vivo. Compounds that inhibit any of the foregoing currents in an in vitro or in vivo assay are characterized as compounds that inhibit a function of TRPV3.

In certain embodiments of any of the foregoing, inhibition of a TRPV3 function means that a function, for example a TRPV3 mediated current, is decreased by at least 50% in the presence of an effective amount of a compound in comparison to in the absence of the compound or in comparison to an ineffective amount of a compound. In certain other embodiments, the inhibition of a TRPV3 function means that a function, for example a TRPV3 mediated current, is decreased by at least 50%, 60%, 70%, 75%, 80%, 85%, or 90% in the presence of an effective amount of a compound in comparison to in the absence of the compound. In still other embodiments, the inhibition of a TRPV3 function means that a function, for example a TRPV3 mediated current, is decreased by at least 92%, 95%, 97%, 98%, 98%, 99%, or 100% in the presence of an effective amount of a compound in comparison to in the absence of the compound.

In certain embodiments of any of the foregoing, the TRPV3 inhibitor is used to treat or ameliorate pain. Exemplary classes of pain that can treated using a TRPV3 inhibitor include, but are not limited to nociceptive pain, inflammatory pain, and neuropathic pain. Pain that can be treated with a TRPV3 inhibitor can be chronic or acute. Throughout the specification, a variety of conditions and diseases characterized, at least in part, by pain are discussed in detail. The invention contemplates that the pain associated with any of these diseases or conditions can be treated using any of the TRPV3 inhibitors described herein. The inhibitor can be formulated in a pharmaceutical preparation appropriate for the intended route of administration.

In certain embodiments of any of the foregoing, the TRPV3 inhibitor can be used to treat or ameliorate pain with fewer side effects. For example, the TRPV3 inhibitor can be used to treat or ameliorate pain without the narcotic effects of, for example, morphine.

In any of the foregoing embodiments, $IC_{50}$ values are measured in vitro using, for example, patch clamp analysis or standard measurements of calcium flux. Exemplary in vitro methods that can be used to measure $IC_{50}$ values of a compound are described in Examples 2 and 3.

Without being bound by theory, a compound may inhibit a function of TRPV3 by binding covalently or non-covalently to a portion of TRPV3. Alternatively, a compound may inhibit a function of TRPV3 indirectly, for example, by associating with a protein or non-protein cofactor necessary for a function of TRPV3. One of skill in the art will readily appreciate that an inhibitory compound may associate reversibly or irreversibly with TRPV3 or a cofactor thereof. Compounds that reversibly associate with TRPV3 or a cofactor thereof may continue to inhibit a function of TRPV3 even after dissociation.

The subject TRPV3 inhibitors can be used alone or in combination with other pharmaceutically active agents. Examples of such other pharmaceutically active agents include, but are not limited to, anti-inflammatory agents (e.g., NSAIDS, hormones and autacoids such as corticosteroids), anti-acne agents (e.g., retinoids), anti-wrinkle agents, anti-scarring agents, anti-psoriatic agents, anti-proliferative agents (e.g., anti-eczema agents), anti-fungal agents, anti-viral agents, anti-septic agents (e.g., antibacterials), local anesthetics, anti-migraine agents, keratolytic agents, hair growth stimulants, hair growth inhibitors, and other agents used for the treatment of skin diseases or conditions. Certain active agents belong to more than one category.

The subject TRPV3 inhibitors can be used alone or as part of a therapeutic regimen combined with other treatments, therapies, or interventions appropriate for the particular disease, condition, injury or disorder being treated. When used as part of a therapeutic regimen, the invention contemplates use of TRPV3 inhibitors in combination with one or more of the following treatment modalities: administration of non-TRPV3 inhibitor pharmaceuticals, chemotherapy, radiotherapy, homeopathic therapy, diet, stress management, and surgery.

When administered alone or as part of a therapeutic regimen, in certain embodiments, the invention contemplates administration of TRPV3 inhibitors to treat a particular primary disease, injury, disorder, or condition. Additionally or alternatively, the invention contemplates administration of TRPV3 inhibitors to treat pain associated with a disease, injury, disorder, or condition. In still other embodiments, the invention contemplates administration of TRPV3 inhibitors to treat symptoms secondary to the primary disease, injury, disorder, or conditions.

The invention contemplates pharmaceutical preparations and uses of TRPV3 antagonists having any combination of the foregoing or following characteristics, as well as any combination of the structural or functional characteristics of the TRPV3 antagonists described herein. Any such antagonists or preparations can be used in the treatment of any of the diseases or conditions described herein. Additionally, the invention contemplates the use of any such antagonists or preparations for inhibiting a TRPV3 mediated current in vitro. Combinations of any of the foregoing or following aspects and embodiments of the invention are also contemplated. For example, the invention contemplates that TRPV3 antagonists having any of the particular potencies and specificities outlined herein can be formulated for the appropriate route of administration and can be used in treating any of the conditions or diseases detailed herein. In certain embodiments, the invention contemplates pharmaceutical preparations and uses of any of the TRPV3 antagonists presented in FIGS. 14A-19C.

DEFINITIONS

The terms "antagonist" and "inhibitor" are used interchangeably to refer to an agent that decreases or suppresses a biological activity, such as to repress an activity of an ion channel, such as TRPV3.

An "effective amount" of, e.g., a TRPV3 antagonist, with respect to the subject method of treatment, refers to an amount of the antagonist in a preparation which, when applied as part of a desired dosage regimen brings about a desired clinical or functional result. Without being bound by theory, an effective amount of a TRPV3 antagonist for use in the methods of the present invention, includes an amount of a TRPV3 antagonist effective to decrease one or more in vitro or in vivo function of a TRPV3 channel. Exemplary functions include, but are not limited to, intracellular calcium levels, membrane polarization (e.g., an antagonist may promote hyperpolarization of a cell), Phase I outward current, Phase II outward current, Phase I inward current, and Phase II inward current. Compounds that antagonize TRPV3 function include compounds that antagonize an in vitro or in vivo functional activity of TRPV3. When a particular functional activity is only readily observable in an in vitro assay, the ability of a compound to inhibit TRPV3 function in that in vitro assay serves as a reasonable proxy for the activity of that compound.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The present invention provides compounds which are in prodrug form. The term "prodrug" is intended to encompass compounds that, under physiological conditions, are converted into the therapeutically active agents of the present invention. A common method for making a prodrug is to include selected moieties that are hydrolyzed under physiological conditions to reveal the desired molecule. In other embodiments, the prodrug is converted by an enzymatic activity of the host animal. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

The term "oxidative metabolite" is intended to encompass compounds that are produced by metabolism of the parent compound under normal physiological conditions. Specifically, an oxidative metabolite is formed by oxidation of the parent compound during metabolism. For example, a thioether group may be oxidized to the corresponding sulfoxide or sulfone.

The term "solvate" as used herein, refers to a compound formed by solvation (e.g., a compound formed by the combination of solvent molecules with molecules or ions of the solute).

The term "hydrate" as used herein, refers to a compound formed by the union of water with the parent compound.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The terms "TRPV3", "TRPV3 protein", and "TRPV3 channel" are used interchangeably throughout the application. These terms refer to an ion channel (e.g., a polypeptide) comprising the amino acid sequence, for example, the amino acid sequence of a human TRPV3 protein, or an equivalent polypeptide, or a functional bioactive fragment thereof. In certain embodiments, the term refers to a polypeptide comprising, consisting of, or consisting essentially of, a TRPV3 amino acid sequence set forth, for example, in any of the patent applications referenced herein. TRPV3 protein may also include orthologs, for example, mouse, rat, horse, or *Drosophila* TRPV3.

TRPV3 includes polypeptides that retain a function of TRPV3 and comprise (i) all or a portion of a TRPV3 amino acid sequence (ii) a TRPV3 amino acid sequence with 1 to about 2, 3, 5, 7, 10, 15, 20, 30, 50, 75 or more conservative amino acid substitutions; (iii) an amino acid sequence that is at least 70%, 75%, 80%, 85%, 90%, 95%, 96%, 97%, 98%, or 99% identical to a TRPV3 amino acid sequence; and (iv) functional fragments thereof. Polypeptides of the invention also include homologs, e.g., orthologs and paralogs, of a human TRPV3 polypeptide. TRPV3 polypeptides and amino acid sequences include, for example, the sequences set forth in any of the patent applications referenced herein.

The term "TRPV3" further refers to a nucleic acid encoding a polypeptide of the invention, e.g., a nucleic acid comprising a sequence consisting of, or consisting essentially of, a TRPV3 polynucleotide sequence. A nucleic acid of the invention may comprise all, or a portion of: (i) a TRPV3 nucleotide sequence; (ii) a nucleotide sequence at least 70%, 75%, 80%, 85%, 90%, 95%, 96%, 97%, 98% or 99% identical to a TRPV3 nucleotide sequence; (iii) a nucleotide sequence that hybridizes under stringent conditions to a TRPV3 nucleotide sequence; (iv) nucleotide sequences encoding polypeptides that are functionally equivalent to polypeptides of the invention; (v) nucleotide sequences encoding polypeptides at least about 70%, 75%, 80%, 85%, 90%, 95%, 98%, 99% homologous or identical with a TRPV3 polypeptide sequence; (vi) nucleotide sequences encoding polypeptides having an activity of a polypeptide of the invention and having at least about 70%, 75%, 80%, 85%, 90%, 95%, 98%, 99% or more homology or identity with a TRPV3 polypeptide sequence; (vii) nucleotide sequences that differ by 1 to about 2, 3, 5, 7, 10, 15, 20, 30, 50, 75 or more nucleotide substitutions, additions or deletions, such as allelic variants, of a TRPV3 nucleotide sequence; (viii) nucleic acids derived from and evolutionarily related to a TRPV3 nucleotide sequence; and (ix) complements of, and nucleotide sequences resulting from the degeneracy of the genetic code, for all of the foregoing and other nucleic acids of the invention. Nucleic acids of the invention also include homologs, e.g., orthologs and paralogs, of a TRPV3 nucleic acid sequence and also variants which have been codon optimized for expression in a particular organism (e.g., host cell). TRPV3 nucleic acid sequences include, for example, the sequences set forth in any of the patent applications referenced herein. Where not explicitly stated, one of skill in the art can readily assess whether TRPV3 refers to a nucleic acid or a protein.

The terms "compound" and "agent" are used interchangeably to refer to the inhibitors/antagonists of the invention. In certain embodiments, the compounds are small organic or inorganic molecules, e.g., with molecular weights less than 7500 amu, preferably less than 5000 amu, and even more preferably less than 2000, 1500, 1000, or 500 amu. One class of small organic or inorganic molecules are non-peptidyl, e.g., containing 2, 1, or no peptide and/or saccharide linkages. On class of small or organic or inorganic molecules are non-peptidyl and non-nucleic acid containing (e.g., do not include a DNA or RNA moiety). In certain other embodiments, the compounds are proteins, for example, antibodies or aptamers. Such compounds can bind to and inhibit a function of TRPV3. In certain other embodiments, the compounds are nucleic acids, for example, TRPV3 antisense oligonucleotides or TRPV3 RNAi constructs. Such compounds can inhibit the expression of TRPV3, thereby inhibiting the activity of TRPV3. Other exemplary compounds that may act as inhibitors include ribozymes and peptide fragments.

The term "acylamino" is art-recognized and refers to a moiety that can be represented by the general formula:

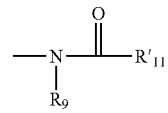

wherein $R_9$ is as defined above, and $R'_{11}$ represents a hydrogen, an alkyl, an alkenyl or —$(CH_2)_m$—$R_8$, where m and $R_8$ are as defined above.

Herein, the term "aliphatic group" refers to a straight-chain, branched-chain, or cyclic aliphatic hydrocarbon group and includes saturated and unsaturated aliphatic groups, such as an alkyl group, an alkenyl group, and an alkynyl group.

The terms "alkenyl" and "alkynyl" refer to unsaturated aliphatic groups analogous in length and possible substitution to the alkyls described above, but that contain at least one double or triple bond respectively.

The terms "alkoxyl" or "alkoxy" as used herein refers to an alkyl group, as defined below, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer, and most preferably 10 or fewer. Likewise, preferred cycloalkyls have from 3-10 carbon atoms in their ring structure, and more preferably have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethylthio, and the like.

The terms "amine" and "amino" are art-recognized and refer to both unsubstituted and substituted amines, e.g., a moiety that can be represented by the general formula:

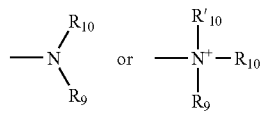

wherein $R_9$, $R_{10}$ and $R'_{10}$ each independently represent a hydrogen, an alkyl, an alkenyl, —$(CH_2)_m$—$R_8$, or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In certain such embodiments, neither $R_9$ and $R_{10}$ is attached to N by a carbonyl, e.g., the amine is not an amide or imide, and the amine is preferably basic, e.g., its conjugate acid has a $pK_a$ above 7. In even more preferred embodiments, $R_9$ and $R_{10}$ (and optionally $R'_{10}$) each independently represent a hydrogen, an alkyl, an alkenyl, or —$(CH_2)_m$—$R_8$. Thus, the term "alkylamine" as used herein means an amine group, as defined above, having a substituted or unsubstituted alkyl attached thereto, i.e., at least one of $R_9$ and $R_{10}$ is an alkyl group.

The term "amido" is art-recognized as an amino-substituted carbonyl and includes a moiety that can be represented by the general formula:

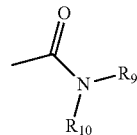

wherein $R_9$, $R_{10}$ are as defined above. Preferred embodiments of the amide will not include imides that may be unstable.

The term "aralkyl", as used herein, refers to an alkyl group substituted with an aryl group (e.g., an aromatic or heteroaromatic group).

The term "aryl" as used herein includes 5-, 6-, and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphate, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The term "carbocycle", as used herein, refers to an aromatic or non-aromatic ring in which each atom of the ring is carbon.

The term "carbonyl" is art-recognized and includes such moieties as can be represented by the general formula:

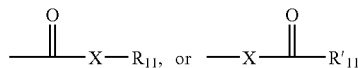

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiocarbonyl" group. Where X is a sulfur and $R_{11}$ or $R'_{11}$ is not hydrogen, the formula represents a "thioester." Where X is a sulfur and $R_{11}$ is hydrogen, the formula represents a "thiocarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The term "electron withdrawing group" refers to chemical groups which withdraw electron density from the atom or group of atoms to which electron withdrawing group is attached. The withdrawal of electron density includes withdrawal both by inductive and by delocalization/resonance effects. Examples of electron withdrawing groups attached to aromatic rings include perhaloalkyl groups, such as trifluoromethyl, halogens, azides, carbonyl containing groups such as acyl groups, cyano groups, and imine containing groups.

The term "heteroatom" as used herein means an atom of any element other than carbon or hydrogen. Preferred heteroatoms are boron, nitrogen, oxygen, phosphorus, sulfur and selenium.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991).

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds (e.g., alkyl, alkenyl, alkynyl, cycloalkyl, heterocyclyl, aryl, heteroaryl, cycloalkylalkyl, heterocyclylalkyl, aralkyl, or heteroaralkyl, any of which may itself be further substituted), as well as halogen, carbonyl (e.g., ester, carboxyl, or formyl), thiocarbonyl (e.g., thioester, thiocarboxylate, or thioformate), ketone, aldehyde, amino, acylamino, amido, amidino, cyano, nitro, azido, sulfonyl, sulfoxido, sulfate, sulfonate, sulfamoyl, sulfonamido, and phosphoryl. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

The term "sulfamoyl" is art-recognized and includes a moiety that can be represented by the general formula:

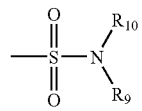

in which $R_9$ and $R_{10}$ are as defined above.

The term "sulfate" is art recognized and includes a moiety that can be represented by the general formula:

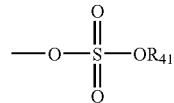

in which $R_{41}$ is as defined above.

The term "sulfonamido" is art recognized and includes a moiety that can be represented by the general formula:

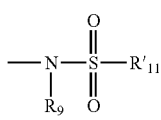

in which $R_9$ and $R'_{11}$ are as defined above.

The term "sulfonate" is art-recognized and includes a moiety that can be represented by the general formula:

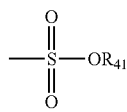

in which $R_{41}$ is an electron pair, hydrogen, alkyl, cycloalkyl, or aryl.

The terms "sulfoxido" or "sulfinyl", as used herein, refers to a moiety that can be represented by the general formula:

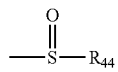

in which $R_{44}$ is selected from the group consisting of hydrogen, alkyl, alkenyl, alkynyl, cycloalkyl, heterocyclyl, aralkyl, or aryl.

As used herein, the definition of each expression, e.g., alkyl, m, n, etc., when it occurs more than once in any structure, is intended to be independent of its definition elsewhere in the same structure.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations. The abbreviations contained in said list, and all abbreviations utilized by organic chemists of ordinary skill in the art are hereby incorporated by reference.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Methods of preparing substantially isomerically pure compounds are known in the art. If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts may be formed with an appropriate optically active acid or base, followed by resolution of the diastereomers thus formed by fractional crystallization or chromatographic means well known in the art, and subsequent recovery of the pure enantiomers. Alternatively, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Techniques for inverting or leaving unchanged a particular stereocenter, and those for resolving mixtures of stereoisomers are well known in the art, and it is well within the ability of one of skill in the art to choose an appropriate method for a particular situation. See, generally, Furniss et al. (eds.), *Vogel's Encyclopedia of Practical Organic Chemistry* 5$^{th}$ Ed., Longman Scientific and Technical Ltd., Essex, 1991, pp. 809-816; and Heller, *Acc. Chem. Res.* 23: 128 (1990).

Contemplated equivalents of the compounds described above include compounds which otherwise correspond thereto, and which have the same general properties thereof (e.g., the ability to inhibit TRPV3 activity), wherein one or more simple variations of substituents are made which do not adversely affect the efficacy of the compound. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and non-aromatic organic compounds which can be substituted or unsubstituted.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

The symbol ∿ , whether utilized as a bond or displayed perpendicular to a bond indicates the point at which the displayed moiety is attached to the remainder of the molecule, solid support, etc.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Wherein substituent groups are specified by their conventional chemical formulae, written from left to right, they equally encompass the chemically identical substituents, which would result from writing the structure from right to left, e.g., —CH$_2$O— is intended to also recite —OCH$_2$—; —NHS(O)$_2$— is also intended to represent —S(O)$_2$HN—; etc.

The term "pharmaceutically acceptable salts" includes salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, trifluoroacetic, propionic, isobutyric, maleic, malonic, benzoic, succinic, suberic, fumaric, lactic, mandelic, phthalic, benzensulfonic, p-tolylsulfonic, citric, tartaric, methanesulfonic, and the like. Also included are the salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs form the various salt forms in certain physical properties, such as solubility in polar solvents, but otherwise the salts are equivalent to the parent form of the compound for the purposes of the present invention.

The term "low enough pyrogen activity", with reference to a pharmaceutical preparation, refers to a preparation that does not contain a pyrogen in an amount that would lead to an adverse effect (e.g., irritation, fever, inflammation, diarrhea, respiratory distress, endotoxic shock, etc.) in a subject to which the preparation has been administered. For example, the term is meant to encompass preparations that are free of, or substantially free of, an endotoxin such as, for example, a lipopolysaccharide (LPS).

Diseases, Disorders, or Conditions Related to TRPV3 Function

In an embodiment of the methods for preventing or treating a disease or disorder or condition, the agent being administered is one that modulates the level and/or activity of a TRPV3 protein. In certain embodiments, the compound inhibits the expression and/or activity of a TRPV3 protein. In other embodiments, the compound selectively inhibits the expression of a TRPV3 protein. In other words, in certain embodiment, the compound inhibits the activity of a TRPV3 protein preferentially in comparison to the activity of one or more other ion channels.

In particular embodiments of the methods for preventing or treating diseases and disorders provided herein, the disease or disorder can be, for example, a pain or sensitivity to touch such as pain related to a disease or disorder, e.g., cancer pain, a dermatological disease or disorder, e.g., psoriasis and basal cell and squamous cell carcinomas, a neurodegenerative disease or disorder, e.g., Alzheimer's disease (AD), Parkinson's disease, Huntington's disease, amyotrophic lateral sclerosis (ALS), and other brain disorders caused by trauma or other insults including aging, an inflammatory disease (e.g., asthma, chronic obstructive pulmonary disease, rheumatoid arthritis, osteoarthritis, inflammatory bowel disease, glomerulonephritis, neuroinflammatory diseases, multiple sclerosis, and disorders of the immune system), cancer or other proliferative disease, kidney disease and liver disease, a metabolic disorder such as diabetes. Further diseases and conditions include post-surgical pain, post herpetic neuraligia, fibromyalgia, and shingles.

Because of the important role that calcium regulation plays in many cellular processes including cellular activation, gene expression, cellular trafficking and apoptotic cell death, calcium dyshomeostasis is implicated in the many diseases and disorders involving such cellular activities. These diseases and disorders include dermatological diseases and disorders; neurological and neurodegenerative diseases and disorders; fever associated with various diseases, disorders or conditions; incontinence; inflammatory diseases and disorders such as inflammatory bowel disease and Crohn's disease; respiratory diseases and disorders such as chronic cough, asthma and chronic obstructive pulmonary disease (COPD); digestive disorders such as ulcers and acid reflux; metabolic diseases and disorders including obesity and diabetes; liver and kidney diseases and disorders; malignancies including cancers; aging-related disorders; and sensitivity to pain and touch.

Additional diseases or conditions that can be treated include ATP-related diseases or disorders including epilepsy, cognition, emesis, pain (e.g., migraine), asthma, peripheral vascular disease, hypertension, immune and inflammatory conditions, irritable bowel syndrome, cystitis, depression, aging-associated degenerative diseases, urinary incontinence, premature ejaculation, cystic fibrosis, diabetes, contraception and sterility, and wound healing (see, for example, Foresta et al. (1992) J. Biol. Chem. 257:19443-19447; Wang et al. (1990) Biochim. Biophys. Res. Commun. 166:251-258; Burnstock and Williams, (2000) J. Pharmacol. Exp. Ther. 295: 862-869; and Burnstock, Pharmacol Rev (2006) 58:58-86).

TRPV3 inhibitors described herein can be used in the treatment of any of the foregoing or following diseases or conditions, including in the treatment of pain associated with any of the foregoing or following diseases or conditions. When used in a method of treatment, an inhibitor can be selected and formulated based on the intended route of administration.

a. Sensitivity to Pain and Touch, or Pain-Related Diseases or Disorders

Compositions and methods provided herein may be used in connection with prevention or treatment of pain or sensitivity to pain and touch. Pain or sensitivity to pain and touch may be indicated in a variety of diseases, disorders or conditions, including, but not limited to, diabetic neuropathy, breast pain, psoriasis, eczema, dermatitis, burn, post-herpetic neuralgia (shingles), nociceptive pain, peripheral neuropathic and central neuropathic pain, chronic pain, cancer and tumor pain, spinal cord injury, crush injury and trauma induced pain, migraine, cerebrovascular and vascular pain, Sickle cell disease pain, pancreatitis related pain, rheumatoid arthritis pain, musculoskeletal pain including treating signs and symptoms of osteoarthritis and rheumatoid arthritis, orofacial and facial pain, including dental and cancer related, lower back or pelvic pain, surgical incision related pain, inflammatory and non-inflammatory pain, visceral pain, psychogenic pain and soft tissue inflammatory pain, fibromyalgia-related pain, and reflex sympathetic dystrophy (complex regional pain syndrome). The compounds and methods of the invention may be used in the treatment of chronic, as well as acute pain. Chronic or acute pain may be the result of injury, age, or disease.

Other ion channels have been implicated in reception or transmission of pain. For example, the involvement of N-type calcium channels in the synaptic transmissions that convey pain signals from sensory afferent nerve cells to the central nervous system has been recognized. Certain naturally occurring peptide neurotoxins that specifically block N-type calcium channel have been shown to act as extremely potent and efficient analgesics in a wide range of animal pain models, including models of inflammatory and neuropathic pain. The available evidence suggests that N-type calcium channel blockers are at least as efficacious as opiates, are devoid of a number of the typical opiate side effects (e.g. respiratory depression) and that the analgesic effect is not subject to tolerance development.

It has also been shown that potent peripheral analgesia induced by 5-alpha-reduced neurosteroid is mediated in part by effects on T-type $Ca^{2+}$ channels (Pathirathna et al., Pain. 2005 April; 114(3):429-43).

Ethosuximide, an anti-epileptic and relatively selective T-type calcium channel blocker, has also been shown as being highly effective in reversing neuropathic pain caused by the commonly employed cytotoxics paclitaxel or vincristine (Flatters and Bennett, Pain. 2004 May; 109(1-2):150-61).

Pregabalin, a new drug that interacts with the alpha(2)-delta protein subunit of the voltage-gated calcium channel, is an efficacious and safe treatment for the pain of diabetic neuropathy (Richter et al., J Pain. 2005 April; 6(4):253-60).

The foregoing demonstrate the involvement of various non-TRP channels in the reception or transmission of pain. Specifically, the foregoing demonstrate the involvement of various calcium channels in pain.

TRPV3, as well as TRPV1 and TRPV4, are expressed in a pattern consistent with involvement in pain. TRPV3 is expressed in pain sensitive neurons, and this expression is upregulated following injury (Smith et al., 2002). In addition, TRPV3 is robustly expressed in skin. Accordingly, methods for treating pain include administration of (i) antagonists of a TRPV3 function; (ii) combinations of selective antagonists of a TRPV3 and TRPV1 and/or TRPV4 function; or (iii) a pan-TRP inhibitor that inhibits a function of TRPV3, TRPV1, and TRPV4.

In addition to TRPV family members, other TRP channels have been implicated in pain reception and/or sensation. For example, certain TRPM channels including TRPM8 have been implicated in the reception and/or sensation of pain. Accordingly, in certain embodiments, the methods of the present invention include treating pain by administering (i) a combination of a selective TRPV3 antagonist and a selective TRPM8 antagonist; (ii) a combination of a selective TRPV3 antagonist, a selective TRPM8 antagonist, and one or more of a selective TRPV1 and/or TRPV3 antagonist; (iii) a cross-TRP inhibitor that antagonizes a function of TRPV3 and TRPM8; or (iv) a pan inhibitor that antagonizes a function of TRPV3, TRPM8, and one or more of TRPV1 and TRPV4.

Without being bound by theory, we propose one possible mechanism for how a TRPV3 antagonist may help reduce pain. TRPV3 antagonists can lead to hyperpolarization of the cell. This may lead to a reduction in the firing of neurons and/or a decrease in action potential frequency. In addition, TRPV3 inhibitors may reduce calcium influx into injured cells and could prevent the calcium dependent changes in gene expression that sometimes accompany injury. However, regardless of the mechanism of action, available expression analysis, electrophysiology and pharmacological efficacy studies support the use of TRPV3 antagonists for the treatment of pain.

These findings are somewhat unanticipated because of the uncertainty and controversy generated by analysis of TRPV3 knock out mice. It has been reported that TRPV3 null mice have deficits in their ability to sense temperature, but not in their ability to sense pain (Moqrich et al., 2005, Science 307: 1468-1472). This finding contradicted an earlier report that suggested that TRPV3 null mice had normal thermal thresholds, but were unable to develop thermal hyperalgesia in response to carrageenan or CFA (Smith et al., 2004, Society for Neuroscience Abstracts).

b. Dermatological Diseases or Disorders

Influx of calcium across plasma membrane of skin cells is a critical signaling element involved in cellular differentiation in the skin epidermis (Dotto, 1999 Crit Rev Oral Biol Med 10:442-457). Regulating or modulating the calcium entry pathway, and thus a critical control point for skin cell growth, can treat or prevent skin diseases or disorders that are characterized by epidermal hyperplasia, a condition in which skin cells both proliferate too rapidly and differentiate poorly. Such diseases include psoriasis, and basal and squamous cell carcinomas. Psoriasis, estimated to affect up to 7 million Americans, afflicts sufferers with mild to extreme discomfort, enhanced susceptibility to secondary infections, and psychological impact due to disfigurement of the affected areas (Lebwohl and Ali, 2001 J Am Acad Dermatol 45:487-498). Basal cell carcinomas (BCC) and squamous cell carcinomas (SCC) of the skin represent at least one-third of all cancers diagnosed in the United States each year. More than 1 million new cases are reported annually and incidence is increasing. Despite being relatively non-aggressive, slow-growing cancers, BCCs are capable of significant local tissue destruction and disfigurement. SCCs are more aggressive and thus present even greater complications. Further, given that 80% of lesions are on the head and neck with another 15% on shoulders, back or chest, BCCs and SCCs of the skin can have a significant impact on the appearance and quality of life of the afflicted patient.

Many dermatological disorders are accompanied by itch (pruritus). Pruritus and pain share many mechanistic similarities. Both are associated with activation of C-fibers, both are potentiated by increases in temperature and inflammatory mediators and both can be quelled with opiates. Decreasing neuronal excitability, particularly C-fiber excitability may alleviate pruritus associated with dialysis, dermatitis, pregnancy, poison ivy, allergy, dry skin, chemotherapy and eczema.

Acne is a dermatological disorder of complex etiology. Among other factors, secretion of oils from the sebaceous glands that contribute to the development of acne, Since TRPV3 is also expressed in the sebaceous gland and has been shown to be able to regulate secretion in other skin cells, antagonizing TRPV3 function might reduce the signs and symptoms of acne.

c. Neurological or Neurodegenerative Diseases and Disorders

Neurodegenerative diseases and disorders include but are not limited to Alzheimer's disease (AD), Parkinson's disease, Huntington's disease, amyotrophic lateral sclerosis (ALS), and other brain disorders caused by trauma or other insults including aging.

Mechanisms associated with calcium signaling may be altered in many neurodegenerative diseases and in disorders resulting from brain injury. For example, fibroblasts or T-lymphocytes from patients with AD have consistently displayed an increase in $Ca^{2+}$ release from intracellular stores compared to controls (Ito et al. (1994) Proc. Natl. Acad. Sci. U.S.A. 91:534-538; Gibson et al. (1996) Biochem. Biophys. ACTA 1316:71-77; Etchenberrigaray et al. (1998) Neurobiology of Disease, 5:37-45). Consistent with these observations, mutations in presenilin genes (PS1 or PS2) associated with familial AD (FAD) have been shown to increase InsP3-mediated $Ca^{2+}$ release from internal stores (Guo et al. (1996) Neuro Report, 8:379-383; Leissring et al. (1999) J. Neurochemistry, 72:1061-1068; Leissring et al. (1999) J. Biol. Chem. 274(46): 32535-32538; Leissring et al. (2000) J. Biol. Chem. 149(4): 793-797; Leissring et al. (2000) Proc. Natl. Acad. Sci. U.S.A. 97(15):8590-8593). Furthermore, mutations in PS1 or PS2 associated with an increase in amyloidogenic amyloid β peptide generation in AD are reported to be associated with a decrease in intracellular calcium level (Yoo et al. (2000) Neuron, 27(3):561-572).

Experimental traumatic brain injury has been shown to initiate massive disturbances in $Ca^{2+}$ concentrations in the brain that may contribute to further neuronal damage. Intracellular $Ca^{2+}$ may be elevated by many different ion channels. It has been further shown that channel blockers may be beneficial in the treatment of neurological motor dysfunction when administered in the acute posttraumatic period (Cheney et al. (2000) J. Neurotrauma, 17(1):83-91).

d. Inflammatory Diseases and Disorders

Compositions and methods provided herein may also be used in connection with treatment of inflammatory diseases. These diseases include but are not limited to asthma, chronic obstructive pulmonary disease, rheumatoid arthritis, osteoarthritis, inflammatory bowel disease, glomerulonephritis, neuroinflammatory diseases such as multiple sclerosis, and disorders of the immune system.

The activation of neutrophils (PMN) by inflammatory mediators is partly achieved by increasing cytosolic calcium concentration ($[Ca^{2+}]_i$). Certain calcium channel-mediated calcium influx in particular is thought to play an important role in PMN activation. It has been shown that trauma increases PMN store-operated calcium influx (Hauser et al. (2000) J. Trauma Injury Infection and Critical Care 48 (4): 592-598) and that prolonged elevations of $[Ca^{2+}]_i$ due to enhanced store-operated calcium influx may alter stimulus-response coupling to chemotaxins and contribute to PMN dysfunction after injury. Modulation of PMN $[Ca^{2+}]_i$ through store-operated calcium channels might therefore be useful in regulating PMN-mediated inflammation and spare cardiovascular function after injury, shock or sepsis (Hauser et al. (2001) J. Leukocyte Biology 69 (1):63-68).

Peripheral neuropathy, for example diabetic neuropathy, is a particular condition that involves both a neuronal and an inflammatory component. Without being bound by a mechanistic theory, the TRPV3 antagonists of the invention may be useful in treating peripheral neuropathies including, but not limited to, diabetic neuropathy. In addition to their use in the treatment of peripheral neuropathies (e.g., reducing inflammation), the subject inhibitors may also be useful in reducing the pain associated with peripheral neuropathy.

e. Cancer and Other Proliferative Diseases

Compositions and methods provided herein may also be used in connection with treatment of malignancies, including, but not limited to, malignancies of lymphoreticular origin, bladder cancer, breast cancer, colon cancer, endometrial cancer, head and neck cancer, lung cancer, melanoma, ovarian cancer, prostate cancer and rectal cancer, in addition to skin cancers described above. Intracellular calcium level may play an important role in cell proliferation in cancer cells (Weiss et al. (2001) International Journal of Cancer 92 (6):877-882).

In addition, pain associated with cancer or with cancer treatment is a significant cause of chronic pain. Cancers of the bone, for example, osteosarcoma, are considered exceptionally painful, and patients with advanced bone cancer may require sedation to tolerate the intense and persistent pain. Accordingly, TRPV3 antagonists of the invention represent a significant possible therapeutic for the treatment of pain, for example, the pain associated with cancer or with cancer treatment.

Cancer treatments are not only painful, but they may even be toxic to healthy tissue. Some chemotherapeutic agents can cause painful neuropathy. Accordingly, TRPV3 antagonists of the invention represent a significant possible therapeutic for the treatment of the pain and/or inflammation associated with cancer treatments that cause neuropathy.

A major function of prostaglandins is to protect the gastric mucosa. Included in this function is the modulation of intracellular calcium level in human gastric cells which plays a critical role in cell proliferation. Consequently, inhibition of prostaglandins by nonsteroidal anti-inflammatory drugs (NSAIDs) can inhibit calcium influx in gastric cells (Kokoska et al. (1998) Surgery (St Louis) 124 (2):429-437). The NSAIDs that relieve inflammation most effectively also produce the greatest gastrointestinal damage (Canadian Family Physician, January 1998, p. 101). Thus, the ability to independently modulate calcium channels in specific cell types may help to alleviate such side effect of anti-inflammatory therapy.

f. Liver Diseases and Disorders

Compositions and methods provided herein may also be used in connection with treatment of liver diseases and disorders. These diseases and disorders include but are not limited to alcoholic liver disease, liver injury, for example, due to transplantation, hepatitis, cancer, and cirrhosis.

Intracellular calcium level has been implicated in chronic liver disease (Tao et al. (1999) J. Biol. Chem., 274(34):23761-23769) as well as transplantation injury after cold preservation-warm reoxygenation (Elimadi et al. (2001) Am J. Physiology, 281(3 Part 1):G809-G815). Chronic ethanol consumption has been shown to impair liver regeneration, in part, by modulating intracellular calcium level (Zhang et al. (1996) J. Clin. Invest. 98(5):1237-1244).

g. Kidney Diseases and Disorders

Compositions and methods provided herein may also be used in connection with treatment of kidney diseases and disorders. Mesangial cell hyperplasia is often a key feature of such diseases and disorders. Such diseases and disorders may be caused by immunological or other mechanisms of injury, including IgAN, membranoproliferative glomerulonephritis or lupus nephritis. Imbalances in the control of mesangial cell replication also appear to play a key role in the pathogenesis of progressive renal failure.

The turnover of mesangial cells in normal adult kidney is very low with a renewal rate of less than 1%. A prominent feature of glomerular/kidney diseases is mesangial hyperplasia due to elevated proliferation rate or reduced cell loss of mesangial cells. When mesangial cell proliferation is induced without cell loss, for example due to mitogenic stimulation, mesangioproliferative glomerulonephritis can result. Data have indicated that regulators of mesangial cell growth, particularly growth factors, may act by regulating certain calcium channels (Ma et al. (2001) J. Am. Soc. of Nephrology, 12:(1) 47-53). Modulators of intracellular calcium level may aid in the treatment of glomerular diseases by inhibiting mesangial cell proliferation. The epithelial calcium channel CaT2 has also been implicated in hypercalciuria and resultant renal stone formation (Peng et al. (2000) J. Biol. Chem., 275(36):28186-28194).

h. Incontinence

Incontinence is a significant social and medical problem affecting both men and women. Incontinence has many causes including, but not limited to, age, pregnancy, radiation exposure, surgery, injury, and diseases of the bladder or musculature that supports the urethra.

Compositions and methods provided herein may be useful in connection with the treatment of incontinence. Animal models of incontinence are often associated with an increase in the frequency of spontaneous action potentials and a chronic depolarization of the smooth muscle cells. Evidence suggests that a non-selective cation current could lead to this depolarization. Since TRPV3 mRNA is known to be expressed in bladder, a TRPV3 antagonist may be useful in treating incontinence i. Temperature Regulation Because of the effects of ion flux on arterial tension and relaxation, the subject compounds can also be used to affect body temperature regulation, for example, to reduce fever. Furthermore, given that TRPV3 channels are heat responsive channels involved in the reception and sensation of heat stimuli, TRPV3 antagonists can be used to modulate the sensation of heat, warmth, or elevated temperatures.

During menopause, many women experience hot flashes. Hot flashes are marked by sweating, discomfort, and a generally disproportionate experience of the temperature of one's environment. The symptoms of hot flashes can be very severe, and may interfere with sleep and other daily activities. Furthermore, menopause is not only a condition experienced by women as they age. Premature menopause, and the accompanying symptoms, can be induced by hormonal imbalances, certain medications, cancers or other diseases of the female reproductive tract, and partial or total hysterectomies. Thus, menopause and its symptoms may be experienced by large numbers of women across a diverse age range.

In certain embodiments, TRPV3 antagonists of the present invention can be used to decrease the perception of heat and temperature associated with hot flashes. TRPV3 antagonists of the present invention can be administered alone, or as part of a therapeutic regimen to decrease the symptoms associated with menopause. By way of example, TRPV3 antagonists of the present invention can be administered alone or together with hormone therapy (e.g., estrogen-replacement therapy) used to decrease the severity of symptoms associated with menopause.

j. Hypertension

Blockers of voltage-gated calcium channels belong to a class of medications originally developed to treat hypertension. Such blockers inhibit the movement of calcium into the muscle cells of the heart and arteries. Because calcium is needed for these muscles to contract, such blockers lower blood pressure by decreasing the force of cardiac contractile response and relaxing the muscle walls of the arteries. Although TRPV3 is not a voltage-gated calcium channel, it is still instrumental in regulating calcium homeostasis, as well as the balance of other ions, in cells and tissues. Accordingly, TRPV3 antagonists of the invention may be used to treat hypertension. Additional uses of the subject compounds include other conditions that may be ameliorated, in whole or in part, by relaxing the muscle walls of blood vessels. Exemplary conditions include headaches and migraine attacks.

k. Hair Loss

TRPV3 knock-out mice have a significant hair loss phenotype. Accordingly, the TRPV3 antagonists of the present invention can be used to promote hair loss or to otherwise inhibit the growth of body hair. By way of example, TRPV3 antagonists can be applied topically to the skin to promote the loss of or to otherwise inhibit the growth of body hair. In such embodiments, the TRPV3 antagonists act as a depilatory agent to promote the loss of or to otherwise inhibit the growth body hair. When used in this manner, one or more TRPV3 antagonist can be used alone or in combination with an additional depilatory agent. Additionally, one or more TRPV3 antagonist can be used to supplement other hair removal techniques such as waxing or shaving. In such a way, a TRPV3 antagonist can be used alone or as part of a hair removal regimen to reduce or eliminate unwanted body hair. Exemplary unwanted body hair includes, but is not limited to, hair on the legs, arms, back, upper lip, chest, bikini area, underarms, and buttocks.

Additionally or alternatively, TRPV3 antagonists can be administered systemically to promote the loss of or to prevent the growth of body hair.

In any of the foregoing, TRPV3 antagonists likely provide an improved method for reducing or eliminating unwanted body hair. Given the pain inhibiting activity of TRPV3 antagonists, their use alone or as part of a hair removal regimen provides an improved method for removing body hair with less discomfort than currently available waxes and chemical depilatories.

As outlined above, compounds that antagonize a function of TRPV3 can be used in the treatment of many diseases, injuries, disorders, and conditions. In certain embodiments, TRPV3 inhibitors can be used in the treatment of pain. As outlined above, TRPV3 inhibitors can be used in the treatment of pain resulting from injury or disease, as well as pain experienced as a consequence of treatment. Exemplary classes of pain include nociceptive pain, inflammatory pain, and neuropathic pain. Such pain can be chronic or acute. TRPV3 inhibitors can be used in the treatment of one or more of any of the foregoing classes of pain. In certain embodiments, TRPV3 inhibitors can be used in the treatment of nociceptive pain. In certain other embodiments, TRPV3 inhibitors can be used in the treatment of inflammatory pain. In certain other embodiments, TRPV3 inhibitors can be used in the treatment of neuropathic pain.

As outlined above, TRPV3 inhibitors may be particularly useful in the treatment of pain associated with cancer, osteoarthritis, rheumatoid arthritis, post-herpetic neuralgia, burns, and other indications detailed above. To further illustrate, additional exemplary indications for which compounds of the present invention can be used include oral pain, Fabry's disease, complex regional pain syndrome, pancreatitis, and fibromyalgia syndrome.

Fabry's Disease

Vague complaints of pain in hands and feet may be a presenting feature. These symptoms are called acroparesthesias, as they reflect the peripheral neuropathy that is a frequent manifestation of the disease. This pain may be both episodic and chronic. Acute episodes may be triggered by exposure to extremes of temperature, stress, emotion, and/or fatigue.

Fibromyalgia

Fibromyalgia (FMS; fibromyalgia syndrome) is a widespread musculoskeletal pain and fatigue disorder. Fibromyalgia is characterized by pain in the muscles, ligaments, and tendons. The condition affects more women than men, and occurs in people of all ages. Overall, FMS is estimated to afflict 3-6% of the population.

Patients have described the pain associated with fibromyalgia as deep muscular aching, throbbing, shooting, and stabbing. The pain sometimes includes an intense burning sensation. The pain and stiffness are often worse in the morning or after repetitive use of a particular muscle group.

Additionally, varying levels of fatigue ranging from mild to incapacitating are often associated with fibromyalgia. Other symptoms of fibromyalgia include gastrointestinal symptoms. Irritable bowel syndrome and IBS-like symptoms such as constipation, diarrhea, frequent abdominal pain, abdominal gas, and nausea occur in roughly 40 to 70% of FMS patients. Acid reflux or gastroesophageal reflux disease (GERD) occurs at a similar frequency.

Another frequent and debilitating symptom of FMS is chronic headaches, including migraine and tension-type headaches. Such headaches are experienced by approximately 70% of FMS patients. Additionally, FMS patients often experience temporomandibular joint dysfunction syndrome (also known as TMJ) which produces pain in the jaw, teeth, and mouth. TMJ may also exacerbate headaches.

Other common symptoms of FMS include, but are not limited to, premenstrual syndrome and painful periods; chest pain; morning stiffness; cognitive or memory impairment; numbness and tingling sensations; muscle twitching; irritable bladder; the feeling of swollen extremities; skin sensitivities; dry eyes and mouth; dizziness; and impaired coordination. Additionally, patients are often sensitive to odors, loud noises, and bright lights.

The cause of FMS remains unknown. However, the onset of the disorder has been linked to infections (viral or bacterial), rheumatoid arthritis, lupus, and hypothyroidism. The link between these and other possible triggers is unclear.

The impact of FMS on the patient is directly correlated with the level of pain and fatigue. Pain may be so severe as to interfere with normal work or family functioning. There is currently no cure for FMS, and current therapies focus primarily on improving sleep (to decrease fatigue) and treating pain. Compounds of the present invention could be used to help manage the pain associated with FMS. Such pain includes, but is not limited to, oral pain in the jaw, teeth, and mouth. Such pain also includes non-oral musco-skeletal pain, pain due to headaches, and pain due to gastrointestinal symptoms.

Complex Regional Pain Syndrome (CRPS; also known as chronic regional pain syndrome) is a chronic pain condition. CRPS was formerly known as reflex sympathetic dystrophy (RSD). CRPS is a chronic, painful, and progressive neurological condition that affects skin, muscles, joints, and bones. The syndrome usually develops in an injured limb, such as a broken leg or following surgery. However, many cases involve only a minor injury, such as a sprain, and sometimes no precipitating injurious event can be identified. CRPS involves continuous, intense pain that is disproportionate to the severity of the injury. The pain worsens, rather than improves, over time.

Although CRPS can affect a variety of regions of the body, it most often affects the arms, legs, hands, or feet. Often the pain begins in one portion of a limb, but spreads over time to include the entire limb or even to include a different limb. Typical features include dramatic changes in the color and temperature of the skin over the affected limb or body part, accompanied by intense burning pain, skin sensitivity, sweating, and swelling.

Generally, CRPS is characterized into two categories. Type I occurs in the absence of a precipitating nerve injury—although there may have been some other type of precipitating injury. Type II (formerly called causalgia) occurs following a nerve injury. These categories are merely descriptive, and do not correlate with symptomology or prognosis.

The National Institute of Neurological Disorders and Strokes (NINDS) reports that 2% to 5% of peripheral nerve injury patients and 12% to 21% of patients with paralysis on one side of the body (hemiplegia) develop reflex sympathetic dystrophy as a complication. The Reflex Sympathetic Dystrophy Syndrome Association of America (RSDSA) reports that the condition occurs following 1-2% of bone fractures.

Precipitating events associated with the onset of CRPS include the following: cerebral lesions, heart disease, heart attack, infection, paralysis on one side of the body (hemiplegia), radiation therapy, repetitive motion disorder (e.g., carpal tunnel syndrome), spinal cord disorders, surgery, and trauma (e.g., bone fracture, gunshot, car accident). However, in 10-20% of cases, no precipitating event can be found. Note that the injury that precedes the onset of CRPS may or may not be significant.

The symptoms of CRPS may progress in three stages. An acute stage occurs during the first 1-3 months and may include burning pain, swelling, increased sensitivity to touch, increased hair and nail growth in the affected region, joint pain, and color and temperature changes. A dystrophic stage may involve constant pain and swelling. The effected limb often feels cool to the touch and looks bluish. There is typically muscle stiffness and wasting (atrophy), as well as early bone loss (osteoporosis). These symptoms usually occur 3-6 months after development of the disorder. During an atrophic stage, the skin becomes cool and shiny, increased muscle stiffness and weakness occur, and symptoms may spread to another limb.

Other symptoms include: burning pain, extreme sensitivity to touch, skin color changes (red or bluish), skin temperature changes (hot or cold), joint pain, swelling (edema), frequent infections, muscle stiffness, muscle spasm, tremor, weakness, dermatitis, eczema, excessive sweating, and migraine headache. A TRPV3 inhibitor can be useful not only in treating the pain associated with CRPS, but also in relieving many of these other symptoms including dermatitis, eczema, and migraines.

Patients with CRPS often suffer from depression and anxiety due to the impact of the disease of their quality of life.

There is currently no cure for CRPS, and thus treatment typically aims to relieve painful symptoms. Doctors may prescribe topical analgesics, antidepressants, corticosteroids, and opioids to relieve pain. However, to this point, no single drug or combination of drugs has produced consistent long-lasting improvement in symptoms. Other treatments may include physical therapy, sympathetic nerve block, spinal cord stimulation, and intrathecal drug pumps to deliver opioids and local anesthetic agents via the spinal cord.

The goals of treatment are to control pain and to maintain as much mobilization of the affected limb as possible. An individualized treatment plan is designed, which often combines treatment modalities. Currently, physical therapy, medications, nerve blocks, and psychosocial support are used. TRPV3 inhibitors according to the present invention can be used instead of or in addition to one or more of the current treatment modalities. For example, a TRPV3 inhibitor can be used as an alternative to current medications, but combined with physical therapy.

TRPV3 inhibitors provide an alternative for managing pain in CRPS patients. TRPV3 inhibitors may be used in combination with any of the current medications used to treat CRPS patients. Alternatively, TRPV3 inhibitors may be used as an alternative medication.

In addition to drug therapy, CRPS patients often receive physical therapy. TRPV3 inhibitors can be used in addition to physical therapy. Physical therapy may be important for helping retain range of motion and function in the affected limb. Appropriate pain management, for example using a TRPV3 inhibitor, not only increases patient comfort, but also facilitates involvement in physical therapy.

Regardless of the particular combination of therapies used to manage pain in CRPS patients, psychological support is often critical. TRPV3 inhibitors can be used in combination with psychological support.

TRPV3 inhibitors of the present invention may be used in the treatment of CRPS. For example, TRPV3 inhibitors of the present invention may be used to help relieve the pain associated with CRPS. TRPV3 inhibitors can be used alone or as part of an overall treatment regimen to help manage the pain and other symptoms associated with CRPS. Pain management for CRPS sufferers is critical for maintaining a meaningful quality of life. Furthermore, effective pain management may allow sufferers to participate in physical therapy to help retain mobility and use of the effected limbs.

Pancreatitis is an inflammation of the pancreas. The pancreas is a large gland behind the stomach and close to the duodenum. Normally, digestive enzymes do not become active until they reach the small intestine, where they begin digesting food. But if these enzymes become active inside the pancreas, they start "digesting" the pancreas itself.

Acute pancreatitis occurs suddenly, lasts for a short period of time, and usually resolves. Chronic pancreatitis does not resolve itself and results in a slow destruction of the pancreas. Either form can cause serious complications including bleeding, tissue damage, and infection.

Acute pancreatitis can be a severe, life-threatening illness with many complications. About 80,000 cases occur in the United States each year, and approximately 20 percent of these cases are characterized as severe.

Acute pancreatitis is usually, although not exclusively, caused by gallstones or by alcohol abuse. Acute pancreatitis usually begins with pain in the upper abdomen that may last for a few days. The pain may be severe and may become constant. The pain may be isolated to the abdomen or it may reach to the back and other areas. Sometimes, and for some patients, the pain is sudden and intense. Other times, or for other patients, the pain begins as a mild pain that worsens after eating. Someone with acute pancreatitis often looks and feels very sick. Other symptoms may include swollen and tender abdomen, nausea, vomiting, fever, and rapid pulse. Severe cases of acute pancreatitis may cause dehydration and low blood pressure, and may even lead to organ failure, internal bleeding, or death.

During acute pancreatitis attacks, the blood levels of amylase and lipase are often increased by at least 3-fold. Changes may also occur in blood levels of glucose, calcium, magnesium, sodium, potassium, and bicarbonate.

The current treatment depends on the severity of the attack. Treatment, in general, is designed to support vital bodily functions, manage pain, and prevent complications. Although acute pancreatitis typically resolved in a few days, pain management during an attack is often required. TPRV3 inhibitors can be used to relieve the pain associated with acute pancreatitis.

Chronic pancreatitis—If injury to the pancreas continues, chronic pancreatitis may develop. Chronic pancreatitis occurs when digestive enzymes attack and destroy the pancreas and nearby tissues, causing scarring and pain. Chronic pancreatitis may be caused by alcoholism, or by blocked, damaged, or narrowed pancreatic ducts. Additionally, hereditary factors appear to influence the disease, and in certain cases, there is no identifiable cause (so called idiopathic pancreatitis).

Most people with chronic pancreatitis have abdominal pain. The pain may get worse when eating or drinking, spread to the back, or become constant and disabling. Other symptoms include nausea, vomiting, weight loss, and fatty stools.

Relieving pain is the first step in treating chronic pancreatitis. Once the pain has been managed, a high carbohydrate and low fat dietary plan is put in place. Pancreatic enzymes may be used to help compensate for decrease enzyme production from the injured pancreas. Sometimes insulin or other drugs are needed to control blood glucose.

Although pain is typically managed using drug therapy, surgery may be necessary to relieve pain. Surgery may be necessary to drain an enlarged pancreatic duct or even to removing a portion of a seriously injured pancreas.

Pain is frequently present with chronic pancreatitis. For example, pain is present for approximately 75% of patients with alcoholic chronic pancreatitis, 50% of patients with late-onset idiopathic chronic pancreatitis, and 100% of patients with early-onset idiopathic chronic pancreatitis (DiMagno, 1999, Gastroenterology 116(5): 1252-1257).

A minority of patients with pain have readily identifiable lesions which are relatively easy to treat surgically or endoscopically. In other patients, pain is often thought to result from a variety of causes, including elevated intrapancreatic pressure, ischemia, and fibrosis. Without being bound by theory, however, these phenomena are not likely the underlying cause of the pain. Rather, pain may result from a background of neuronal sensitization induced by damage to the perineurium and subsequent exposure of the nerves to mediators and products of inflammation.

Given the importance of effective pain management in patients with chronic pancreatitis, additional therapies for treating painful symptoms are important and useful. TRPV3 inhibitors can be used to manage the pain associated with chronic pancreatitis. TRPV3 inhibitors can be used alone or as part of an overall therapeutic treatment plan to manage patients with chronic pancreatitis. For example, TRPV3 inhibitors can be administered with pancreatic enzymes and/or insulin as part of a therapeutic regimen designed to manage patients with chronic pancreatitis.

Oral pain is a particular category of pain that may be treated using the TRPV3 inhibitors of the present invention. The term "oral pain" refers to any pain in the mouth, throat, lips, gums, teeth, tongue, or jaw. The term is used regardless of the cause of the pain and regardless of whether the oral pain is a primary or secondary symptom of a particular disease, injury, or condition.

Oral pain has a large number of possible causes. In certain embodiments, oral pain is caused by an injury or disease of the mouth, jaw, teeth, gums, throat, lips, or tongue. In certain other embodiments, oral pain is a consequence of an injury or disease that primarily affects another part of the body. In still other embodiments, oral pain is a side effect of a therapy used to treat an injury or disease of the mouth or another part of the body. TRPV3 inhibitors are useful in treating oral pain regardless of its cause.

All pain has a serious negative impact on the health and well being of the sufferer. However, oral pain may have a particularly deleterious impact on patient health and quality of life. In particular, oral pain can interfere with appropriate eating and drinking. Thus, individuals with oral pain are susceptible to weight loss, malnutrition, and dehydration. In some instances, oral pain may interfere with hydration and nutrition so significantly as to require intravenous, nasogastric, or other artificial support (e.g., tube feeding and/or hydration). Additionally, oral pain can interfere with proper oral hygiene. Poor oral hygiene may further exacerbate many of the causes of oral pain, for example, oral pain due to infection or abscess.

In certain embodiments, oral pain is caused by ulcers, sores, or other lesions in the mouth. For example, oral pain may be caused by ulcers, sores, or other lesions on the tongue, gums, lips, throat, or other tissues of the mouth. Alternatively or additionally, oral pain may be caused by inflammation of the throat, tongue, gums, lips, or other tissues of the mouth. Inflammation may accompany ulcers or other lesions, or inflammation may occur prior to or in the absence of formation of ulcers or other lesions.

The invention contemplates treatment of oral pain by administering a TRPV3 inhibitor by any route of administration described herein. In certain embodiments, TRPV3 inhibitors for use in the treatment of oral pain are administered orally. Preferred preparations for oral administration of TRPV3 inhibitors for use in treating oral pain are as a mouthwash, a gel, a tooth paste or other paste, a liquid, a lozenge, via a swab, or in association with a mouth guard or dental apparatus. The preparation and particular method of administration will depend on the cause of the oral pain, the overall health and underlying medical conditions of the patient, the severity of the pain, and other medications or therapies the patient is concurrently receiving. A medical practitioner can readily determine the optimal formulation for use in a particular patient.

The conditions provided below are intended to illustrate the range of injuries and diseases of diverse etiology that may lead to oral pain. The invention contemplates administration of a TRPV3 inhibitor, according to the present invention, to treat or prevent oral pain. In certain embodiments, compounds of the invention can be orally administered, for example as a gel, paste, mouth wash, or other oral preparation, to help treat or prevent oral pain associated with any injury, disease, or condition. Regardless of the particular formulation, the invention contemplates administration by, for example, direct application to the affected area of the mouth, rinsing of the entire mouth, via a swab, via a syringe, or on a mouth guard or other dental apparatus.

For any of these conditions, the invention contemplates administration of a TRPV3 inhibitor alone, or in combination with one or more other compounds or treatment regimens appropriate for the particular injury or condition.

Oral Mucositis

Oral mucositis, also known as stomatitis, is a common complication of many cancer treatments. Patients receiving systemic chemotherapy and/or local radiotherapy often develop extremely painful ulcers of the oral mucosa. This side effect is not limited to patients suffering from cancers of the head and neck, but rather is a debilitating side effect afflicting approximately 40% of all chemotherapy patients (Prevention and Treatment of Oral Mucositis in Cancer Patients, 1998, *Best Practice:* 2, pages 1-6.)

Oral mucositis is extremely painful. Additionally, oral mucositis interferes with proper nutrition and hydration of cancer patients. Given the already compromised status of patients undergoing chemotherapy and/or radiotherapy, further interference with nutrition and hydration may seriously undermine patient health. Furthermore, these ulcers present an increased risk of infection. This risk is particularly acute in patients with compromised immune systems. Examples of patients at particular risk of developing an opportunistic infection are patients whose treatment included removal of one or more lymph nodes, patients who previously received high-dose chemotherapy in preparation for a bone marrow or stem cell transplant, and patients with an underlying immunosuppressive disorder (e.g., HIV or hepatitis).

Canker Sores

Canker sores, also known as aphthous ulcers (aphthae), may be relatively small and out-of-sight. However, they are often painful, persistent and annoying. Canker sores are shallow ulcers in the mouth that can make eating and talking uncomfortable. They may occur on the tongue, soft palate, inside the cheek or lip, or at the base of the gums. Canker sores differ from cold sores in that they occur on the internal soft tissues of the mouth and aren't contagious. Conversely, cold sores almost always start out on the lips and don't often spread to the soft tissues of the mouth. In addition, cold sores are caused by a form of the herpes virus, making them extremely contagious.

Researchers generally believe that stress or tissue injury may cause the eruption of canker sores. In some cases a minor injury, for example biting the inside of the mouth or eating rough foods, may trigger a canker sore. Other causes may include: (i) faulty immune system function; (ii) nutritional problems, such as a deficiency of vitamin B-12, zinc, folic acid or iron; (iii) diseases of the gastrointestinal tract; (iv) food allergies; or (v) the menstrual cycle.

Canker sores can occur at any age, but often they first appear between the ages of 10 and 40 years. Although canker sores typically resolve on their own, they can be very uncomfortable.

Dental/Tooth Abscess

Infection or decay can lead to an abscess. An abscess may have serious dental and medical consequences. For example, a severe infection caused by a dental abscess may lead to a sinus or systemic infection. Furthermore, an abscess may lead to the need to extract one or more teeth. Extraction may be necessary due to significant tooth decay, or because the infection is too severe to fully treat in the presence of the offending tooth.

Regardless of the ultimate outcome, a dental abscess may be extremely painful. Not only is the pain uncomfortable, but it may interfere with proper nutrition and hydration. Methods and compositions for reducing the pain associated with dental abscess would provide significant benefits for their management.

Gastroesophageal Reflux Disease

Gastroesophageal reflux disease, or GERD, occurs when the lower esophageal sphincter (LES) does not close properly and stomach contents leak back into the esophagus. The LES is a ring of muscle at the bottom of the esophagus that acts like a valve between the esophagus and stomach. When refluxed stomach acid touches the lining of the esophagus, it causes a burning sensation in the chest or throat. This is often experienced as heartburn. The refluxed fluid may even be tasted in the back of the mouth, a sensation commonly referred to as acid indigestion.

Although occasional heartburn is uncommon and not necessarily indicative of GERD, heartburn that occurs more than twice a week may be a sign of GERD. In addition to the discomfort of heartburn and indigestion, GERD may lead to other serious health problems. For example, over time, acid refluxed to the back of the throat can lead to oral sores, lesions, or ulcers in the mouth, gums, tongue, throat, or lips. The lesions can cause significant pain, can interfere with nutrition and hydration, and can leave a person vulnerable to infection.

Administration of TRPV3 inhibitors, according to the present invention, may be useful in treating oral pain from lesions caused by GERD. TRPV3 inhibitors may be used as part of a treatment regimen where the TRPV3 inhibitor is administered to help manage the discomfort of the oral lesion, while other agents or therapeutics interventions are used to manage the GERD.

Gingivostomatitis

Gingivostomatitis is a disorder involving sores on the mouth and gums that result from a viral infection. Gingivostomatitis is characterized by inflammation of the gums and mucosa and multiple oral ulcers. The inflammation and ulcers are caused by viral infections, particularly those that cause common childhood illness such as herpes virus (cold sores and acute herpetic stomatitis), and Coxsackie viruses (hand, foot and mouth disease and herpangina). These viruses cause shallow ulcers with a grayish or yellowish base and a slightly red margin, on the tissues of the gums (gingiva), the lining of the cheeks (buccal mucosa), or other soft tissues of the mouth. Although this condition can occur in patients of any age, it is particularly common in children.

The oral ulcers caused by these viruses can be very painful. The ulcers are often accompanied by a fever. Overall, the condition can take several weeks to resolve. The recognized treatments for gingivostomatitis focus on reducing the pain caused by the oral ulcers. This is particularly important for children who may refuse food or liquids because of their discomfort, thus making them especially susceptible to dehydration. Compounds of the present invention can be used to treat the pain associated with these oral ulcers.

Oral Thrush

Oral thrush is a fungal infection generally caused by the yeast fungus, *Candida albicans*, in the mucous membranes of the mouth. Strictly speaking, thrush is only a temporary *Candida* infection in the oral cavity of babies. However, the term is used generally to refer to fungal infections in the mouths and throats of children and adults.

*Candida* is present in the oral cavity of almost half of the population. For example, everyone who wears dentures has *Candida*, without necessarily suffering any ill effects. Generally, *Candida* does not create problems until there is a change in the chemistry of the oral cavity such that the growth of *Candida* is favored over the other microorganisms that typically inhabit the mouth and throat. Changes in oral chemistry sufficient to permit the growth of *Candida* may occur as a side effect to taking antibiotics or chemotherapeutics. Overall patient health may also influence the chemistry of the mouth. HIV infection, diabetes, malnutrition, age, and immunodeficiency are exemplary conditions that can shift oral chemistry enough to permit the overgrowth of *Candida* in the mouth and throat.

In addition to shifts in oral chemistry, people whose dentures don't fit well can sustain breaks in the mucous membranes in their mouth. These breaks provide an opportunity for *Candida* infection in the mouth and lips.

Thrush causes white, cream-colored, or yellow spots in the mouth. The spots are slightly raised. If these spots are scraped they tend to bleed. Thrush can be very uncomfortable, and may cause a burning sensation in the mouth and throat. The discomfort may interfere with hydration and nutrition. Furthermore, the discomfort may interfere with proper oral hygiene such as brushing and flossing.

Standard treatment of thrush is by administration of antifungal agents. These agents can be administered directly to the mouth, for example, in the form of pastilles that are sucked or oral suspensions that are held in the mouth before swallowing. Examples include nystatin (e.g., Nystan oral suspension), amphotericin (e.g., Fungilin lozenges) or miconazole (e.g., Daktarin oral gel). In addition to standard antifungal therapy, compounds of the present invention can be administered to manage the pain and discomfort associated with thrush.

Glossitis

Glossitis is an abnormality of the tongue that results from inflammation. Glossitis occurs when there is acute or chronic inflammation of the tongue. It causes the tongue to swell and change color. Finger-like projections on the surface of the tongue (papillae) are lost, causing the tongue to appear smooth. Glossitis has a number of causes including, but not limited to, the following: bacterial infections; viral infections (including oral herpes simplex); injury or trauma; exposure to irritants (e.g., tobacco, alcohol, hot foods, spices); allergic reactions; vitamin or mineral deficiencies (e.g., iron deficiency anemia, pernicious anemia and other B-vitamin deficiencies); or as a side effect of other diseases or disorders.

The symptoms of glossitis include swelling, soreness, and tenderness of the tongue. Additionally, the tongue often changes appearance, becoming smooth and dark red in color. As a consequence of the swelling and discomfort, glossitis often makes chewing, swallowing, and speaking difficult.

The typical treatment for glossitis depends on the underlying cause of the inflammation. Regardless of the particular antibiotics, anti-inflammatories, or anti-viral agents that may be administered to combat the underlying cause of glossitis, compounds according to the present invention may be administered to decrease the pain and discomfort associated with glossitis. Decreasing the pain associated with glossitis is especially important when it interferes with proper nutrition and hydration, or when it interferes with or prevents proper oral hygiene.

Cutaneous Diseases

Oral ulcers may result from any of a number of cutaneous diseases. For example, lichen planus, pemphigus, pemphigoid, and erythema multiforme may lead to oral ulcers. Such oral ulcers may cause significant pain that can be treated using the compounds of the present invention.

Reduction of pain may help facilitate healing. This is especially important for patients with pemphigus and pemphigoid who develop oral ulcers. Such patients are already immunosuppressed, and may thus be more susceptible to opportunistic infections from lesions in the mouth.

Gastrointestinal Diseases

Oral ulcers may result from any of a number of gastrointestinal diseases. Conditions which interfere with proper digestion, management and flow of stomach and other digestive acids, motility, and elimination may lead to oral ulcers and other lesions. In some instances, the oral ulcers are the results of acids or partially digested food refluxing into the esophagus. In other instances, the oral ulcers result from frequent vomiting. In still other instances, oral ulcers occur due to vitamin deficiency, mineral deficiency or other nutritional deficiency secondary to the gastrointestinal disease. In still other instances, oral ulcers are part of the complex etiology that characterizes the gastrointestinal disease.

Oral ulcers resulting from or experienced as part of a gastrointestinal disease may be extremely painful. They may undermine proper nutrition and hydration for a patient whose underlying gastrointestinal disease may already impose multiple limitations on diet. Accordingly, methods and compositions for decreasing the discomfort and pain associated with these oral ulcers offer substantial benefits for patients with an underlying gastrointestinal condition.

Exemplary gastrointestinal conditions which may lead to oral inflammation, lesions, or ulcers include, but are not limited to, Crohn's disease, ulcerative colitis, irritable bowel syndrome, celiac sprue, and dermatitis herpetiformis. The primary symptoms of these conditions may be managed with diet, stress management, and medications. The TRPV3 inhibitors of the present invention may be used to help manage the pain and discomfort of oral inflammation, lesions, or ulcers caused by any of these gastrointestinal conditions.

Rheumatoid Diseases

A consequence of several rheumatoid diseases is oral ulcers. For example, lupus, Behcet's syndrome, Sweet's syndrome, and Reiter's disease may all lead to oral ulcers. Such oral ulcers may cause significant mouth pain that can be treated using the compounds of the present invention.

Sjogren's Syndrome

Dry mouth is a common symptom associated with Sjögren's syndrome. Dry mouth is caused by a decrease in the production of saliva. Saliva is an essential body fluid for protection and preservation of the oral cavity and oral functions. Although saliva is mostly water, it also contains over 60 substances which serve the following important functions: protect, lubricate and cleanse the oral mucosa; aid chewing, swallowing and talking; protect the teeth against decay; protect the mouth, teeth, and throat from infection by bacteria, yeasts, and viruses; support and facilitate our sense of taste.

Given the important functions of saliva, decreased salivation can lead to many problems. If the condition persists for months or years, a patient may develop oral complications such as difficulty swallowing, severe and progressive tooth decay, oral infections (particularly fungal), or combinations of these. Many of the conditions can cause discomfort, in their own right, and may also lead to oral lesions or ulcers.

Several medications are available to help increase salivary secretion in patients with dry mouth. Pilocarpine (Salagen®) and cevimeline (Evoxac®) reduce symptoms of dry mouth and increase salivary secretion. However, these drugs don't prevent tooth decay or treat the oral pain associated with the symptoms or effects of dry mouth. Compounds of the present invention can be used to treat the pain associated with dry mouth.

Vitamin or Mineral Deficiencies

In some instances, vitamin or mineral deficiencies may lead to ulcers or other sores in the mouth. For example, deficiency in vitamin C may lead to the oral lesions characteristic of scurvy. Deficiencies in vitamins B1, B2, B6, or B12 may also lead to oral lesions. Additionally, deficiencies in zinc, folic acid, iron, selenium, or calcium may lead to oral lesions.

In certain embodiments, a vitamin or mineral deficiency is a precipitating factor leading to a canker sore. However, a vitamin or mineral deficiency may also lead to other types of oral ulcers and lesions. Regardless of the nature of the lesion, compounds of the present invention can be used to help manage the associated pain.

Allergies

Allergies can sometimes lead to canker sores and other oral lesions. Oral lesions due to an allergy may be more likely when a person's oral tissues come into contact with the causative allergen. However, contact between the allergen and oral tissue is not necessarily required to produce an oral lesion. Exemplary allergens that can lead to oral lesions include food allergens such as fruits and vegetables (e.g., strawberries, lemons, oranges, pineapples, apples, figs, tomatoes); shellfish; chocolate; nuts; dairy (e.g., milk and cheese); cereal grains (e.g., buckwheat, wheat, oats, rye, barley, gluten protein found in grains); additives (e.g., cinnamonaldehyde (a flavoring agent), benzoic acid (a preservative); toothpastes (e.g., some people have a sensitivity to sodium laurel sulfate found in certain toothpastes and mouthwashes); nonsteroidal anti-inflammatory drugs (NSAIDs; some people have a sensitivity leading to canker sores in response to this class of drug).

Other Exemplary Conditions and Injuries

The foregoing are merely exemplary of diseases and conditions that cause or lead to inflammation, lesions, ulcers, or other sources of oral pain. In other embodiments, the oral pain is due to an injury to the mouth, jaw, lips, gums, or teeth. In other embodiments, the oral pain is due to oral surgery, for example, surgery for cancer, tooth extraction, or jaw remodeling. Other conditions that may lead to oral ulcers, and thus oral pain, include, but are not limited to chickpox, herpes zoster, infectious mononucleosis, syphilis, tuberculosis, acute necrotizing gingivitis, and burning mouth syndrome. Additionally, conditions that lead to a compromised immune system put patients at risk for, among other complications, oral inflammation, lesions, or ulcers. HIV infection, AIDS, and hepatitis are all conditions that undermine the immune system and may lead to oral lesions or ulcers. Additionally, individuals taking immunosuppressants (e.g., organ transplant recipients, bone marrow recipients, stem cells recipients, patients with an autoimmune disease) are at increased risk of developing painful oral lesions.

The invention contemplates the use of TRPV3 inhibitors, according to the present invention, in the treatment of oral pain regardless of the underlying cause. In certain embodiments, TRPV3 inhibitors for treating oral pain can be administered orally, for example, as a paste, mouth wash, gel, or other liquid preparation. In certain embodiments, the paste, mouth wash, gel, or other liquid preparation is administered via a swab, mouth guard, or other dental apparatus. In certain embodiments, the preparation is applied locally to the mouth, but is not otherwise ingested. For example, a mouth wash formulation that is not swallowed may be used. Regardless of the formulation and route of administration, the invention contemplates administration of the subject TRPV3 inhibitors as part of an overall treatment strategy that also includes therapies appropriate for the particular disease or condition that caused the oral inflammation, lesion, or ulcer.

TRPV3 inhibitors may be used to treat oral pain resulting from any of the foregoing injuries, diseases, or conditions. Additionally, Applicants note that the subject TRPV3 inhibitors may also be useful in the treatment of the underlying aforementioned diseases and conditions themselves. Specifically, TRPV3 inhibitors may be useful in the treatment of inflammation, and thus diseases or conditions with an inflammatory component, whether the symptoms manifest themselves in the mouth or in other parts of the body, may themselves be treatable with the subject TRPV3 inhibitors.

Accordingly, the invention contemplates and recognizes that for some conditions the therapeutic affects of administering a TRPV3 inhibitor may be two-fold: (i) decreasing pain (oral or otherwise) associated with one or more symptoms of a disease or condition and (ii) treating the underlying symptoms or disease.

Disease and Injury Models

Compounds that antagonize TRPV3 function may be useful in the prophylaxis and treatment of any of the foregoing injuries, diseases, disorders, or conditions. In addition to in vitro assays of the activity of these compounds, their efficacy can be readily tested in one or more animal models. By way of example, numerous well known animal models exist. One or more suitable animal models (e.g., suitable in light of the particular indication) can be selected.

Pain can be generally categorized as chronic pain and acute pain. The two categories of pain differ in duration, as well as underlying mechanism. Chronic pain is not only persistent, but also does not generally respond well to treatment with currently available analgesics, non-steroidal anti-inflammatory drugs, and opioids.

Two broad sub-categories of chronic pain are neuropathic pain and cancer pain. Wang and Wang (2003) Advanced Drug Delivery Reviews 55: 949-965. Neuropathic pain refers to pain resulting from damage (e.g., from disease, injury, age) to the nervous system (e.g., nerves, spinal cord, CNS, PNS). Cancer-related pain may be caused by tumor infiltration, nerve compression, substances secreted by tumors, or the particular treatment regimen (e.g., radiation, chemotherapeutics, surgery).

Pain is also often classified mechanistically as nociceptive, inflammatory, or neuropathic. Nociceptive pain is pain experienced following, for example, changes or extremes in temperature, exposure to acids, exposure to chemical agents, exposure to force, and exposure to pressure. Reception of painful stimuli sends impulses to the dorsal root ganglia. The response is typically a combination of a reflexive response (e.g., withdrawal from the stimuli) and an emotional reaction. Inflammation is the immune system's response to injury or disease. In response to injury or disease, macrophages, mast cells, neutrophils, and other cells of the immune system are recruited. This infiltration of cells, along with the release of cytokines and other factors (e.g., histamine, serotonin, bradykinin, prostaglandins, ATP, H+, nerve growth factor, TNFα, endothelins, interleukins), can cause fever, swelling, and pain. Current treatments for the pain of inflammation include Cox2 inhibitors and opioids. Neuropathic pain refers to pain resulting from damage (e.g., from disease, injury, age) to the nervous system (e.g., nerves, spinal cord, CNS, PNS). Current treatment for neuropathic pain includes tricyclic antidepressants, anticonvulsants, Na+ channel blockers, NMDA receptor antagonists, and opioids.

There are numerous animal models for studying pain. Generally, the animal models mimic one of the foregoing mechanisms of pain, rather than the pain associated with any one disease or injury. Such models provide evidence of whether a drug or therapy would be effective in treating any of a number of injuries, diseases, or conditions that generate pain via a particular mechanism (e.g., nociceptive, inflammatory, or neuropathic).

The various models use various agents or procedures to simulate pain resulting from injuries, diseases, or other conditions. Blackburn-Munro (2004) Trends in Pharmacological Sciences 25: 299-305 (see, for example, Table 1). Behavioral characteristics of challenged animals can then be observed. Compounds or procedures that may reduce pain in the animals can be readily tested by observing behavioral characteristics of challenged animals in the presence versus the absence of the test compound(s) or procedure.

Exemplary behavioral tests used to study chronic pain include tests of spontaneous pain, allodynia, and hyperalgesia. Id. To assess spontaneous pain, posture, gait, nocifensive signs (e.g., paw licking, excessive grooming, excessive exploratory behavior, guarding of the injured body part, and self-mutilation) can be observed. To measure evoked pain, behavioral responses can be examined following exposure to heat (e.g., thermal injury model).

Exemplary animal models of pain include, but are not limited to, the Chung model, the carageenan induced hyperalgesia model, the Freund's complete adjuvant (CFA) induced hyperalgesia model, the thermal injury model, the formalin model and the Bennett Model. The Chung model of neuropathic pain (without inflammation) involves ligating one or more spinal nerves. Chung et al. (2004) Methods Mol Med 99: 35-45; Kim and Chung (1992) Pain 50: 355-363. Ligation of the spinal nerves results in a variety of behavioral changes in the animals including heat hyperalgesia, cold allodynia, and ongoing pain. Compounds that antagonize TRPV3 can be administered to ligated animals to assess whether they diminish these ligation induced behavioral changes in comparison to that observed in the absence of compound.

Carageenan induced hyperalgesia and Freund's complete adjuvent (CFA) induced hyperalgesia are models of inflammatory pain. Walker et al. (2003) Journal of Pharmacol Exp Ther 304: 56-62; McGaraughty et al. (2003) Br J Pharmacol 140: 1381-1388; Honore et al. (2005) J Pharmacol Exp Ther. Compounds that antagonize TRPV3 can be administered to carrageenan or FCA challenged animals to assess whether they diminish thermal hyperalgesia in comparison to that observed in the absence of compound. In addition, the ability of compounds that antagonize TRPV3 function to diminish cold and/or mechanical hypersensitivity can also be assessed in these models. Typically, the carrageenan induced hyperalgesia model is believed to mimic acute inflammatory pain and the CFA model is believed to mimic chronic pain and chronic inflammatory pain.

The Bennett model uses prolonged ischemia of the paw to mirror chronic pain. Xanthos et al. (2004) J Pain 5: S1. This provides an animal model for chronic pain including post-operative pain, complex regional pain syndrome, and reflex sympathetic dystrophy. Prolonged ischemia induces behavioral changes in the animals including hyperalgesia to mechanical stimuli, sensitivity to cold, pain behaviors (e.g., paw shaking, licking, and/or favoring), and hyperpathia. Compounds that antagonize TRPV3 can be administered to challenged animals to assess whether they diminish any or all of these behaviors in comparison to that observed in the absence of compound. Similar experiments can be conducted in a thermal injury model which can be used to mimic post-operative pain.

Additional models of neuropathic pain include central pain models based on spinal cord injury. Chronic pain is generated by inducing a spinal cord injury, for example, by dropping a weight on a surgically exposed area of spinal cord (e.g., weight-drop model). Spinal cord injury can additionally be induced by crushing or compressing the spinal cord, by delivering neurotoxin, using photochemicals, or by hemisecting the spinal cord. Wang and Wang (2003).

Additional models of neuropathic pain include peripheral nerve injury models. The term peripheral neuropathy encompasses a variety of diseases, conditions, and injuries. One of skill in the art can readily select an appropriate model in light of the particular condition or disease under investigation. Exemplary models include, but are not limited to, the neuroma model, the Bennett model, the Seltzer model, the Chung model (ligation at either L5 or L5/L6), the sciatic cryoneurolysis model, the inferior caudal trunk resection model, and the sciatic inflammatory neuritis model. Id.

Exemplary models of neuropathic pain associated with particular diseases are also available. Diabetes and shingles are two diseases often accompanied by neuropathic pain. Even following an acute shingles episodes, some patients continue to suffer from postherpetic neuralgia and experience persistent pain lasting years. Neuropathic pain caused by shingles and/or postherpetic neuralgia can be studied in the postherpetic neuralgia model (PHN). Diabetic neuropathy can be studied in diabetic mouse models, as well as chemically induced models of diabetic neuropathy. Wang and Wang (2003).

As outlined above, cancer pain may have any of a number of causes, and numerous animal models exist to examine cancer pain related to, for example, chemotherapeutics or tumor infiltration. Exemplary models of toxin-related cancer pain include the vincristine-induced peripheral neuropathy model, the taxol-induced peripheral neuropathy model, and the cisplatin-induced peripheral neuropathy model. Wang and Wang (2003). An exemplary model of cancer pain caused by tumor infiltration is the cancer invasion pain model (CIP). Id.

Primary and metastatic bone cancers are associated with tremendous pain. Several models of bone cancer pain exist including the mouse femur bone cancer pain model (FBC), the mouse calcaneus bone cancer pain model (CBC), and the rat tibia bone cancer model (TBC). Id.

An additional model of pain is the formalin model. Like the carrageenan and CFA models, the formalin model involves injection of an irritant intradermally or intraperitoneally into an animal. Injection of formalin, a 37 percent solution of formaldehyde, is the most commonly used agent for intradermal paw injection (the formalin test). Injection of a 0.5 to 15 percent solution of formalin (usually about 3.5%) into the dorsal or plantar surface of the fore- or hindpaw produces a biphasic painful response of increasing and decreasing intensity for about 60 minutes after the injection. Typical responses include the paw being lifted, licked, nibbled, or shaken. These responses are considered nociceptive. The initial phase of the response (also known as the Early Phase), which lasts 3 to 5 minutes, is probably due to direct chemical stimulation of nociceptors. This is followed by 10 to 15 minutes during which animals display little behavior suggestive of nociception. The second phase of this response (also known as the Late Phase) starts about 15 to 20 minutes after the formalin injection and lasts 20 to 40 minutes, initially rising with both number and frequency of nociceptive behaviors, reaching a peak, then falling off. The intensities of these nociceptive behaviors are dependent on the concentration of formalin used The second phase involves a period of sensitization during which inflammatory phenomena occur. The two phases of responsiveness to formalin injection makes the formalin model an appropriate model for studying mociceptive and acute inflammatory pain. It may also model, in some respects, neuropathic pain.

In addition to any of the foregoing models of chronic pain, compounds that antagonize TRPV3 function can be tested in one or more models of acute pain. Valenzano et al. (2005) Neuropharmacology 48: 658-672. Regardless of whether compounds are tested in models of chronic pain, acute pain, or both, these studies are typically (though not exclusively) conducted, for example, in mice, rats, or guinea pigs. Additionally, compounds can be tested in various cell lines that provide in vitro assays of pain. Wang and Wang (2003).

The foregoing animal models are relied upon extensively in the study of pain. The following provide additional exemplary references describing the use of these models in the study of pain: thermal injury model (Jones and Sorkin, 1998, Brain Res 810: 93-99; Nozaki-Taguchi and Yaksh, 1998, Neuroscience Lett 254: 25-28; Jun and Yaksh, 1998, Anesth Analg 86: 348-354), formalin model (Yaksh et al., 2001, J Appl Physiol 90: 2386-2402), carrageenan model (Hargreaves et al., 1988, Pain 32: 77-88), and CFA model (Nagakura et al., 2003, J Pharmacol Exp Ther 306: 490-497).

For testing the efficacy of TRPV3 antagonists for the treatment of cough, experiments using the conscious guinea pig model of cough can be readily conducted. Tanaka and Maruyama (2003) Journal Pharmacol Sci 93: 465-470; McLeod et al. (2001) Br J Pharmacol 132: 1175-1178. Briefly, guinea pigs serve as a useful animal model for cough because, unlike other rodents such as mice and rats, guinea pigs actually cough. Furthermore, guinea pig coughing appears to mimic human coughing in terms of the posture, behavior, and appearance of the coughing animal.

To induce cough, conscious guinea pigs are exposed to an inducing agent such as citric acid or capsaicin. The response of the animal is measured by counting the number of coughs. The effectiveness of a cough suppressing agent, for example a compound that inhibits TRPV3, can be measured by administering the agent and assessing the ability of the agent to decrease the number of coughs elicited by exposure to citric acid, capsaicin, or other similar cough-inducing agent. In this way, TRPV3 inhibitors for use in the treatment of cough can be readily evaluated and identified.

Additional models of cough include the unconscious guinea pig model. Rouget et al. (2004) Br J Pharmacol 141: 1077-1083. Either of the foregoing models can be adapted for use with other animals capable of coughing. Exemplary additional animals capable of coughing include cats and dogs.

As detailed above, TRPV3 inhibitors can be used to treat the symptoms of pain associated with pancreatitis. The efficacy of TRPV3 inhibitors in pancreatitis pain management may be tested in one or more animal models. Inhibitors may be tested in general animal models of pain, for example models of inflammatory pain or visceral pain. Alternatively or additionally, TRPV3 inhibitors may be tested in animal models that specifically mimic pain accompanying pancreatitis or other pancreatic injury.

Several rat models of pancreatic pain have recently been described (Lu, 2003, Anesthesiology 98(3): 734-740; Winston et al., 2003, Journal of Pain 4(6): 329-337). Lu et al. induced pancreatitis by systemic delivery of dibutylin dichloride in rats. Rats showed an increase in withdrawal events after von Frey filament stimulation of the abdomen and decreased withdrawal latency after thermal stimulation during a period of 7 days. The pain state induced in these animals was also characterized by increased levels of substance P in spinal cords (Lu, et al., 2003). To test the efficacy of a TRPV3 inhibitor in this model, a TRPV3 inhibitor can be administered following or concurrently with delivery of dibutylin dichloride. Control animals can be administered a carrier or a known pain reliever. Indicia of pain can be measured. Efficacy of a TRPV3 inhibitor can be evaluated by comparing the indicia of pain observed in animals receiving a TRPV3 inhibitor to that of animals that did not receive a TRPV3 inhibitor. Additionally, efficacy of a TRPV3 inhibitor can be compared to that of known pain medicaments.

The efficacy of von Frey filament testing as a means to measure nociceptive behavior was also shown by inducing pancreatitis by systemic L-arginine administration (Winston et al., 2003). The efficacy of a TRPV3 inhibitor can similarly be tested following pancreatitis induced by systemic L-arginine administration.

Lu et al. also described direct behavioral assays for pancreatic pain using acute noxious stimulation of the pancreas via an indwelling ductal canula in awake and freely moving rats. These assays included cage crossing, rearing, and hind limb extension in response to intrapancreatic bradykinin infusion. Intrathecal administration of either D-APV (NMDA receptor antagonist) or morphine alone partially reduced visceral pain behaviors in this model. Combinations of both reduced pain behaviors to baseline. The efficacy of a TRPV3 inhibitor can similarly be tested in this system.

Any of the foregoing animal models may be used to evaluate the efficacy of a TRPV3 inhibitor in treating pain associated with pancreatitis. The efficacy can be compared to a no treatment or placebo control. Additionally or alternatively, efficacy can be evaluated in comparison to one or more known pain relieving medicaments.

Optimizing the Treatment of Pain

TRPV3 inhibitors, according to the present invention, can be used in the treatment of a variety of injuries, diseases, conditions, and disorders. One important therapeutic use for TRPV3 inhibitors is in the treatment of pain. As illustrated by the extensive list of injuries, conditions, and diseases for which pain is a significant and sometimes debilitating symptom, improved methods and compositions for use in the treatment of pain provide substantial benefits for an enormous range of patients. Such methods and compositions have the potential to improve the quality of care and the quality of life for patients afflicted with a diverse range of injuries, diseases, and conditions.

TRPV3 is a good target for modulating pain. TRPV3 is expressed in tissues that contribute to transmission of painful stimuli. Additionally, TRPV3 expression is upregulated, for example in dorsal root ganglia, following injury. Finally, TRPV3 knockout mice exhibit abnormal responses to painful stimuli. These characteristics of TRPV3 suggest that inhibitors of TRPV3 will be useful in the treatment of pain.

Many of these characteristics are shared by TRPV1, and inhibitors of TRPV1 are being developed for the treatment of pain. However, although TRPV1 and TRPV3 share certain characteristics consistent with the development of effective therapeutics for the treatment of pain, TRPV3 possesses certain characteristics that makes it a better target for therapeutic compounds for the treatment of pain. For example, TRPV3 sensitizes upon repeated stimulation. In contrast, TRPV1 desensitizes upon repeated stimulation with the agonist capsaicin. In addition to expression in dorsal root ganglia, TRPV3 is expressed in skin. Given the significant involvement of skin in many types of pain, this expression pattern is suggestive of potential effectiveness of TRPV3 inhibitors in pain involving the skin.

An important issue with the treatment of pain is how to manage pain while reducing the side effects experienced with many analgesics. For example, although many opiates and other narcotics effectively diminish pain, patients are often unable to drive, work, or concentrate while taking these medications. Thus, while opiates such as morphine or dilaudin may be suitable for short term use or for use during hospitalization, they are not optimal for long term use. Additionally, opiates and other narcotics are habit forming, and patients typically develop a tolerance for these drugs. These characteristics of opioids and other narcotics make them sub-optimal for pain management.

The present invention provides TRPV3 inhibitors for use in vitro and in vivo. The present invention also provides compositions and pharmaceutical compositions comprising particular classes of compounds that inhibit TRPV3 activity. In certain embodiments, the subject TRPV3 inhibitors are selective. In other words, in certain embodiments, the compound inhibits TRPV3 activity preferentially over the activity of other ion channels. In certain embodiments, the compound inhibits TRPV3 activity preferentially over TRPV1, TRPV2, TRPV4, and/or TRPM8 activity. In certain other embodiments, the compound is selected because it cross reacts with one or more other TRP channels involved with pain. For example, in certain embodiments, the compound inhibits the activity of TRPV3 and also inhibits the activity of one or more of TRPV1, TRPV2, TRPV4, and TRPM8.

Combination Therapy

Another aspect of the invention provides a conjoint therapy wherein one or more other therapeutic agents are administered with the TRPV3 modulators. Such conjoint treatment may be achieved by way of the simultaneous, sequential, or separate dosing of the individual components of the treatment.

In certain embodiments, a compound of the invention is conjointly administered with an analgesic. Suitable analgesics include, but are not limited to, opioids, glucocorticosteroids, non-steroidal anti-inflammatories, naphthylalkanones, oxicams, para-aminophenol derivatives, propionic acids, propionic acid derivatives, salicylates, fenamates, fenamate derivatives, pyrozoles, and pyrozole derivatives. Examples of such analgesic compounds include, but are not limited to, codeine, hydrocodone, hydromorphone, levorpharnol, morphine, oxycodone, oxymorphone, butorphanol, dezocine, nalbuphine, pentazocine, etodolac, indomethacin, sulindac, tolmetin, nabumetone, piroxicam, acetaminophen, fenoprofen, flurbiprofen, ibuprofen, ketoprofen, naproxen, diclofenac, oxaprozin, aspirin, diflunisal, meclofenamic acid, mefanamic acid, prednisolone, and dexamethasone. Preferred analgesics are non-steroidal anti-inflammatories and opioids (preferably morphine).

In certain embodiments, a compound of the invention is conjointly administered with a non-steroidal anti-inflammatory. Suitable non-steroidal anti-inflammatory compounds include, but are not limited to, piroxicam, diclofenac, etodolac, indomethacin, ketoralac, oxaprozin, tolmetin, naproxen, flubiprofen, fenoprofen, ketoprofen, ibuprofen, mefenamic acid, sulindac, apazone, phenylbutazone, aspirin, celecoxib and rofecoxib.

In certain embodiments, a compound of the invention is conjointly administered with an antiviral agent. Suitable antiviral agents include, but are not limited to, amantadine, acyclovir, cidofovir, desciclovir, deoxyacyclovir, famciclovir, foscamet, ganciclovir, penciclovir, azidouridine, anasmycin, amantadine, bromovinyldeoxusidine, chlorovinyldeoxusidine, cytarbine, didanosine, deoxynojirimycin, dideoxycitidine, dideoxyinosine, dideoxynucleoside, edoxuidine, enviroxime, fiacitabine, foscamet, fialuridine, fluorothymidine, floxuridine, hypericin, interferon, interleukin, isethionate, nevirapine, pentamidine, ribavirin, rimantadine, stavirdine, sargramostin, suramin, trichosanthin, tribromothymidine, trichlorothymidine, vidarabine, zidoviridine, zalcitabine 3-azido-3-deoxythymidine, 2',3'-dideoxyadenosine (ddA), 2',3'-dideoxyguanosine (ddG), 2',3'-dideoxycytidine (ddC), 2',3'-dideoxythymidine (ddT), 2',3'-dideoxy-dideoxythymidine (d4T), 2'-deoxy-3'-thia-cytosine (3TC or lamivudime), 2',3'-dideoxy-2'-fluoroadenosine, 2',3'-dideoxy-2'-fluoroinosine, 2',3'-dideoxy-2'-fluorothymidine, 2',3'-dideoxy-2'-fluorocytosine, 2',3'-dideoxy-2',3'-didehydro-2'-fluorothymidine (Fd4T), 2',3'-dideoxy-2'-beta-fluoroadenosine (F-ddA), 2',3'-dideoxy-2'-beta-fluoro-inosine (F-ddI), and 2',3'-dideoxy-2'-beta-fluorocytosine (F-ddC), trisodium phosphomonoformate, trifluorothymidine, 3'azido-3'thymidine (AZT), dideoxyinosine (ddI), and idoxuridine.

In certain embodiments, a compound of the invention is conjointly administered with an antibacterial agent. Suitable antibacterial agents include, but are not limited to, amanfadine hydrochloride, amanfadine sulfate, amikacin, amikacin sulfate, amoglycosides, amoxicillin, ampicillin, amsamycins, bacitracin, beta-lactams, candicidin, capreomycin, carbenicillin, cephalexin, cephaloridine, cephalothin, cefazolin, cephapirin, cephradine, cephaloglycin, chilomphenicols, chlorhexidine, chloshexidine gluconate, chlorhexidine hydrochloride, chloroxine, chlorquiraldol, chlortetracycline, chlortetracycline hydrochloride, ciprofloxacin, circulin, clindamycin, clindamycin hydrochloride, clotrimazole, cloxacillin, demeclocycline, diclosxacillin, diiodohydroxyquin, doxycycline, ethambutol, ethambutol hydrochloride, erythromycin, erythromycin estolate, erhmycin stearate, farnesol, floxacillin, gentamicin, gentamicin sulfate, gramicidin, giseofulvin, haloprogin, haloquinol, hexachlorophene, iminocylcline, iodochlorhydroxyquin, kanamycin, kanamycin sulfate, lincomycin, lineomycin, lineomycin hydrochloride, macrolides, meclocycline, methacycline, methacycline hydrochloride, methenine, methenamine hippurate, methenamine mandelate, methicillin, metonidazole, miconazole, miconazole hydrochloride, minocycline, minocycline hydrochloride, mupirocin, nafcillin, neomycin, neomycin sulfate, netimicin, netilmicin sulfate, nitrofurazone, norfloxacin, nystatin, octopirox, oleandomycin, orcephalosporins, oxacillin, oxyteacline, oxytetracycline hydrochloride, parachlorometa xylenol, paromomycin, paromomycin sulfate, penicillins, penicillin G, penicillin V, pentamidine, pentamidine hydrochloride, phenethicillin, polymyxins, quinolones, streptomycin sulfate, tetracycline, tobramycin, tolnaftate, triclosan, trifampin, rifamycin, rolitetracycline, spectinomycin, spiramycin, struptomycin, sulfonamide, tetracyclines, tetracycline, tobramycin, tobramycin sulfate, triclocarbon, triclosan, trimethoprim-sulfamethoxazole, tylosin, vancomycin, and yrothricin.

In certain embodiments, a compound of the invention is conjointly administered with a cough suppressant, decongestant, or expectorant.

Examples of retinoids that be administered with the subject TRPV3 inhibitors, e.g., where the TRPV3 inhibitor can be used to reduce the pain and/or inflammatory effect of the retinoid, include, but are not limited to, compounds such as retinoic acid (both cis and trans), retinol, adapalene, vitamin A and tazarotene. Retinoids are useful in treating acne, psoriasis, rosacea, wrinkles and skin cancers and cancer precursors such as melanoma and actinic keratosis.

Similarly, the subject TRPV3 inhibitors can be used in conjunction with keratolytic agents include benzoyl peroxide, alpha hydroxyacids, fruit acids, glycolic acid, salicylic acid, azelaic acid, trichloroacetic acid, lactic acid and piroctone.

The subject TRPV3 inhibitors can also be administered along with depilatory agents (hair loss).

The subject TRPV3 inhibitors can be used with anti-acne agents, anti-eczema agents and anti-psoratic agents. Compounds particularly useful in treating acne include azelaic acid (an aliphatic diacid with antiacne properties), anthralin (a diphenolic compound with antifungal and antipsoriatic properties), and masoprocol (nordihydroguaiaretic acid, a tetraphenolic compound with antioxidant properties, also useful in the treatment of actinic keratosis) and analogs thereof (such as austrobailignan 6, oxoaustrobailignan 6,4'-O-methyl-7,7'-dioxoaustrobailignan 6, macelignan, demethyldihydroguaiaretic acid, 3,3',4-trihydroxy-4'-methoxylignan, Saururenin, 4-hydroxy-3,3',4'-trimethoxylignan, and isoanwulignan). Anti-eczema agents include pimecrolimus and tacrolimus. Anti-psoriatic active agents suitable for use in the present invention include retinoids (including isomers and derivatives of retinoic acid, as well as other compounds that bind to the retinoic acid receptor, such as retinoic acid, acitretin, 13-cis-retinoic acid (isotretinoin), 9-cis-retinoic acid, tocopheryl-retinoate (tocopherol ester of retinoic acid (trans- or cis-)), etretinate, motretinide, 1-(13-cis-retinoyloxy)-2-propanone, 1-(13-cis-retinoyloxy)-3-decanoyloxy-2-propanone, 1,3-bis-(13-cis-retinoyloxy)-2-propanone, 2-(13-cis-retinoyloxy)-acetophenone, 13-cis-retinoyloxymethyl-2,2-dimethyl propanoate, 2-(13-cis-retinoyloxy)-n-methylacetamide, 1-(13-cis-retinoyloxy)-3-hydroxy-2-propanone, 1-(13-cis-retinoyloxy)-2,3-dioleoylpropanone, succinimdyl 13-cis-retinoate, adapalene, and tazarotene), salicylic acid (monoammonium salt), anthralin, 6-azauridine, vitamin D derivatives (including but not limited to Rocaltrol (Roche Laboratories), EB 1089 (24α,26α,27α-trihomo-22,24-diene-1α,25-$(OH)_2$-$D_3$), KH 1060 (20-epi-22-oxa-24α,26α,27α-trihomo-1α,25-$(OH)_2$-$D_3$), MC 1288, GS 1558, CB 1093, 1,25-$(OH)_2$-16-ene-$D_3$, 1,25-$(OH)_2$-16-ene-23-yne-$D_3$, and 25-(OH)2-16-ene-23-yne-$D_3$, 22-oxacalcitriol; 1α-(OH)$D_5$ (University of Illinois), ZK 161422 and ZK 157202 (Institute of Medical Chemistry-Schering AG), alfacalcidol, calcifediol, calcipotriol (calcipotriene), maxacalcitriol, colecalciferol, doxercalciferol, ergocalciferol, falecalcitriol, lexacalcitol, maxacalcitol, paricalcitol, secalciferol, seocalcitol, tacalcitol, calcipotriene, calcitriol, and other analogs as disclosed in U.S. Pat. No. 5,994,332), pyrogallol, and tacalcitol.

The subject TRPV3 inhibitors can also be administered with vitamins and derivatives thereof including Vitamin A, ascorbic acid (Vitamin C), alpha-tocopherol (Vitamin E), 7-dehydrocholesterol (Vitamin D), Vitamin K, alpha-lipoic acid, lipid soluble anti-oxidants, and the like.

The subject TRPV3 inhibitors can also be used with skin protectants, such allantoin and esculin.

In certain embodiments, two or more compounds of the invention are conjointly administered. When two or more compounds of the invention are conjointly administered, the two or more compounds may have a similar selectivity profile and functional activity, or the two or more compounds may have a different selectivity profile and functional activity. By way of example, the two or more compounds may both be approximately 10, 100, or 1000 fold selective for antagonizing a function of TRPV3 over TRPV1, TRPV5, and TRPV6 (e.g., the two or more compounds have a similar selectivity profile), and further may inhibit a function of TRPV3 with a similar $IC_{50}$ (e.g., a similar functional activity). Alternatively, the one of the two or more compounds may selectively inhibit TRPV3 while the other of the two or more compounds inhibits both TRPV3 and TRPV1 (e.g., the two or more compounds have differing selectivity profiles). Administration of combinations of two or more compounds of the invention having similar or differing properties are contemplated.

In certain embodiments, a compound of the invention is conjointly administered with one or more additional compounds that antagonize the function of a different channel. By way of example, a compound of the invention may be conjointly administered with one or more compounds that antagonize TRPV1 and/or TRPV4. The compound(s) that antagonize TRPV1 or TRPV4 may be selective for TRPV1 or TRPV4 (e.g, inhibit TRPV1 or TRPV4 10, 100, or 1000 fold more strongly than TRPV3). Alternatively, the compound(s) that antagonize TRPV1 or TRPV4 may cross react with other TRP channels.

In certain other embodiments, a compound of the invention is conjointly administered with one or more additional agents or therapeutic regimens appropriate for the particular injury, disease, condition, or disorder being treated.

When combinations of a TRPV3 inhibitor and one or more other compounds, agents, or therapeutic regimens are administered, the invention contemplates administration via the same route of administration or via differing routes of administration.

Pharmaceutical Compositions While it is possible for a compound of the present invention to be administered alone, it is preferable to administer the compound as a pharmaceutical formulation (composition). The compounds according to the invention may be formulated for administration in any convenient way for use in human or veterinary medicine. In certain embodiments, the compound included in the pharmaceutical preparation may be active itself, or may be a prodrug, e.g., capable of being converted to an active compound in a physiological setting.

Regardless of the route of administration selected, the compounds of the present invention, which may be used in a suitable hydrated form, and/or the pharmaceutical compositions of the present invention, are formulated into pharmaceutically acceptable dosage forms such as described below or by other conventional methods known to those of skill in the art.

Thus, another aspect of the present invention provides pharmaceutically acceptable compositions comprising a therapeutically effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions); tablets; boluses; powders; granules; pastes for application to the tongue, teeth, lips, gums; mouth washes; gels; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) for inhalation. However, in certain embodiments the subject compounds may be simply dissolved or suspended in sterile water. In certain embodiments, the pharmaceutical preparation is non-pyrogenic, i.e., does not elevate the body temperature of a patient.

The phrase "therapeutically effective amount" as used herein means that amount of a compound, material, or composition comprising a compound of the present invention which is effective for producing some desired therapeutic effect by inhibiting TRPV3 function in at least a sub-population of cells in an animal and thereby blocking the biological consequences of that function in the treated cells, at a reasonable benefit/risk ratio applicable to any medical treatment.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject antagonists from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As set out above, certain embodiments of the present compounds may contain a basic functional group, such as amino or alkylamino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. Oral formulations include those delivered to and maintained in the mouth without swallowing, as well as formulations that are swallowed as part of or following use. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for oral administration may be administered directly to the mouth in the presence or absence of a device to aid administration or local delivery. For example, a liquid formulation or suspension may be directly delivered via a mouthwash. Alternatively, the liquid formulation or suspension may be directly applied to all or a portion of the mouth using a syringe or swab. In another embodiment, an oral formulation may be applied to a mouth guard or other dental device, and delivered to the mouth via the mouth guard or device. The present invention contemplates that preparations suitable for oral delivery can be formulated to facilitate any of these modes of delivery. For any of the foregoing, the oral formulation may optionally be ingested or may be maintained in the mouth and later expectorated.

It is known that sterols, such as cholesterol, will form complexes with cyclodextrins. Thus, in preferred embodiments, where the inhibitor is a steroidal alkaloid, it may be formulated with cyclodextrins, such as α-, β- and γ-cyclodextrin, dimethyl-β cyclodextrin and 2-hydroxypropyl-β-cyclodextrin.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W.H. Freedman and CO., San Francisco, U.S.A., 1969 or "Livestock Feeds and Feeding" O and B books, Corvallis, Oreg., U.S.A., 1977).

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous, intracerebroventricular and subcutaneous doses of the compounds of this invention for a patient will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable and/or sterile carriers and can also be administered in conjunction with other agents. Exemplary other agents include penicillins, cephalosporins, aminoglycosides, glycopeptides, anti-inflammatories, anti-virals, anti-fungals, anti-bacterials, or any agents appropriate for the treatment of the particular injury, disease, or condition. Conjunctive therapy, thus includes sequential, simultaneous and separate administration of the active compound in a way that the therapeutic effects of the first administered compound are still detectable when the subsequent therapy is administered.

Synthetic Schemes and Identification of Active Antagonists

Combinatorial Libraries

The compounds of the present invention, particularly libraries of variants having various representative classes of substituents, are amenable to combinatorial chemistry and other parallel synthesis schemes (see, for example, PCT WO 94/08051). The result is that large libraries of related compounds, e.g. a variegated library of compounds represented above, can be screened rapidly in high throughput assays in order to identify potential TRPV3 agonist or antagonist lead compounds, as well as to refine the specificity, toxicity, and/or cytotoxic-kinetic profile of a lead compound. For instance, TRPV3 bioactivity assays, such as those disclosed herein, can be used to screen a library of compounds for those having agonist activity or antagonist activity towards TRPV3.

Simply for illustration, a combinatorial library for the purposes of the present invention is a mixture of chemically related compounds that may be screened together for a desired property. The preparation of many related compounds in a single reaction greatly reduces and simplifies the number of screening processes that need to be carried out. Screening for the appropriate physical properties can be done by conventional methods.

Diversity in the library can be created at a variety of different levels. For instance, the substrate aryl groups used in the combinatorial reactions can be diverse in terms of the core aryl moiety, e.g., a variegation in terms of the ring structure, and/or can be varied with respect to the other substituents.

A variety of techniques are available in the art for generating combinatorial libraries of small organic molecules such as the subject compounds. See, for example, Blondelle et al. (1995) *Trends Anal. Chem.* 14:83; the Affymax U.S. Pat. Nos. 5,359,115 and 5,362,899: the Ellman U.S. Pat. No. 5,288, 514: the Still et al. PCT publication WO 94/08051; the ArQule U.S. Pat. Nos. 5,736,412 and 5,712,171; Chen et al. (1994) *JACS* 116:2661: Kerr et al. (1993) *JACS* 115:252; PCT publications WO92/10092, WO93/09668 and WO91/07087; and the Lerner et al. PCT publication WO93/20242). Accordingly, a variety of libraries on the order of about 100 to 1,000,000 or more diversomers of the subject compounds can be synthesized and screened for particular activity or property.

Many variations on the above and related pathways permit the synthesis of widely diverse libraries of compounds that may be tested as inhibitors or agonists of TRPV3.

EXAMPLES

Example 1

Synthesis of Compounds of the Invention

Synthesis of 2-Chloro-1-(8-methyl-3,4-dihydro-2H-quinolin-1-yl)ethanone (2)

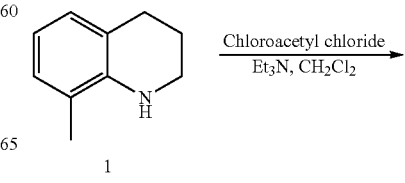

1

2-Chloro-1-(8-methyl-3,4-dihydro-2H-quinolin-1-yl)ethanone (2)

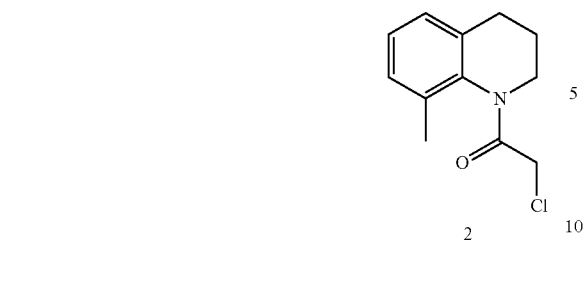

To a solution of 8-methyl-1,2,3,4-tetrahydroquinoline (1) (2.77 g, 18.8 mmol) in dry $CH_2Cl_2$ (50 mL) at 0° C. was added chloroacetyl chloride (1.80 mL, 22.6 mmol) followed by dropwise addition of $Et_3N$ (6.30 mL, 45.2 mmol). The reaction was stirred overnight under $N_2$. The reaction mixture was then diluted with $CH_2Cl_2$ (50 mL), washed with water (2×15 mL), and saturated NaCl (15 mL). Dried over $MgSO_4$, filtered, and concentrated to give compound 2 (3.7 g). This crude material was used in subsequent reactions without further purification.

Synthesis of 2-Chloro-1-(3,4-dihydro-2H-quinolin-1-yl)ethanone (4)

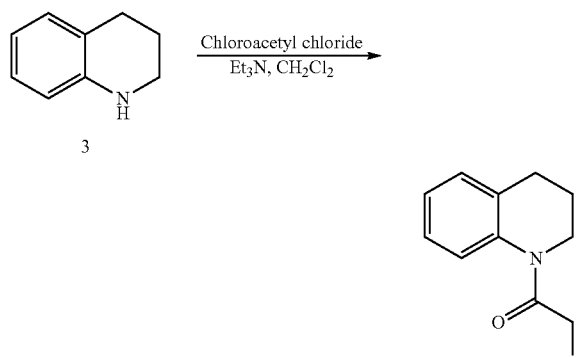

2-Chloro-1-(3,4-dihydro-2H-quinolin-1-yl)ethanone (4)

To a solution of 1,2,3,4-tetrahydroquinoline (3, 2.00 g, 15.0 mmol) in dry $CH_2Cl_2$ (30 mL) at 0° C. was added chloroacetyl chloride (1.80 g, 16.0 mmol) followed by dropwise addition of $Et_3N$ (2.50 mL, 18.0 mmol). The reaction was stirred overnight under $N_2$. The reaction mixture was diluted with $CH_2Cl_2$ (50 mL), washed with 5% HCl (15 mL), water (2×15 mL), and saturated NaCl (15 mL). Dried over $MgSO_4$, filtered, and concentrated to give 3.05 g of 4. This crude material was used in subsequent reactions without further purification.

Synthesis of 2,3,4,5-Tetrahydro-1H-benzo[b]azepine

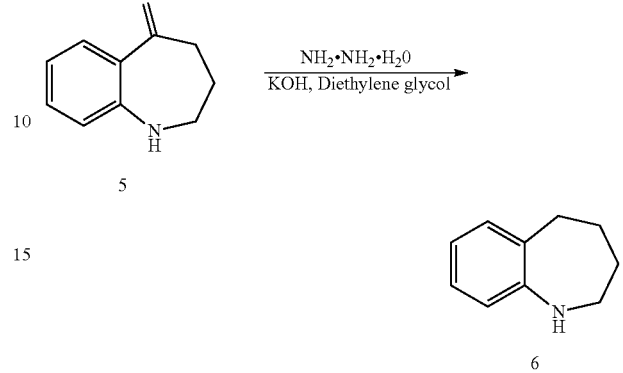

Ref: *J. Med. Chem.*, 2000, 43 (23) 4392

2,3,4,5-Tetrahydro-1H-benzo[b]azepine (6)

A mixture of 1,2,3,4-tetrahydro-benzo[b]azepin-5-one (5) (1.58 g, 9.80 mmol), hydrazine monohydrate (1.92 mL, 40.0 mmol), and KOH (3.3 g, 58.8 mmol) in diethylene glycol (50 mL) was heated to reflux for 6 hr under a $N_2$ atmosphere. After cooling, the reaction was poured onto ice-cold water, neutralized with 1N HCl, and extracted with EtOAc. All the organics were washed with water and saturated NaCl. Dried over $MgSO_4$, filtered, and concentrated to yield compound 6 (0.69 g). This crude material was used in the next step with out further purification.

Synthesis of 5,6-Dichloro-2-mercapto benzothiazole

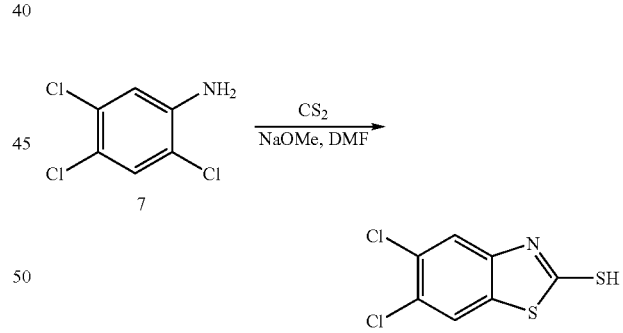

Ref: U.S. Pat. No. 4,431,813 (Feb. 14, 1984)

5,6-Dichloro-2-mercapto benzothiazole (8)

To a suspension of $CS_2$ (0.64 mL, 10.6 mmol) and sodium methylate (0.55 g, 10.2 mmol) in DMF (10 mL) was added 2,4,5-trichloroaniline (7, 1.00 g, 5.09 mmol) in DMF (5 mL) under $N_2$. The reaction mixture was heated at 110-120° C. for 16 h. After cooling, the reaction mixture was diluted with water (30 mL) and acidified with 1N HCl. The precipitate was collected by filtration, washed with water, and dried over

Synthesis of 5-Methyl-2-mercapto benzothiazole

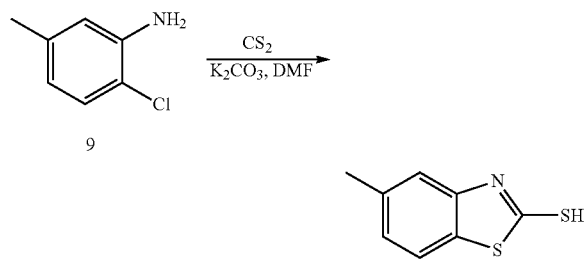

5-Methyl-2-mercapto benzothiazole (10)

To a suspension of 2-chloro-5-methyl aniline (9, 1.00 g, 7.06 mmol) and $K_2CO_3$ (2.80 g, 28.2 mmol) in DMF (20 mL) was added $CS_2$ (0.50 mL, 8.50 mmol) under $N_2$ at room temperature. The reaction mixture was heated at 150° C. for 16 h. After cooling, the reaction mixture was diluted with water (30 mL) and acidified with 1N HCl. The precipitate was collected by filtration, washed with water, and dried over $P_2O_5$ under vacuum to yield compound 10 (0.35 g, 27%).

Synthesis of 5-Nitro-2-mercapto benzothiazole

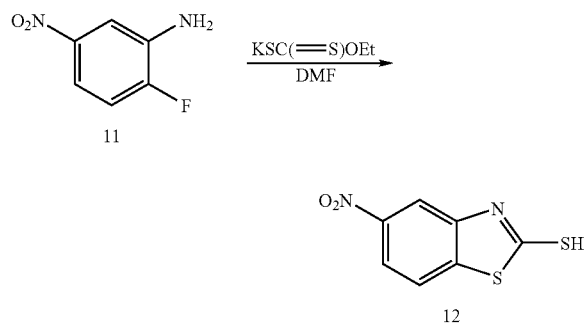

Ref: *J. Heterocyclic Chem.* 42 (4) 727, 2005

5-Nitro-2-mercapto benzothiazole (12)

A mixture of 2-fluoro-5-nitro aniline (11, 1.00 g, 6.40 mmol) and potassium O-ethyl dithiocarbonate (1.53 g, 9.60 mmol) in DMF (15 mL) was heated overnight at 110-110° C. under $N_2$. After cooling, the reaction mixture was diluted with water and acidified with 1N HCl. The precipitate was collected by filtration, washed with water, and dried under vacuum to yield compound 12 (1.27 g, 94%).

Synthesis of 5-Cyano-2-mercaptobenzothiazole

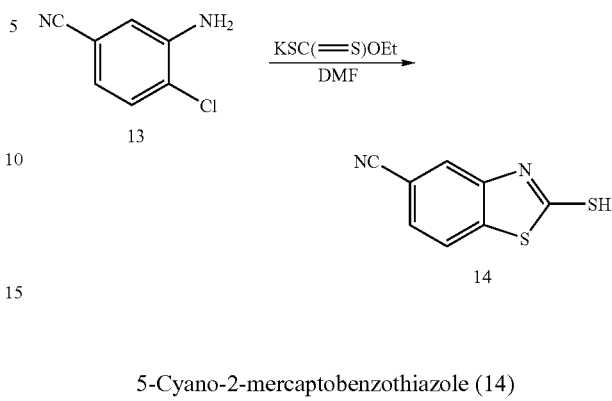

5-Cyano-2-mercaptobenzothiazole (14)

A mixture of 3-amino-4-chloro benzonitrile (13, 0.50 g, 3.28 mmol) and potassium O-ethyl dithiocarbonate (1.05 g, 6.55 mmol) in DMF (15 mL) was heated overnight at 110-120° C. under $N_2$. After cooling, the reaction mixture was diluted with water and acidified with 1N HCl. The precipitate was collected by filtration, washed with water, and dried under vacuum to yield 14 (0.48 g, 76%).

General Procedure A: Nucleophilic Displacement of □-chloro Ketones,

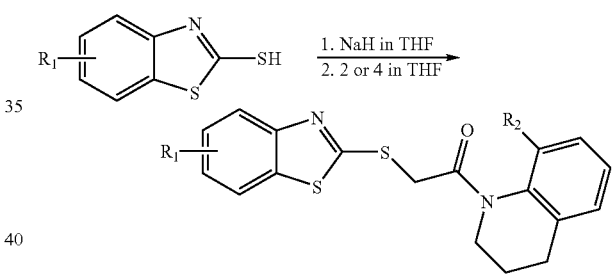

To a solution of a substituted 2-mercaptobenzothiazole (16.5 mmol) in dry THF (50 mL) at 0° C. was added NaH (60% in mineral oil, 18.2 mmol) in small portions. After stirring for 30 min at 0° C., a solution of compound 2 or 4 (16.5 mmol) in THF (10 mL) was added dropwise. The reaction was stirred overnight at room temperature. The reaction mixture was quenched by addition of water (25 mL) and EtOAc (50 mL), the two layers were separated. The aqueous layer was extracted with EtOAc (2×20 mL). All the combined organics were washed with water (2×20 mL), brine (20 mL), and dried over $MgSO_4$. The solvent was removed under reduced pressure and the product was purified by column chromatography to afford the desired product.

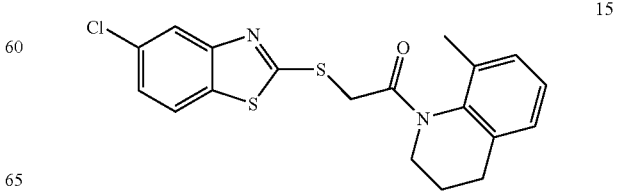

2-(5-Chlorobenzothiazol-2-ylsulfanyl)-1-(8-methyl-3,4-dihydro-2H-quinolin-1-yl)-ethanone (15)

The title compound was synthesized according to General Procedure A using compound 2 as the electrophile and 5-chloro-2-mercaptobenzothiazole as the nucleophile to yield 15 (3.60 g, 56%): MS m/z: 393 (M+H)$^+$. Anal. Calcd. For, $C_{19}H_{17}ClN_2OS_2 \cdot 0.2H_2O$: C, 58.14; H, 4.47; N, 7.14; S, 16.33; Cl, 9.03. Found: C, 57.90; H, 4.40; N, 7.17; S, 16.47; Cl, 9.24.

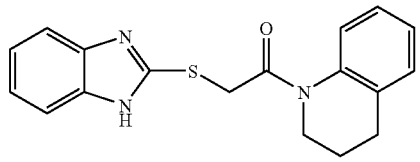

16

2-(1H-Benzoimidazol-2-ylsulfanyl)-1-(3,4-dihydro-2H-quinolin-1-yl)-ethanone (16)

The title compound was synthesized according to General Procedure A using compound 4 as the electrophile and 1H-benzo[d]imidazole-2-thiol as the nucleophile to yield 16 as a white solid (82%): MS m/z: 324 (M+H)$^+$. Anal. Calcd. For, $C_{18}H_{17}N_3OS$: C, 66.85; H, 5.30; N, 12.99; S, 9.91. Found: C, 66.78; H, 5.41; N, 12.90; S, 9.72.

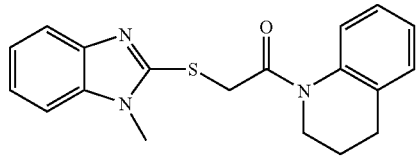

17

1-(3,4-Dihydro-2H-quinolin-1-yl)-2-(1-methyl-1H-benzoimidazol-2-ylsulfanyl)ethanone (17)

The title compound was synthesized according to General Procedure A using compound 4 as the electrophile and 1-methyl-1H-benzo[d]imidazole-2-thiol as the nucleophile to yield 17 as a pale yellow solid (77%): MS m/z: 338 (M+H)$^+$. Anal. Calcd. For, $C_{19}H_{19}N_3OS$: C, 67.63; H, 5.68; N, 12.45; S, 9.50. Found: C, 67.45; H, 5.74; N, 12.25; S, 9.41.

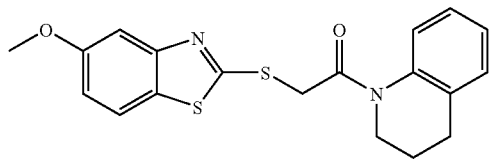

18

1-(3,4-Dihydro-2H-quinolin-1-yl)-2-(5-methoxy-benzothiazol-2-ylsulfanyl)-ethanone (18)

The title compound was synthesized according to General Procedure A using compound 4 as the electrophile and 5-methoxybenzo[d]thiazole-2-thiol as the nucleophile to yield 18 as a pale yellow solid (83%): MS m/z: 371 (M+H)$^+$. Anal. Calcd. For, $C_{19}H_{18}N_2O_2S_2$: C, 61.60; H, 4.90; N, 7.56; S, 17.31. Found: C, 61.40; H, 4.90; N, 7.48; S, 17.26.

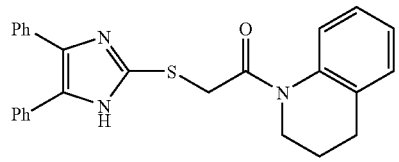

19

1-(3,4-Dihydro-2H-quinolin-1-yl)-2-(4,5-diphenyl-1H-imidazol-2-ylsulfanyl)-ethanone (19)

The title compound was synthesized according to General Procedure A using compound 4 as the electrophile and 4,5-diphenyl-1H-imidazole-2-thiol as the nucleophile to yield 19 as a off-white solid (26%): MS m/z: 426 (M+H)$^+$. Anal. Calcd. For, $C_{26}H_{23}N_3OS \cdot 0.2H_2O$: C, 72.77; H, 5.50; N, 9.79; S, 7.47. Found: C, 72.58; H, 5.33; N, 9.74; S, 7.48.

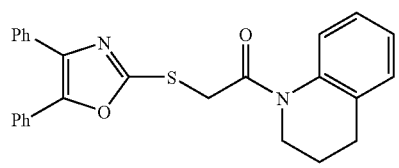

20

1-(3,4-Dihydro-2H-quinolin-1-yl)-2-(4,5-diphenyl-1H-oxazol-2-ylsulfanyl)-ethanone (20)

The title compound was synthesized according to General Procedure A using compound 4 as the electrophile and 4,5-diphenyloxazole-2-thiol as the nucleophile to yield 20 as an off-white solid (40%): MS m/z: 427 (M+H)$^+$. Anal. Calcd. For, $C_{26}H_{22}N_2O_2S$: C, 73.21; H, 5.20; N, 6.57; S, 7.52. Found: C, 73.49; H, 5.13; N, 6.57; S, 7.42.

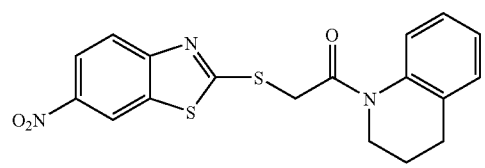

21

1-(3,4-Dihydro-2H-quinolin-1-yl)-2-(6-nitro-benzothiazol-2-ylsulfanyl)-ethanone (21)

The title compound was synthesized according to General Procedure A using compound 4 as the electrophile and 6-nitrobenzo[d]thiazole-2-thiol as the nucleophile to yield 21 as a yellow solid (33%): MS m/z: 386 (M+H)$^+$. Anal. Calcd. For, $C_{18}H_{15}N_3O_3S_2$: C, 56.09; H, 3.92; N, 10.90; S, 16.64. Found: C, 55.98; H, 3.75; N, 10.94; S, 16.41.

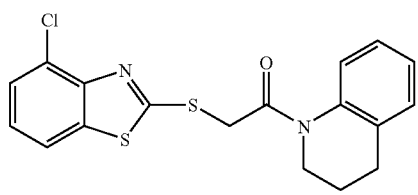

2-(4-Chloro-benzothiazol-2-ylsulfanyl)-1-(3,4-dihydro-2H-quinolin-1-yl)-ethanone (22)

The title compound was synthesized according to General Procedure A using compound 4 as the electrophile and 4-chlorobenzo[d]thiazole-2-thiol as the nucleophile to yield 22 as a white solid (72%): MS m/z: 375 (M+H)$^+$. Anal. Calcd. For, $C_{18}H_{15}ClN_2OS_2$: C, 57.67; H, 4.03; N, 7.47; S, 17.11; Cl, 9.46. Found: C, 57.79; H, 4.08; N, 7.48; S, 17.33; Cl, 9.41.

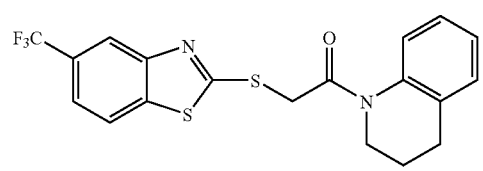

1-(3,4-Dihydro-2H-quinolin-1-yl)-2-(5-trifluoromethyl-benzothiazol-2-ylsulfanyl)-ethanone (23)

The title compound was synthesized according to General Procedure A using compound 4 as the electrophile and 5-(trifluoromethyl)benzo[d]thiazole-2-thiol as the nucleophile to yield 23 as a white solid (80%): MS m/z: 409 (M+H)$^+$. Anal. Calcd. For, $C_{19}H_{15}F_3N_2OS_2$: C, 55.87; H, 3.70; N, 6.86; S, 15.70; F, 13.95. Found: C, 55.79; H, 3.71; N, 6.92; S, 15.67; F, 14.07.

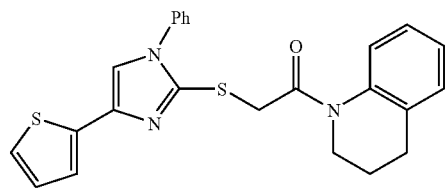

1-(3,4-Dihydro-2H-quinolin-1-yl)-2-(1-phenyl-4-thiophen-2-yl-1H-imidzol-2-Ylsulfanyl)-ethanone (24)

The title compound was synthesized according to General Procedure A using compound 4 as the electrophile and 1-phenyl-4-(thiophen-2-yl)-1H-imidazole-2-thiol as the nucleophile to yield 24 as an off-white solid (47%): MS m/z: 432 (M+H)$^+$. Anal. Calcd. For, $C_{24}H_{21}N_3OS_2$: C, 66.79; H, 4.90; N, 9.74; S, 14.86. Found: C, 66.74; H, 4.78; N, 9.65; S, 15.05.

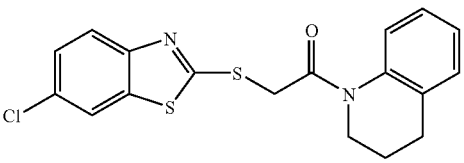

2-(6-Chloro-benzothiazol-2-ylsulfanyl)-1-(3,4-dihydro-2H-quinolin-1-yl)-ethanone (25)

The title compound was synthesized according to General Procedure A using compound 4 as the electrophile and 6-chlorobenzo[d]thiazole-2-thiol as the nucleophile to yield 25 as a white solid (73%): MS m/z: 375 (M+H)$^+$. Anal. Calcd. For, $C_{18}H_{15}ClN_2OS_2$: C, 57.67; H, 4.03; N, 7.47; S, 17.11; Cl, 9.46. Found: C, 57.50; H, 4.05; N, 7.48; S, 16.86; Cl, 9.74.

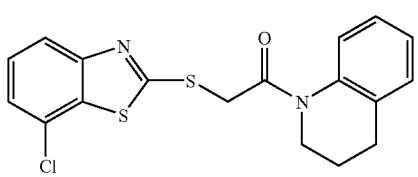

2-(7-Chloro-benzothiazol-2-ylsulfanyl)-1-(3,4-dihydro-2H-quinolin-1-yl)-ethanone (26)

The title compound was synthesized according to General Procedure A using compound 4 as the electrophile and 7-chlorobenzo[d]thiazole-2-thiol as the nucleophile to yield 26 as a white solid (46%): MS m/z: 375 (M+H)$^+$. Anal. Calcd. For, $C_{18}H_{15}ClN_2OS_2$: C, 57.67; H, 4.03; N, 7.47; S, 17.11; Cl, 9.46. Found: C, 57.50; H, 3.99; N, 7.47; S, 17.36; Cl, 9.52.

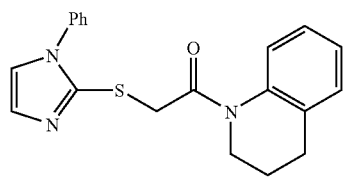

1-(3,4-Dihydro-2H-quinolin-1-yl)-2-(1-phenyl-1H-imidazol-2-ylsulfanyl)-ethanone (27)

The title compound was synthesized according to General Procedure A using compound 4 as the electrophile and 1-phenyl-1H-imidazole-2-thiol as the nucleophile to yield 27 as a yellow gum (69%): MS m/z: 350 (M+H)$^+$. Anal. Calcd. For, $C_{20}H_{19}N_3OS$: C, 68.74; H, 5.48; N, 12.02; S, 9.18. Found: C, 68.47; H, 5.71; N, 11.75; S, 8.96.

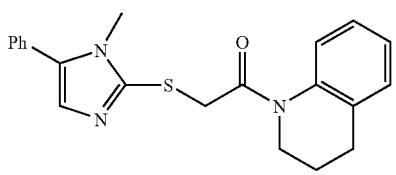

1-(3,4-Dihydro-2H-quinolin-1-yl)-2-(1-methyl-5-phenyl-1H-imidazol-2-ylsulfanyl)-ethanone (28)

The title compound was synthesized according to General Procedure A using compound 4 as the electrophile and 1-methyl-5-phenyl-1H-imidazole-2-thiol as the nucleophile to yield 28 as an off-white solid (42%): MS m/z: 364 (M+H)$^+$. Anal. Calcd. For, $C_{21}H_{21}N_3OS$: C, 69.39; H, 5.82; N, 11.56; S, 8.82. Found: C, 69.29; H, 5.83; N, 11.40; S, 8.83.

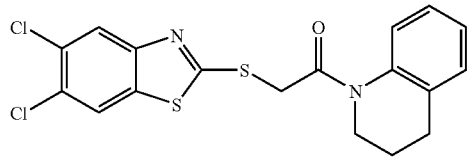

2-(5,6-Dichloro-benzoimidazol-2-ylsulfanyl)-1-(3,4-dihydro-2H-quinolin-1-yl)-ethanone (29)

The title compound was synthesized according to General Procedure A using compound 4 as the electrophile and compound 8 as the nucleophile to yield 29 as a white solid (41%): MS m/z: 409 (M+H)$^+$. Anal. Calcd. For, $C_{18}H_{14}Cl_2N_2OS_2$: C, 52.81; H, 3.45; N, 6.84; S, 15.67. Found: C, 52.75; H, 3.62; N, 6.80; S, 15.56.

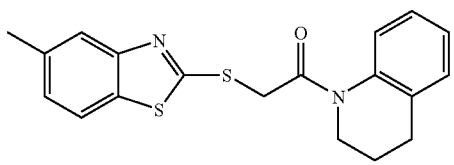

1-(3,4-Dihydro-2H-quinolin-1-yl)-2-(5-methyl-benzoimidazol-2-ylsulfanyl)-ethanone (30)

The title compound was synthesized according to General Procedure A using compound 4 as the electrophile and 5-methylbenzo[d]thiazole-2-thiol (10) as the nucleophile to yield 30 as a white solid (60%): MS m/z: 355 (M+H)$^+$. Anal. Calcd. For, $C_{19}H_{18}N_2OS_2$: C, 64.38; H, 5.12; N, 7.90; S, 18.09. Found: C, 64.54; H, 5.22; N, 7.84; S, 17.88.

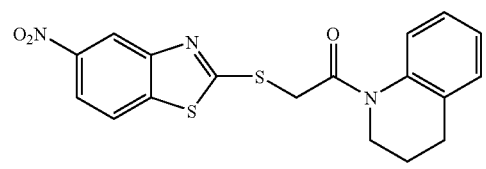

1-(3,4-Dihydro-2H-quinolin-1-yl)-2-(5-nitro-benzothiazol-2-ylsulfanyl)-ethanone (31)

The title compound was synthesized according to General Procedure A using compound 4 as the electrophile and 5-nitrobenzo[d]thiazole-2-thiol (12) as the nucleophile to yield 31 as a pale yellow solid (56%): MS m/z: 386 (M+H)$^+$. Anal. Calcd. For, $C_{18}H_{15}N_3O_3S_2$: C, 56.09; H, 3.92; N, 10.90; S, 16.64. Found: C, 56.22; H, 3.95; N, 10.81; S, 16.67.

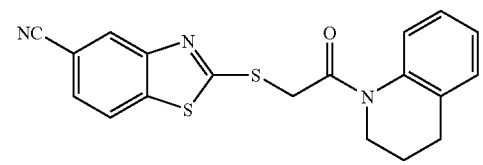

2-[2-(3,4-Dihydro-2H-quinolin-1-yl)-2-oxo-ethylsulfanyl]-benzothiazol-5-carbonitrile (32)

The title compound was synthesized according to General Procedure A using compound 4 as the electrophile and 2-mercaptobenzo[d]thiazole-5-carbonitrile (14) as the nucleophile to yield 32 as a white solid (74%): MS m/z: 366 (M+H)$^+$. Anal. Calcd. For, $C_{19}H_{15}N_3OS_2$: C, 62.44; H, 4.14; N, 11.50; S, 17.55. Found: C, 62.47; H, 4.36; N, 11.35; S, 17.65.

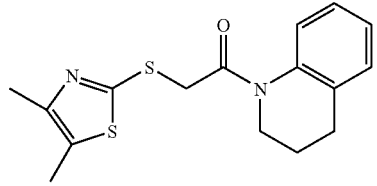

1-(3,4-dihydroquinolin-1(2H)-yl)-2-(4,5-dimethylthiazol-2-ylthio)ethanone (33)

The title compound was synthesized according to General Procedure A using compound 4 as the electrophile and 4,5-dimethylthiazole-2-thiol as the nucleophile to yield 33 as a cream solid (690 mg, 74%). MS (APCI): m/z 319 [M+H]$^+$. Anal. Calcd. for $C_{16}H_{18}N_2OS_2$: C, 60.34; H, 5.70; N, 8.80. Found: C, 60.51; H, 5.71; N, 8.72.

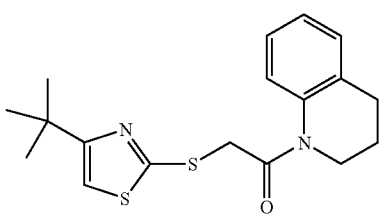

34

2-(4-tert-butylthiazol-2-ylthio)-1-(3,4-dihydroquino-
lin-1(2H)-yl)ethanone (34)

The title compound was synthesized according to General Procedure A using compound 4 as the electrophile and 4-tert-butylthiazole-2-thiol as the nucleophile to yield 34 (37%): MS: m/z⁺ 347.2 [M+H]⁺. Anal. Calcd (found) for $C_{18}H_{22}N_2OS_2$: C, 62.39 (62.60); H, 6.40 (6.43); N, 8.08 (8.06); S, 18.50 (18.39).

Synthesis of 1-(3,4-dihydroquinolin-1(2H)-yl)-2-
(thiazolo[5,4-b]pyridin-2-ylthio)ethanone (36)

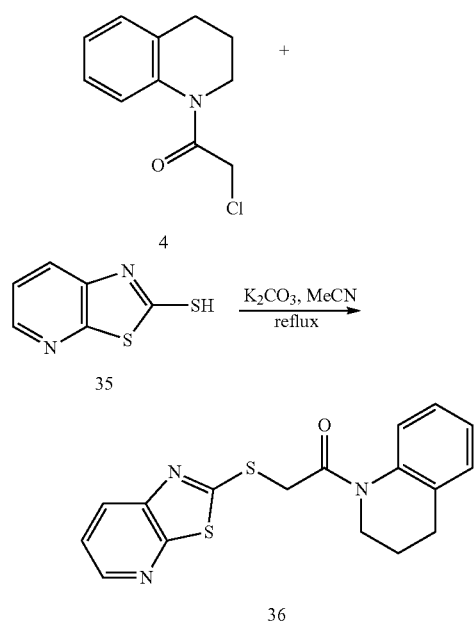

1-(3,4-dihydroquinolin-1(2H)-yl)-2-(thiazolo[5,4-b]
pyridin-2-ylthio)ethanone (36)

The mixture of compound 4 (418 mg, 2.0 mmol), compound 35 (338 mg, 2.0 mmol) and $K_2CO_3$ (276 mg, 2.0 mmol) in MeCN (20 mL) was refluxed over night under $N_2$. After cooling to room temperature, the mixture was partitioned between EtOAc (100 mL) and water (50 mL). The organic layer was separated, washed with water and brine, dried over $Na_2SO_4$ and concentrated. The crude material was purified by flash chromatography on silica gel eluting with EtOAc/hexanes (20~50%). The solid obtained was triturated with ether (5 mL) and hexanes (20 mL) over night. After filtration, compound 36 was obtained as a pale yellow solid (414 mg, 61%). MS (APCI): m/z 342 [M+H]⁺. Anal. Calcd. for $C_{17}H_{15}N_3OS_2$: C, 59.80; H, 4.43; N, 12.31. Found: C, 59.80; H, 4.37; N, 12.16.

General Procedure B: Amide Formation with EDCI—HOBt

To a solution of an acid (1.5 mmol) in DCM (25 mL) was added a disubstituted amine (1.5 mmol). The mixture was cooled in an ice-water bath, then DIPEA (3.75 mmol) was added, followed by HOBt (1.5 mmol) and EDCI (1.5 mmol). The reaction mixture was stirred at room temperature over night (or monitored by TLC). The mixture was diluted with DCM (25 mL), washed with $H_2O$, citric acid (10% in $H_2O$), $NaHCO_3$ (sat.), dried over $Na_2SO_4$ and concentrated in vacuum. The crude product was purified by flash chromatography on silica gel eluting with EtOAc/hexanes (10~40%).

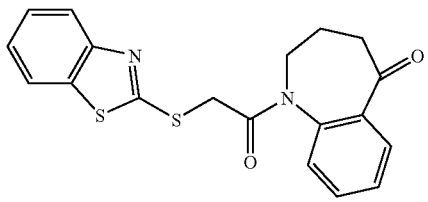

37

1-(2-(Benzo[d]thiazol-2-ylthio)acetyl)-1,2,3,4-tet-
rahydro-benzo[b]azepin-5-one (37)

The title compound was synthesized according to General Procedure B using 2-(benzo[d]thiazol-2-ylthio)acetic acid and 1,2,3,4-tetrahydrobenzo[b]azepin-5-one (5) to yield 37 (160 mg, 29%): MS (APCI): m/z 369 [M+H]⁺. Anal. Calcd. for $C_{19}H_{16}N_2O_2S_2$: C, 61.93; H, 4.38; N, 7.60. Found: C, 61.72; H, 4.31; N, 7.40.

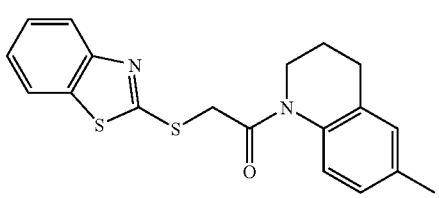

38

2-(Benzo[d]thiazol-2-ylthio)-1-(6-methyl-3,4-dihyd-
roquinolin-1(2H)-yl)ethanone (38)

The title compound was synthesized according to General Procedure B using 2-(benzo[d]thiazol-2-ylthio)acetic acid and 6-methyl-1,2,3,4-tetrahydroquinoline to yield 38 (450.5 mg, 85%): MS (APCI): m/z 355 [M+H]⁺. Anal. Calcd. for $C_{19}H_{18}N_2OS_2$: C, 64.39; H, 5.12; N, 7.90. Found: C, 64.55; H, 5.01; N, 7.88.

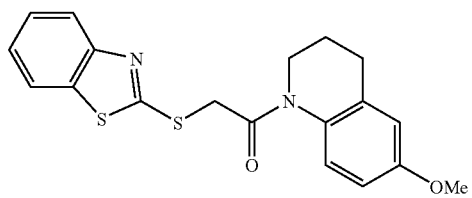

2-(Benzo[d]thiazol-2-ylthio)-1-(6-methoxy-3,4-dihydroquinolin-1(2H)-yl)ethanone (39)

The title compound was synthesized according to General Procedure B using 2-(benzo[d]thiazol-2-ylthio)acetic acid and 6-methoxy-1,2,3,4-tetrahydroquinoline to yield 39 (245 mg, 1.5 mmol). MS (APCI): m/z 371 [M+H]$^+$. Anal. Calcd. for $C_{19}H_{18}N_2O_2S_2$: C, 61.60; H, 4.90; N, 7.56. Found: C, 61.49; H, 4.87; N, 7.59.

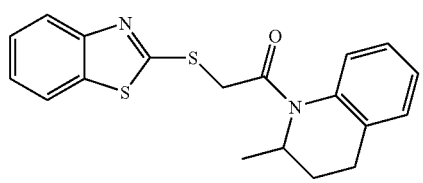

2-(Benzothiazol-2-ylsulfanyl)-1-(2-methyl-3,4-dihydro-2H-quinolin-1-yl)-ethanone (40)

The title compound was synthesized according to General Procedure B using 2-(benzo[d]thiazol-2-ylthio)acetic acid and 2-methyl-1,2,3,4-tetrahydroquinoline to yield 40 as a pale yellow solid (0.32 g, 40%); MS m/z: 355 (M+H)$^+$. Anal. Calcd. For, $C_{19}H_{18}N_2OS_2$: C, 64.38; H, 5.12; N, 7.90; S, 18.09. Found: C, 64.38; H, 5.22; N, 7.85; S, 17.93.

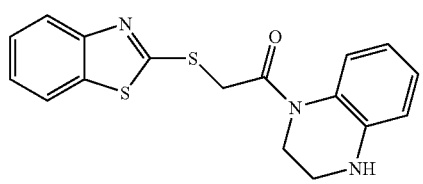

2-(Benzothiazol-2-ylsulfanyl)-1-(3,4-dihydro-2H-quinoxalin-1-yl)-ethanone (41)

The title compound was synthesized according to General Procedure B using 2-(benzo[d]thiazol-2-ylthio)acetic acid and 1,2,3,4-tetrahydroquinoxaline to yield 41 as a white solid (51%) MS m/z: 342 (M+H)$^+$. Anal. Calcd. For, $C_{17}H_{15}N_3OS_2.0.2H_2O$: C, 59.18; H, 4.50; N, 12.18; S, 18.52. Found: C, 59.32; H, 4.65; N, 12.18; S, 18.25.

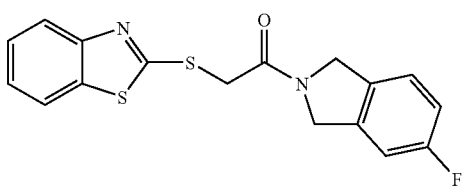

2-(Benzothiazol-2-ylsulfanyl)-1-(5-fluoro-3,4-dihydro-iso-indol-2-yl)-ethanone (42)

The title compound was synthesized according to General Procedure B using 2-(benzo[d]thiazol-2-ylthio)acetic acid and 5-fluoroisoindoline to yield 42 as a white solid (47%): MS m/z: 345 (M+H)$^+$. Anal. Calcd. For, $C_{17}H_{13}FN_2OS_2.0.3H_2O$: C, 58.37; H, 3.92; N, 8.01; S, 18.33. Found: C, 58.15; H, 3.86; N, 7.92; S, 18.05.

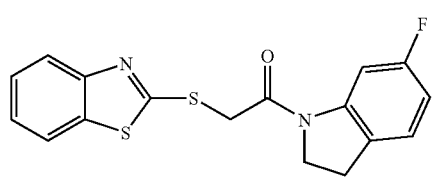

2-(Benzothiazol-2-ylsulfanyl)-1-(6-fluoro-2,3-dihydro-indol-1-yl)-ethanone (43)

The title compound was synthesized according to General Procedure B using 2-(benzo[d]thiazol-2-ylthio)acetic acid and 6-fluoroindoline to yield 43 as a white solid (70%): MS m/z: 345 (M+H)$^+$. Anal. Calcd. For, $C_{17}H_{13}N_2FOS_2$: C, 59.28; H, 3.80; N, 8.13; S, 18.62; F, 5.52. Found: C, 59.51; H, 3.85; N, 8.13; S, 18.73; F, 5.37.

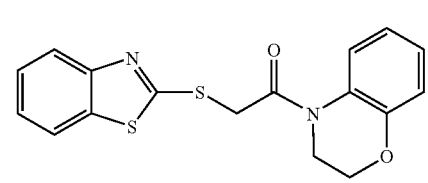

2-(Benzothiazol-2-ylsulfanyl)-1-(2,3-dihydro-benzo[1,4]oxazin-4-yl)-ethanone (44)

The title compound was synthesized according to General Procedure B using 2-(benzo[d]thiazol-2-ylthio)acetic acid and 3,4-dihydro-2H-benzo[b][1,4]oxazine to yield 44 as a white solid (78%): MS m/z: 343 (M+H)$^+$. Anal. Calcd. For, $C_{17}H_{14}N_2O_2S_2$: C, 59.63; H, 4.12; N, 8.18; S, 18.73. Found: C, 59.73; H, 4.17; N, 8.18; S, 18.76.

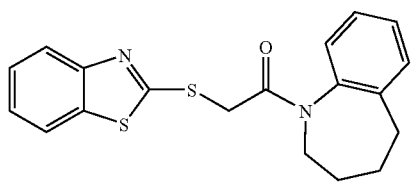

2-(Benzothiazol-2-ylsulfanyl)-1-(2,3,4,5-tetrahydro-benzo[b]-azepin-1-yl)-ethanone (45)

The title compound was synthesized according to General Procedure B using 2-(benzo[d]thiazol-2-ylthio)acetic acid and 2,3,4,5-tetrahydro-1H-benzo[b]azepine (6) to yield 45 as a white solid (23%): MS m/z: 355 (M+H)$^+$. Anal. Calcd. For, $C_{19}H_{18}N_2OS_2$: C, 64.38; H, 5.12; N, 7.90; S, 18.09. Found: C, 64.53; H, 5.06; N, 7.83; S, 17.93.

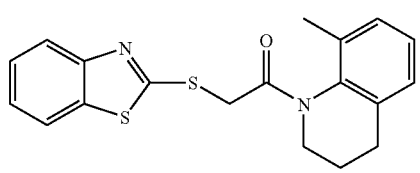

2-(Benzothiazol-2-ylsulfanyl)-1-(8-methyl-3,4-dihydro-2H-quinolin-1-yl)-ethanone (46)

The title compound was synthesized according to General Procedure B using 2-(benzo[d]thiazol-2-ylthio)acetic acid and 8-methyl-1,2,3,4-tetrahydroquinoline to yield 46 as a white solid (39%): MS m/z: 355 (M+H)$^+$. Anal. Calcd. For, $C_{19}H_{18}N_2OS_2$: C, 64.38; H, 5.12; N, 7.90; S, 18.09. Found: C, 64.37; H, 5.02; N, 7.74; S, 18.10.

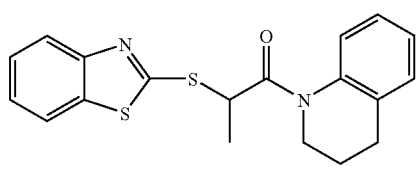

2-(Benzothiazol-2-ylsulfanyl)-1-(3,4-dihydro-2H-quinolin-1-yl)-propan-1-one (47)

The title compound was synthesized according to General Procedure B using 2-(benzo[d]thiazol-2-ylthio)propanoic acid and 1,2,3,4-tetrahydroquinoline to yield 47 as a yellow oil (34%): MS m/z: 355 (M+H)$^+$. Anal. Calcd. For, $C_{19}H_{18}N_2OS_2$: C, 64.38; H, 5.12; N, 7.90; S, 18.09. Found: C, 64.38; H, 5.26; N, 7.97; S, 18.08.

Synthesis of 1-(4-Acetyl-3,4-dihydro-2H-quinoxalin-1-yl)-2-(benzothiazol-2-ylsulfanyl)-ethanone (48)

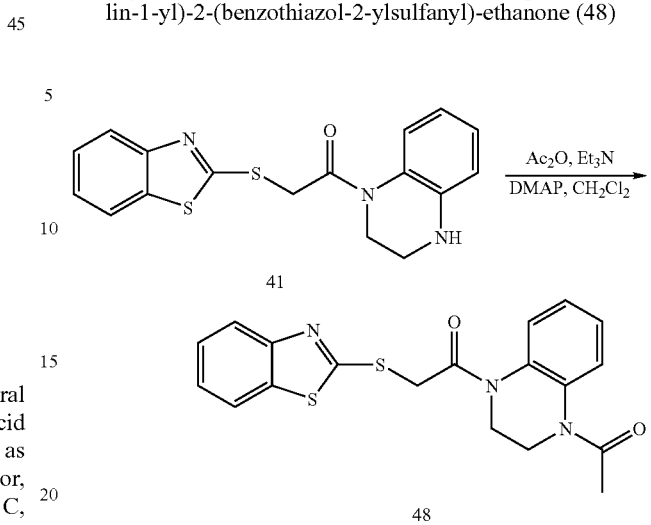

1-(4-Acetyl-3,4-dihydro-2H-quinoxalin-1-yl)-2-(benzothiazol-2-ylsulfanyl)-ethanone (48)

To a 0° C. solution of compound 41 (0.41 g, 1.20 mmol) in dry $CH_2Cl_2$ (20 mL) were added $Ac_2O$ (1.12 mL, 12.0 mmol) followed by dropwise addition of $Et_3N$ (1.12 mL, 8.00 mmol), and DMAP (10 mg) The reaction was stirred for 18 h under $N_2$ at room temperature. The reaction mixture was diluted with $CH_2Cl_2$ (20 mL), washed with saturated $NaHCO_3$ (10 mL), water (2×10 mL), and saturated NaCl (2×10 mL). Dried over $MgSO_4$ and filtered. The solvent was removed under reduced pressure and the product was purified by column chromatography ($CH_2Cl_2$/EtOAc 1:1), and triturated from $CH_2Cl_2$/hexanes to afford 48 as a yellow solid (0.24 g, 52%); MS m/z: 384 (M+H)$^+$. Anal. Calcd. For, $C_{19}H_{17}N_3O_2S_2 \cdot 0.1H_2O$: C, 59.23; H, 4.92; N, 10.91; S, 16.64. Found: C, 58.84; H, 4.55; N, 10.55; S, 16.32.

General Procedure C: Nitro Reduction

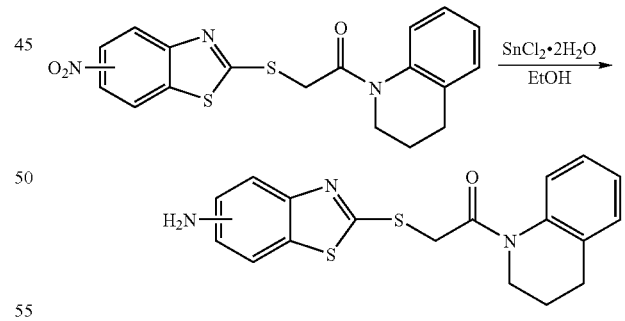

A mixture of the aromatic nitro compound (1.40 g, 3.64 mmol) and $SnCl_2 \cdot 2H_2O$ (4.10 g, 18.2 mmol) in EtOH (40 mL) was heated to reflux for 3 h. The reaction mixture was cooled to room temperature and quenched with saturated $Na_2CO_3$. The solids were filtered through celite. Most of the filtrate was evaporated, and extracted with EtOAc (3×50 mL). All the combined organic extracts were washed with water (2×20 mL), and brine (20 mL). The organic solution was dried over $MgSO_4$, filtered. The solvent was removed under reduced pressure, and the product was purified by column chromatography to yield the desired amine.

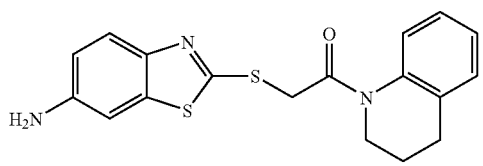

2-(6-Amino-benzothiazol-2-ylsulfanyl)-1-(3,4-dihydro-2H-quinolin-1-yl)-ethanone (49)

The title compound was made according to General Procedure C using 1-(3,4-Dihydro-2H-quinolin-1-yl)-2-(6-nitro-benzothiazol-2-ylsulfanyl)-ethanone (21) and the product was purified by column chromatography (2% Et₃N in EtOAc/hexanes 1:1) to afford compound 49 as a pale yellow solid (0.79 g, 61%); MS m/z: 356 (M+H)⁺. Anal. Calcd. For, $C_{18}H_{17}N_3OS_2$: C, 60.82; H, 4.82; N, 11.82; S, 18.04. Found: C, 61.06; H, 4.92; N, 11.53; S, 17.56.

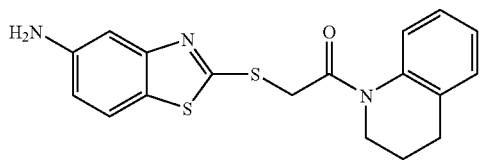

2-(5-Amino-benzothiazol-2-ylsulfanyl)-1-(3,4-dihydro-2H-quinolin-1-yl)-ethanone (50)

The title compound was synthesized according to General Procedure C using 1-(3,4-Dihydro-2H-quinolin-1-yl)-2-(5-nitro-benzothiazol-2-ylsulfanyl)-ethanone (31) to yield 50 as an off-white foam (56%): MS m/z: 356 (M+H)⁺. Anal. Calcd. For, $C_{18}H_{17}N_3OS_2$: C, 60.82; H, 4.82; N, 11.82; S, 18.04. Found: C, 60.51; H, 4.90; N, 11.44; S, 17.69.

Synthesis of N-{2-[2-(3,4-Dihydro-2H-quinolin-1-yl)-2-oxo-ethylsulfanyl]-benzothiazol-6-yl}-acetamide (51)

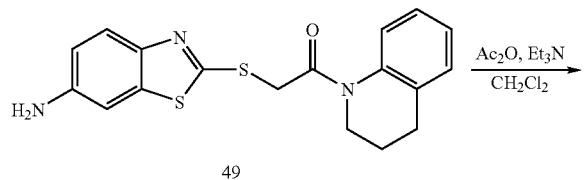
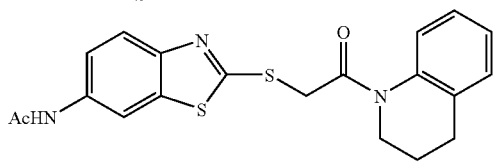

N-{2-[2-(3,4-Dihydro-2H-quinolin-1-yl)-2-oxo-ethylsulfanyl]-benzothiazol-6-yl}-acetamide (51)

To a 0° C. solution of compound 49 (0.16 g, 0.45 mmol) in dry CH₂Cl₂ (5 mL) was added Ac₂O (0.25 mL, 2.70 mmol) followed by dropwise addition of Et₃N (0.25 mL, 1.80 mmol). The reaction was stirred for 2 h under N₂. The reaction mixture was diluted with CH₂Cl₂ (40 mL), washed with saturated NaHCO₃ (10 mL), water (2×10 mL), and saturated NaCl (2×10 mL). Dried over MgSO₄ and filtered. The solvent was removed under reduced pressure and the product was purified by column chromatography (EtOAc/hexanes 3:7) to afford 51 as a white solid (154 mg, 86%); MS m/z: 398 (M+H)⁺. Anal. Calcd. For, $C_{20}H_{19}N_3O_2S_2$: C, 60.43; H, 4.82; N, 10.57; S, 16.13. Found: C, 60.54; H, 4.91; N, 10.41; S, 15.87.

Synthesis of N-{2-[2-(3,4-Dihydro-2H-quinolin-1-yl)-2-oxo-ethylsulfanyl]-benzothiazol-5-yl}-acetamide (52)

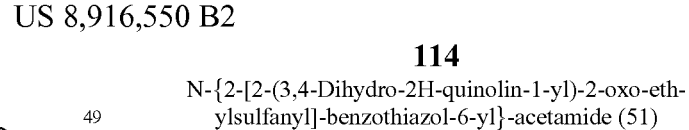

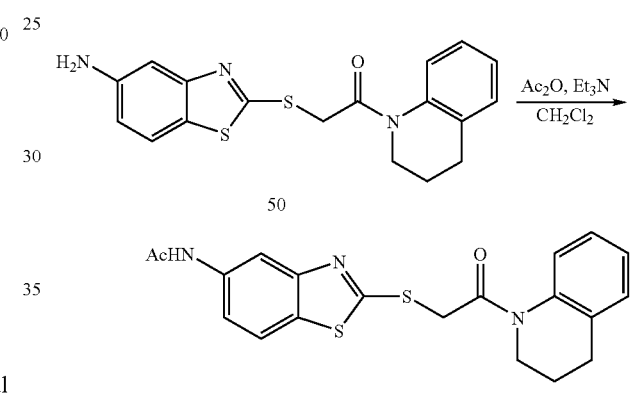

N-{2-[2-(3,4-Dihydro-2H-quinolin-1-yl)-2-oxo-ethylsulfanyl]-benzothiazol-5-yl}-acetamide (52)

Compound 52 was synthesized by the same procedure as above to yield 52 as an off-white solid (53%): MS m/z: 398 (M+H)⁺. Anal. Calcd. For, $C_{20}H_{19}N_3O_2S_2 \cdot 0.1H_2O$: C, 60.13; H, 4.85; N, 10.52; S, 16.05. Found: C, 59.94; H, 4.99; N, 10.35; S, 15.80.

Synthesis of N-{2-[2-(3,4-Dihydro-2H-quinolin-1-yl)-2-oxo-ethylsulfanyl]-benzothiazol-6-yl}-methanesulfonamide (53)

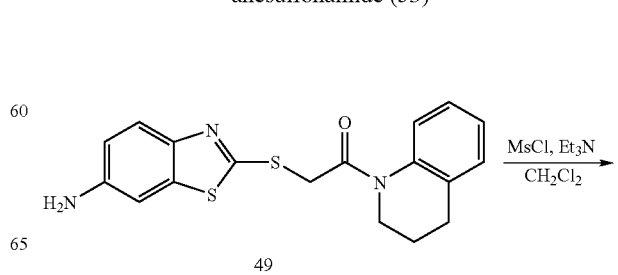

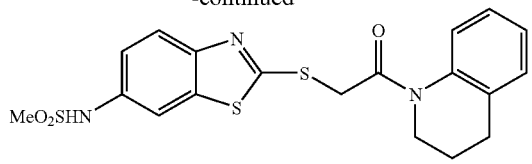

53

N-{2-[2-(3,4-Dihydro-2H-quinolin-1-yl)-2-oxo-ethylsulfanyl]-benzothiazol-6-yl}-methanesulfonamide (53)

To a 0° C. solution of compound 49 (170 mg, 0.48 mmol) in dry CH$_2$Cl$_2$ (5 mL) were added methanesulfonyl chloride (78 μL) followed by dropwise addition of Et$_3$N (0.13 mL). The reaction was stirred for 2.5 h under N$_2$ at room temperature. The reaction mixture was diluted with CH$_2$Cl$_2$ (40 mL), washed with 1N HCl (10 mL), water (2×10 mL), and saturated NaCl (2×10 mL). Dried over MgSO$_4$ and filtered. The solvent was removed under reduced pressure, and the product was purified by column chromatography (EtOAc/hexanes 4:1) to afford a mixture of mono and bis-sulfonamides (215 mg). To a solution of the mixture of mono and bis-sulfonamides (200 mg) in 3 mL of MeOH and THF (2:1) was added NaOH (38 mg in 0.1 mL of H$_2$O). The reaction was stirred for 45 min. at room temperature. Most of the solvent was evaporated under vacuum, the residue was dissolved in water (15 mL), and extracted with EtOAc. The combined organics were dried over MgSO$_4$ and filtered. The solvent was removed under reduced pressure, and the product was purified by column chromatography (EtOAc/hexanes 2:1) to afford 53 as a white solid (120 mg); MS m/z: 434 (M+H)$^+$. Anal. Calcd. For, C$_{19}$H$_{19}$N$_3$O$_3$S$_3$.0.1H$_2$O: C, 52.39; H, 4.86; N, 9.65; S, 22.08. Found: 52.06; H, 4.57; N, 9.45; S, 21.80.

Synthesis of N-{2-[2-(3,4-Dihydro-2H-quinolin-1-yl)-2-oxo-ethylsulfanyl]-benzothiazol-5-yl}-methanesulfonamide (54)

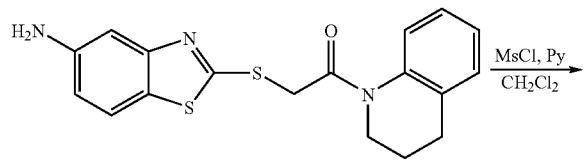

54

N-{2-[2-(3,4-Dihydro-2H-quinolin-1-yl)-2-oxo-ethylsulfanyl]-benzothiazol-5-yl}-methanesulfonamide (54)

To a 0° C. solution of compound 50 (160 g, 0.45 mmol) in dry CH$_2$Cl$_2$ (5 mL) was added methanesulfonyl chloride (70 μL, 0.90 mmol)) followed by dropwise addition of pyridine (100 μL, 1.40 mmol). The reaction was stirred overnight under N$_2$. The reaction mixture was diluted with CH$_2$Cl$_2$ (40 mL), washed with 1N HCl (10 mL), water (2×10 mL), and saturated NaCl (2×10 mL). Dried over MgSO$_4$ and filtered. The solvent was removed under reduced pressure and the product was purified by column chromatography (EtOAc/hexanes 1:1) to afford 54 as a pale yellow solid (117 mg, 60%); MS m/z: 434 (M+H)$^+$. Anal. Calcd. For, C$_{19}$H$_{19}$N$_3$O$_3$S$_2$: C, 52.63; H, 4.42; N, 9.69; S, 22.19. Found: C, 52.69; H, 4.49; N, 9.54; S, 22.11.

Synthesis of N-{2-[2-(3,4-Dihydro-2H-quinolin-1-yl)-2-oxo-ethylsulfanyl]-benzothiazol-6-yl}-benzamide (55)

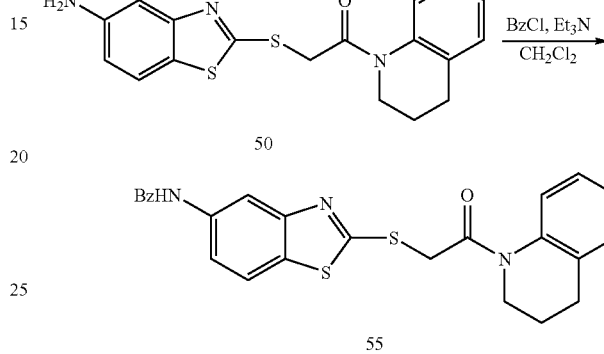

55

N-{2-[2-(3,4-Dihydro-2H-quinolin-1-yl)-2-oxo-ethylsulfanyl]-benzothiazol-6-yl}-benzamide (55)

To a 0° C. solution of compound 50 (0.22 g, 0.62 mmol) in dry CH$_2$Cl$_2$ (6 mL) was added benzoyl chloride (0.10 mL, 0.93 mmol) followed by dropwise addition of Et$_3$N (0.26 mL, 1.86 mmol). The reaction was stirred overnight under N$_2$ at room temperature. The reaction mixture was poured onto ice-water, and extracted with CH$_2$Cl$_2$ (3×20 mL). The combined organics extracts were washed with water (2×10 mL), and saturated NaCl (2×10 mL). Dried over MgSO$_4$ and filtered. The solvent was removed under reduced pressure, and the product was purified by column chromatography (EtOAc/hexanes 1:1) to afford 55 as a white solid (132 mg, 46%); MS m/z: 460 (M+H)$^+$. Anal. Calcd. For, C$_{25}$H$_{21}$N$_3$O$_2$S$_2$: C, 65.33; H, 4.61; N, 9.14; S, 13.95. Found: C, 65.08; H, 4.64; N, 8.99; S, 13.69.

General Procedure D: Amide formation with EDCI

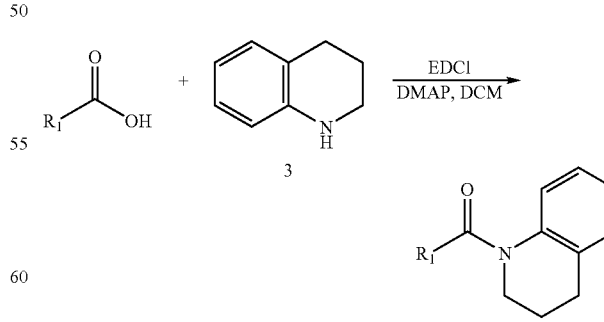

To a mixture of acid (2.5 mmol), aniline (2.5 mmol) and DMAP (2.5 mmol) in DCM (15 mL) was added EDCI (2.5 mmol). The reaction mixture was stirred at room temperature over night (or monitored by TLC). The mixture was diluted with DCM (25 mL), washed with H$_2$O, HCl (1N), NaOH (1N), dried over Na$_2$SO$_4$ and concentrated in vacuo. The crude product was purified by flash chromatography on silica gel eluting with EtOAc/hexanes (10~30%).

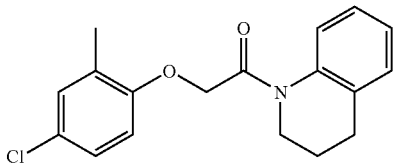

56

2-(4-Chloro-2-methylphenoxy)-1-(3,4-dihydroquinolin-1(2H)-yl)propan-1-one (57)

The title compound was synthesized according to General Procedure D using 2-(4-chloro-2-methylphenoxy)propanoic acid and compound 3 to yield 57 (350 mg, 46%): MS (APCI): m/z 330 [M+H]$^+$. Anal. Calcd. for C$_{19}$H$_{20}$ClNO$_2$: C, 69.19; H, 6.11; N, 4.25. Found: C, 69.09; H, 6.10; N, 4.31.

Synthesis of 2-(Benzo[d]thiazol-2-yloxy)-1-(3,4-dihydroquinolin-1(2H)-yl)ethanone (62)

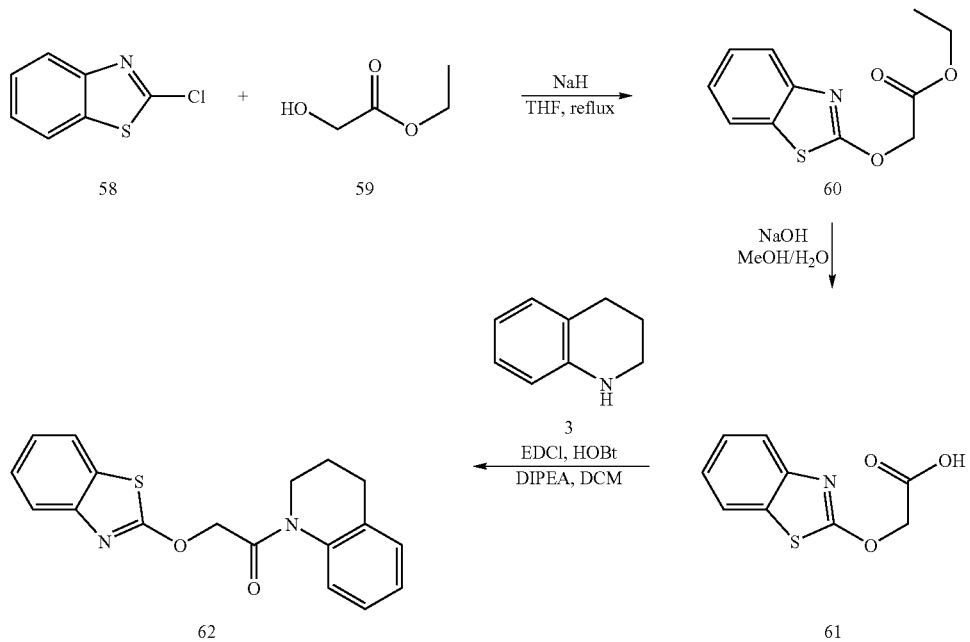

2-(4-Chloro-2-methylphenoxy)-1-(3,4-dihydroquinolin-1(2H)-yl)ethanone (56)

The title compound was synthesized according to General Procedure D using 2-(4-chloro-2-methylphenoxy)acetic acid and compound 3 to yield compound 56 (365 mg, 46%): MS (APCI): m/z 316 [M+H]$^+$. Anal. Calcd. for C$_{18}$H$_{18}$ClNO$_2$: C, 68.46; H, 5.75; N, 4.44. Found: C, 68.41; H, 5.92; N, 4.51.

Ethyl 2-(benzo[d]thiazol-2-yloxy)acetate (60)

To a solution of 59 (1.1 g, 10.6 mmol) in THF (100 mL) cooled in an ice-water bath was added NaH (60%, 465 mg, 11.6 mmol) portionwise under N$_2$. The mixture was then stirred at room temperature for half an hour, cooled in an ice-water bath and a solution of 58 (1.80 g, 10.6 mmol) in THF (10 mL) was added dropwise. It was refluxed for 1 hour and then stirred at room temperature over night. After diluting with EtOAc (150 mL), the solution washed with water (3×) and brine, dried and concentrated. The crude material was purified by flash chromatography on silica gel eluting with EtOAc/hexanes (0~10%) to give 60 as a white solid (1.32 g, 53%).

2-(Benzo[d]thiazol-2-yloxy)acetic acid (61)

To a solution of 60 (1.32 g, 5.6 mmol) in MeOH was added NaOH (3M, 75 mL, 0.22 mol) dropwise. The mixture was stirred at room temperature over night. It was then cooled in an ice-water bath and acidified to pH<2 with HCl (2N). The mixture was then extracted with CHCl$_3$ (3×). The combined organic layers were dried over Na$_2$SO$_4$ and concentrated in vacuum to yield 61 as a white solid (1.0 g, 86%).

2-(Benzo[d]thiazol-2-yloxy)-1-(3,4-dihydroquinolin-1(2H)-yl)ethanone (62)

Compound 62 was synthesized according to General Procedure B using compound 3 and compound 61 to yield 62 (183 mg, 28%): MS (APCI): m/z 325 [M+H]$^+$. Anal. Calcd. for $C_{18}H_{16}N_2O_2S$: C, 66.64; H, 4.97; N, 8.64. Found: C, 66.88; H, 4.94; N, 8.60.

Synthesis of 2-(benzo[d]thiazol-2-ylsulfinyl)-1-(3,4-dihydroquinolin-1(2H)-yl)ethanone (65) and 2-(benzo[d]thiazol-2-ylsulfonyl)-1-(3,4-dihydroquinolin-1(2H)-yl)ethanone (66)

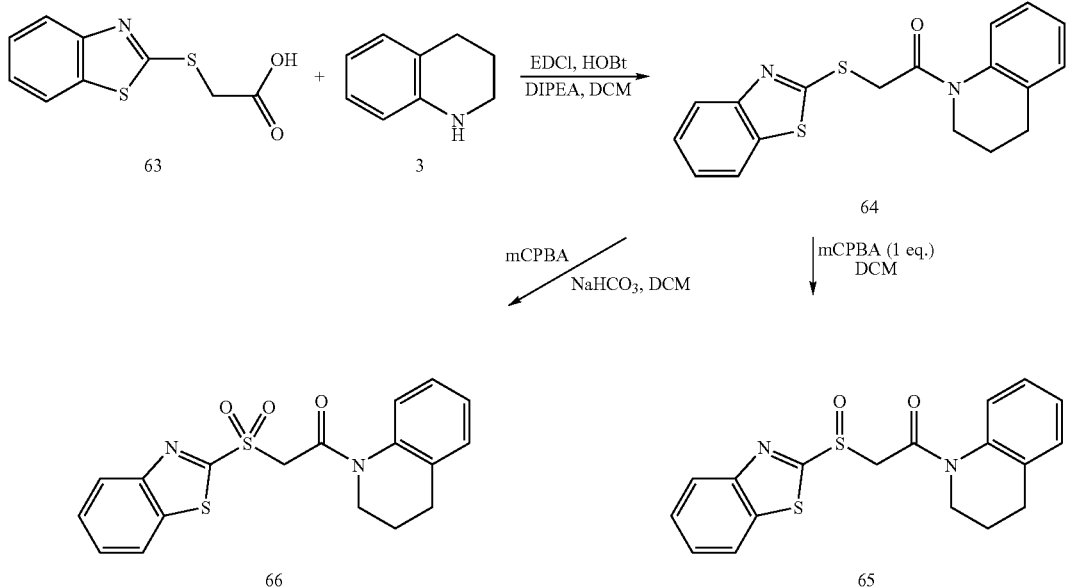

2-(Benzo[d]thiazol-2-ylthio)-1-(3,4-dihydroquinolin-1(2H)-yl)ethanone (64)

Compound 64 was synthesized according to General Procedure B using acid 63 and compound 3 to yield 64 (418 mg, 82%).

2-(Benzo[d]thiazol-2-ylsulfinyl)-1-(3,4-dihydroquinolin-1(2H)-yl)ethanone (65)

To a solution of compound 64 (167 mg, 0.49 mmol) in DCM (4 mL) cooled in a salt-ice bath was added a solution of mCPBA (77%, 110 mg, 0.49 mmol) in DCM (4 mL) drop wise. The reaction mixture was stirred for 1 hr. After diluting with DCM (30 mL), the solution washed with Na$_2$S$_2$O$_3$, NaHCO$_3$, dried over Na$_2$SO$_4$ and concentrated in vacuum. The crude material was purified by flash chromatography on silica gel eluting with EtOAc/hexanes (20~50%) to give compound 65 as a white solid (164 mg, 94%). MS (APCI): m/z 357 [M+H]$^+$. Anal. Calcd for $C_{18}H_{16}N_2O_2S_2$: C, 60.65; H, 4.52; N, 7.86. Found: C, 60.44; H, 4.66; N, 7.73.

2-(Benzo[d]thiazol-2-ylsulfonyl)-1-(3,4-dihydroquinolin-1(2H)-yl)ethanone (66)

To a solution of 64 (167 mg, 0.49 mmol) in DCM (4 mL) in an ice-water bath was added a solution of mCPBA (77%, 412 mg, 1.84 mmol) in DCM (10 mL) drop wise. NaHCO$_3$ (154 mg, 1.84 mmol) was then added portion wise. The reaction mixture was stirred at room temperature over night. After diluting with DCM (50 mL), the solution washed with H$_2$O, Na$_2$S$_2$O$_3$, NaHCO$_3$, dried over Na$_2$SO$_4$ and concentrated in vacuum. The crude material was purified by flash chromatography on silica gel eluting with EtOAc/hexanes (20~40%) to give 66 as a white solid (157 mg, 86%). MS (APCI): m/z 373 [M+H]$^+$. Anal. Calcd for $C_{18}H_{16}N_2O_3S_2$: C, 58.04; H, 4.33; N, 7.52. Found: C, 58.04; H, 4.43; N, 7.50.

Synthesis of 1-(3,4-dihydroquinolin-1(2H)-yl)-2-(thiazolo[4,5-c]pyridine-2-ylthio)ethanone hydrochloride (70)

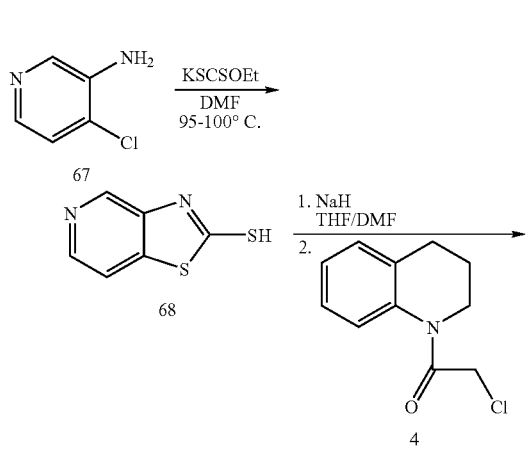

-continued

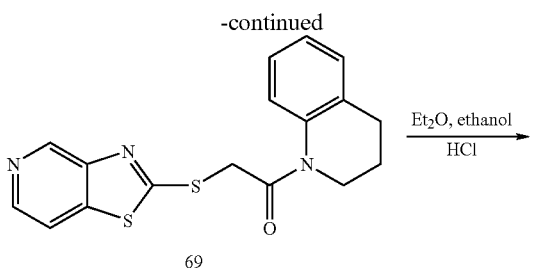

69

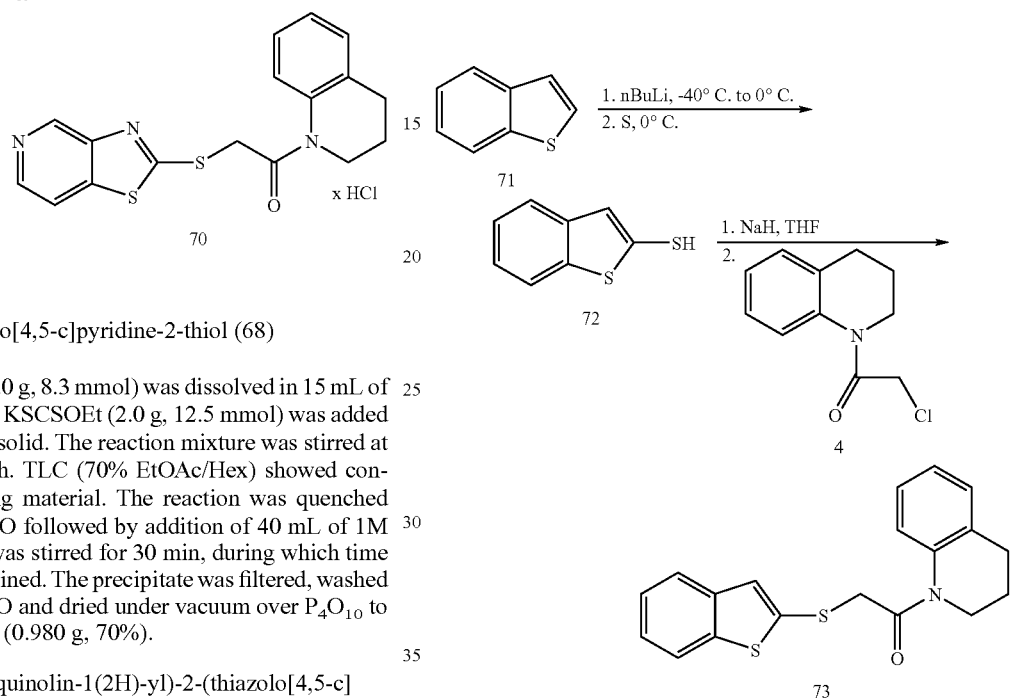

Thiazolo[4,5-c]pyridine-2-thiol (68)

Compound 67 (1.0 g, 8.3 mmol) was dissolved in 15 mL of dry DMF under $N_2$. KSCSOEt (2.0 g, 12.5 mmol) was added to the solution as a solid. The reaction mixture was stirred at 95-100° C. for 15 h. TLC (70% EtOAc/Hex) showed consumption of starting material. The reaction was quenched with ~35 mL of $H_2O$ followed by addition of 40 mL of 1M HCl. The mixture was stirred for 30 min, during which time precipitate was obtained. The precipitate was filtered, washed with 250 mL of $H_2O$ and dried under vacuum over $P_4O_{10}$ to yield compound 68 (0.980 g, 70%).

1-(3,4-Dihydroquinolin-1(2H)-yl)-2-(thiazolo[4,5-c]pyridin-2-ylthio)ethanone (69)

Compound 68 (0.5 g, 3.0 mmol) was mixed with 20 mL of dry THF and 20 mL of dry DMF under $N_2$ and the suspension was stirred for 30 min at RT and then cooled to 0° C. NaH (0.15 g 60% in mineral oil, 3.7 mmol) was added to the ice-cold suspension which became a greenish solution upon stirring for several minutes at 0° C. The reaction mixture was stirred for another 30 min at 0° C. and then 2-chloro-1-(3,4-dihydroquinolin-1(2H)-yl)ethanone (0.63 g, 3.0 mmol) dissolved in 5 ml of dry THF was added. After the reaction mixture was stirred for 16 h at RT (monitored by TLC ($CH_2Cl_2$/EtOAc=1:1 and MS), it was diluted with 100 mL of EtOAc followed by addition of 50 mL of $H_2O$. The organic layer was separated and the aqueous layer was extracted with EtOAc (2×50 mL). The organic layers were combined washed with water, brine, dried over $Na_2SO_4$ and concentrated giving 1.1 g of crude which was purified by flash chromatography ($CH_2Cl_2$/EtOAc) to yield compound 69 (0.5 g, 49%). MS: m/z+ 342.1 [M+H]+; Anal. Calcd (found) for $C_{17}H_{15}N_3OS_2$: C, 59.80 (59.89); H, 4.43 (4.51); N, 12.31 (12.12); S, 18.78 (18.53).

1-(3,4-dihydroquinolin-1(2H)-yl)-2-(thiazolo[4,5-c]pyridine-2-ylthio)ethanone hydrochloride (70)

Compound 69 (162 mg, 4.7 mmol) was dissolved in 10 mL of $Et_2O$ and 2.5 mL of EtOH, stirred for 10 min, then 0.57 mL of 1M HCl (in $Et_2O$) was added slowly. The precipitation started upon addition of the acid. The reaction mixture was stirred for 1 h at RT, 40 min at 0° C., filtered. The precipitate washed with $Et_2O$ and dried under high vacuum over $P_4O_{10}$ overnight, then at 45° C. for 4 h to yield compound 70 (150 mg, 77%): MS: m/z+ 342.1 (M+H)+; Anal. Calcd (found) for $C_{17}H_{16}ClN_3OS_2$: C, 54.03 (53.78); H, 4.27 (4.33); N, 11.12 (10.95); Cl, 9.38 (9.15); S, 16.97 (16.68).

Synthesis of 2-(Benzo[b]thiophen-2-ylthio)-1-(3,4-dihydroquinolin-1(2H)-yl)ethanone (73)

Benzo[b]thiophene-2-thiol (72)

Compound 71 (1.75 g, 13.0 mmol) was dissolved in 40 mL of dry $Et_2O$ under $N_2$ and the solution was cooled to −40° C. nBuLi (2.5 M solution in hexane, 5.7 mL, 14.3 mmol) was added and the reaction mixture was allowed to warm up to 0° C. during 1 h and then sulfur (0.414 g, 13.0 mmol) was added in one portion. The solution was allowed to slowly warm up to RT over 3 h. Excess of 10% HCl was added and the reaction mixture was stirred for 20 min. The thiol was extracted with ether, washed with brine, dried over $Na_2SO_4$ and concentrated to afford 2.0 g of crude compound 72 which was used in the next step without further purification.

2-(Benzo[b]thiophen-2-ylthio)-1-(3,4-dihydroquinolin-1(2H)-yl)ethanone (73)

Crude compound 72 (0.71 g, 4.3 mmol) was dissolved in 40 mL of dry THF under $N_2$, stirred for 30 min at RT and then cooled down to 0° C. NaH (60% in mineral oil, 0.224 g, 5.5 mmol) was added to the ice-cold solution which became a yellowish suspension. The formed suspension was stirred for 40 min at 0° C. and then 2-chloro-1-(3,4-dihydroquinolin-1 (2H)-yl)ethanone (0.89 g, 4.3 mmol) was added as a solution in 4 mL of dry THF. The reaction mixture was stirred at RT for 16 h. The work-up, the same as for compound 5, gave crude material which was purified by flash chromatography (CH$_2$Cl$_2$/EtOAc) giving 0.56 g of the crude product. Pumping the crude product under high vacuum over P$_4$O$_{10}$ at 45° C. for 4 h removed the co-crystallized EtOAc to yield the desired product 73 (36%): MS: m/z$^+$ 340.1 [M+H]$^+$; Anal. Calcd (found) for C$_{19}$H$_{17}$NOS$_2$: C, 67.22 (67.18); H, 5.05 (5.11); N, 4.13 (4.08); S, 18.89 (18.70).

Synthesis of 1-(3,4-dihydroquinolin-1(2H)-yl)-2-(3-methylbenzo[b]thiophen-2-ylthio)-ethanone (76)

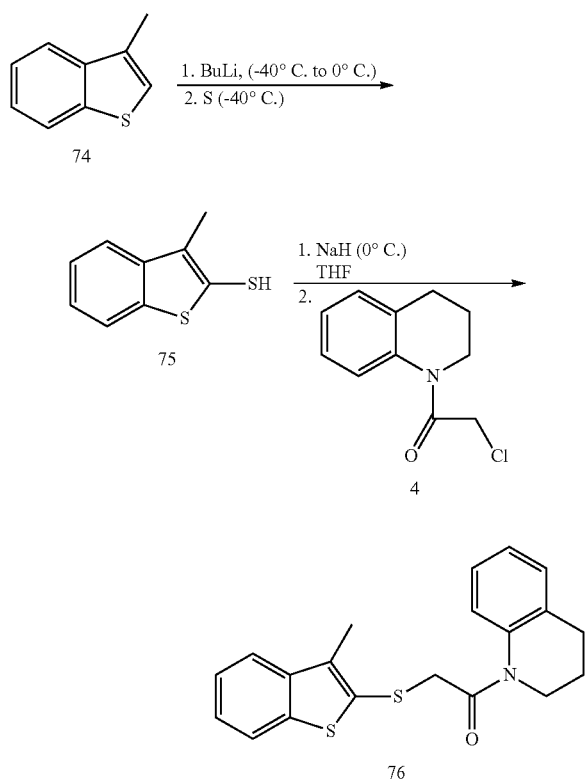

Methylbenzo[b]thiophene-2-thiol (75)

Compound 75 was obtained according to the procedure used to synthesize compound 72, except the addition of sulfur was done at −40° C. in an attempt to avoid significant formation of disulfide. The obtained crude material (75) was used for the next step without further purification.

1-(3,4-dihydroquinolin-1(2H)-yl)-2-(3-methylbenzo[b]thiophen-2-ylthio)-ethanone (76)

Crude compound 75 (0.55 g, 3.0 mmol) was coupled with compound 4 (0.48 g, 2.3 mmol) according to procedure used to synthesize compound 73. The product was purified by column chromatography to yield compound 76 (95 mg, 5% for two steps): MS: m/z+ 354.1 [M+H]$^+$; Anal. Calcd (found) for C20H19NOS2.0.1H$_2$O: C, 67.61 (67.59); H, 5.45 (5.48); N, 3.94 (3.94); S, 18.05 (17.75).

Synthesis of 2-(2-(3,4-dihydroquinolin-1(2H)-yl)-2-oxoethylthio)-1H-benzo[d]imidazole-1-carbonitrile (79)

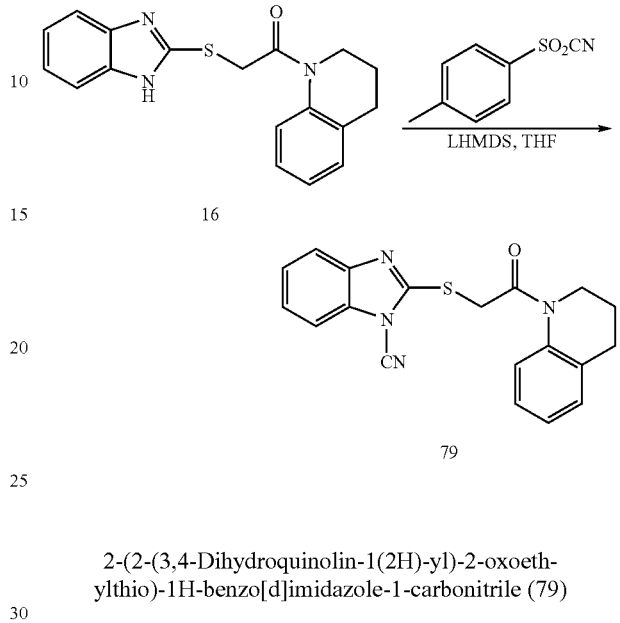

2-(2-(3,4-Dihydroquinolin-1(2H)-yl)-2-oxoethylthio)-1H-benzo[d]imidazole-1-carbonitrile (79)

To a solution of compound 16 (0.52 g, 1.6 mmol, 1.0 eq) in 6 mL of dry THF stirred at −78° C. under N$_2$ LiHMDS (1.7 mL, 1.05 eq) was added. The mixture was stirred for 15 min. at −78° C. and then TosCN (306 mg, 1.05 eq. in 1 mL of THF) was added dropwise. The reaction mixture was quickly allowed to warmed up to RT. The reaction mixture was quenched with 10 mL of NH$_4$Cl (sat.), extracted into ethyl acetate, washed with brine and concentrated to give creamy solid. The crude was purified by column chromatography (ethyl acetate/hexanes) to give 79 (330 mg, 59%). MP=153.3-154.2° C. Anal/Calcd. for C$_{19}$H$_{16}$N$_4$OS: C, 65.50; H, 4.63; N, 16.08; S, 9.20. Found C, 65.59; H, 4.66; N, 16.06; S, 9.16.

Synthesis of Benzo[d]thiazol-2-yl(2-(3,4-dihydroquinolin-1(2H)-yl)-2-oxoethyl)cyanamide (84)

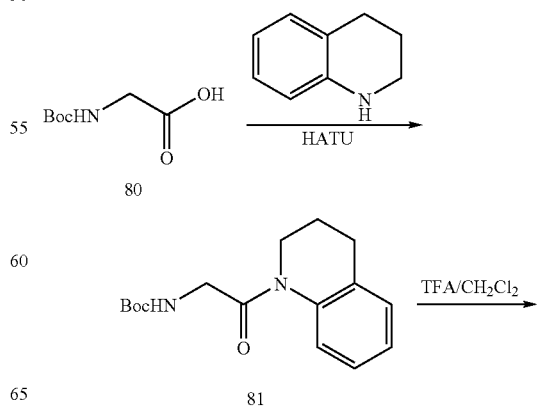

125

-continued

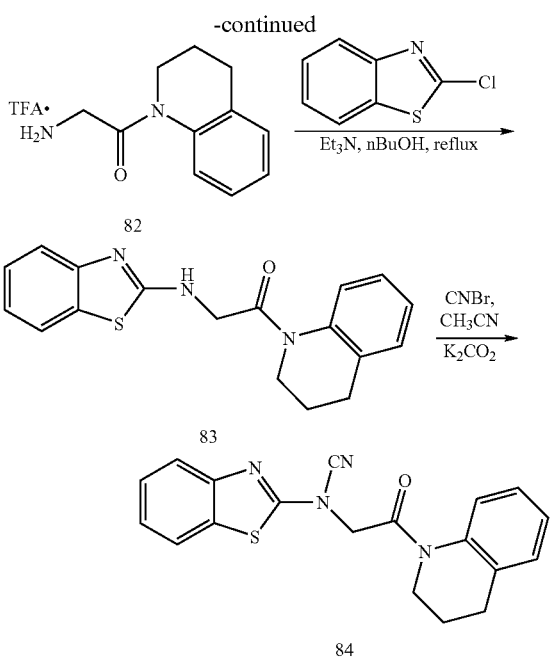

Tert-butyl 2-(3,4-dihydroquinolin-1(2H)-yl)-2-oxoethylcarbamate (81)

To a solution of Boc-Gly-OH (80) (4.0 g, 22.83 mmol) in dry $CH_2Cl_2$ (50 mL) at 0° C. under $N_2$ was added HATU (8.70 g, 22.9 mmol). After stirring for 15 min at r.t., 1,2,3,4-tetrahydroquinoline (2.9 mL, 23.0 mmol), and DIPEA (12 mL, 68.8 mmol) were added. The reaction was stirred for 36 h at room temperature. The reaction mixture was diluted with $CH_2Cl_2$ (100 mL) and washed with saturated $NaHCO_3$, 5% HCl, water, and saturated NaCl. Dried over $MgSO_4$, and filtered. The solvent was removed under reduced pressure and the product was purified by column chromatography (10-50% EtOAc in hexanes) to afford 81 as a solid (5.76 g, 87%).

2-Amino-1-(3,4-dihydroquinolin-1(2H)-yl)ethanone, TFA salt (82)

Compound 81 (2.8 g, 9.66 mmol) was dissolved in 20 mL of $TFA/CH_2Cl_2$ (1:3) at 0° C. under $N_2$. After stirring for 1 h, the solvents were removed under reduced pressure. 5 mL of $CH_2Cl_2$/hexanes were added and removed again under reduced pressure to afford 82 (3.0 g). This crude material was used in the next step with out further purification.

2-(Benzo[d]thiazol-2-ylamino)-1-(3,4-dihydroquinolin-1(2H)-yl)ethanone (83)

To a 0° C. solution of 2-chlorobenzothiazole (1.20 mL, 9.66 mmol) in 1-butanol (25 mL) was added compound 82 (2.94 g, 9.66 mmol)) followed by dropwise addition of $Et_3N$ (4.5 mL, 32 mmol). The reaction was heated to reflux for 24 h under $N_2$. The solvent was removed under reduced pressure and the product was purified by column chromatography (20-50% EtOAc in hexanes) to afford 83 as a white foam (2.58 g, 82%); MS m/z: 324 (M+H)+. Anal. Calcd. For, $C_{18}H_{17}N_3OS$: C, 66.85; H, 5.30; N, 12.99; S, 9.91. Found: C, 67.01; H, 5.42; N, 12.78; S, 9.85.

126

Benzo[d]thiazol-2-yl(2-(3,4-dihydroquinolin-1(2H)-yl)-2-oxoethyl)cyanamide (84)

To a suspension of compound 83 (340 g, 1.05 mmol) in dry $CH_3CN$ (10 mL) were added cyanogen bromide (5M in $CH_3CN$) (0.42 mL, 2.1 mmol) and $K_2CO_3$ (580 g, 4.2 mmol). The reaction was heated to reflux for 4 h under $N_2$. 0.84 mL (4.2 mmol) of cyanogen bromide was added and the reflux was continued for 12 h. The reaction mixture was diluted with EtOAc (50 mL). The solids were filtered off, filtrate was concentrated, and the yellow residue was purified by column chromatography (20% EtOAc in hexanes) to afford 84 as an off-white solid (80 mg, 28%). MS m/z: 349 (M+H)+. Anal. Calcd. For, $C_{19}H_{16}N_4OS \cdot 0.6\ H_2O$: C, 63.53; H, 4.83; N, 15.60; S, 8.92. Found: C, 63.24; H, 4.67; N, 15.25; S, 8.76.

Example 2

High-Throughput Screening Assay

The assay depends on detection of the rise in intracellular $Ca^{2+}$ concentration ($[Ca^{2+}]_i$) following channel activation in cells inducibly expressing the TRPV3 channel. $Ca^{2+}$ rise is quantified with the use of fluorescent $Ca^{2+}$ indicators that are loaded into cells and thereafter indicated the $[Ca^{2+}]_i$. $Ca^{2+}$ influx follows activation of the TRPV3 channel. Compounds inhibiting this $[Ca^{2+}]_i$ rise are considered hits for further investigation.

The commercially available HEK293/TREx line (Invitrogen) was stably transfected with a TRPV3 construct and screened by immunostaining to find clones with TRPV3 expression following stimulation with 1 μg/ml tetracycline. Clonal TRPV3-expressing cells were maintained in the growth medium recommended by the manufacturer supplemented with 100 μg/ml hygromycin to promote retention of the TRPV3 construct. After growing to near confluency, cells are plated at a density of ~25,000 cells/well in 384 well plates in the presence of 1 μg/ml tetracycline, and allowed to grow for 20-30 hrs. A nearly confluent monolayer results. Cells are then loaded with $Ca^{2+}$ dye: Fura-2/AM or Fluo4/AM are added to the wells to a final concentration of 2 μM or 1 μM, respectively, and incubated for 80 min or 60 min, respectively, at room temperature. Supernatant is then removed from the cells by inverting plates with a sharp flick, and 40 μl Ringer's solution (140 mM NaCl, 4.5 mM KCl, 2 mM $CaCl_2$, 1 mM $MgCl_2$, 10 mM HEPES, 10 mM glucose, pH 7.4) is then added to each well. Following ~1 hour for recovery from loading, cells are assayed using the Hamamatsu FDSS 6000 system, which permits illumination alternately at 340 nM and 380 nM for Fura-2 experiments, or at 485 nM for Fluo4 experiments. Frames were acquired at a rate of 0.2 Hz. During the assay, the plates are continuously vortexed, with pipette mixing of wells following addition of each reagent. For the screening assay, 13 μl of a diluted stock of each compound to be tested (at 50 μM) was added to each well for 2 minutes following the collection of a short (4 frame) baseline. 13 μl 750 μM 2-APB (2-aminoethyldiphenylborinate) was added to each well, achieving a final concentration of 10 μM each compound and 150 μM 2-APB. Data were collected for ~3 minutes following addition of 2-APB, where the fluorescent intensity (for Fluo4) and the F340/F380 ratio (for Fura-2) are proportional to the $[Ca^{2+}]_i$. Negative controls consisted of HEK293/TREx TRPV3 cells exposed to 2-APB, but no test compound. Positive control cells were usually HEK293/TREx ("parental") cells exposed to 2-APB but no test compound, but sometimes normal HEK/293 TREx TRPV3 cells were also used, but not exposed to 2-APB or test compound.

These controls defined a screening window, and "hits" were defined as those test compounds inhibiting the fluorescence response by at least 40%.

Example 3

Patch Clamp Experiments

Whole-cell patch clamp experiments permit the detection of currents through the TRPV3 channel in the cell line described above. A glass electrode is brought into contact with a single cell and the membrane is then ruptured, permitting control of the voltage of the cell membrane and measurement of currents flowing across the membrane using the amplifier attached to the electrode. A perfusion system permits control of the extracellular solution, including the addition of blockers and activators of the current. The current can be activated by heating this solution to 28° C. or warmer or by addition of 20 µM 2-APB to the solution.

TRPV3 cells were induced 20-48 hours, removed from growth plates, and replated at low density (to attain good single-cell physical separation) on glass coverslips for measurement. In some cases, cells were grown in low density overnight on glass coverslips. Patch clamp recordings were made in the whole-cell mode with a holding potential of −40 mV. Every 5 seconds, a voltage ramp was applied from −120 to +100 mV, 400 ms in duration. Currents elicited were quantified at −80 mV and +80 mV. The internal solution consisted of 140 mM cesium aspartate, 10 mM EGTA, 2.27 mM $MgCl_2$, 1.91 mM $CaCl_2$ and 10 mM HEPES, pH to 7.2 with KOH; with 50 nM calculated free $Ca^{2+}$. External solution was Ringer's solution described above. Upon addition of 2-APB or upon heating of the extracellular solution as described above, TRPV3 current was induced only in TRPV3-expressing cells and not in parental HEK293 TREx cells. This current showed a small inward component, reversal near +10 mV and a strong outward rectification, and is referred to as Phase I. Upon continued or repeated readdition of 2-APB or heat as a stimulus, current characteristics change, resulting in a Phase II that is linear through +10 mV. Removal of the stimulus caused most of the current to go away, and inhibitor addition could still inhibit this current.

FIGS. 14A-19C summarize data collected for various tested compounds. The data includes approximate IC50 values for inhibition of TRPV3 mediated inward and outward current (phase 1 and phase 2) as assessed by patch-clamp, as well as comparative data for inhibition of other ion channels. Note that several of the compounds inhibit at least one function of TRPV3 with an 1050 of 1000 nM (1 uM) or less. These compounds include at least one small molecule that inhibits a function of TRPV3 with an IC50 of 500 nM or less. These compounds include at least two small molecules that inhibits a function of TRPV3 with an IC50 of 20 nM or less.

To determine whether compounds were selective for TRPV3 inhibition over inhibition of other ion channel types, the human ERG (hERG), NaV1.2, and TRPV1 (hTRPV1) channels and the rat TRPV6 (rTRPV6) channel were also stably transfected and expressed or induced to express in mammalian cell lines. The methods for measuring currents from these channels are well-established and have been described in numerous publications (See, Weerapura et al., 2002, J Physiology 540: 15-27; Rush et al., 2005, J Physiology 564: 808-815; Caterina et al., 1997, Nature 389: 816-824; Hoenderhop et al., 2001, J Physiology 537: 747-761; Clapham et al., 2003, Pharmacol Rev 55: 591-596). Compounds of interest were tested against these channels at concentrations up to 30 µM, and the resulting data were used to estimate $IC_{50}$. Selectivity data for ruthenium red and for selected compounds are provided in the following Table. Data is presented as fold selective.

| Fold Selectivity of Blockers for TRPV3 Over Other Channels | | | | |
|---|---|---|---|---|
| Compound | TRPV3:hERG | TRPV3:NaV1.2 | TRPV3:TRPV1 | TRPV3:TRPV6 |
| Compound 64 | >40 fold selective | >40 fold selective | >40 fold selective | >40 fold selective |
| Compound 15 | >1000 fold selective | >1000 fold selective | >1000 fold selective | >1000 fold selective |
| Compound 46 | >100 fold selective | N/D | >200 fold selective | N/D |
| Compound 101 | >1000 fold selective | N/D | >1000 fold selective | N/D |
| Compound 102 | >300 fold selective | N/D | N/D | N/D |
| Ruthenium Red | >40 fold selective | N/D | 3 fold selective | 10 fold (Clapham et al.) |

Example 4

Other Screening Assays

Although the exemplary TRPV3 inhibitors provided herein were identified using the assays described in Examples 2 and 3, other cell-based assays can be used to identify and/or characterize TRPV3 inhibitors. One such assay is described in U.S. application Ser. No. 11/078,188, filed Mar. 11, 2005, the contents of which are hereby incorporated by reference in their entirety. TRPV3 protein can be expressed in the prokaryotic cell system described in application Ser. No. 11/078,188, and this system can be used to screen for compounds that modulate an activity of the TRPV3 protein. Alternatively, an ion channel other than TRPV3 can be expressed in the prokaryotic cell system, and the system can be used to evaluate the activity profile of an identified TRPV3 inhibitors with respect to other ion channels.

Any assays performed to identify and/or characterize compounds that inhibit an activity of TRPV3 can be performed in a high-throughput fashion, or can be performed on a smaller scale examining individual compounds or small numbers of compounds. Additionally, any of these assays can be performed (i) as a primary assay to identify compounds that inhibit a function of TRPV3; (ii) as a secondary assay to assess the specificity of a compound with respect to its activity against other ion channels; (iii) as an assay used in a medicinal chemistry program to optimize subject compounds.

Example 5

TRPV3 Antagonist Diminishes Pain from Thermal Injury

Figure 1:
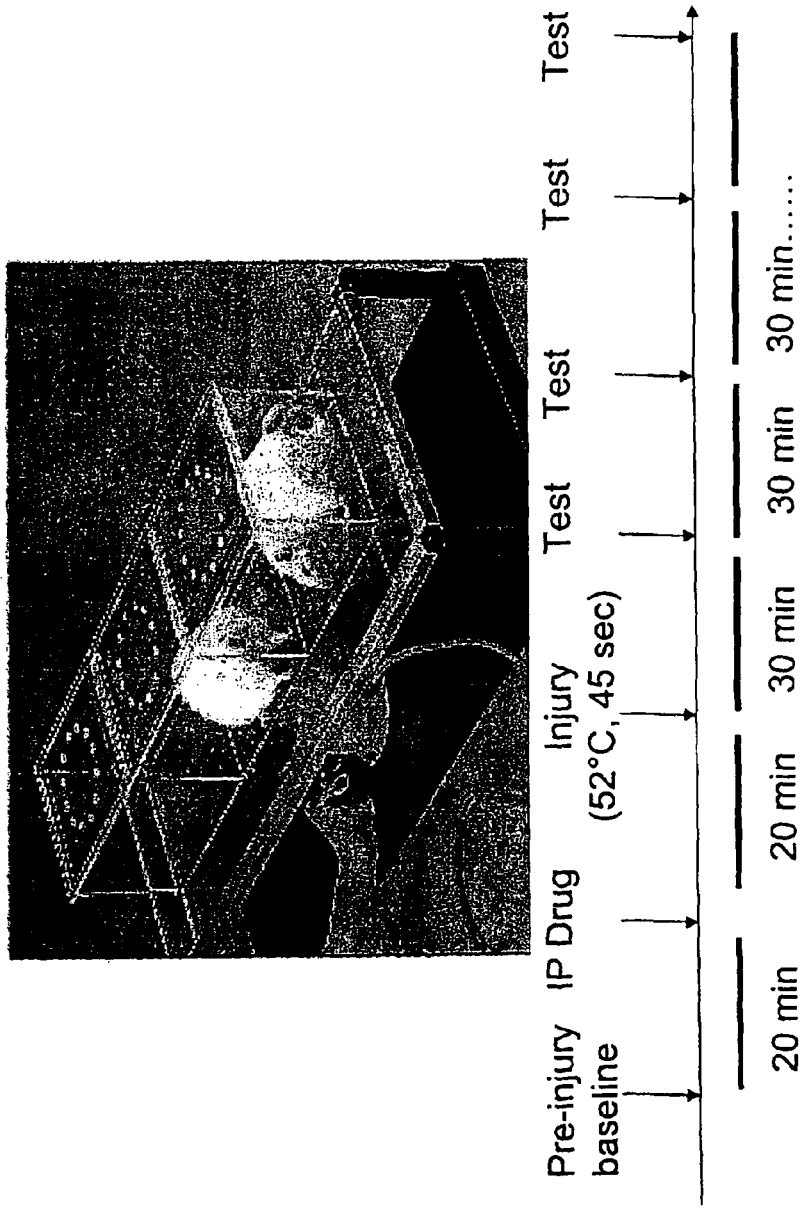

The thermal injury model was used to evaluate the effectiveness of an exemplary TRPV3 inhibitor in the treatment of nociceptive pain. FIG. 1 provides a schematic representation of the protocol used to evaluate a TRPV3 inhibitor in the thermal injury model.

Briefly, the following protocol was followed. Male Holtzman rats (approximately 300 grams) were tested on thermal escape using a Hargreaves type apparatus. Under light anesthesia, a thermal injury (52° C. for 45 seconds) was applied to one heel. The animals were tested for thermal escape latency of the injured and uninjured paw before and at 30, 60, 80 and 120 minutes after injury. Drug (a TRPV3 inhibitor or morphine) or vehicle (0.5% methylcellulose) was administered after the baseline measurement and approximately 15-20 minutes prior to the thermal injury. In addition to the escape latency measurement, behavioral observations were made throughout the experiment.

Figure 2:
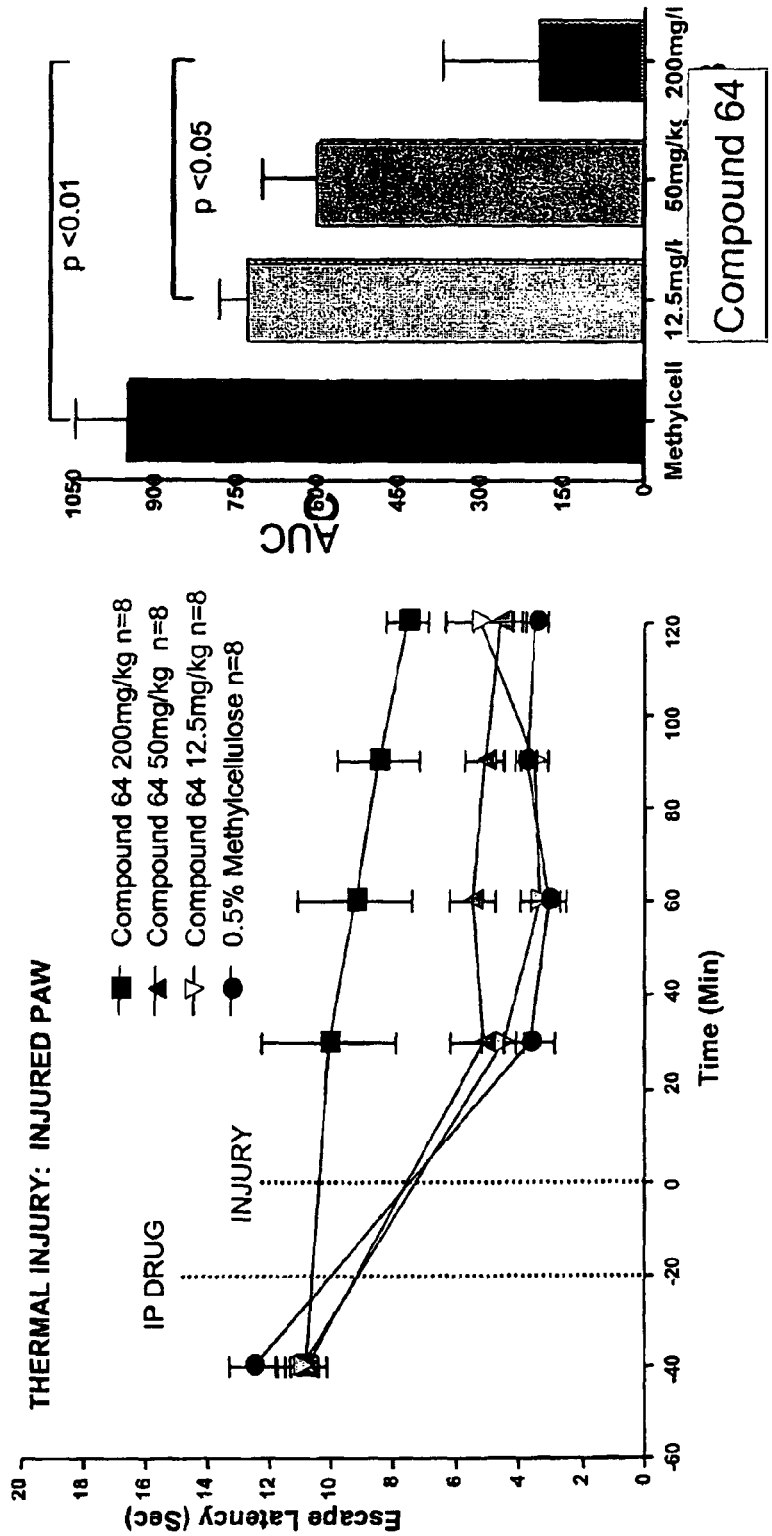

The results of one series of experiments are summarized in FIG. 2. FIG. 2 shows the effects of various concentrations of a TRPV3 inhibitor (inhibitor 64) on escape latency in the injured paw of treated mice following thermal injury, in comparison to a methylcellulose control. Note the significant sensitivity to pain in the vehicle injected injured paw, evidenced by the very fast (4 second) escape latency after injury. Increasing concentrations of the TRPV3 inhibitor significantly diminished pain in the injured animals. This is evidenced by the increasing escape latency measurements. In fact, administration of 200 mg/kg of TRPV3 inhibitor resulted in an escape latency comparable to that observed prior to injury. The reduction of pain observed in the injured paw of animals injected with the TRPV3 inhibitor are statistically significant.

Figure 3:
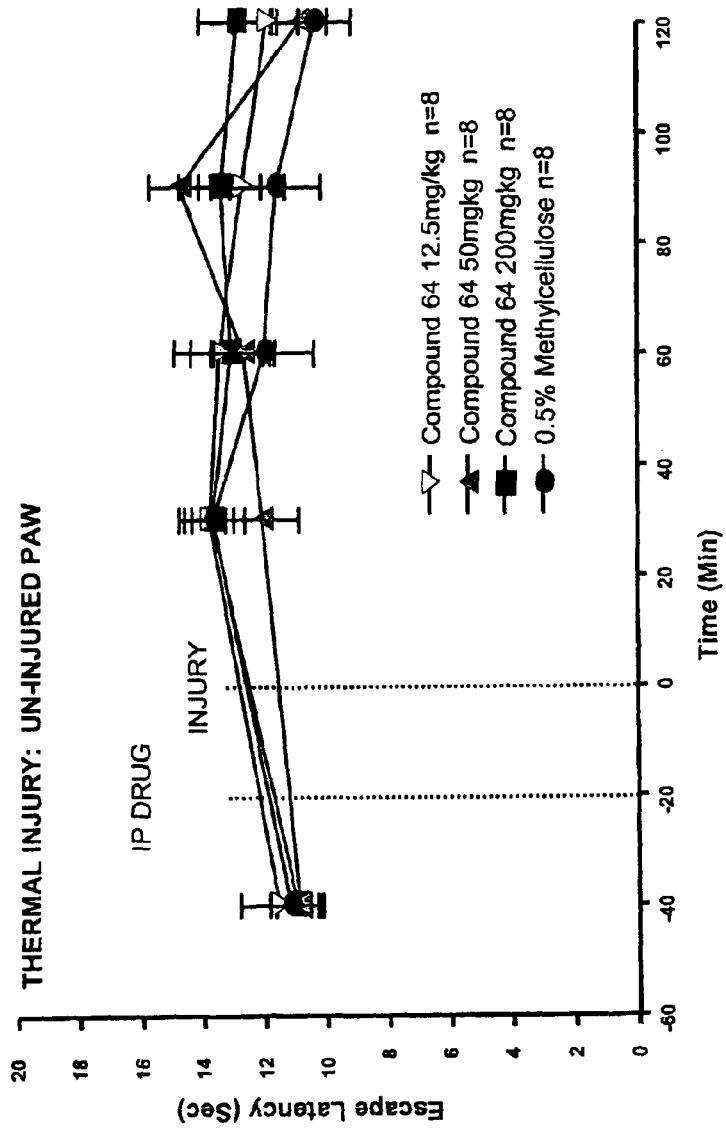
FIG. 3 shows that the efficacy of a TRPV3 inhibitor in diminishing pain in the thermal injury model is specific, and that a TRPV3 inhibitor diminishes pain without affecting the uninjured paw. This suggests that TRPV3 inhibitors are specific for the facilitated state and are non-narcotic.
Figure 4:
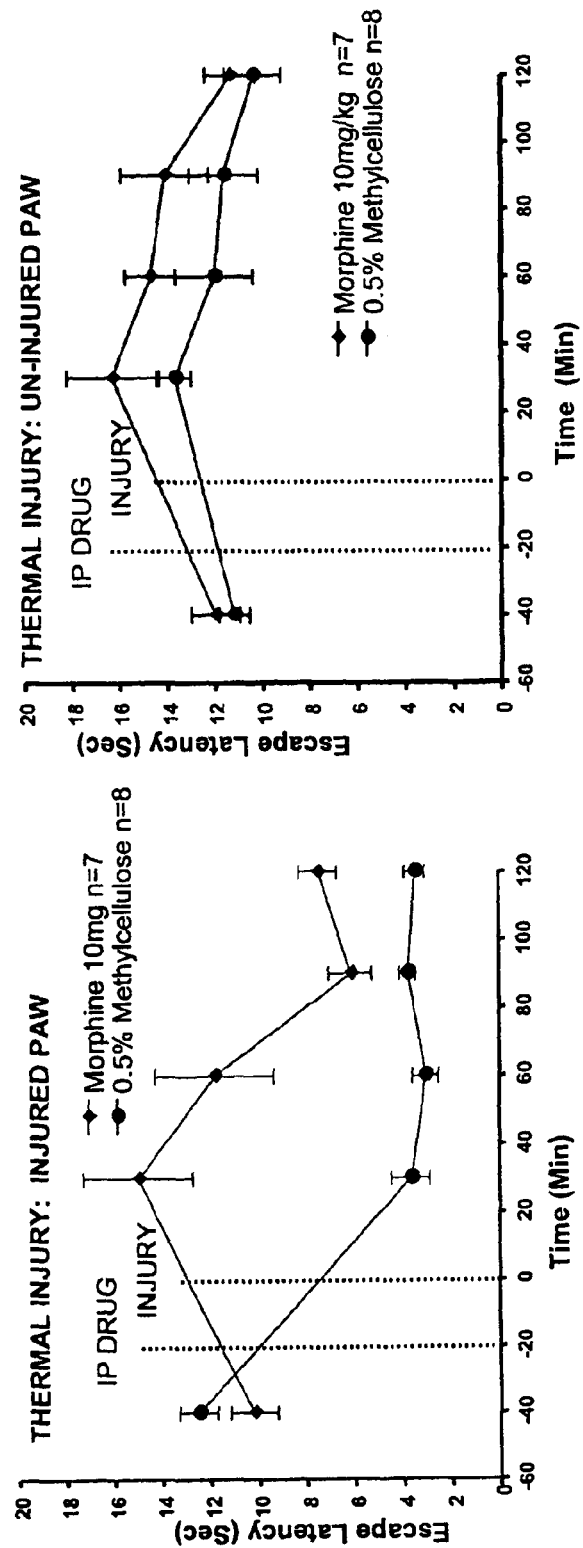
FIG. 4 shows that, in contrast to a TRPV3 inhibitor, morphine reduces pain but has a narcotic effect. Note the thermal escape latency after treatment with morphine is elevated above the baseline.

The effects observed in the injured paw, and summarized in FIG. 2, are specific to the injured paw. FIG. 3 summarizes experiments measuring escape latency in the uninjured paw. Even at the highest concentrations administered, TRPV3 inhibitor had no effect on the uninjured paw. This indicates that TRPV3 inhibitors may have fewer deleterious side-effects than other analgesic compounds. For example, and as shown in FIG. 4, the narcotic morphine does have an effect on both the injured and un-injured paw.

Table A provides further data indicating that a TRPV3 inhibitor with efficacy in reducing pain following thermal injury, specifically inhibitor 64, has few side effects then morphine.

TABLE A

| Behavioral deficits | Pre Injury Observation | t = 30 min | t = 60 min | t = 90 min | t = 120 min |
|---|---|---|---|---|---|
| TRPV3 Inhibitor 64 - Side Effects Observed at Various Concentrations of Compound | | | | | |
| Spontaneous agitation | 0 of 8 (200 mg) | 0 of 8 (200 mg) | 0 of 8 (200 mg) | 0 of 8 (200 mg) | 0 of 8 (200 mg) |
| | 0 of 8 (50 mg) | 0 of 8 (50 mg) | 0 of 8 (50 mg) | 0 of 8 (50 mg) | 0 of 8 (50 mg) |
| | 0 of 8 (12.5 mg) | 0 of 8 (12.5 mg) | 0 of 8 (12.5 mg) | 0 of 8 (12.5 mg) | 0 of 8 (12.5 mg) |
| Tactile allodynia | 0 of 8 (200 mg) | 0 of 8 (200 mg) | 0 of 8 (200 mg) | 0 of 8 (200 mg) | 0 of 8 (200 mg) |
| | 0 of 8 (50 mg) | 0 of 8 (50 mg) | 0 of 8 (50 mg) | 0 of 8 (50 mg) | 0 of 8 (50 mg) |
| | 0 of 8 (12.5 mg) | 0 of 8 (12.5 mg) | 0 of 8 (12.5 mg) | 0 of 8 (12.5 mg) | 0 of 8 (12.5 mg) |
| Pinna response | 0 of 8 (200 mg) | 0 of 8 (200 mg) | 0 of 8 (200 mg) | 0 of 8 (200 mg) | 0 of 8 (200 mg) |
| | 0 of 8 (50 mg) | 0 of 8 (50 mg) | 0 of 8 (50 mg) | 0 of 8 (50 mg) | 0 of 8 (50 mg) |
| | 0 of 8 (12.5 mg) | 0 of 8 (12.5 mg) | 0 of 8 (12.5 mg) | 0 of 8 (12.5 mg) | 0 of 8 (12.5 mg) |
| Corneal response | 0 of 8 (200 mg) | 0 of 8 (200 mg) | 0 of 8 (200 mg) | 0 of 8 (200 mg) | 0 of 8 (200 mg) |
| | 0 of 8 (50 mg) | 0 of 8 (50 mg) | 0 of 8 (50 mg) | 0 of 8 (50 mg) | 0 of 8 (50 mg) |
| | 0 of 8 (12.5 mg) | 0 of 8 (12.5 mg) | 0 of 8 (12.5 mg) | 0 of 8 (12.5 mg) | 0 of 8 (12.5 mg) |
| Exopthalmos | 0 of 8 (200 mg) | 0 of 8 (200 mg) | 0 of 8 (200 mg) | 0 of 8 (200 mg) | 0 of 8 (200 mg) |
| | 0 of 8 (50 mg) | 0 of 8 (50 mg) | 0 of 8 (50 mg) | 0 of 8 (50 mg) | 0 of 8 (50 mg) |
| | 0 of 8 (12.5 mg) | 0 of 8 (12.5 mg) | 0 of 8 (12.5 mg) | 0 of 8 (12.5 mg) | 0 of 8 (12.5 mg) |
| Catalepsy | 0 of 8 (200 mg) | 0 of 8 (200 mg) | 0 of 8 (200 mg) | 0 of 8 (200 mg) | 0 of 8 (200 mg) |
| | 0 of 8 (50 mg) | 0 of 8 (50 mg) | 0 of 8 (50 mg) | 0 of 8 (50 mg) | 0 of 8 (50 mg) |
| | 0 of 8 (12.5 mg) | 0 of 8 (12.5 mg) | 0 of 8 (12.5 mg) | 0 of 8 (12.5 mg) | 0 of 8 (12.5 mg) |
| Sedate | 0 of 8 (200 mg) | 0 of 8 (200 mg) | 2 of 8 (200 mg) | 2 of 8 (200 mg) | 2 of 8 (200 mg) |
| | 0 of 8 (50 mg) | 0 of 8 (50 mg) | 0 of 8 (50 mg) | 0 of 8 (50 mg) | 0 of 8 (50 mg) |
| | 0 of 8 (12.5 mg) | 0 of 8 (12.5 mg) | 0 of 8 (12.5 mg) | 0 of 8 (12.5 mg) | 0 of 8 (12.5 mg) |
| Blistered paw | 0 of 8 (200 mg) | 0 of 8 (200 mg) | 0 of 8 (200 mg) | 1 of 8 (200 mg) | 1 of 8 (200 mg) |
| | 0 of 8 (50 mg) | 0 of 8 (50 mg) | 3 of 8 (50 mg) | 4 of 8 (50 mg) | 5 of 8 (50 mg) |
| | 0 of 8 (12.5 mg) | 0 of 8 (12.5 mg) | 2 of 8 (12.5 mg) | 3 of 8 (12.5 mg) | 4 of 8 (12.5 mg) |
| Morphine - Side Effects Observed at Following Adminstration of 10 mg/kg | | | | | |
| Spontaneous agitation | 0 of 7 | 0 of 7 | 0 of 7 | 0 of 7 | 0 of 7 |
| Tactile allodynia | 0 of 7 | 0 of 7 | 0 of 7 | 0 of 7 | 0 of 7 |
| Pinna response | 0 of 7 | 5 of 7 | 2 of 7 | 0 of 7 | 0 of 7 |
| Corneal response | 0 of 7 | 0 of 7 | 0 of 7 | 0 of 7 | 0 of 7 |
| Exopthalmos | 0 of 7 | 6 of 7 | 6 of 7 | 6 of 7 | 0 of 7 |
| Catalepsy | 0 of 7 | 4 of 7 | 3 of 7 | 1 of 7 | 0 of 7 |
| Blistered paw | 0 of 7 | 0 of 7 | 0 of 7 | 0 of 7 | 0 of 7 |
| 0.5% Methycellulose - Administration of Control | | | | | |
| Spontaneous agitation | 0 of 8 | 0 of 8 | 0 of 8 | 0 of 8 | 0 of 8 |
| Tactile allodynia | 0 of 8 | 0 of 8 | 0 of 8 | 0 of 8 | 0 of 8 |
| Pinna response | 0 of 8 | 0 of 8 | 0 of 8 | 0 of 8 | 0 of 8 |
| Corneal response | 0 of 8 | 0 of 8 | 0 of 8 | 0 of 8 | 0 of 8 |
| Catalepsy | 0 of 8 | 0 of 8 | 0 of 8 | 0 of 8 | 0 of 8 |
| Blistered paw | 0 of 8 | 0 of 8 | 6 of 8 | 7 of 8 | 7 of 8 |

Table A provides a comparison of the side-effects observed in rats following administration of TRPV3 inhibitor 64, at varying concentrations, versus the side-effects observed in rats administered 10 mg/kg of morphine. Side-effects of rats administered 0.5% methycellulouse were observed and served as a control.

Briefly, some of the side-effects of morphine administration include exopthalmos (bulging eyes), catalepsy (a near catatonic state), and the pinna response. These side-effects were not observed in rats administered 12.5, 50, or 200 mg/kg of TRPV3 inhibitor 64.

These experiments demonstrated that a TRPV3 inhibitor diminished pain in the injured paw following thermal injury. The effectiveness of the TRPV3 inhibitor was specific to the injured paw. This specificity indicates that TRPV3 inhibitors diminish pain without producing many of the side-effects of narcotics such as morphine. The efficacy of the TRPV3 inhibitor in this model of nociceptive pain supports the use of TRPV3 inhibitors in the treatment of severe pain, including chronic and acute pain.

Example 6

TRPV3 Antagonist Diminishes Pain Following Formalin

As outlined above, the formalin model involves injection of a formalin solution intradermally or intraperitoneally. Injection of formalin solution invokes a biphasic response, and thus provides a model for both nociceptive and inflammatory pain. The formalin model was used to evaluate the effectiveness of an exemplary TRPV3 inhibitor in the treatment of pain. FIG. 5 provides a schematic representation of the protocol used to evaluate a TRPV3 inhibitor in the formalin model.

Briefly, the following protocol was followed. Male Holtzmann rats received intraplantar injections of 50 µL of 2% formalin. Paw flinching was detected by an automated sensor detecting movement of a small metal band placed on the injected hind paw. Drug or vehicle was administered approximately 15 minutes prior to the injection of formalin. The animal's response to injection of the irritant was measured by counting flinches per minutes during the Early Phase (the first 5 minutes following injection of formalin), during the Late Phase (approximately 30 minutes after injection of formalin), and during the intervening pain free phase.

The results of exemplary experiments are summarized in FIG. 6. Flinches per minute, a measure of the pain and discomfort experienced by the animal, was measured following formalin injection in animals receiving either 200 mg/kg TRPV3 inhibitor or a vehicle control (0.5% methylcellulose). Administration of a TRPV3 inhibitor substantially reduced the flinches per minute during both Early Phase and Late Phase. These results indicated that a TRPV3 inhibitor diminished both phases of pain in the formalin model. Note that these results are similar to the published data reporting the effectiveness of morphine in the formalin model. However, further experiments indicated that TRPV3 diminished pain without producing any of the narcotic side-effects of morphine. The efficacy of the TRPV3 inhibitor in both phases of this model of nociceptive pain and inflammatory pain supports the use of TRPV3 inhibitors in the treatment of severe pain, including chronic and acute pain.

Example 7

TRPV3 Antagonist Diminishes Pain in the Carrageenan Model of Acute Inflammatory Pain As outlined above, the carrageenan model is a model of acute inflammatory pain. As such, it may be used to evaluate effectiveness in relieving pain caused by inflammation, for example, pain due to arthritis. FIG. 7 provides a schematic representation of the protocol used to evaluate a TRPV3 inhibitor in the carrageenan model.

Briefly, naive rats were pretested for sensitivity to a heat stimulus using the Hargreaves apparatus. The next day, 100 µL of λ-carrageenan was injected into the plantar surface of the right hindpaw approximately 4.5 hours before testing. 30-60 minutes before testing the rats were injected intraperitoneally with vehicle or drug. In this study, the drug administered was either a TRPV3 inhibitor or the TRPV1 inhibitor, A-425619 (produced by Abbott; maximal efficacious dose, 40 mg/kg IP; El Kouhen et al., 2005, J Pharmacol Exp Ther 314: 400-4091; Honore et al., 2005, J Pharmacol Exp Ther 314: 410-421). Following injection of both carrageenan and drug or vehicle control, the thermal escape latency was measured. Data are expressed as the recorded Paw Withdrawal Latencies (PWLs) in seconds).

FIG. 8 summarizes the results of these experiments. For each "drug" (vehicle, TRPV3 inhibitor, TRPV1 inhibitor), the results of the control paw are shown at the left and the results of the experimental (carrageenan-injected) paw are shown at the right. The results show that the TRPV3 inhibitor diminished pain in the carrageenan model. Specifically, the TRPV3 inhibitor reduced thermal hyperalgesia in this model of inflammatory pain. At the higher tested concentration of TRPV3 inhibitor (200 mg/kg), the TRPV3 inhibitor was as effective as the TRPV1 inhibitor in diminishing pain. The efficacy of the TRPV3 inhibitor in this model of inflammatory pain supports the use of TRPV3 inhibitors in the treatment of inflammatory pain, for example, pain due to arthritis.

Example 8

TRPV3 Antagonists Diminish Pain in the CFA Model of Inflammatory Pain

As outlined above, the Complete Freund's Adjuvant (CFA) model is a model of inflammatory pain. As such, it may be used to evaluate effectiveness in relieving pain caused by inflammation, for example, pain due to arthritis and other inflammatory conditions. FIG. 9 provides a schematic representation of the protocol used to evaluate a TRPV3 inhibitor in the CFA model.

Naive rats were pretested for sensitivity to a heat stimulus in the Hargreaves apparatus. The next day, 100 µL of complete Freund's adjuvant (CFA) was injected into the plantar surface of the right hindpaw. Two days later, in the morning, the rats were again pretested. In the afternoon, rats were injected with either vehicle control (methylcellulose or PEG-400) or with drug (TRPV3 inhibitor 64, TRPV3 inhibitor 15, TRPV1 inhibitor A-425619, or the non-steroidal anti-inflammatory diclofenac). Drugs or vehicle were injected intraperitoneally, and 45 minutes later rats were tested for hyperalgesia by applying the heat source to the CFA injected and uninjected hindpaw and measuring latency to withdrawal.

FIG. 10 summarizes the results of experiments showing that the TRPV3 inhibitor 64 reduced pain in the CFA model of inflammatory pain. Specifically, the TRPV3 inhibitor reduced thermal hyperalgesia in this model of inflammatory pain. The efficacy of this TRPV3 inhibitor was similar to that of diclofenac (a non-steroidal anti-inflammatory) and to the TRPV1 inhibitor. In fact, at the highest dose of the TRPV3 inhibitor (200 mg/kg) tested, the effects of the TRPV3 inhibitor were more potent than the effects of either the non-steroidal anti-inflammatory or the TRPV1 inhibitor.

FIG. 11 shows that the TRPV3 inhibitor 64 returns pain sensitivity to baseline levels. Specifically, the TRPV3 inhibitor reduces pain in the inflamed paw back to where it was before the CFA was injected. The control paw (uninflamed) was not affected showing that the TRPV3 antagonist does not prevent normal sensation (data not shown).

FIG. 12 summarizes the results of experiments showing that a second TRPV3 inhibitor, 15, also reduces pain in the CFA model of inflammatory pain. Specifically, this second TRPV3 inhibitor reduced thermal hyperalgesia in the CFA model of inflammatory pain. The efficacy of this TRPV3 inhibitor was similar to that of diclofenac (a non-steroidal anti-inflammatory). In fact, at the highest dose of the TRPV3 inhibitor (200 mg/kg) tested, the effects of the TRPV3 inhibitor were more potent than the effects of the non-steroidal anti-inflammatory.

The efficacy of multiple TRPV3 inhibitors in this model of inflammatory pain supports the use of TRPV3 inhibitors in the treatment of inflammatory pain, for example, pain due to arthritis. The tested TRPV3 inhibitors appear to reduce pain without toxicity and without dulling normal sensation (See, FIG. 11); the uninflamed paw was unaffected by treatment with the TRPV3 antagonist (data not shown). Additionally, the tested TRPV3 inhibitors reduce pain with similar or greater efficacy than a non-steroidal anti-inflammatory or a TRPV1 inhibitor. Given the observed side-effects of both of these classes of compounds, TRPV3 inhibitors may reduce pain without the side-effects experienced with available analgesics.

Example 9

Plasma Levels of TRPV3 Inhibitors

The plasma levels of TRPV3 inhibitor 15 were determined via HPLC/MS/MS following administration to male Sprague-Dawley rats. Rats were administered a single intravenous bolus dose of 1.2 mg/kg, an intraperitoneal dose of a suspension of 30 or 60 mg/kg, an oral dose of a solution of 8.6 mg/kg, or an oral dose of a suspension of 6.9 mg/kg.

For intravenous administration, TRPV3 inhibitor 15 solutions were formulated in Solutol at a target concentration of 0.25 mg/mL. The solution was administered as a rapid bolus (approximately 2-3 seconds) via the tail vein of conscious rats or via jugular vein catheter in anesthetized rats. The solution was administered at a dose volume of 4 mL/kg.

For intraperitoneal administration, TRPV3 inhibitor 15 was formulated as a uniform suspension in CMC (carboxymethylcellulose) at a target concentration of 5 mg/mL. The suspension was administered at a dose volume of 10 mL/kg.

For oral administration, TRPV3 inhibitor 15 was formulated as either a uniform suspension in CMC or as a solution in Solutol. The target concentration was 1 mg/mL. Oral administration was by gavage at a dose volume of 10 mL/kg to conscious, fasted, male Sprague-Dawley rats.

FIGS. 13A and 13B summarize the results of experiments conducted following intravenous administration (FIG. 13A) or oral administration of a suspension (FIG. 13B). Data for experiments conducted following administration via other route are not shown. Briefly, the estimated half-life of TRPV3 inhibitor 15 is 1.6 hours. The estimated plasma clearance was 41 mL/kg/min. The estimated volume of distribution was 5510 mL/kg.

Estimated bioavailability in fasted rats was approximately 5%, regardless of whether a solution or suspension was administered. The profile of the plasma-concentration-time curve (FIGS. 13A and 13B) suggests that TRPV3 inhibitor 15 was absorbed rapidly. This rapid absorption was highlighted by the observation that Cmax occurred after just 15 minutes. Such rapid absorption is an advantageous characteristic for a drug useful in the treatment of pain.

TRPV3 inhibitor 15 was prepared in formulations and administered via several different routes of administration. This indicated that TRPV3 inhibitors could be formulated in any of a number of ways and adapted to most effectively treat particular diseases or injuries. These properties, coupled to the minimal side-effects observed following administration of TRPV3 inhibitors to rats, indicated that TRPV3 inhibitors have characteristics of suitable drugs and drug candidates.

Example 10

TRPV3 Inhibitors have a Unique Therapeutic Profile

Based on the foregoing experiments performed in multiple animal models of various types of pain, TRPV3 inhibitors have a unique profile in comparison to non-TRPV3 modulators used in the treatment of pain. The unique profile of TRPV3 inhibitors, along with the absence of narcotic side-effects observed in these studies, makes TRPV3 inhibitors particularly well suited for use in the treatment of pain.

To briefly summarize, the foregoing experiments indicated that the tested TRPV3 antagonists are non-narcotic. The tested compounds were effective in an acute thermal injury model, a formalin model, the carrageenan model, and the CFA model.

Table B provides a comparison, based on our data as well as data available in the literature, between the test TRPV3 antagonists and the following agents: morphine, COX-2 inhibitors (Vioxx® and Celebrex®), gabapentin, and a TRPV1 antagonist (A-425619)

In addition to the differences outlined in Table B, the non-TRPV3 compounds have particular side-effects that must be considered before using them for the treatment of pain. For example, morphine has narcotic and addictive effects that can impede daily functioning. COX-2 inhibitors have been linked to an increased risk of cardiovascular complications. Gabapentin, also known as neurontin, was traditionally used in the treatment of epilepsy. However, it has also been approved for and used in the treatment of post-herpetic neuralgia. Although effective, gabapentin does have numerous side-effects.

TABLE B

| | TRPV3 Antagonist | Morphine | COX-2 Inhibitors | Gabapentin | TRPV1 Antagonist |
|---|---|---|---|---|---|
| | Non-narcotic | Non-narcotic | Narcotic | Non-narcotic | Non-narcotic | Non-narcotic |
| Acute thermal injury | Effective | Effective | Ineffective | Effective | Effective |

TABLE B-continued

| | TRPV3 Antagonist | Morphine | COX-2 Inhibitors | Gabapentin | TRPV1 Antagonist |
|---|---|---|---|---|---|
| Formalin Model | May be effective in Phase I response. Effective in Phase II response | Effective in both Phase I response and Phase II response | Effective in Phase II response only | Effective in Phase II response only | Ineffective |
| Carrageenan Model | Effective | Effective | Effective | Slightly effective | Effective |
| CFA Model | Effective | Effective | Effective | Ineffective | Effective |

Example 11

TRPV3 Antagonist Reduces Pain in the Formalin Model Following Intrathecal Delivery As outlined above, the formalin model involves injection of a formalin solution intradermally or intraperitoneally. Injection of formalin solution invokes a biphasic response, and thus provides a model for both nociceptive and inflammatory pain. The formalin model was used to evaluate the effectiveness of an exemplary TRPV3 inhibitor in the treatment of pain following intrathecal (IT) delivery. Efficacy following intrathecal delivery provides evidence that the compound can act centrally.

Briefly, the following protocol was followed. Male Holtzmann rats received intraplantar injections of 50 μL of 2% formalin. Paw flinching was detected by an automated sensor detecting movement of a small metal band placed on the injected hind paw. Drug or vehicle was administered intrathecally approximately 15 minutes prior to the injection of formalin. The animal's response to injection of the irritant was measured by counting flinches per minutes during the Early Phase and during the Late Phase.

The results of exemplary experiments are summarized in FIG. 20. Flinches per minute, a measure of the pain and discomfort experienced by the animal, was measured following formalin injection in animals receiving either 10 mg/kg TRPV3 inhibitor (Compound 64) or a vehicle control (0.5% DCC). The TRPV3 inhibitor was formulated in 20% DMSO/20% cremaphore/10% cyclodextrin (DCC) and administered intrathecally. Note that in FIG. 20 Phase I refers to the Early Phase and Phase II refers to the Late Phase.

Administration of a TRPV3 inhibitor substantially reduced the flinches per minute. A statistically significant reduction in fliches per minute was observed during the Late Phase. These results indicated that a TRPV3 inhibitor diminished pain in the formalin model following intrathecal delivery.

Example 12

TRPV3 Antagonist Diminishes Pain in the Substance P Induced Thermal Hyperalgesia The efficacy of a TRPV3 antagonist in diminishing hyperalgesia was assessed in a model of intrathecal administered substance-P induced thermal hyperalgesia. Male Holtzman rats were used in this study and thermal escape was measured using a Hargreaves apparatus. Thermal escape was measured pre-treatment (baseline), and at intervals following intrathecal administration of substance-P (tested at 15, 30, 45, and 60 minutes post substance-P administration). Control animals were administered vehicle intraperitoneally after baseline assessment and 30 minutes prior to substance P administration. Experimental animals receiving a TRPV3 inhibitor (compound 64) were administered compound intraperitoneally after baseline assessment and 30 minutes prior to substance P administration.

Substance-P induced rats were surgically prepared with a lumbar intrathecal catheter using clean surgical technique while under inhalation anesthesia (isoflurane). The catheter was externalized at the back of the head to minimize handling of the animal during drug delivery. If the animal remained healthy for three to four days following catheter placement, it was used into the study.

A modified Hargreaves apparatus was used to determine the thermal escape latencies for each paw. The glass surface on which the rat stands is maintained at 30° C. Thermal nociceptive stimulus originates from a focused projection bulb that is manually manipulated to permit the stimulus to be delivered separately to either hind paw.

Briefly, baseline mean paw latencies were determined prior to substance-P administration. Rats received a single intraperitoneal injection of 200 mg/kg of compound 64 or vehicle (0.5% CMC), 30 minutes prior to substance-P administration. After injection of substance P intrathecally via the previously placed catheter (counted as time=0), measurements of escape latency were taken at 15, 30, 45, and 60 minutes post-substance-P administration. Each time point signifies the time at which the left hind paw was tested, with the right hind paw tested one minute later. The mean of the two response latencies were taken as the latency for that testing time. Note that substance-P was administered at a concentration of 200 nmol/66 μl in saline. Substance-P was delivered at a dose of 30 nmol/10 μl followed by a 10 μg saline flush over a period of about 5 seconds.

In addition to assessing thermal escape latency, general behavioral assessments were made during each period of observation. Observations included: tactile allodynia (vocalization/agitation induced by light touch applied to the body surface), spontaneous vocalization, biting and chewing of body surface, loss of hind limb placing and stepping reflex, loss of hind limb weight bearing, and loss of righting reflex. All assessments were noted as "present", "absent" or ranked according to a graded scale.

As summarized in FIG. 21, intrathecal administration of substance-P evoked a fall in the mean paw latency in vehicle treated animals. In other words, intrathecal administration of substance-P resulted in thermal hyperalgesia. Pre-treatment with 200 mg/kg TRPV3 inhibitor (compound 64; delivered IP) reversed the hyperalgesia observed in comparison to control animals. These results are statistically significant ($p<0.05$) between groups.

Intrathecal substance-P produces thermal hyperalgesia by the central activation of NK1 receptors. This hyperalgesia reflects the initiation of a central (spinal) facilitated states. These experiments indicated that a TRPV3 inhibitor was capable of reversing hyperalgesia induced by substance-P. This is consistent with a conclusion that systemically administered TRPV3 inhibitor can exert a central antihyperalgesic effect.

INCORPORATION BY REFERENCE

All publications and patents mentioned herein, are hereby incorporated by reference in their entirety as if each individual publication or patent was specifically and individually indicated to be incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method for treating pain, comprising administering to a patient in need thereof an effective amount of a compound of Formula I or a salt thereof:

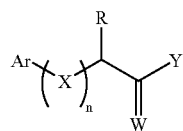

wherein
Ar represents an aryl or heteroaryl group;
Y represents

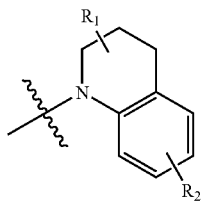

wherein $R_1$ and $R_2$ each, independently, are absent or represent one or more substituents on the ring to which they are attached;
R represents H or a lower alkyl;
X represents O, S, $NR_{10}$, $CF_2$, or $C(CN)_2$;
W represents S or NR';
n is 1;
R', independently for each occurrence, represents H or a lower alkyl;
$R_{10}$ represents H, lower alkyl, or cyano; and
wherein said compound inhibits TRPV3 with an $IC_{50}$ of 10 micromolar or less.

2. The method of claim 1, wherein each $R_1$ is independently selected from H, lower alkyl, alkoxy, carboxyl, ester, amido, sulfonamido, heterocyclyl, cycloalkyl, hydroxyl, amino, acylamino, thioether, sulfonylamino, or $R_1$ taken together with the carbon to which it is attached forms a carbonyl or thiocarbonyl; and each R2 is independently selected from H, lower alkyl, alkoxy, carboxyl, ester amido, sulfonamido, heterocyclyl, cycloalkyl, hydroxyl, amino, acylamino, thioether, sulfonylamino, halogen, $CF_3$, or cyano.

3. The method of claim 1, wherein Y represents

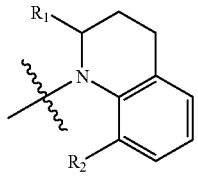

wherein
$R_1$ represents H, lower alkyl, alkoxy, carboxyl, ester, amido, sulfonamido, heterocyclyl, cycloalkyl, hydroxyl, amino, acylamino, thioether, sulfonylamino, or $R_1$ taken together with the carbon to which it is attached forms a carbonyl or thiocarbonyl; and
$R_2$ represents H, lower alkyl, alkoxy, carboxyl, ester, amido, sulfonamido, heterocyclyl, cycloalkyl, hydroxyl, amino, acylamino, thioether, sulfonylamino, halogen, $CF_3$, or cyano.

4. The method of claim 3, wherein $R_1$ represents H, lower alkyl, alkoxy, or $R_1$ taken together with the carbon to which it is attached forms a carbonyl, and $R_2$ represents H, lower alkyl, alkoxy or halogen.

5. The method of claim 1, wherein Ar represents

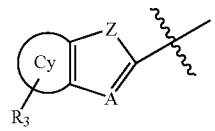

wherein
Cy represents an aryl or heteroaryl ring;
Z represents O, S, $NR_{11}$, $CF_2$, or $C(CN)_2$;
$R_3$ is absent or represents one or more substituents on the ring to which it is attached;
$R_{11}$ represents H, lower alkyl, or cyano;
A represents N or $C(R_{2a})$; and
$R_{2a}$ represents H, lower alkyl, alkoxy, or halogen.

6. The method of claim 5, wherein Cy represents a phenyl, thiophene, imidazole, thiazole, furan, oxazole, tetrazole, thiadiazole, pyridine, pyrimadine, or triazole.

7. The method of claim 5, wherein $R_3$ is absent, or independently for each occurrence, is selected from lower alkyl, alkoxy, carboxyl, ester, amido, sulfonamido, heterocyclyl, cycloalkyl, hydroxyl, amino, acylamino, thioether, sulfonylamino, nitro, halogen, $CF_3$, or cyano.

8. The method of claim 5, wherein Ar represents

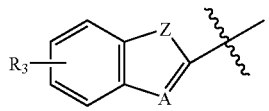

wherein
Z represents O, S, $NR_{11}$, $CF_2$, NR, or $C(CN)_2$;
A represents N or $C(R_{2a})$;
$R_3$ is absent or represents one or more substituents on the ring to which it is attached;
$R_{11}$ represents H, lower alkyl, or cyano; and
$R_{2a}$ represents H, lower alkyl, alkoxy, or halogen.

9. The method of claim 8, wherein $R_3$ is absent or each $R_3$ is independently selected from lower alkyl, alkoxy, carboxyl, ester, amido, sulfonamido, heterocyclyl, cycloalkyl, hydroxyl, amino, acylamino, thioether, sulfonylamino, nitro, halogen, $CF_3$, or cyano.

10. The method of claim 8, wherein Ar represents

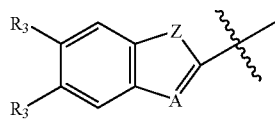

wherein
Z represents O, S, $NR_{11}$, $CF_2$, or $C(CN)_2$;
A represents N or $C(R_{2a})$;
$R_3$ independently for each occurrence represents H, lower alkyl, alkoxy, carboxyl, ester, amido, sulfonamido, heterocyclyl, cycloalkyl, hydroxyl, amino, acylamino, thioether, sulfonylamino, nitro, halogen, $CF_3$, or cyano;
$R_{11}$ represents H, lower alkyl, or cyano; and
$R_{2a}$ represents H, lower alkyl, alkoxy, or halogen.

11. The method of claim 10, wherein $R_3$ independently for each occurrence represents H, lower alkyl, alkoxy, $CF_3$, nitro, or halogen.

12. The method of claim 1, wherein said compound inhibits a TRPV3-mediated current with an $IC_{50}$ of 10 micromolar or less.

13. The method of claim 1, wherein said compound inhibits at least 95% of TRPV3-mediated current at 5 micromolar or less.

14. The method of claim 1, wherein said compound inhibits TRPV3 with an $IC_{50}$ of 100 nanomolar or less.

15. The method of claim 1, wherein said compound inhibits TRPV3 with an $IC_{50}$ at least one order of magnitude lower than its $IC_{50}$ for inhibition of one or more of TRPV5, TRPV6, NaV 1.2, mitochondrial uniporter and hERG channel activities.

16. The method of claim 1, wherein said compound inhibits TRPV3 with an $IC_{50}$ at least one order of magnitude lower than its $IC_{50}$ for inhibition of TRPV1.

17. The method of claim 12, wherein said compound inhibits a TRPV3 mediated current with an $IC_{50}$ at least one order of magnitude lower than its $IC_{50}$ for inhibition of one or more of TRPV5, TRPV6, NaV 1.2, mitochondrial uniporter and hERG channel activities.

18. The method of claim 12, wherein said compound inhibits a TRPV3 mediated current with an $IC_{50}$ at least one order of magnitude lower than its $IC_{50}$ for inhibition of TRPV1.

19. The method of claim 1, wherein the compound is administered topically.

20. The method of claim 1, wherein the compound is administered orally.

21. The method of claim 1, wherein the compound is administered transdermally, parenterally, rectally, vaginally, intranasally, intraocularly, intravenously, intramuscularly, intraarterially, intrathecally, intracapsularly, intraorbitally, intracardiacly, intradermally, intraperitoneally, transtracheally, subcutaneously, subcuticularly, intraarticularly, subcapsularly, subarachnoidly, intraspinally, intrasternally or by inhallation.

22. The method of claim 1, used to reduce the frequency of, delay the onset of, treat or alleviate symptoms of acute pain, chronic pain, touch sensitivity, itching sensitivity, or as part of treating a burn.

23. The method of claim 9, wherein the pain is post-surgical pain, cancer pain, or neuropathic pain.

24. The method of claim 1, used to reduce the frequency of, delay the onset of, treat or alleviate symptoms of migraine.

25. The method of claim 1, used to reduce the frequency of, delay the onset of, treat or alleviate symptoms of oral mucositis.

26. The method of claim 17, used to reduce the frequency of, delay the onset of, treat or alleviate symptoms of a disorder or condition selected from one or more members of the group consisting of acute or chronic pain, touch sensitivity, burns, inflammation, diabetic neuropathy, psoriasis, eczema, dermatitis, post-herpetic neuralgia (shingles), migraine, pancreatitis, incontinence, fever, chronic regional pain syndrome, hot flashes, osteoarthritis, rheumatoid arthritis and cough, or is used as a depilatory to promote loss of or inhibit the growth of hair on a patient.

* * * * *